US005891905A

United States Patent [19]
Romanczyk, Jr. et al.

[11] Patent Number: 5,891,905
[45] Date of Patent: Apr. 6, 1999

[54] METHODS OF TREATMENT USING PROCYANIDIN ANTIOXIDANTS

[75] Inventors: Leo J. Romanczyk, Jr., Hackettstown, N.J.; John F. Hammerstone, Jr., Nazareth, Pa.; Margaret M. Buck, Morristown, N.J.

[73] Assignee: Mars, Incorporated, McLean, Va.

[21] Appl. No.: 839,446

[22] Filed: Apr. 14, 1997

Related U.S. Application Data

[62] Division of Ser. No. 687,885, Jul. 26, 1996, Pat. No. 5,712,305, which is a division of Ser. No. 317,226, Oct. 3, 1994, Pat. No. 5,554,645.

[51] Int. Cl.$^6$ .......................... A01N 43/02; A01N 43/16; A61K 31/35; A61K 31/335
[52] U.S. Cl. .......................... 514/449; 514/451; 514/453; 514/456; 514/577; 252/397; 252/399; 252/404; 252/407
[58] Field of Search ...................................... 514/449, 451, 514/453, 456, 577; 252/397, 399, 404, 407

[56] References Cited

PUBLICATIONS

Phenolic Compounds in Foods and Their Effects on Health II, Antioxidants & Cancer Prevention, Huang, M.T., Ho, C.T., and Lee, C.Y. editors, ACS Symposium Series 507, American Chemical Society, Washington, D.C. (1992).

Phenolic Compounds in Foods and Their Effects on Health I, Analysis, Occurrence & Chemistry, Ho, E.T., Lee, C.Y., and Huang, M.T. editors, ACS Symposium Series 506, American Chemical Society, Washington, D.C. (1992).

Barrows, L.R., Borchers, A.H., and Paxton, M.B., Transfectant CHO Cells Expressing $O^6$–alkylguanine –DNA–alkyltransferase Display Increased Resistance to DNA Damage Other than $O^6$–guanine Alkylation, Carcinogenesis, 8:1853 (1987).

Boukharta, M., Jalbert, G. and Castonguay, A. Efficacy of Ellagitannins and Ellagic Acid as Cancer Chemopreventive Agents—Presented at the XVI$^{th}$ International Conference of the Groupe Polyphenols, Lisbon, Portugal, Jul. 13–16, 1992.

Burres, N.S., Sazesh, J., Gunawardana, G.P., and Clement, J.J., Antitumor Activity and Nucleic Acid Binding Properties of Dercitin, a New Acridine Alkaloid Isolated from a Marine Dercitus species Sponge, Cancer Research, 49, 5267–5274 (1989).

Caragay, A.B., Cancer Preventive Foods and Ingredients, Food Technology, 46;4, 65–79 (1992).

Chu, S.–C., Hsieh, Y.–S. and Lim, J.–Y., Inhibitory Effects of Flavonoids on Maloney Murine Leukemia Virus Reverse Transcriptase Activity, J. of Natural Products, 55:2, 179–183 (1992).

Clapperton, J., Hammerstone, J.F. Jr., Romanczyk, L.J. Jr., Chan, J., Yow, S., Lim, D. and Lockwood, R., Polyphenols and Cocoa Flavor—Presented at the XVI$^{th}$ International Conference of the Groupe Polyphenols, Lisbon, Portugal, Jul. 13–16, 1992.

Danks, M.K., Schmidt, C.A., Cirtain, M.C., Suttle, D.P., and Beck, W.T., Altered Catalytic Activity of and DNA Cleavage by DNA Topoisomerase II from Human Leukemic Cells Selected for Rsistance to VM–26, Biochem., 27;8861 (1988).

Delcour, J.A., Ferreira, D. and Roux, D.G., Synthesis of Condensed Tannins, Part 9, The Condensation Sequence of Leucocyanidin with (+Catechin and with the Resultant Procyanidins, J. Chem. Soc. Perkin Trans. I, 1711–1717 (1983).

Deschner, E.E., Ruperto, J., Wong, G. and Newmark, H.L., Quercetin and Rutin as Inhibitors of Azoxymethanol—Induced Colonic Neoplasia, Carcinogenesis, 7, 1193–1196 (1991).

Designing Foods, Manipulating Foods to Promote Health, Inform, 4:4, 344–369 (1993).

Drake, F.H., Hofmann, G.A., Mong., S.–M., Bartus, J.O., Hertzberg, R.P., Johnson, R.K. Mattern, M.R., and Mirabelli, C.K., In vitro and Intercellular Inhibition of Topoisomerase II by the Antitumor Agent Membrane, Cancer Research, 49, 2578–2583 (1989).

Engels J.M.M., Genetic Resources of Cacao: A Catalogue of the CATIE Collection, Tech. Bull. 7, Turrialba, Costa Rica (1981).

Enriquez G.A. and Soria J.V., Cocoa Cultivars Register IICA, Turrialba, Costa Rica (1967).

Ferreira, D., Steynberg, J.P. Roux, D.G. and Brandt, E.V., Diversity of Structure and Function in Oligomeric Flavanoids, Tetrahedron, 48:10, 1743–1803 (1992).

Fesen, M. and Pommier, Y., Mammalian Topoisomerase II Activity is Modulated by the DNA Minor Groove Binder—Distainycin in Simian Virus 40 DNA, J. Biol. Chem., 264, 11354–11359 (1989).

Fry, D.W., Boritzki, T.J., Besserer, J.A., and Jackson, R.C. in vitro Strand Scission and Inhibition of Nucleic Acid Synthesis on L1210 Leukemia Cells by a New Class of DNA Complexes, the anthra [1, 9–CD]pyrazol–6(2H)–ones (anthrapyrazoles), Biochem. Pharmacol., 34, 3499–3508 (1985).

(List continued on next page.)

Primary Examiner—Nathan M. Nutter
Attorney, Agent, or Firm—Fitzpatrick, Cella, Harper & Scinto

[57] ABSTRACT

Disclosed and claimed are cocoa extracts such as polyphenols or procyanidins, methods for preparing such extracts, as well as uses for them, especially as antineoplastic agents and antioxidants. Disclosed and claimed are antineoplastic compositions containing cocoa polyphenols or procyanidins and methods for treating patients employing the compositions. Additionally disclosed and claimed is a kit for treating a patient in need of treatment with an antineoplastic agent containing cocoa polyphenols or procyanidins as well as a lyophilized antineoplastic composition containing cocoa polyphenols or procyanidins. Further, disclosed and claimed is the use of the invention in antioxidant, preservative and topiosomerase-inhibiting compositions and methods.

11 Claims, 91 Drawing Sheets

PUBLICATIONS

Hsiang, Y.-H., Jiang, J.B., and Liu, L.F., Topoisomerase II Mediated DNA Cleavage by Amonafide and Its Structural Analogs, Mol. Pharmacol., 36, 371–376 (1989).

Jalal, M.A.F. and Collin, H.A., Polyphenols of Mature Plant, Seedling and Tissue Cultures of *Theobroma Cacoa*, Phytochemistry, 6, 1377–1380 (1978).

Jeggo, P.A., Caldecott, K., Pidsley, S., and Banks, G.R., Sensitivity of Chinese Hamster Ovary Mutants Defective in DNA Double Strand Break Repair to Topoisomerase II Inhibitors, Cancer Res., 49:7057 (1989).

Kashiwada, T., Nonaka, G.-I., Nishioka, I., Lee, K.J.-H., Bori, I., Fukushima, Y., Bastow, K.F., and Lee, K.-H., Tannin as Potent Inhibitors of DNA Topoisomerase II in vitro, J. Pharm. Sci., 82:5, 487–492 (1993).

Kato, R., Nakadate, T., Yamamoto, S. and Sugimura, T., Inhibition of 12–O–tetradecanoylphorbol–13–acetate Induced Tumor Promotion and Ornithine Decarboxylase Activity by Quercitin: Possible Involvement of Lipoxygenase Inhibition, Carcinogenesis, 4, 1301–1305 (1983).

Kawada, S.-Z., Yamashita, Y., Fujii, N. and Nakano, H., Induction of Heat Stable Topoisomerase II–DNA Cleavable Complex by Nonintercalative Terpenoids, Terpentecin and Clerocidin, Cancer Research, 51, 2922–2929 (1991).

Kemp, L.M., Sedgwick, S.G. and Jeggo, P.A., X–ray Sensitive Mutants of Chinese Hamster Ovary Cells Defective in Double Strand Break Rejoining, Mutat. Res., 132:189 (1984).

Kikkoman Corporation, Antimutagenic Agent Containing Proanthocyandin Oligomer Preferably Having Flavan–3–ol–Diol Structure, JP 04190774–A, Jul. 7, 1992.

Lehrian, D.W., Patterson, G.R. In Biotechnology; Reed, G., Ed.; Verlag Chemie: Weinheim, 1983, vol.5, Chapter 12.

Leonessa, F., Jacobson, M., Boyle, B., Lippman, J., McGarvey, M., and Clarke, R. Effect of Tamoxifen on the Multidrug–Resistant Phenotype in Human Breast Cancer Cells: Isobolograms, Drug Accumulation, and $M_r$ 170,000 Glycoprotein (gp 170) Binding Studies, Cancer Research, 54, 441–447 (1994).

Liu, L.F., DNA Toposimerase Poisions as Antitumor Drugs, Ann. Rev. Biochem., 58, 351–375 (1989).

McCord, J.D. and Kilara A. Control of Enzymatic Browning in Processed Mushrooms (*Agaricus bisporus*). J. Food Sci., 48:1479 (1983).

Miller, K.G., Liu, L.F. and Englund, P.A., Homogeneous Type II DNA Topoisomerase from Hela Cell Nuclei, J. Biol. Chem., 256:9334 (1981).

Mosmann, T., Rapid Colorimetric Assay for Cellular Growth and Survival: Application to Proliferation and Cytoxicity Assays, J. Immunol. Methods, 65, 55 (1983).

Muller, M.T., Helal, K., Soisson, S. and Spitzer, J.R., A Rapid and Quantitative Microtiter Assay for Eukaryotic Topoisomerase II, Nuc. Acid Res., 17:9499 (1989).

Nawata, H., Chong, M.T., Bronzert, D. and Lippman, M.E. Estradiol–Independent growth of a Subline of MCF–7 Human Breast Cancer Cells in Culture, J. Biol. Chem., 256:13, 6895–6902 (1981).

Okuda, T., Yoshida, T., and Hatano, T., Molecular Structures and Pharmacological Activities of Polyphenols—Oligomeric Hydrolyzable Tannins and Others—Presented at the XVIth International Conference of the Groupe Polyphenols, Lisbon, Portugal, Jul. 13–16, 1992.

Porter, L.J., Ma, Z. and Chan, B.G., Cocoa Procyanidins: Major Flavanoids and Identification of Some Minor Metabolites, Phytochemistry, 30, 1657–1663 (1991).

Revilla, E., Bourzeix, M. and Alonso, E., Analysis of Catechins and Procyanidins in Grape Seeds by HPLC with Photodiode Array Detection, Chromatographia. 31, 465–468 (1991).

Scudiero, D.A., Shoemaker, R.H., Paull, K.D., Monks, A. Tierney, S., Nofziger, T.H., Currens, M.J., Seniff, D., and Boyd, M.R. Evaluation of a Soluble Tetrazolium/Formazan Assay for Cell Growth and Drug Sensitivity in Culture Using Human and Other Tumor Cell Lines, Canur Research, 48, 4827–4833 (1988).

Self, R., Eagles, J., Galletti, G.C., Mueller–Harvey, I., Hartley, R.D., Lee, A.G.H., Magnolato, D., Richli, U., Gujur, R. and Haslam, E., Fast Atom Bombardment Mass Spectrometry of Polyphenols (syn. Vegetable Tannins), Biomed Environ. Mass Spec. 13, 449–468 (1986).

Tanabe, K., Ikegami, Y., Ishda, R. and Andoh, T., Inhibition of Topoisomerase II by Antitumor Agents bis(2,6–dioxopiperazine) Derivatives, Cancer Research, 51, 4903–4908 (1991).

Van Oosten, C.W., Poot, C. and A.C. Hensen, The Precision of the Swift Stability Test, Fette, Seifen, Anstrichmittel, 83:4, 133–135 (1981).

Wang, J.C., DNA Topoisomerases, Ann. Rev. Biochem., 54, 665–697 (1985).

Warters, R.L., Lyons, B.W., Li, T.M. and Chen, D.J., Topoisomerase II Activity in a DNA Double–Strand Break Repair Deficient Chinese Hamster Ovary Cell Line, Mutat. Res., 254:167 (1991).

Yamashita, Y., Kawada, S.-Z. and Nakano, H., Induction of Mammalian Topoismerase II Dependent DNA Cleavage by Nonintercalative Flavanoids, Genisten and Orbol., Biochem Pharm, 39:4, 737–744 (1990).

Yamashita, Y., Kawada, S.-Z., Fujii, N. Nakano, H., Induction of Mammalian DNA Topoisomerase I and II Mediated DNA Cleavage by Saintopin, a New Antitumor Agent from Fungus, Biochem., 30, 5838–5845 (1991).

Oliveira et al., Antitumor Activity of Condensed Flavanols, An. Acad, brasil Cien, (1972), 44(1).

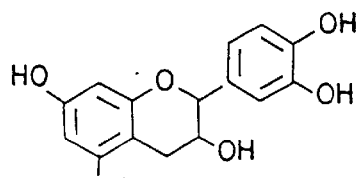
(−) EPICATECHIN
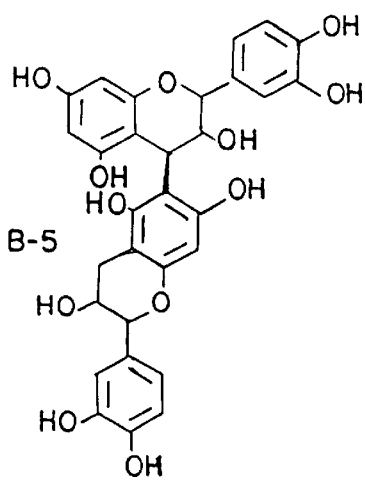
PROCYANIDIN B-5
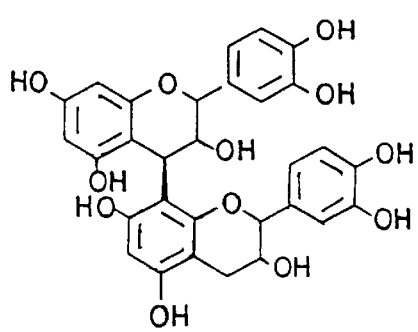
PROCYANIDIN B-2
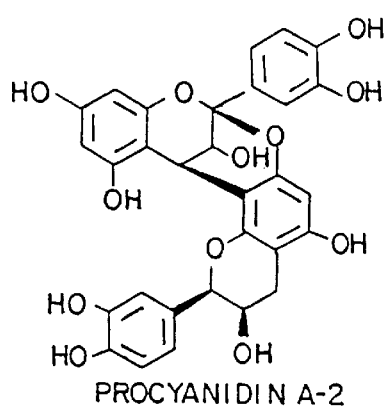
PROCYANIDIN A-2
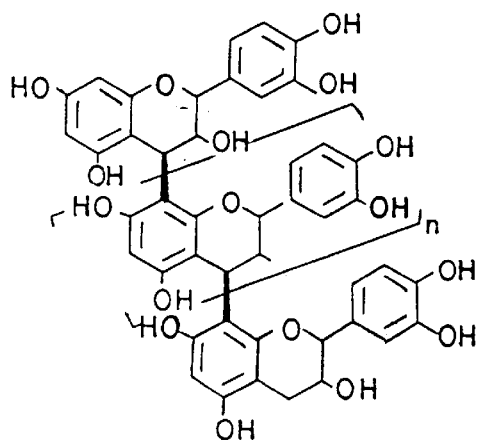
PROCYANIDIN OLIGOMERS n= 2 THROUGH 5
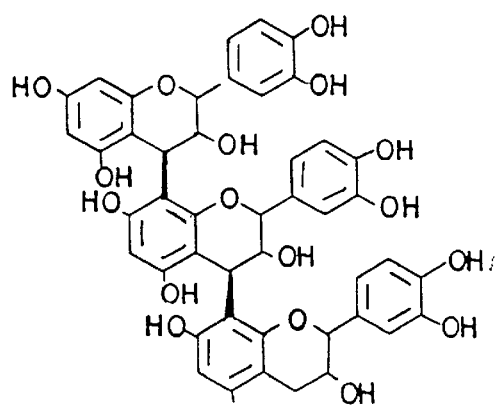
PROCYANIDIN C-1
FIG.3

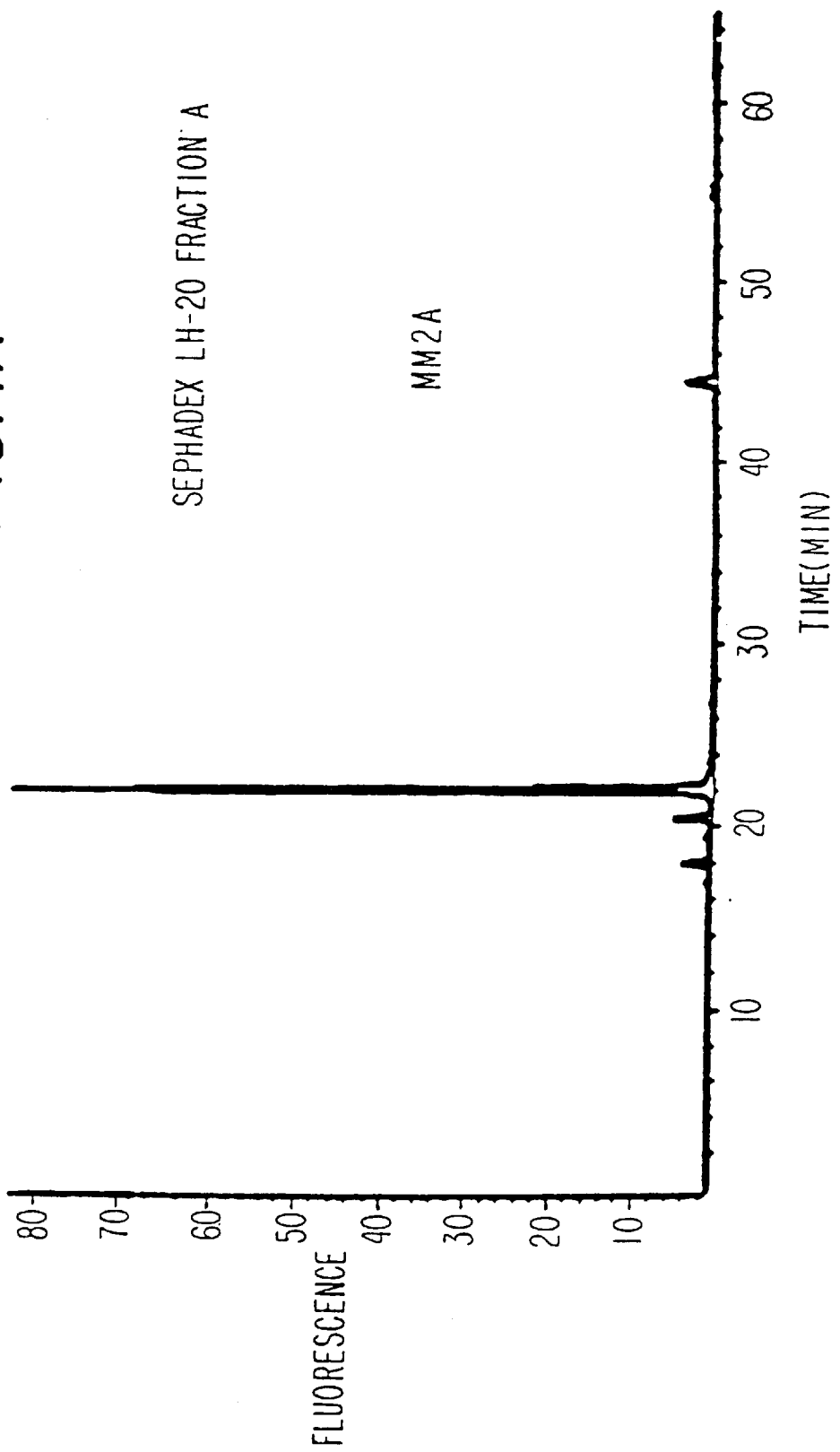

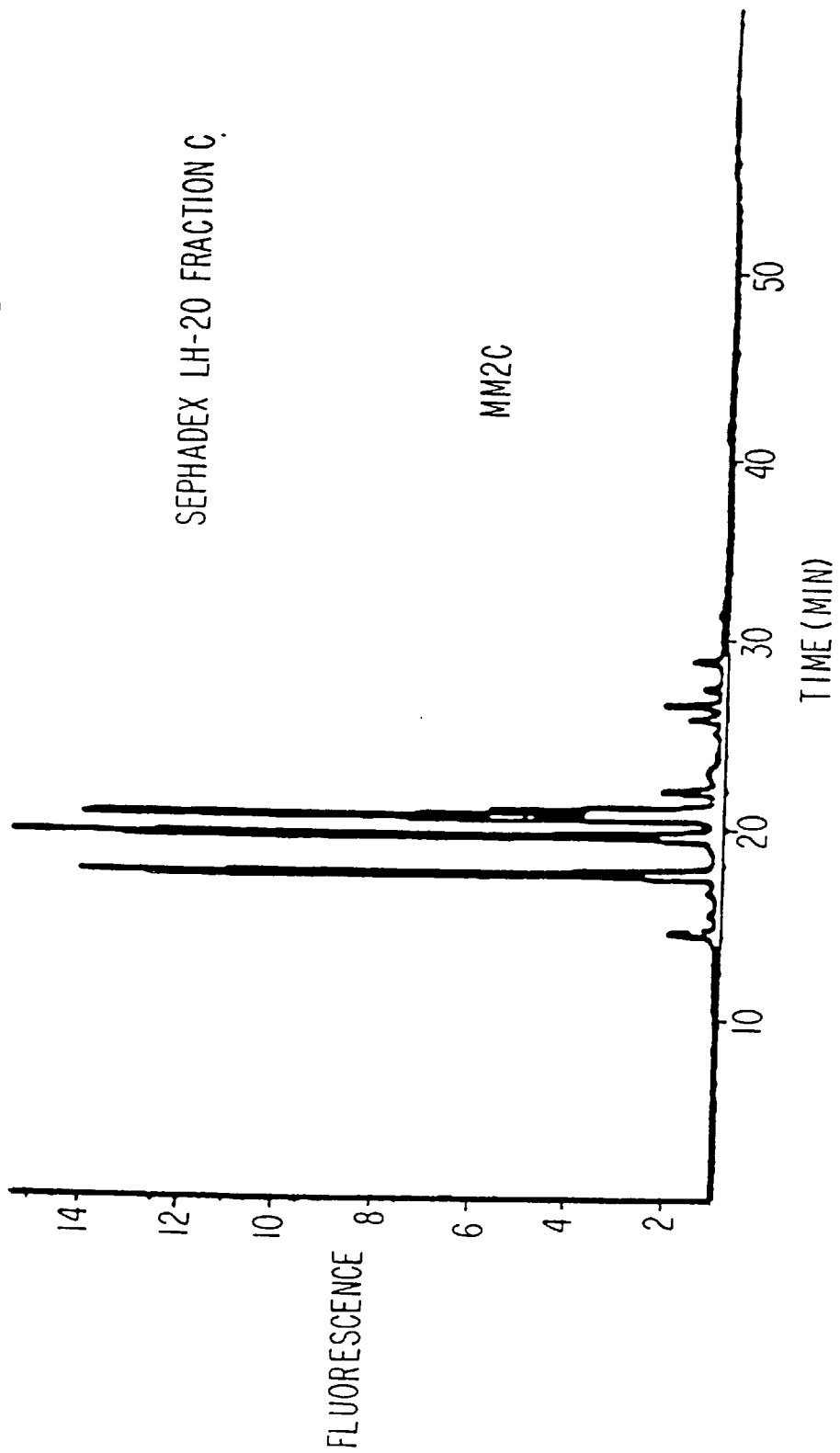

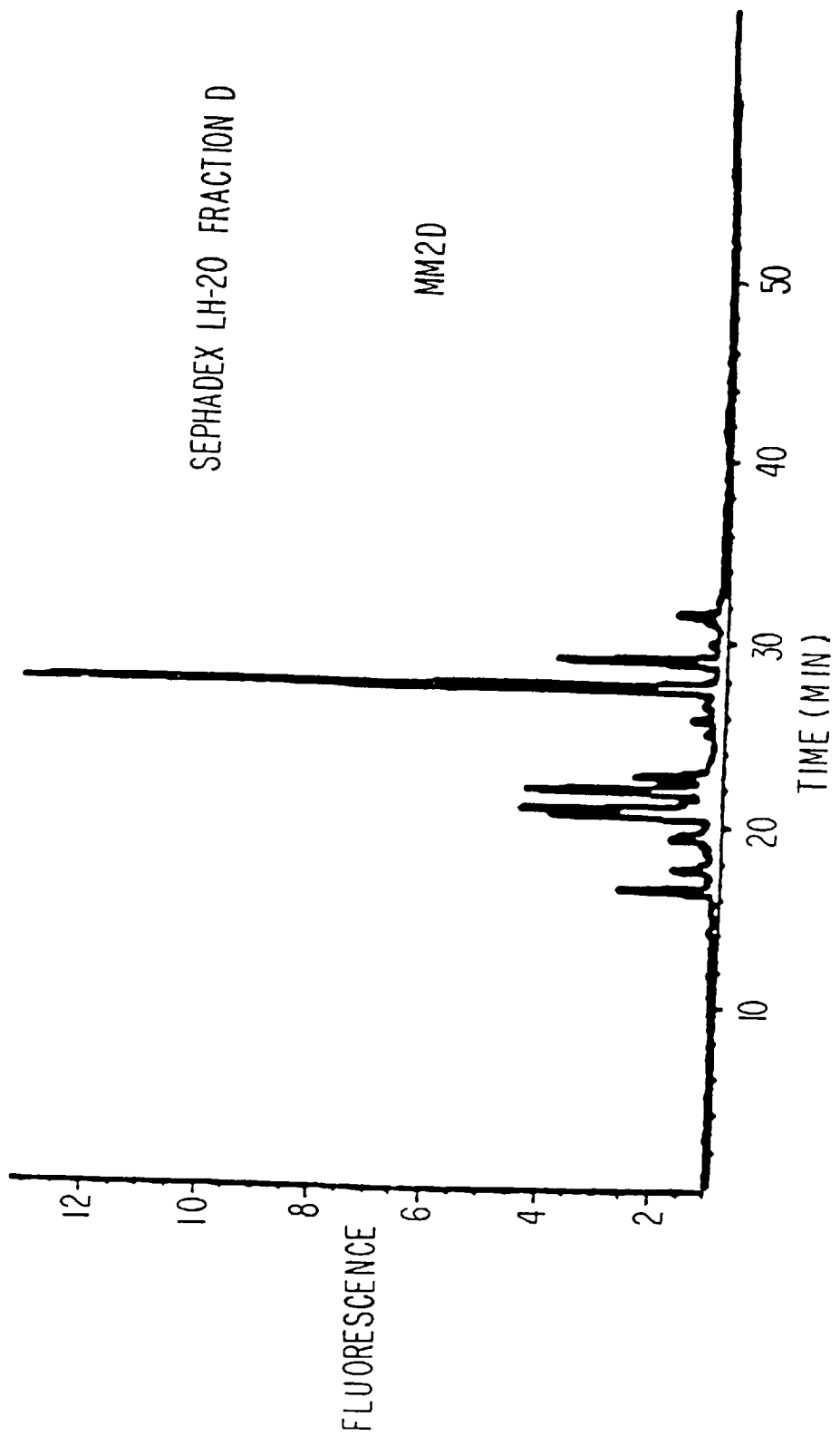

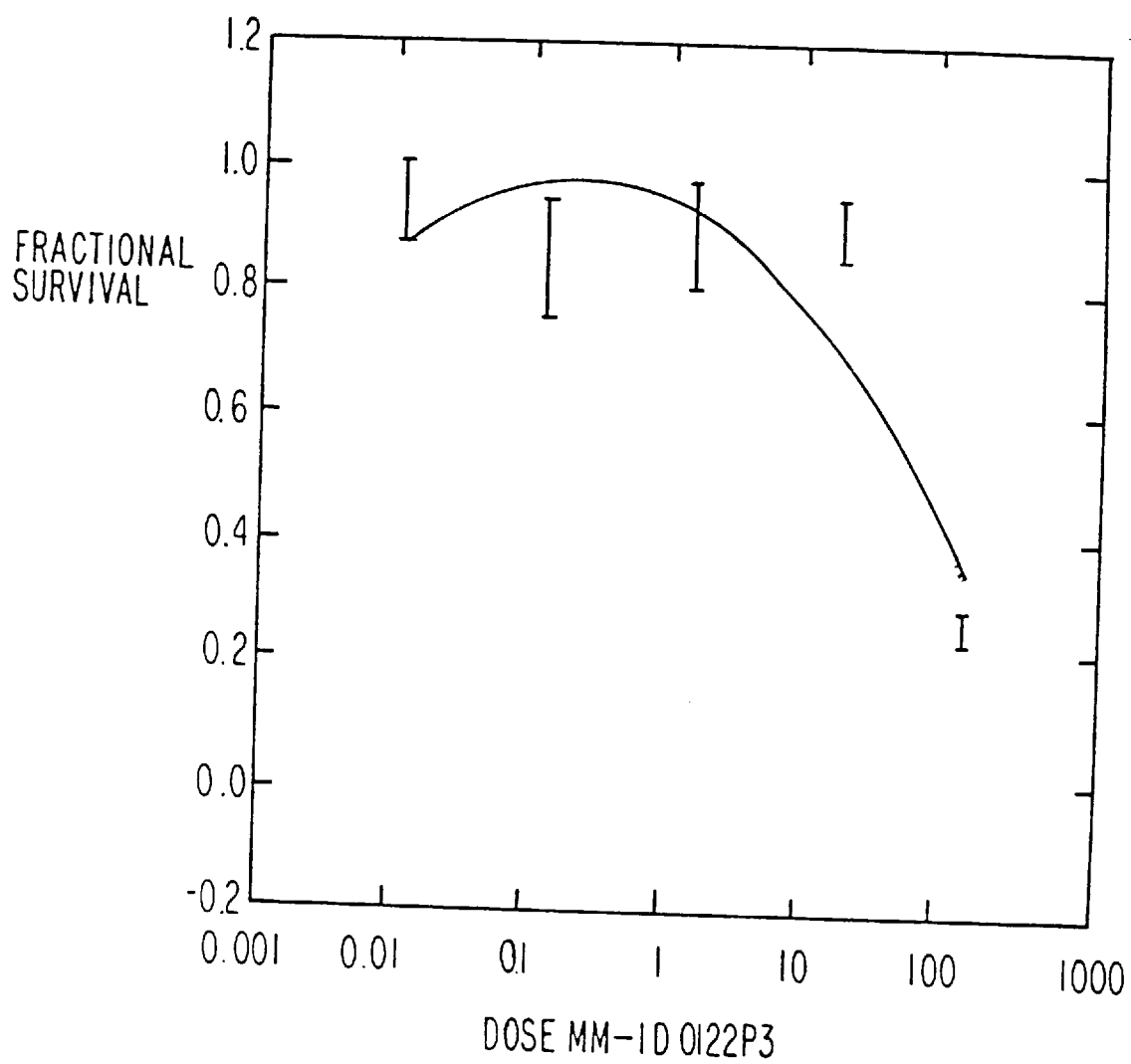

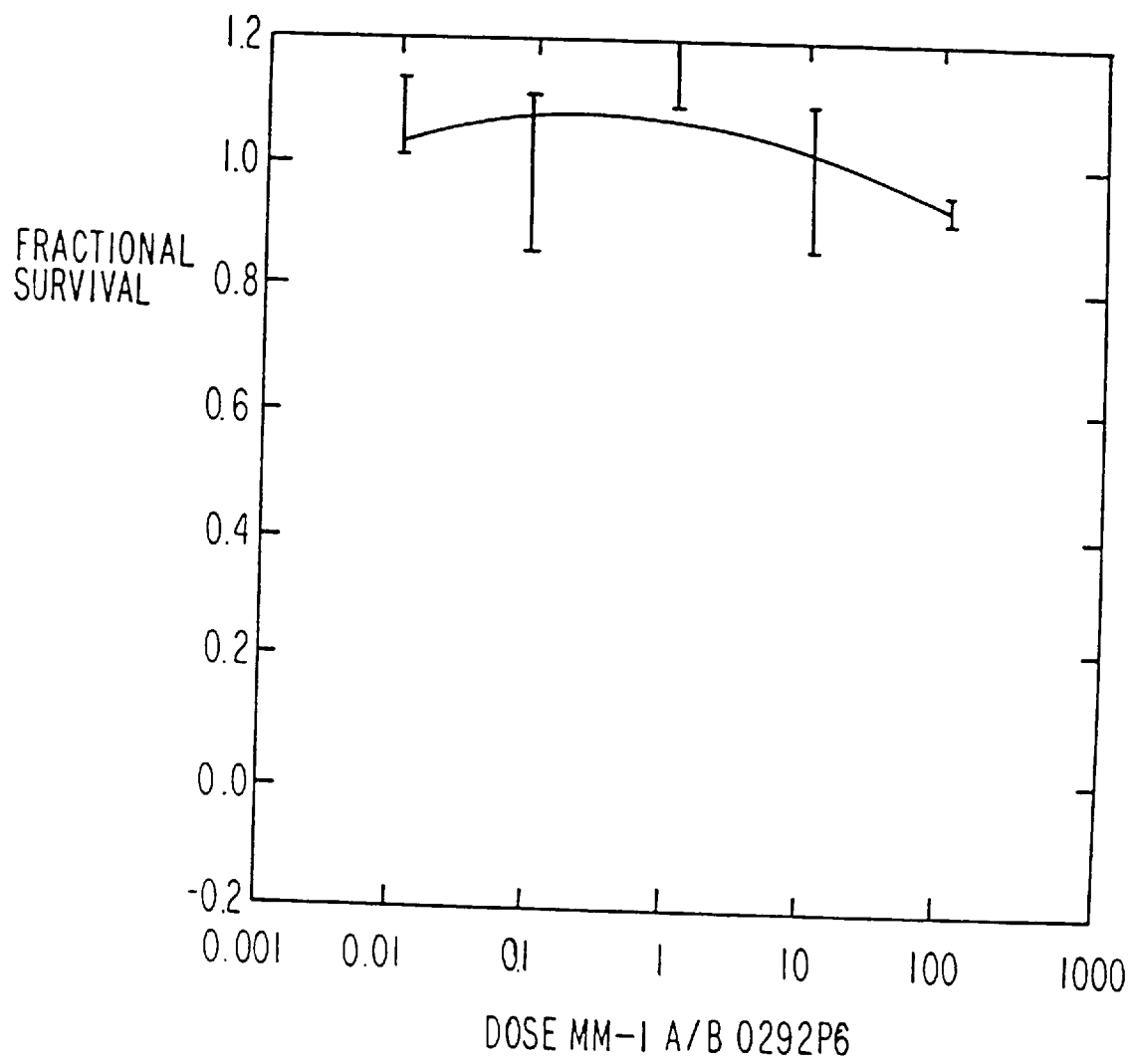

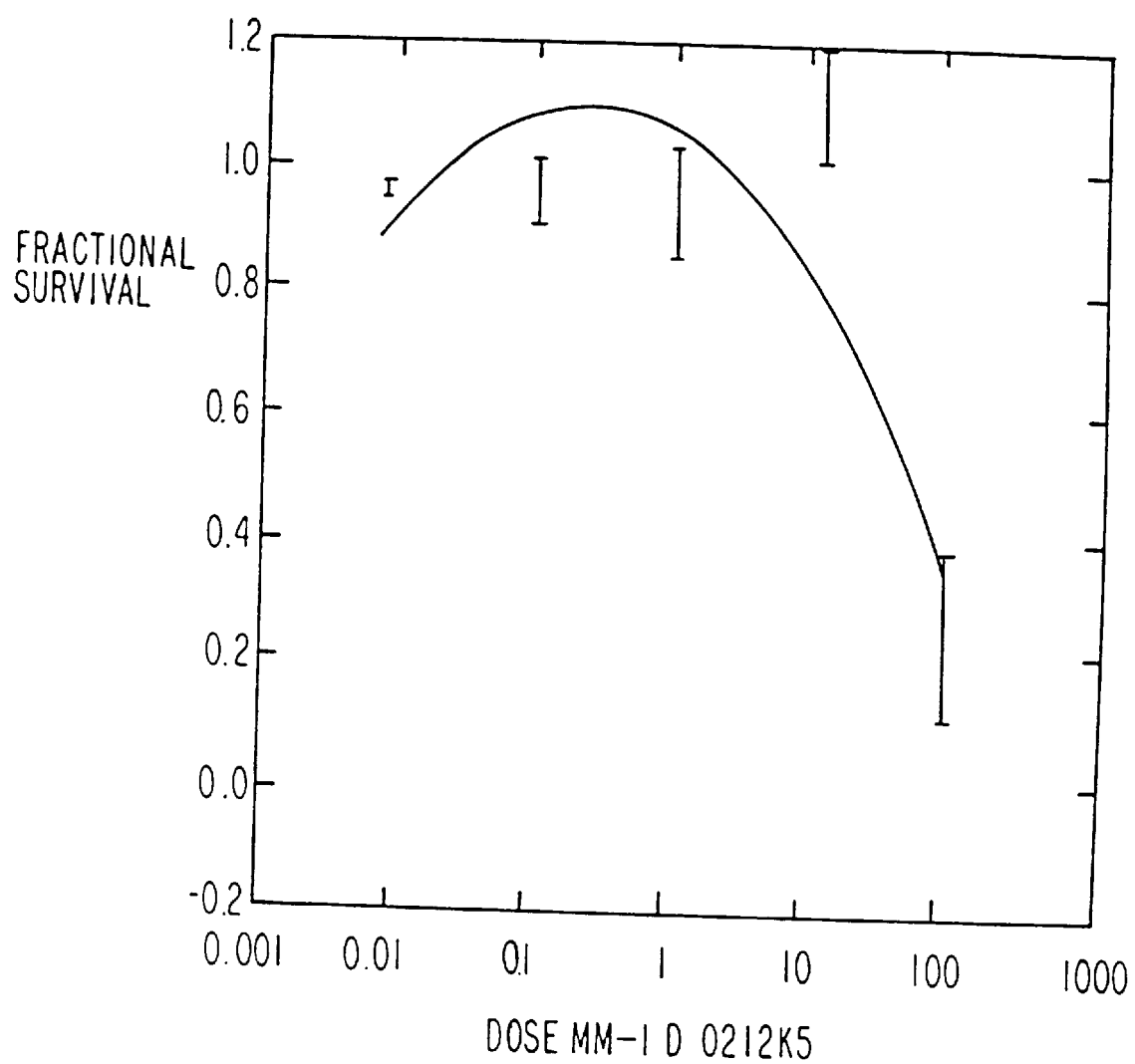

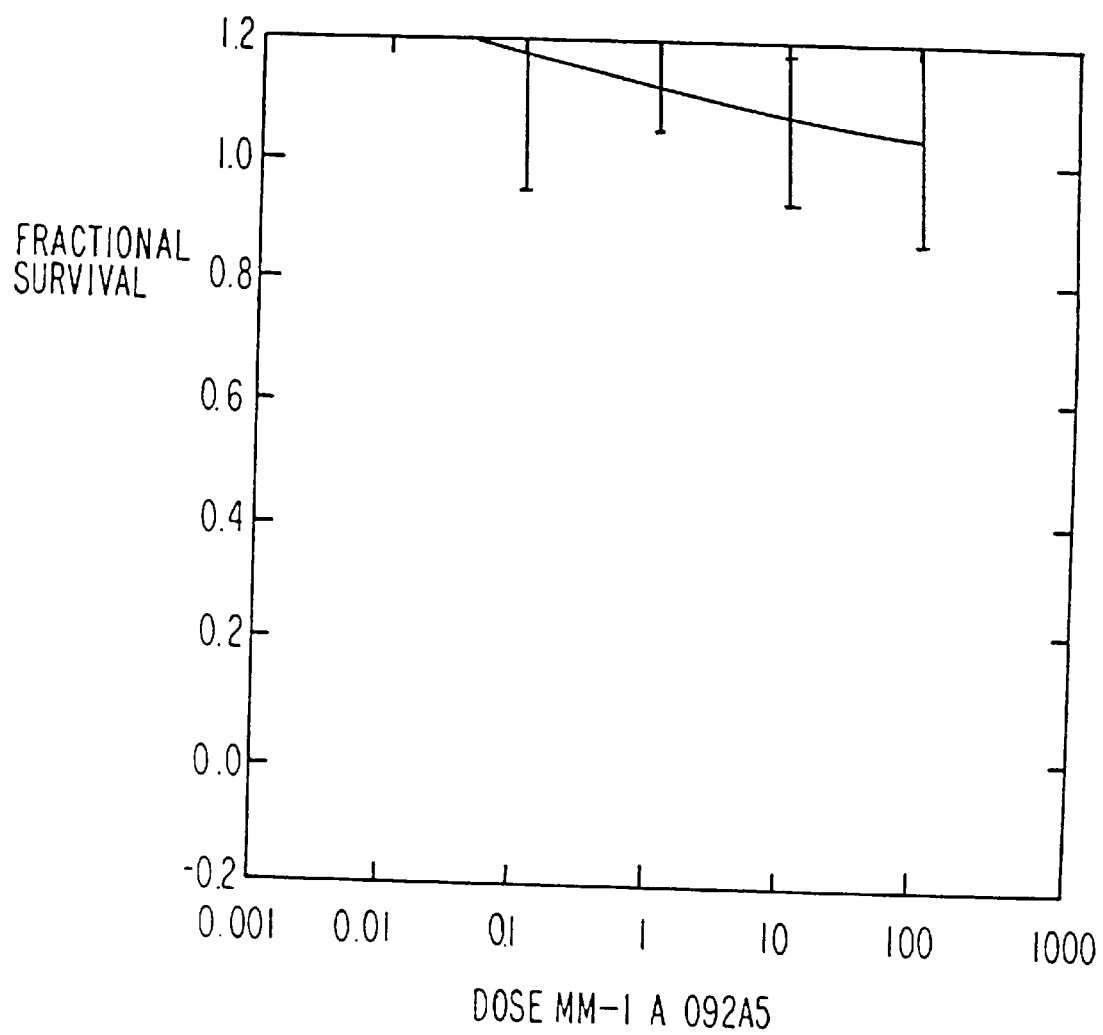

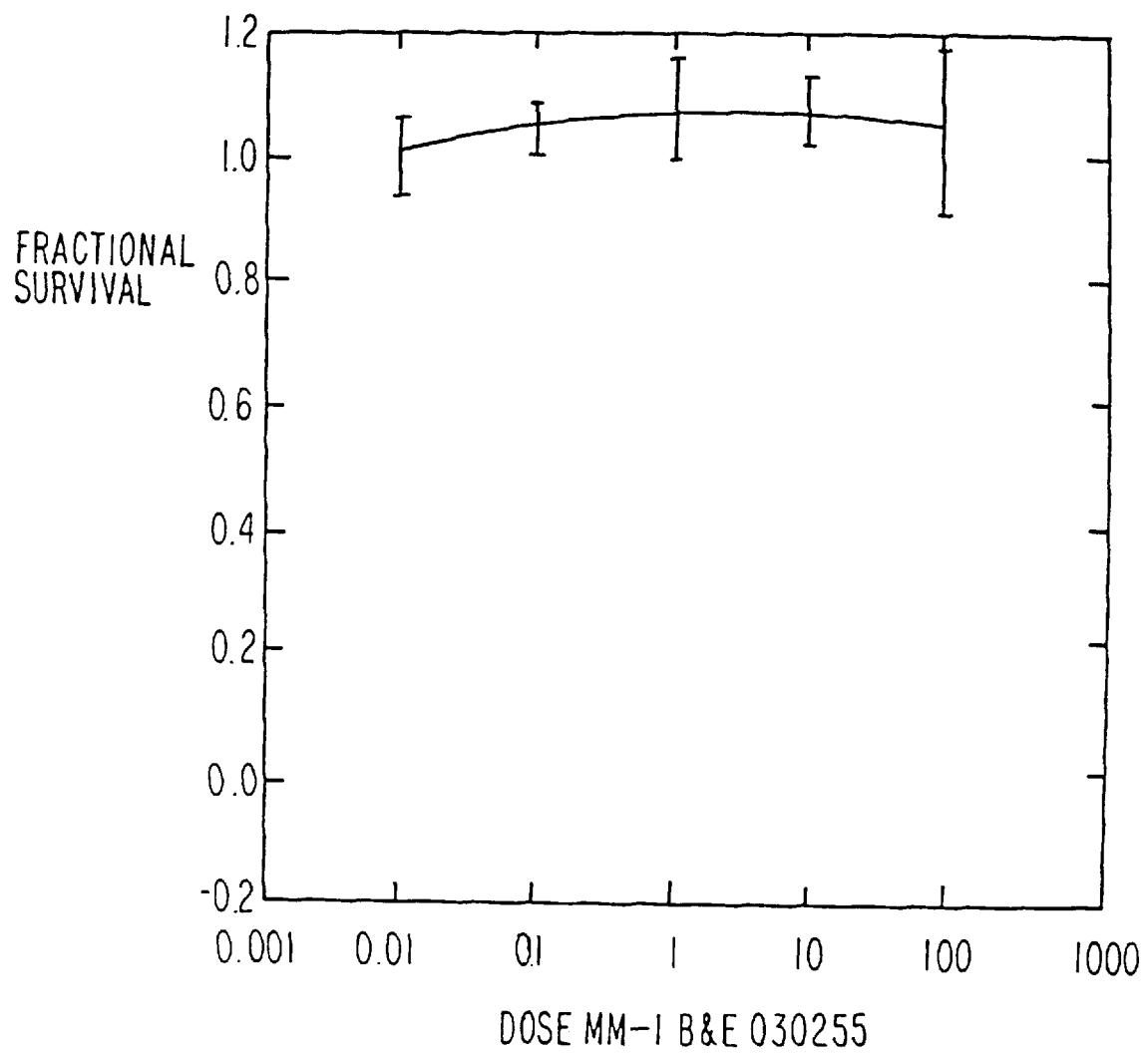

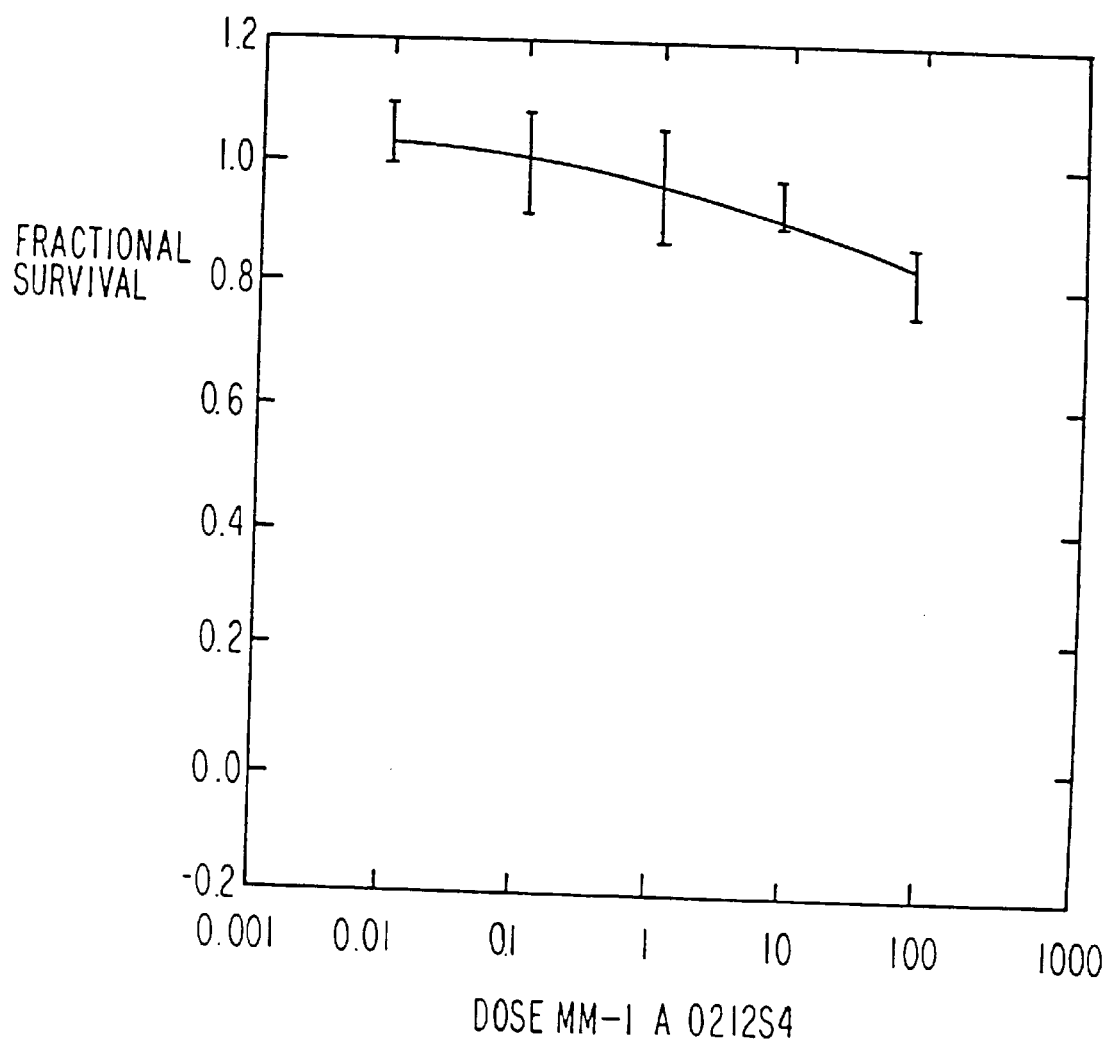

○ XTT STAINING
● CRYSTAL VIOLET STAINING

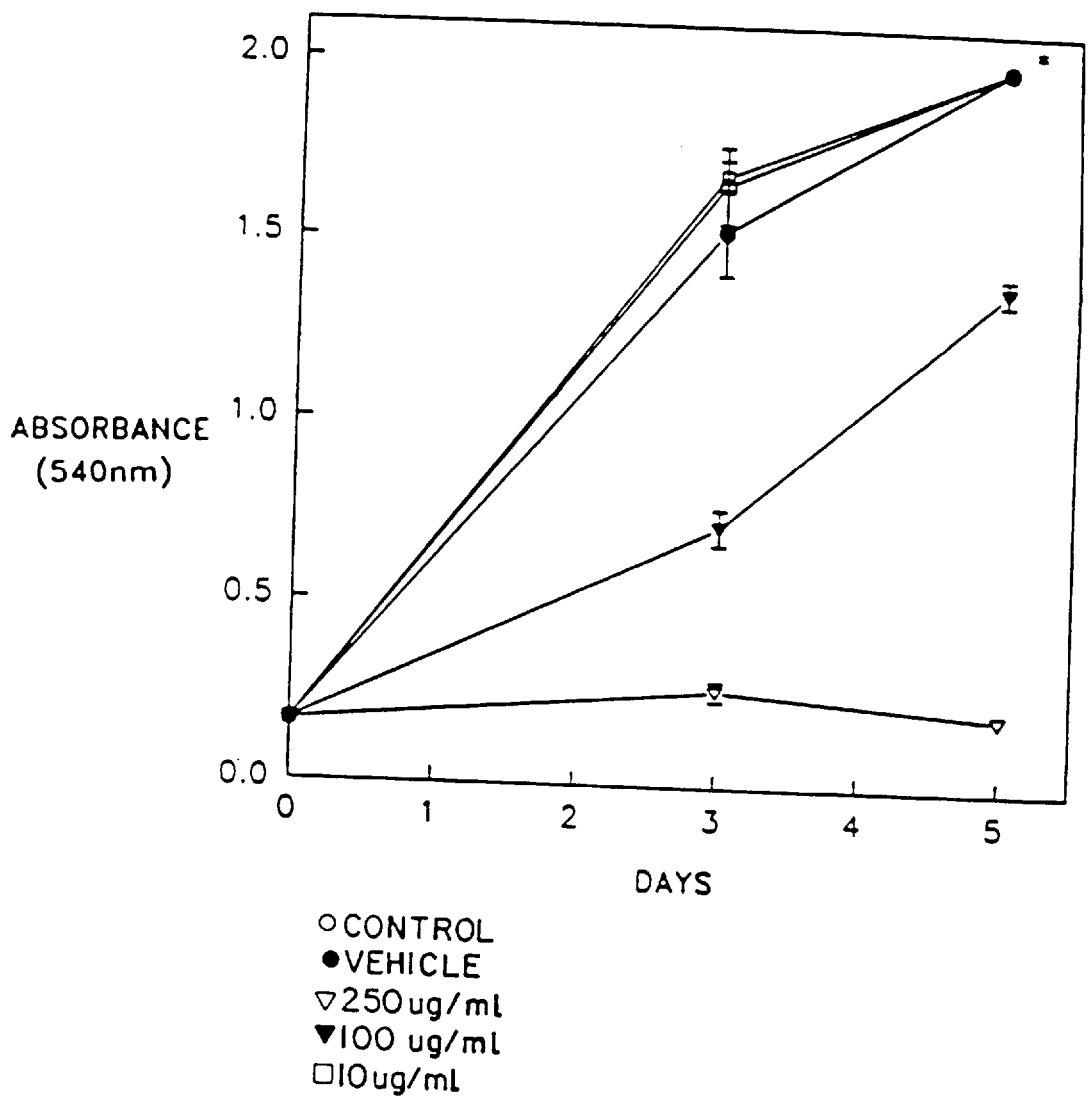

○ CONTROL
● VEHICLE
▽ 250 ug/mL
▼ 100 ug/mL
□ 10 ug/mL

*NOTE: ABSORBANCE OF 2.0 INDICATES THE MAXIMUM ABSORBANCE OF THE PLATE READER. IT IS NOT REPRESENTATIVE OF CELL NUMBER.

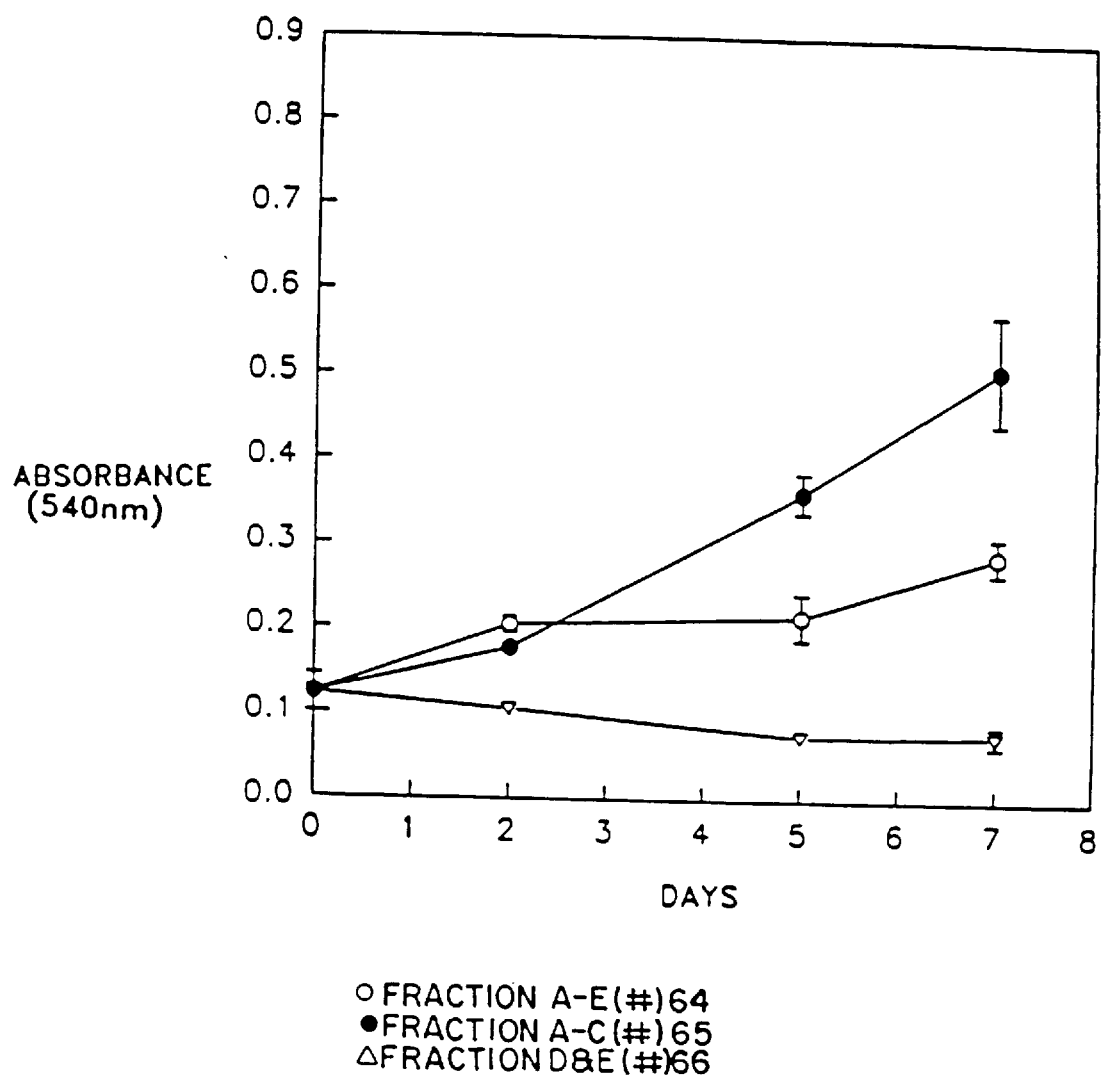

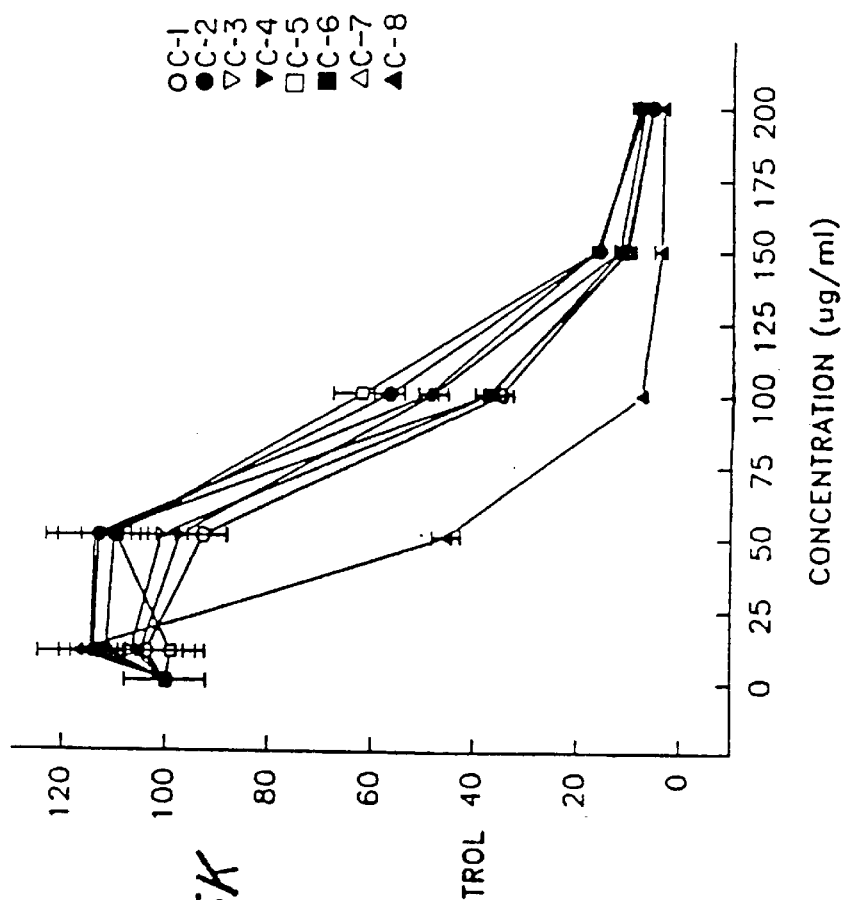

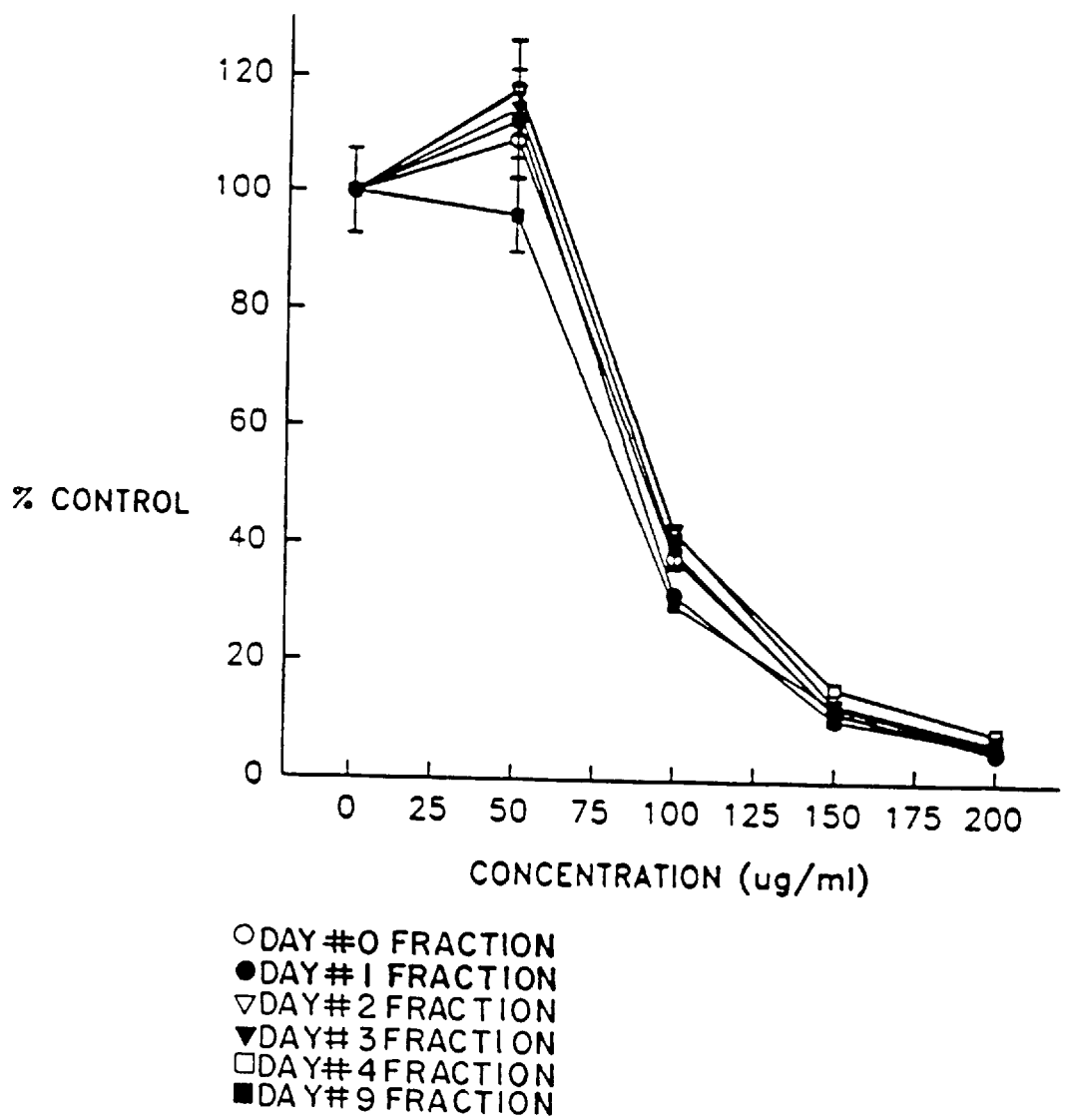

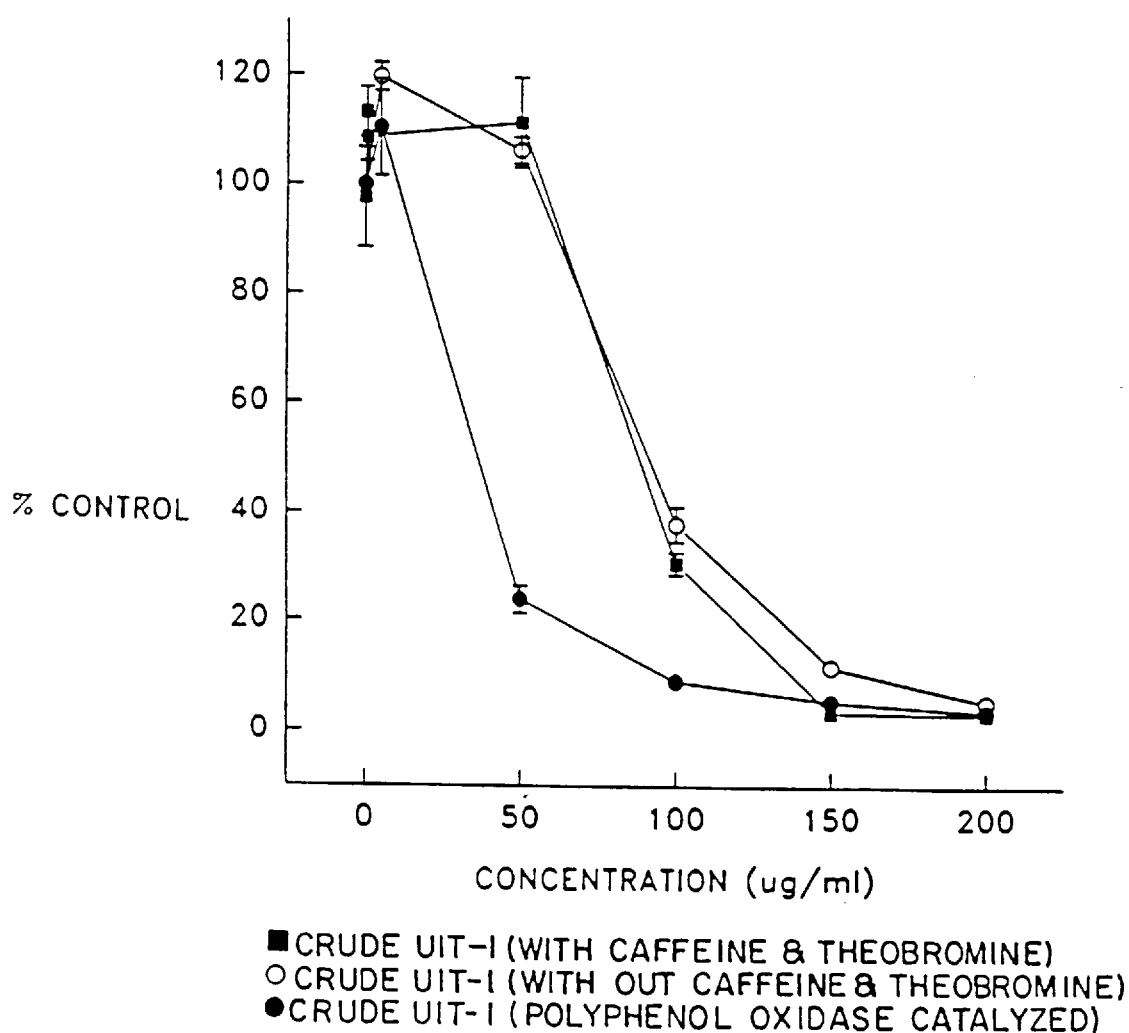

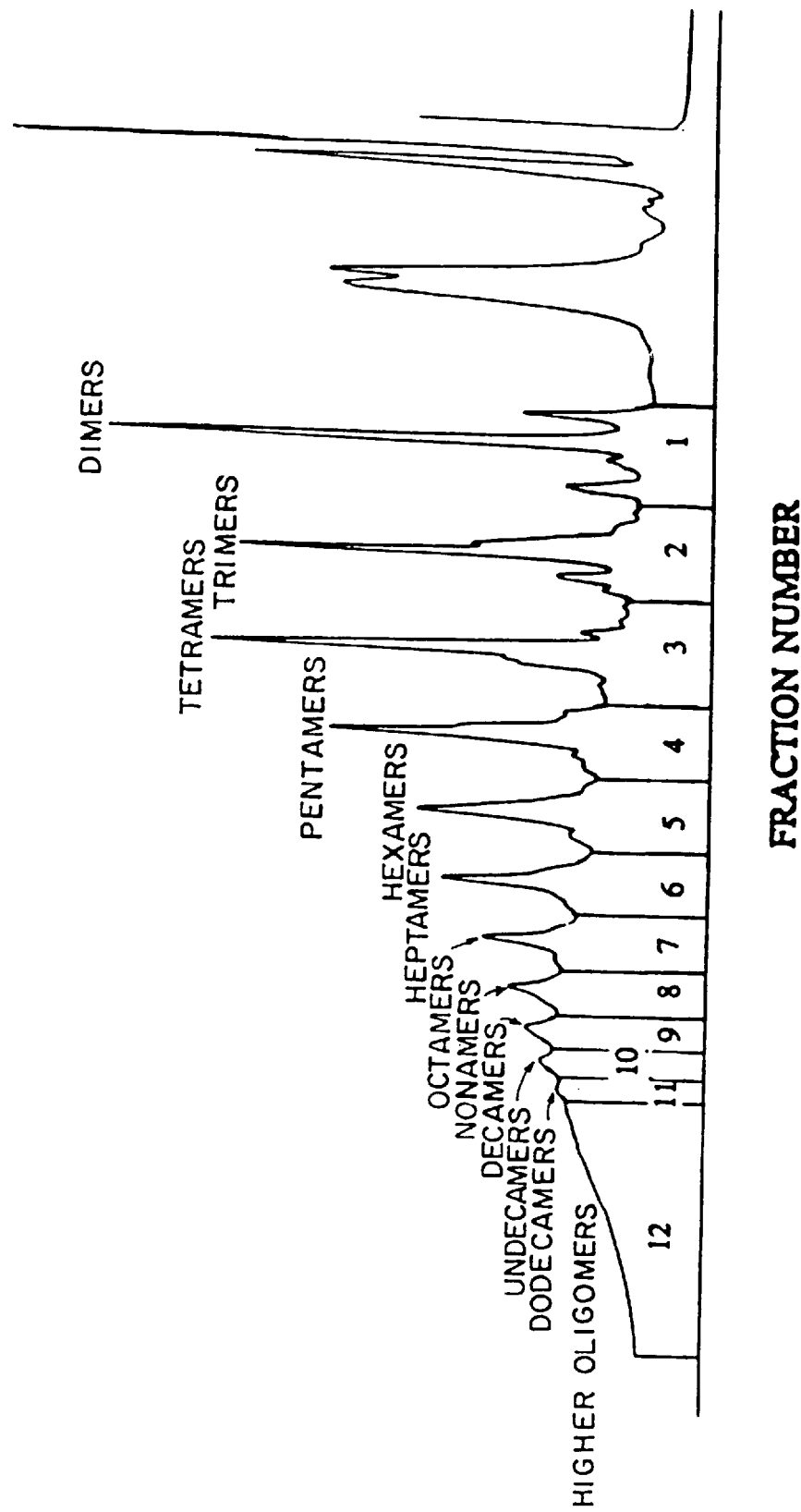

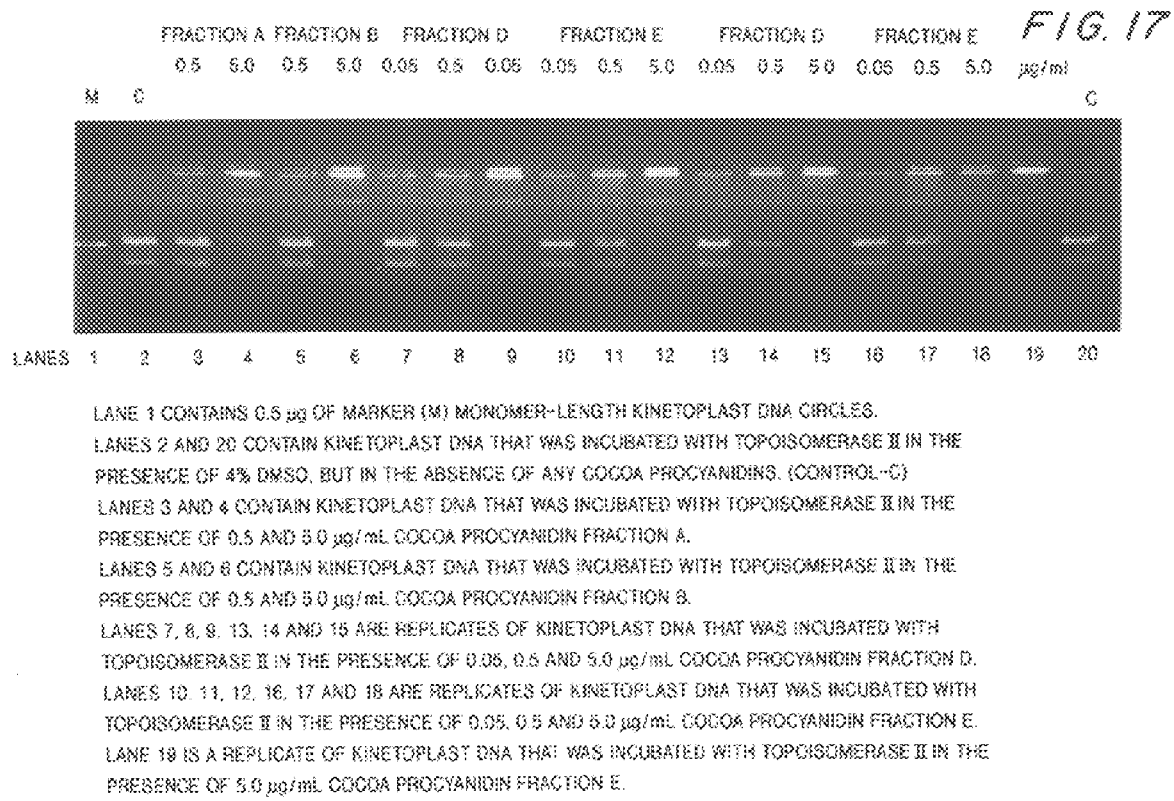

FIG. 17

LANE 1 CONTAINS 0.5 μg OF MARKER (M) MONOMER-LENGTH KINETOPLAST DNA CIRCLES.
LANES 2 AND 20 CONTAIN KINETOPLAST DNA THAT WAS INCUBATED WITH TOPOISOMERASE II IN THE PRESENCE OF 4% DMSO, BUT IN THE ABSENCE OF ANY COCOA PROCYANIDINS. (CONTROL-C)
LANES 3 AND 4 CONTAIN KINETOPLAST DNA THAT WAS INCUBATED WITH TOPOISOMERASE II IN THE PRESENCE OF 0.5 AND 5.0 μg/mL COCOA PROCYANIDIN FRACTION A.
LANES 5 AND 6 CONTAIN KINETOPLAST DNA THAT WAS INCUBATED WITH TOPOISOMERASE II IN THE PRESENCE OF 0.5 AND 5.0 μg/mL COCOA PROCYANIDIN FRACTION B.
LANES 7, 8, 9, 13, 14 AND 15 ARE REPLICATES OF KINETOPLAST DNA THAT WAS INCUBATED WITH TOPOISOMERASE II IN THE PRESENCE OF 0.05, 0.5 AND 5.0 μg/mL COCOA PROCYANIDIN FRACTION D.
LANES 10, 11, 12, 16, 17 AND 18 ARE REPLICATES OF KINETOPLAST DNA THAT WAS INCUBATED WITH TOPOISOMERASE II IN THE PRESENCE OF 0.05, 0.5 AND 5.0 μg/mL COCOA PROCYANIDIN FRACTION E.
LANE 19 IS A REPLICATE OF KINETOPLAST DNA THAT WAS INCUBATED WITH TOPOISOMERASE II IN THE PRESENCE OF 5.0 μg/mL COCOA PROCYANIDIN FRACTION E.

5,891,905

METHODS OF TREATMENT USING PROCYANIDIN ANTIOXIDANTS

This application is a division of application Ser. No. 08/687,885, filed Jul. 26, 1996 and now U.S. Pat. No. 5,712,305 which is a division of application Ser. No. 08/312,226, filed Oct. 3, 1994 (now U.S. Pat. No. 5,554,645).

FIELD OF THE INVENTION

This invention relates to cocoa extracts such as polyphenols preferably polyphenols enriched with procyanidins. This invention also relates to methods for preparing such extracts, as well as to uses for them; for instance, as antineoplastic agents and antioxidants.

Documents are cited in this disclosure with a full citation for each appearing in a References section at the end of the specification, preceding the claims. These documents pertain to the field of this invention; and, each document cited herein is hereby incorporated herein by reference.

BACKGROUND OF THE INVENTION

Polyphenols are an incredibly diverse group of compounds (Ferreira et al., 1992) which widely occur in a variety of plants, some of which enter into the food chain. In some cases they represent an important class of compounds for the human diet. Although some of the polyphenols are considered to be nonnutrative, interest in these compounds has arisen because of their possible beneficial effects on health. For instance, quercitin (a flavonoid) has been shown to possess anticarcinogenic activity in experimental animal studies (Deshner et al., 1991 and Kato et al., 1983). (+)-Catechin and (−)-epicatechin (flavan-3-ols) have been shown to inhibit Leukemia virus reverse transcriptase activity (Chu et al., 1992). Nobotanin (an oligomeric hydrolyzable tannin) has also been shown to possess anti-tumor activity (Okuda et al., 1992). Statistical reports have also shown that stomach cancer mortality is significantly lower in the tea producing districts of Japan. Epigallocatechin gallate has been reported to be the pharmacologically active material in green tea that inhibits mouse skin tumors (Okuda et al., 1992). Ellagic acid has also been shown to possess anticarcinogen activity in various animal tumor models (Bukharta et al., 1992). Lastly, proanthocyanidin oligomers have been patented by the Kikkoman Corporation for use as antimutagens. Indeed, the area of phenolic compounds in foods and their modulation of tumor development in experimental animal models has been recently presented at the 202nd National Meeting of The American Chemical Society (Ho et al., 1992; Huang et al., 1992).

However, none of these reports teaches or suggests cocoa extracts, any methods for preparing such extracts, or, any uses as antineoplastic agents for cocoa extracts.

Since unfermented cocoa beans contain substantial levels of polyphenols, the present inventors considered it possible that similar activities of and uses for cocoa extracts, e.g., compounds within cocoa, could be revealed by extracting such compounds from cocoa and screening the extracts for activity. The National Cancer Institute has screened various Theobroma and Herrania species for anti-cancer activity as part of their massive natural product selection program. Low levels of activity were reported in some extracts of cocoa tissues, and the work was not pursued. Thus, in the antineoplastic or anti-cancer art, cocoa and its extracts were not deemed to be useful; i.e., the teachings in the antineoplastic or anti-cancer art lead the skilled artisan away from employing cocoa and its extracts as cancer therapy. Since a number of analytical procedures were developed to study the contributions of cocoa polyphenols to flavor development (Clapperton et al., 1992), the present inventors decided to apply analogous methods to prepare samples for anti-cancer screening, contrary to the knowledge in the antineoplastic or anti-cancer art. Surprisingly, and contrary to the knowledge in the art, e.g., the National Cancer Institute screening, the present inventors discovered that cocoa polyphenol extracts which contain procyanidins, have significant utility as anti-cancer or antineoplastic agents. Additionally, the inventors demonstrate that cocoa extracts containing procyanidins have utility as antioxidants.

OBJECTS AND SUMMARY OF THE INVENTION

It is an object of the present invention to provide a method for producing cocoa extract.

It is another object of the invention to provide a cocoa extract.

It is another object of the invention to provide an antioxidant composition.

It is another object of the invention to demonstrate inhibition of DNA topoisomerase II enzyme activity.

It is yet another object of the present invention to provide a method for treating tumors or cancer.

It is still another object of the invention to provide an anti-cancer, anti-tumor or antineoplastic composition.

It is a further object of the invention to provide a method for making an anti-cancer, anti-tumor or antineoplastic composition.

And, it is an object of the invention to provide a kit for use in treating tumors or cancer.

It has been surprisingly discovered that cocoa extract has anti-tumor, anti-cancer or antineoplastic activity; or, is an antioxidant composition or, inhibits DNA topoisomerase II enzyme activity. Accordingly, the present invention provides a substantially pure cocoa extract. The extract preferably comprises polyphenol(s) such as polyphenol(s) enriched with cocoa procyanidin(s), such as polyphenols of at least one cocoa procyanidin selected from (−) epicatechin, procyanidin B-2, procyanidin oligomers 2 through 12, preferably 2 through 5 or 4 through 12, procyanidin B-5, procyanidin A-2 and procyanidin C-1. The present invention also provides an anti-tumor, anti-cancer or antineoplastic or antioxidant or DNA topoisomerase II inhibitor composition comprising a substantially pure cocoa extract or synthetic cocoa polyphenol(s) such as polyphenol(s) enriched with procyanidin(s) and a suitable carrier. The extract preferably comprises cocoa procyanidin(s). The cocoa extract is preferably obtained by a process comprising reducing cocoa beans to powder, defatting the powder and, extracting active compound(s) from the powder.

The present invention further comprehends a method for treating a patient .in need of treatment with an anti-tumor, anti-cancer, or antineoplastic agent or an antioxidant or a DNA topoisomerase II inhibitor comprising administering to the patient a composition comprising an effective quantity of a substantially pure cocoa extract or synthetic cocoa polyphenol(s) or procyanidin(s) and a carrier. The cocoa extract can be cocoa procyanidin(s); and, is preferably obtained by reducing cocoa beans to powder, defatting the powder and, extracting active compound(s) from the powder.

Additionally, the present invention provides a kit for treating a patient in need of treatment with an anti-tumor, anti-cancer, or antineoplastic agent or antioxidant or DNA topoisomerase II inhibitor comprising a substantially pure cocoa extract or synthetic cocoa polyphenol(s) or procyanidin(s) and a suitable carrier for admixture with the extract or synthetic polyphenol(s) or procyanidin(s).

These and other objects and embodiments are disclosed or will be obvious from the following Detailed Description.

BRIEF DESCRIPTION OF THE DRAWINGS

The following Detailed Description will be better understood by reference to the accompanying drawings wherein:

FIG. 3 shows several representative procyanidin structures;

FIGS. 4A–4E show representative HPLC chromatograms of five fractions employed in screening for anti-cancer or antineoplastic activity;

FIGS. 7A to 7H show the typical dose response relationships between cocoa procyanidin fractions A, B, C, D, E, A+B, A+E, and A+D, and the PC-3 cell line (fractional survival vs. dose, µg/ml); MM-1A 0212P3, MM-1 B 0162P1, MM-1 C 0122P3, MM-1 D 0122P3, MM-1 E 0292P8, MM-1 A/B 0292P6, MM-1 A/E 0292P6, MM-1 A/D 0292P6;

FIGS. 8A to 8H show the typical dose response relationships between cocoa procyanidin fractions A, B, C, D, E, A+B, B+E, and D+E and the KB Nasopharyngeal/HeLa cell line (fractional survival vs. dose, µg/ml); MM-1A092K3, MM-1 B 0212K5, MM-1 C 0162K3, MM-1 D 0212K5, MM-1 E 0292K5, MM-1 A/B 0292K3, MM-1 B/E 0292K4, MM-1 D/E 0292K5;

FIGS. 10A to 10H show typical dose response relationships between cocoa procyanidin fractions A, B, C, D, E, B+D, C+D and A+E and the ACHN renal cell line (fractional survival vs. dose, µg/ml); MM-1 A 092A5, MM-1 B 092A5, MM-1 C 0192A7, MM-1 D 0192A7, M&M1 E 0192A7, MM-1 B&D 0302A6, MM-1 C&D 0302A6, MM-1 A&E 0262A6;

FIGS. 11A to 11H show typical dose response relationships between cocoa procyanidin fractions A, B, C, D, E, A+E, B+E and C+E and the A-549 lung cell line (fractional survival vs. dose, µg/ml); MM-1 A 019258, MM-1 B 09256, MM-1 C 019259, MM-1 D 019258, MM-1 E 019258, A/E 026254, MM-1 B&E 030255, MM-1 C&E N6255;

FIGS. 12A to 12H show typical dose response relationships between cocoa procyanidin fractions A, B, C, D, E, B+C, C+D and D+E and the SK-5 melanoma cell line (fractional survival vs. dose µg/ml); MM-1 A 0212S4, MM-1 B 0212S4, MM-1 C 0212S4, MM-1 b 0212S4, MM-1 E N32S1, MM-1 B&C N32S2, MM-1 C&D N32S3, MM-1 D&E N32S3;

FIG. 15B shows a typical dose response curve obtained from MDA MB231 breast cell line treated with varying levels of crude polyphenols obtained from UIT-1 cocoa genotype (absorbance (540 nm) vs. Days; open circle is control, darkened circle is vehicle, open inverted triangle is 250 µg/ml, darkened inverted triangle is 100 µg/ml, open square is 10 µg/ml; absorbance of 2.0 is maximum of plate reader and may not be necessarily representative of cell number);

FIG. 15G shows cytotoxic effects at 100 ul/ml against SKBR-3 breast cancer cell line treated with different cocoa polyphenol fractions (absorbance (540 nm) vs. Days; open circle is fractions A–E, darkened circle is fractions A–C, open inverted triangle is fractions D&E);

FIG. 15I shows typical dose-response relationship between cocoa procyanidin fraction D+E on SKBR-3 cells (absorbance (540 nm) vs. Days; open circle is control, darkened circle is 100 µg/ml, open inverted triangle is 75 µg/ml, darkened inverted triangle is 50 µg/ml, open square is 25 µg/ml, darkened square is 10 µg/ml);

FIG. 15K shows the growth inhibition of Hela cells when treated with crude polyphenol extracts obtained from eight different cocoa genotypes (% control vs. concentration, µg/ml; open circle is C-1, darkened circle is C-2, open inverted triangle is C-3, darkened inverted triangle is C-4, open square is C-5, darkened square is C-6, open triangle is C-7, darkened triangle is C-8; C-1=UF-12: horti race=Criollo and description is crude extracts of UF-12 (Brazil) cocoa polyphenols (decaffeinated/detheobrominated); C-2=NA-33: horti race=Forastero and description is crude extracts of NA-33 (Brazil) cocoa polyphenols (decaffeinated/detheobrominated); C-3=EEG-48: horti race=Forastero and description is crude extracts of EEG-48 (Brazil) cocoa polyphenols (decaffeinated/detheobrominated); C-4=unknown: horti race=Forastero and description is crude extracts of unknown (W. African) cocoa polyphenols (decaffeinated/detheobrominated); C-5=UF-613: horti race=Trinitario and description is crude extracts of UF-613 (Brazil) cocoa polyphenols (decaffeinated/detheobrominated); C-6=ICS-100: horti race=Trinitario and description is crude extracts of ICS-100 (Brazil) cocoa polyphenols (decaffeinated/detheobrominated); C-7=ICS-139: horti race=Trinitario and description is crude extracts of ICS-139 (Brazil) cocoa polyphenols (decaffeinated/detheobrominated); C-8=UIT-1: horti race=Trinitario and description is crude extracts of UIT-1 (Malaysia) cocoa polyphenols (decaffeinated/detheobrominated));

FIG. 15L shows the growth inhibition of Hela cells when treated with crude polyphenol extracts obtained from fermented cocoa beans and dried cocoa beans (stages throughout fermentation and sun drying; % control vs. concentration, µg/ml; open circle is day zero fraction, darkened circle is day 1 fraction, open inverted triangle is day 2 fraction, darkened inverted triangle is day 3 fraction, open square is day 4 fraction and darkened square is day 9 fraction);

FIG. 15M shows the effect of enzymically oxidized cocoa procyanidins against Hela cells (dose response for polyphenol oxidase treated crude cocoa polyphenol; % control vs. concentration, µg/ml; darkened square is crude UIT-1 (with caffeine and theobromine), open circle crude UIT-1 (without caffeine and theobromine) and darkened circle is crude UIT-1 (polyphenol oxidase catalyzed));

FIG. 15O shows a representative normal phase semi-preparative HPLC separation of a crude cocoa polyphenol extract;

FIG. 17 shows a typical Agarose Gel indicating inhibition of topoisomerase II catalyzed decatenation of kinetoplast DNA by cocoa procyanidin fractions (Lane 1 contains 0.5 µg of marker (M) monomer-length kinetoplast DNA circles; Lanes 2 and 20 contain kinetoplast DNA that was incubated with Topoisomerase II in the presence of 4% DMSO, but in the absence of any cocoa procyanidins. (Control –C); Lanes 3 and 4 contain kinetoplast DNA that was incubated with Topoisomerase II in the presence of 0.5 and 5.0 µg/mL cocoa procyanidin fraction A; Lanes 5 and 6 contain kinetoplast DNA that was incubated with Topoisomerase II in the presence of 0.5 and 5.0 µg/mL cocoa procyanidin fraction B; Lanes 7, 8, 9, 13, 14 and 15 are replicates of kinetoplast DNA that was incubated with Topoisomerase II in the presence of 0.05, 0.5 and 5.0 µg/mL cocoa procyanidin fraction D; Lanes 10, 11, 12, 16, 17 and 18 are replicates of kinetoplast DNA that was incubated with Topoisomerase II in the presence of 0.05, 0.5, and 5.0 µg/mL cocoa procyanidin fraction E; Lane 19 is a replicate of kinetoplast DNA that was incubated with Topoisomerase II in the presence of 5.0 µg/mL cocoa procyanidin fraction E);

DETAILED DESCRIPTION

Figure 1:
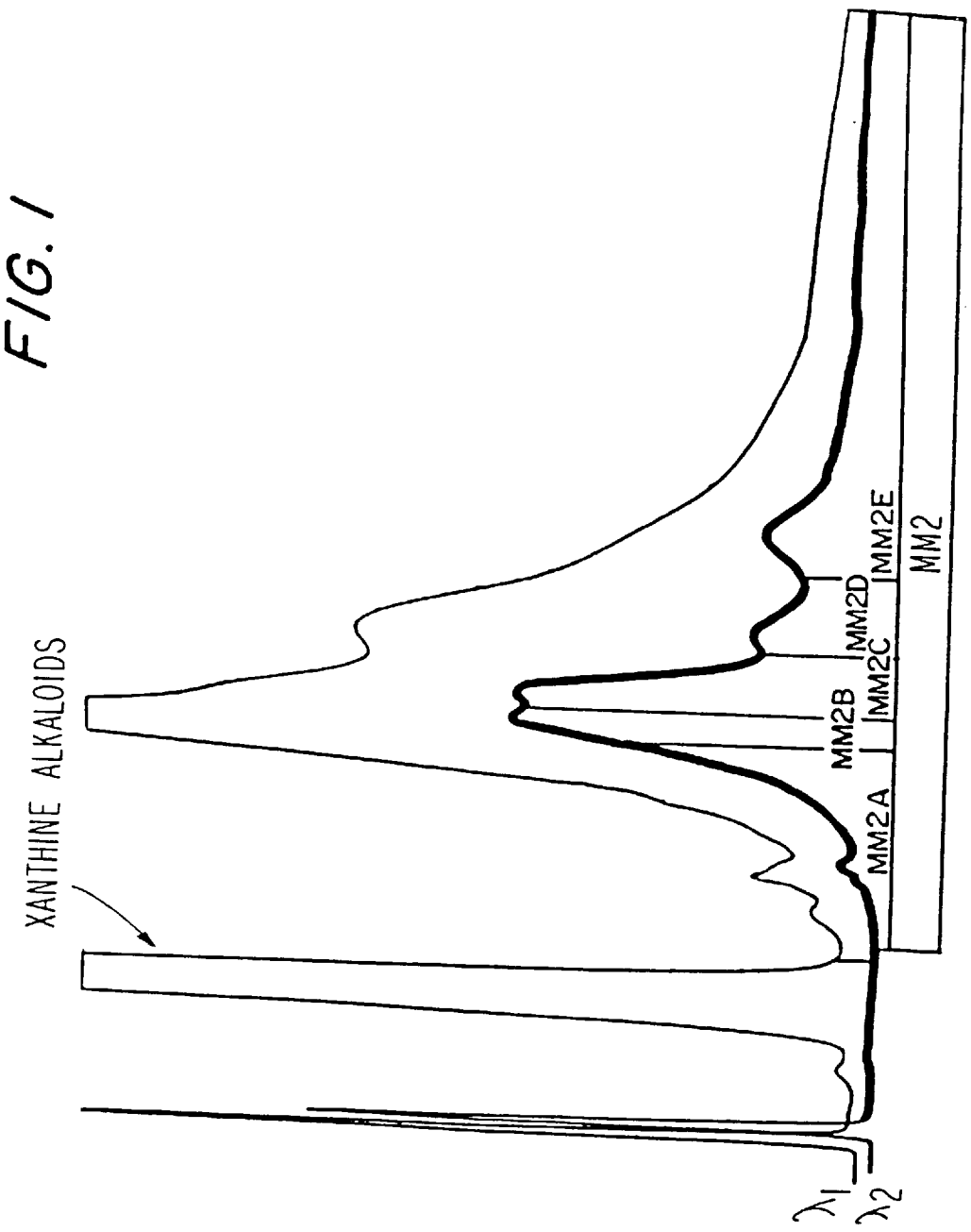
FIG. 1 shows a representative gel permeation chromatogram from the fractionation of crude cocoa procyanidins.

As discussed above, it has now been surprisingly found that cocoa extracts exhibit anti-cancer, anti-tumor or anti-neoplastic activity, antioxidant activity and, inhibit DNA topoisomerase II enzyme. The extracts are generally prepared by reducing cocoa beans to a powder, defatting the powder, and extracting the active compound(s) from the defatted powder. The powder can be prepared by freeze-drying the cocoa beans and pulp, depulping the cocoa beans and pulp, dehulling the freeze-dried cocoa beans, and grinding the dehulled beans. The extraction of active compound(s) can be by solvent extraction techniques. The extracts can be purified; for instance, by gel permeation chromatography or by preparative High Performance Liquid Chromatography (HPLC) techniques or by a combination of such techniques. The extracts having activity, without wishing to necessarily be bound by any particular theory, have been identified as cocoa polyphenol(s) such as procyanidins. These cocoa procyanidins have significant anti-cancer, anti-tumor or antineoplastic activity; antioxidant activity; and inhibit DNA topoisomerase II enzyme.

Anti-cancer, anti-tumor or antineoplastic or, antioxidant or DNA topoisomerase II enzyme inhibiting compositions containing the inventive cocoa polyphenols or procyanidins can be prepared in accordance with standard techniques well known to those skilled in the pharmaceutical art. Such compositions can be administered to a patient in need of such administration in dosages and by techniques well known to those skilled in the medical arts taking into consideration such factors as the age, sex, weight, and condition of the particular patient, and the route of administration. The compositions can be co-administered or sequentially administered with other antineoplastic, anti-tumor or anti-cancer agents or antioxidant or DNA topoisomerase II enzyme inhibiting agents and/or with agents which reduce or alleviate ill effects of antineoplastic, anti-tumor or anti-cancer agents or antioxidant or DNA topoisomerase II enzyme inhibiting agents; again, taking into consideration such factors as the age, sex, weight, and condition of the particular patient, and, the route of administration.

Examples of compositions of the invention include solid compositions for oral administration such as capsules, tablets, pills and the like, as well as chewable solid formulations, to which the present invention may be well-suited since it is from an edible source (e.g., cocoa or chocolate flavored solid compositions); liquid preparations for orifice, e.g., oral, nasal, anal, vaginal etc., administration such as suspensions, syrups or elixirs; and, preparations for parental, subcutaneous, intradermal, intramuscular or intravenous administration (e.g., injectable administration) such as sterile suspensions or emulsions. However, the active ingredient in the compositions may complex with proteins such that when administered into the bloodstream, clotting may occur due to precipitation of blood proteins; and, the skilled artisan should take this into account. In such compositions the active cocoa extract may be in admixture with a suitable carrier, diluent, or excipient such as sterile water, physiological saline, glucose or the like. The active cocoa extract of the invention can be provided in lyophilized form for reconstituting, for instance, in isotonic aqueous, saline buffer.

Further, the invention also comprehends a kit wherein the active cocoa extract is provided. The kit can include a separate container containing a suitable carrier, diluent or excipient. The kit can also include an additional anti-cancer, anti-tumor or antineoplastic agent or antioxidant or DNA topoisomerase II enzyme inhibiting agent and/or an agent which reduces or alleviates ill effects of antineoplastic, anti-tumor or anti-cancer agents or antioxidant or DNA topoisomerase II enzyme inhibiting agents for co- or sequential-administration. The additional agent(s) can be provided in separate container(s) or in admixture with the active cocoa extract. Additionally, the kit can include instructions for mixing or combining ingredients and/or administration.

Furthermore, while the invention is described with respect to cocoa extracts preferably comprising cocoa procyanidins, from this disclosure the skilled organic chemist will appreciate and envision synthetic routes to obtain the active compounds. Accordingly, the invention comprehends synthetic cocoa polyphenols or procyanidins or their derivatives which include, but are not limited to glycosides, gallates, esters, etc. and the like.

The following non-limiting Examples are given by way of illustration only and are not to be considered a limitation of this invention, many apparent variations of which are possible without departing from the spirit or scope thereof.

EXAMPLES

Example 1

Cocoa Source and Method of Preparation

Several *Theobroma cacao* genotypes which represent the three recognized horticultural races of cocoa (Enriquez, 1967; Engels, 1981) were obtained from the three major cocoa producing origins of the world. A list of those genotypes used in this study are shown in Table 1. Harvested cocoa pods were opened and the beans with pulp were removed for freeze drying. The pulp was manually removed from the freeze dried mass and the beans were subjected to analysis as follows. The unfermented, freeze dried cocoa beans were first manually dehulled, and ground to a fine powdery mass with a TEKMAR Mill. The resultant mass was then defatted overnight by Soxhlet extraction using redistilled hexane as the solvent. Residual solvent was removed from the defatted mass by vacuum at ambient temperature.

TABLE 1

Description of *Theobroma cacao* Source Material

| GENOTYPE | ORIGIN | HORTICULTURAL RACE |
| --- | --- | --- |
| UIT-1 | Malaysia | Trinitario |
| Unknown | West Africa | Forastero |
| ICS-100 | Brazil | Trinitario |
| ICS-39 | Brazil | Trinitario |
| UF-613 | Brazil | Trinitario |
| EEG-48 | Brazil | Forastero |
| UF-12 | Brazil | Criollo |
| NA-33 | Brazil | Forastero |

Example 2

Procyanidin Extraction Procedures

A. Method 1

Procyanidins were extracted from the defatted, unfermented, freeze dried cocoa beans of Example 1 using a modification of the method described by Jalal and Collin (1977). Procyanidins were extracted from 50 gram batches of the defatted cocoa mass with 2×400 mL 70% acetone/deionized water followed by 400 mL 70% methanol/deionized water. The extracts were pooled and the solvents removed by evaporation at 45° C. with a rotary evaporator held under partial vacuum. The resultant aqueous phase was diluted to 1 L with deionized water and extracted 2× with 400 mL $CHCl_3$. The solvent phase was discarded. The aqueous phase was then extracted 4× with 500 mL ethyl acetate. Any resultant emulsions were broken by centrifugation on a Sorvall RC 28S centrifuge operated at 2,000×g for 30 min. at 10° C. To the combined ethyl acetate extracts, 100–200 mL deionized water was added. The solvent was removed by evaporation at 45° C. with a rotary evaporator held under partial vacuum. The resultant aqueous phase was frozen in liquid $N_2$ followed by freeze drying on a LAB-CONCO Freeze Dry System. The yields of crude procyanidins that were obtained from the different cocoa genotypes are listed in Table 2.

TABLE 2

Crude Procyanidin Yields

| GENOTYPE | ORIGIN | YIELDS (g) |
|---|---|---|
| UIT-1 | Malaysia | 3.81 |
| Unknown | West Africa | 2.55 |
| ICS-100 | Brazil | 3.42 |
| ICS-39 | Brazil | 3.45 |
| UF-613 | Brazil | 2.98 |
| EEG-48 | Brazil | 3.15 |
| UF-12 | Brazil | 1.21 |
| NA-33 | Brazil | 2.23 |

B. Method 2

Alternatively, procyanidins are extracted from defatted, unfermented, freeze dried cocoa beans of Example 1 with 70% aqueous acetone. Ten grams of defatted material was slurried with 100 mL solvent for 5–10 min. The slurry was centrifuged for 15 min. at 4° C. at 3000×g and the supernatant passed through glass wool. The filtrate was subjected to distillation under partial vacuum and the resultant aqueous phase frozen in liquid $N_2$, followed by freeze drying on a LABCONCO Freeze Dry System. The yields of crude procyanidins ranged from 15–20%.

Without wishing to be bound by any particular theory, it is believed that the differences in crude yields reflected variations encountered with different genotypes, geographical origin, horticultural race, and method of preparation.

Example 3

Partial Purification of Cocoa Procyanidins

A. Gel Permeation Chromatography

Procyanidins obtained from Example 2 were partially purified by liquid chromatography on Sephadex LH-20 (28×2.5 cm). Separations were aided by a step gradient into deionized water. The initial gradient composition started with 15% methanol in deionized water which was followed step wise every 30 min. with 25% methanol in deionized water, 35% methanol in deionized water, 70% methanol in deionized water, and finally 100% methanol. The effluent following the elution of the xanthine alkaloids (caffeine and theobromine) was collected as a single fraction. The fraction yielded a xanthine alkaloid free subfraction which was submitted to further subfractionation to yield five subfractions designated MM2A through MM2E. The solvent was removed from each subfraction by evaporation at 45° C. with a rotary evaporator held under partial vacuum. The resultant aqueous phase was frozen in liquid $N_2$ and freeze dried overnight on a LABCONCO Freeze Dry System. A representative gel permeation chromatogram showing the fractionation is shown in FIG. 1. Approximately, 100 mg of material was subfractionated in this manner.

FIG. 1: Gel Permeation Chromatogram of Crude Procyanidins on Sephadex LH-20

Chromatographic Conditions: Column; 28×2.5 cm Sephadex LH-20, Mobile Phase: Methanol/Water Step Gradient, 15:85, 25:75, 35:65, 70:30, 100:0 Stepped at ½ Hour Intervals, Flow Rate; 1.5 ml/min, Detector; UV @ $\lambda_1$=254 nm and $\lambda_2$=365 nm, Chart Speed: 0.5 mm/min, Column Load; 120 mg.

B. Semi-preparative High Performance Liquid Chromatography-(HPLC)

Method 1: Reverse Phase Separation

Procyanidins obtained from Example 2 and/or 3A were partially purified by semi-preparative HPLC. A Hewlett Packard 1050 HPLC System equipped with a variable wavelength detector, Rheodyne 7010 injection valve with 1 mL injection loop was assembled with a Pharmacia FRAC-100 Fraction Collector. Separations were effected on a Phenomenex Ultracarb $10\mu$ ODS column (250×22.5 mm) connected with a Phenomenex $10\mu$ ODS Ultracarb (60×10 mm) guard column. The mobile phase composition was A=water; B=methanol used under the following linear gradient conditions: [Time, % A]; (0,85), (60,50), (90,0), and (110,0) at a flow rate of 5 mL/min.

Figure 15A:
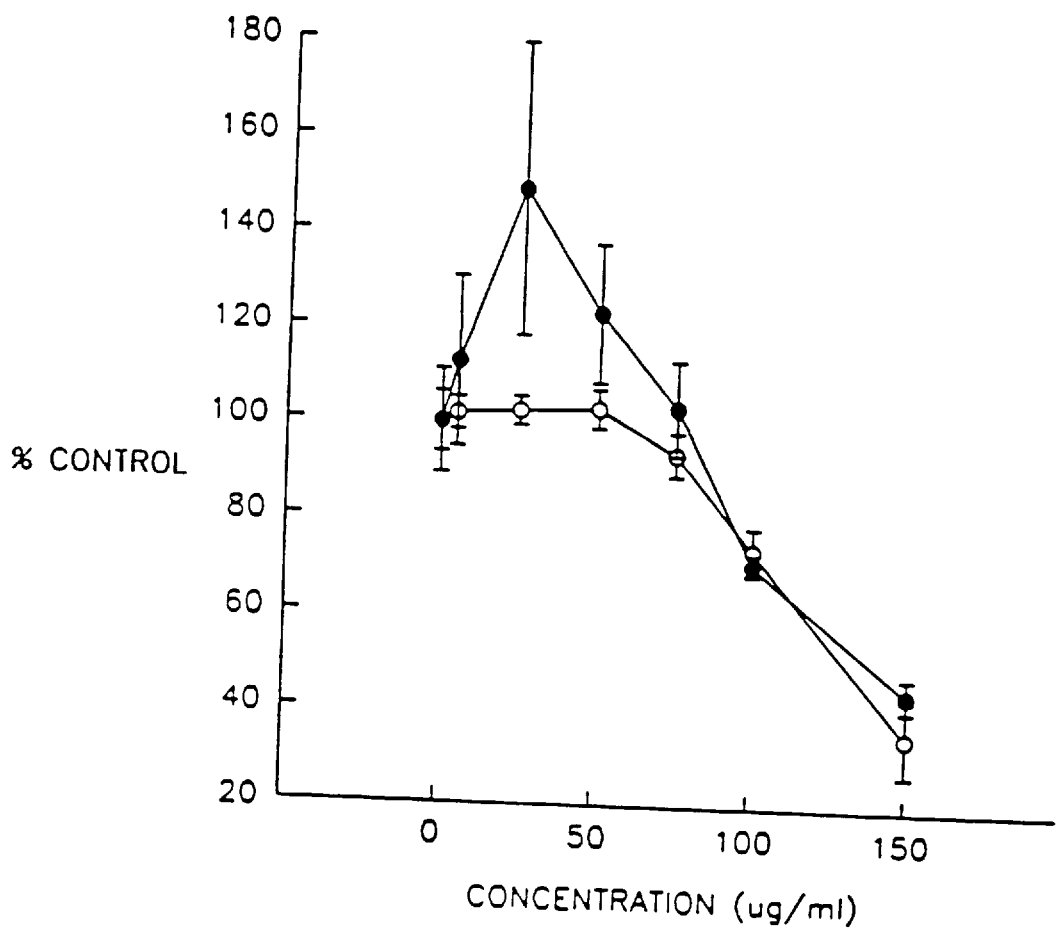
FIG. 15A shows a comparison of the XTT and Crystal Violet cytotoxicity assays against MCF-7 p168 breast cancer cells treated with fraction D+E (open circle is XTT and darkened circle is Crystal Violet)
Figure 15C:
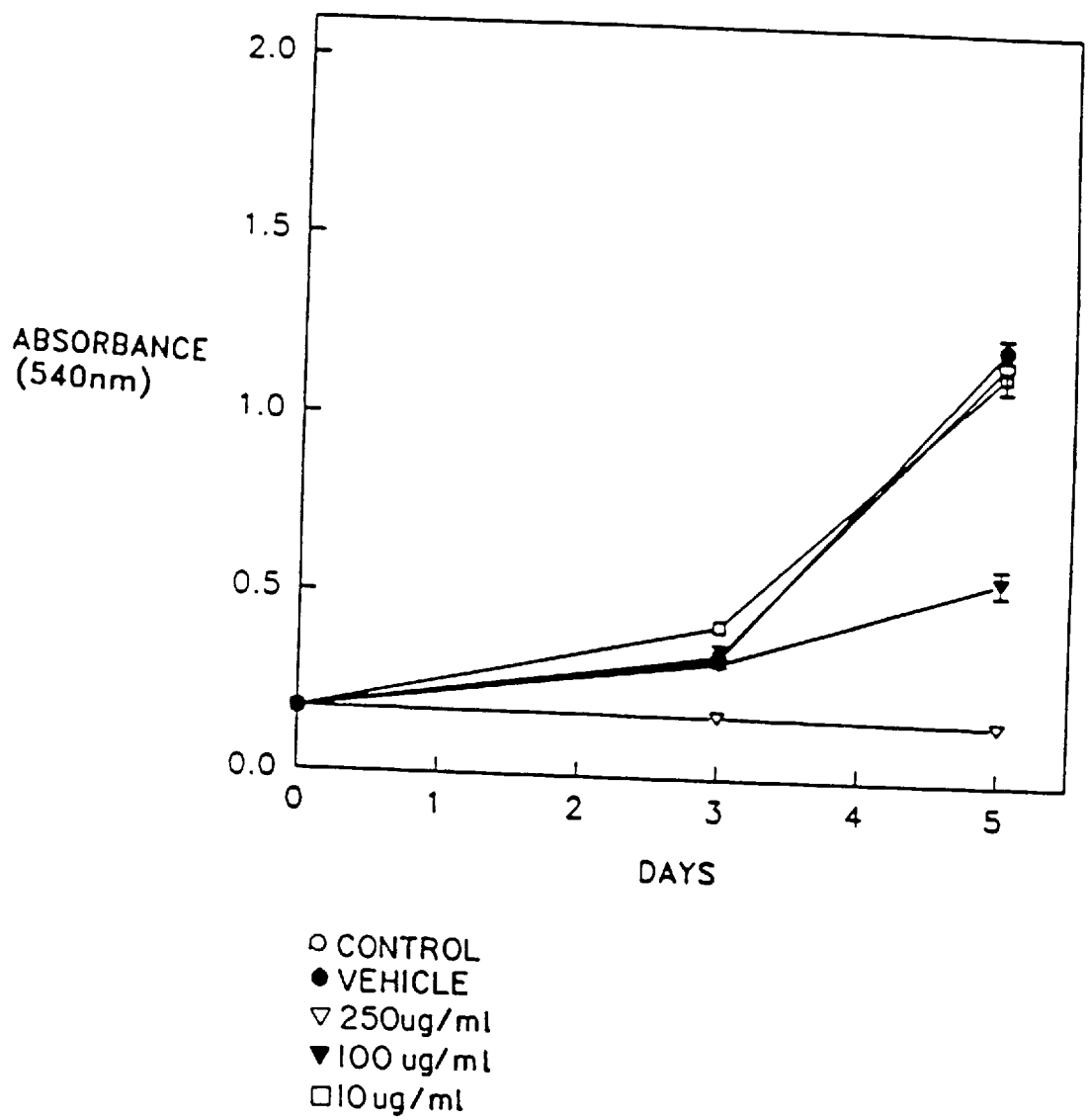
FIG. 15C shows a typical dose response curve obtained from PC-3 prostate cancer cell line treated with varying levels of crude polyphenols obtained from UIT-1 cocoa genotype (absorbance (540 nm) vs. Days; open circle is control, darkened circle is vehicle, open inverted triangle is 250 µg/ml, darkened inverted triangle is 100 µg/ml and open square is 10 µg/ml)
Figure 15D:
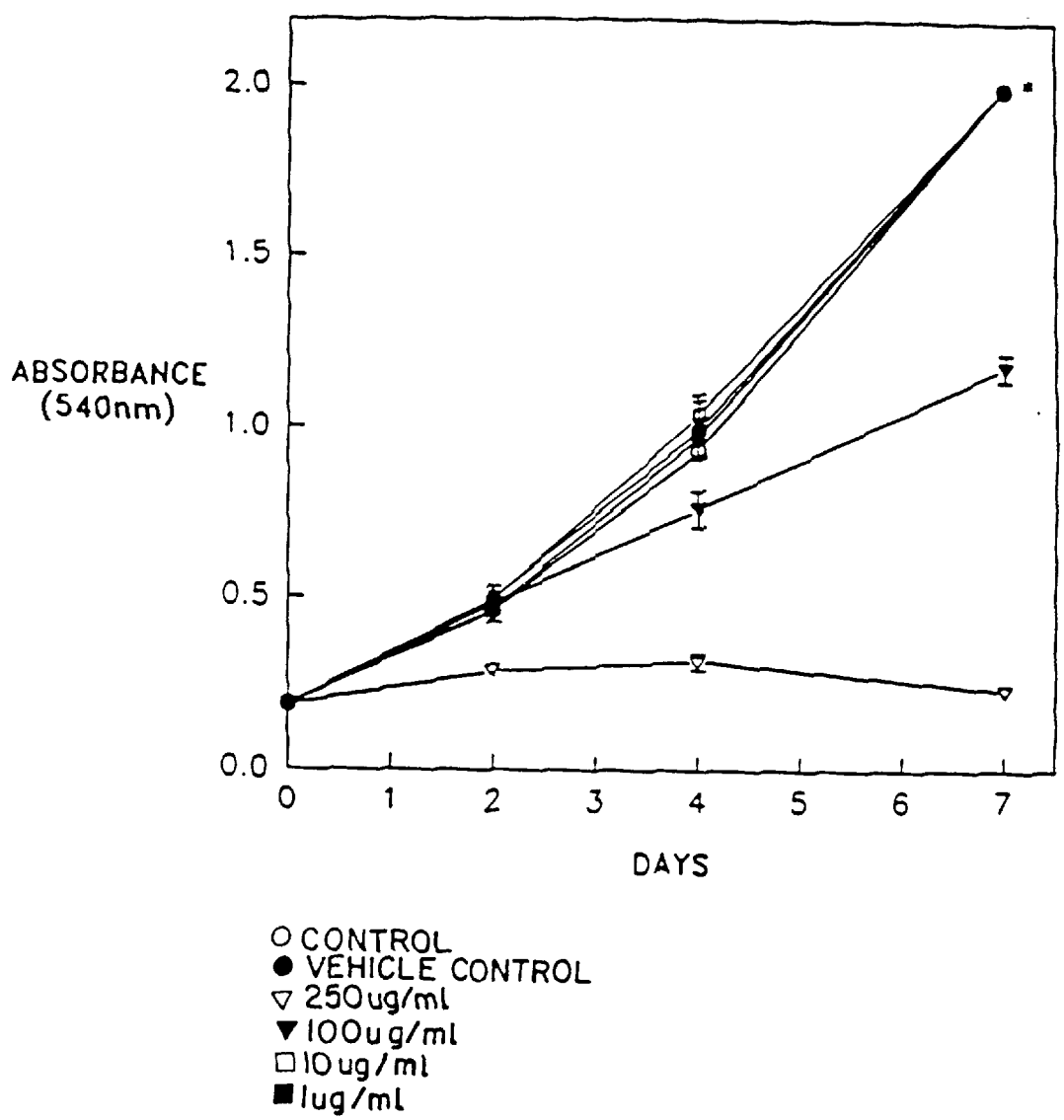
FIG. 15D shows a typical dose-response curve obtained from MCF-7 p168 breast cancer cell line treated with varying levels of crude polyphenols obtained from UIT-1 cocoa genotype (absorbance (540 nm) vs. Days; open circle is control, darkened circle is vehicle, open inverted triangle is 250 µg/ml, darkened inverted triangle is 100 µg/ml, open square is 10 µg/ml, darkened square is 1 µg/ml; absorbance of 2.0 is maximum of plate reader and may not be necessarily representative of cell number)
Figure 15E:
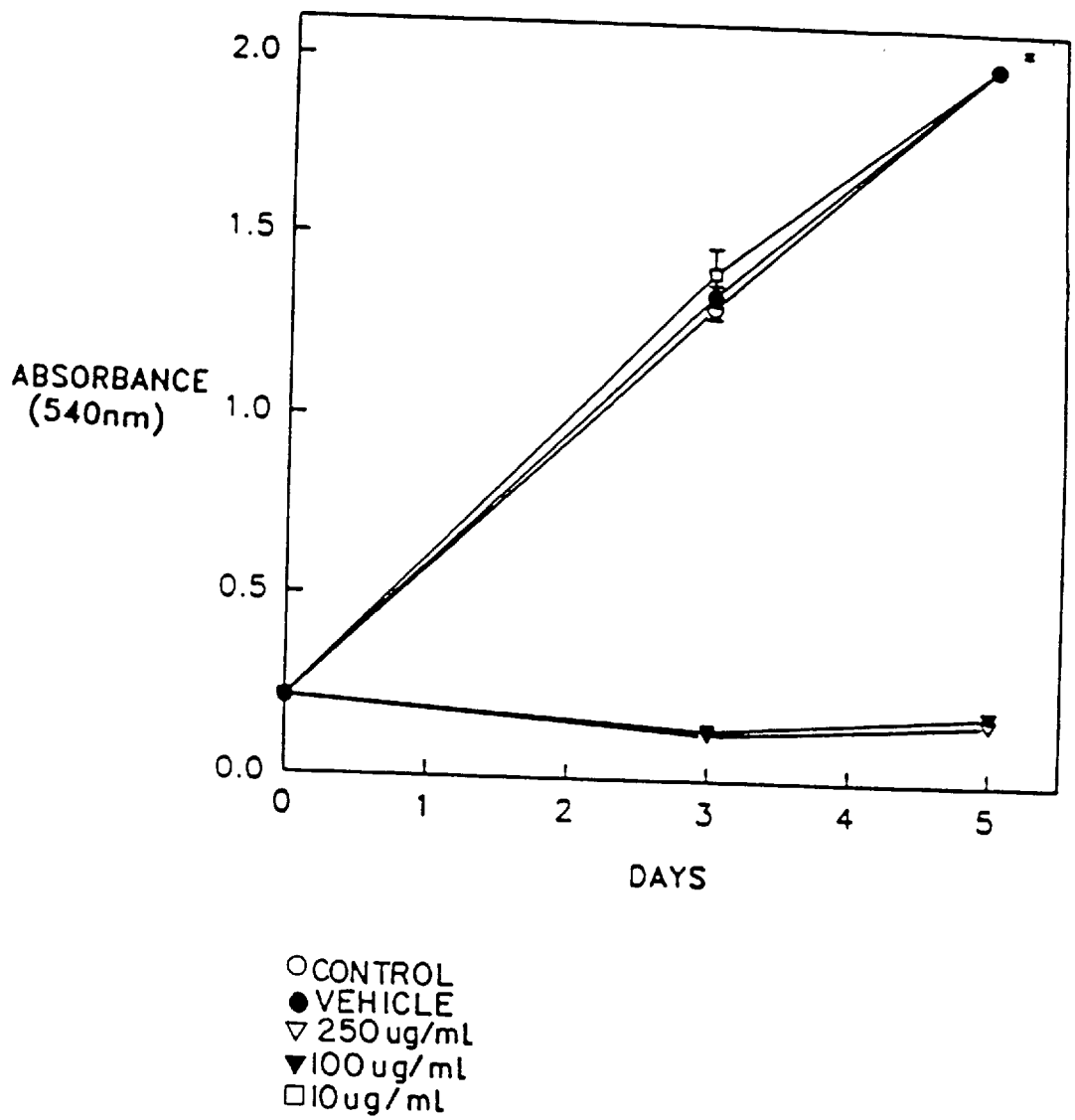
FIG. 15E shows a typical dose response curve obtained from Hela cervical cancer cell line treated with varying levels of crude polyphenols obtained from UIT-1 cocoa genotype (absorbance (540 nm) vs. Days; open circle is control, darkened circle is vehicle, open inverted triangle is 250 µg/ml, darkened inverted triangle is 100 µg/ml, open square is 10 µg/ml; absorbance of 2.0 is maximum of plate reader and may not be necessarily representative of cell number)
Figure 15F:
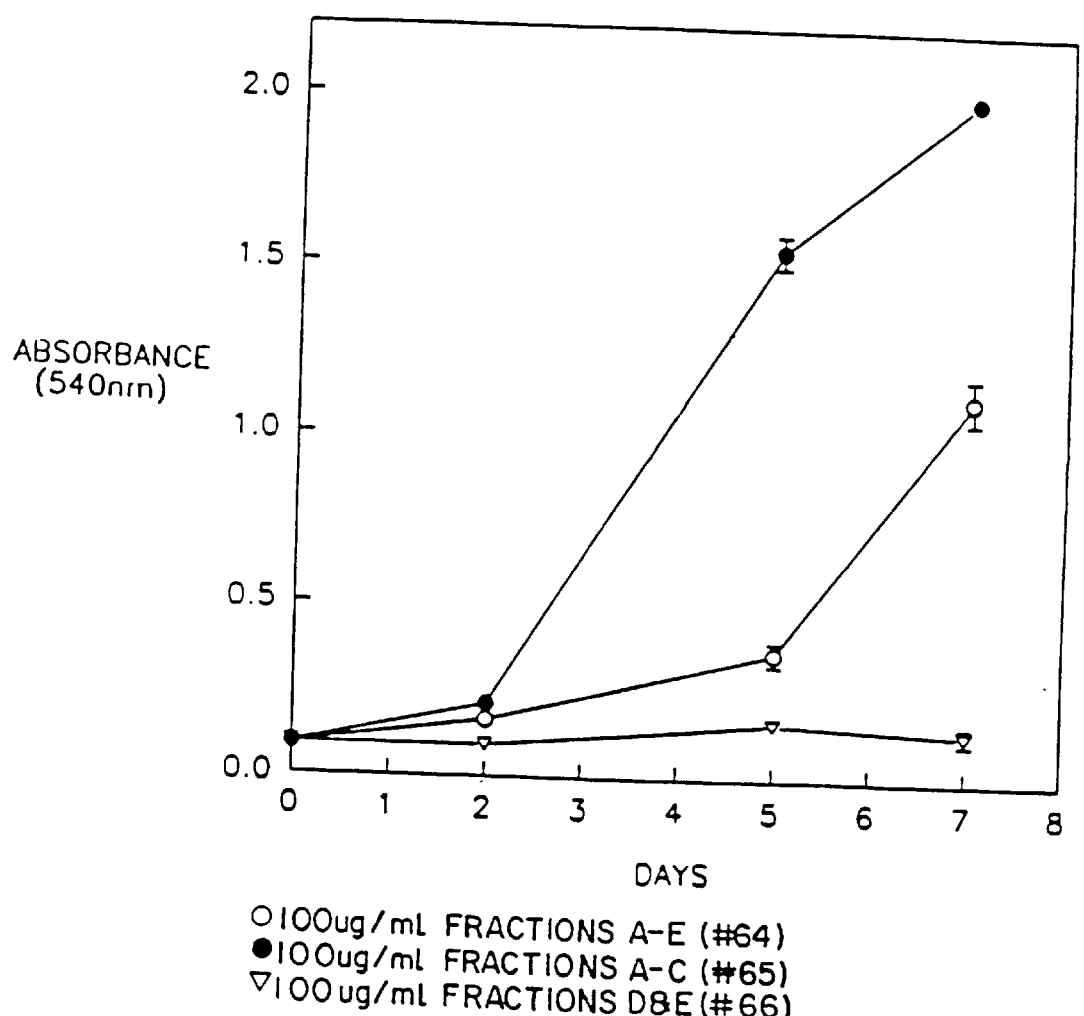
FIG. 15F shows cytotoxic effects against Hela cervical cancer cell line treated with different cocoa polyphenol fractions (absorbance (540 nm) vs. Days; open circle is 100 µg/ml fractions A–E, darkened circle is 100 µg/ml fractions A–C, open inverted triangle is 100 µg/ml fractions D&E; absorbance of 2.0 is maximum of plate reader and not representative of cell number)
Figure 15H:
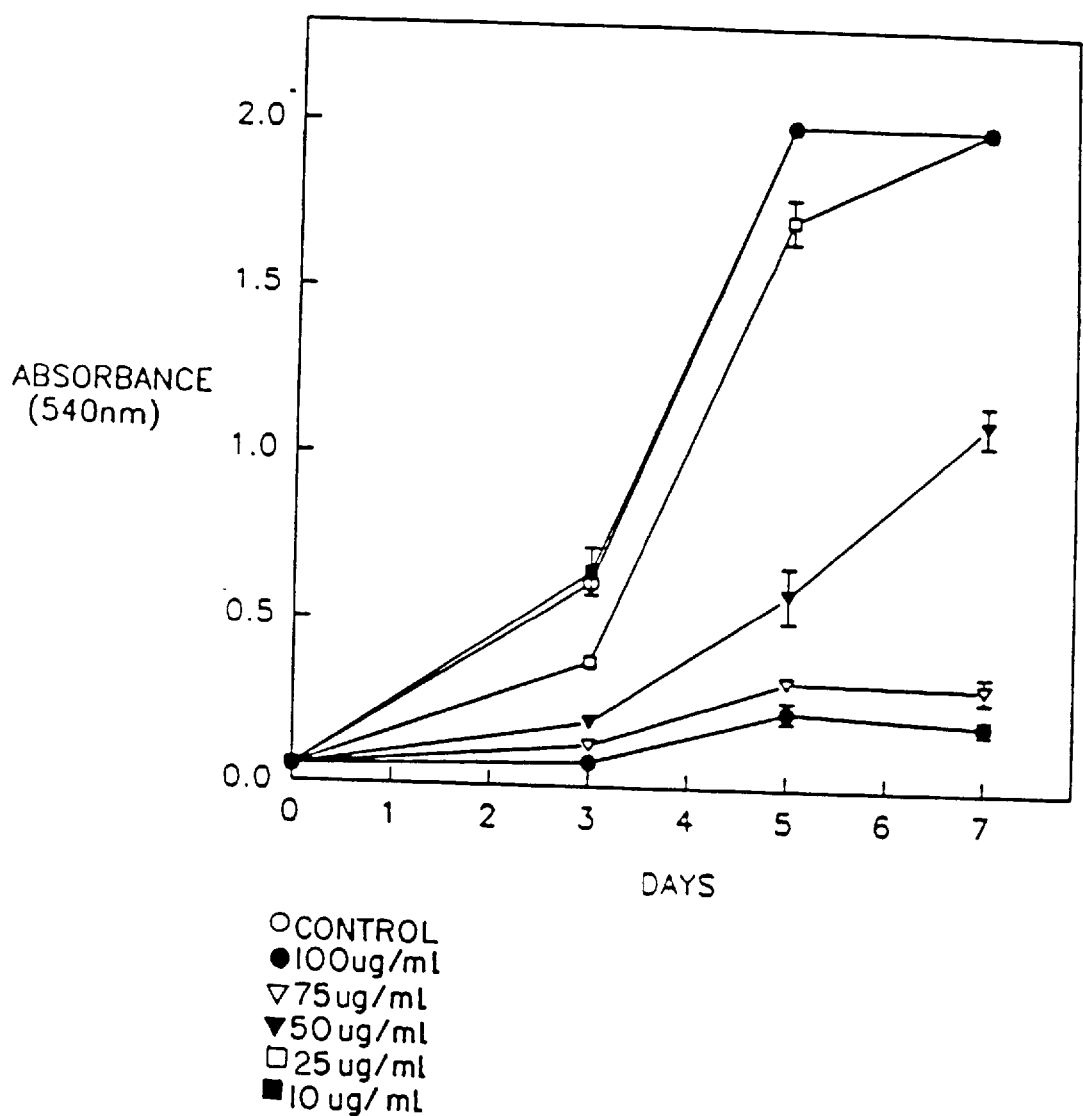
FIG. 15H shows typical dose-response relationships between cocoa procyanidin fraction D+E on Hela cells (absorbance (540 nm) vs. Days; open circle is control, darkened circle is 100 µg/ml, open inverted triangle is 75 µg/ml, darkened inverted triangle is 50 µg/ml, open square is 25 µg/ml, darkened square is 10 µg/ml; absorbance of 2.0 is maximum of plate reader and is not representative of cell number)
Figure 151:
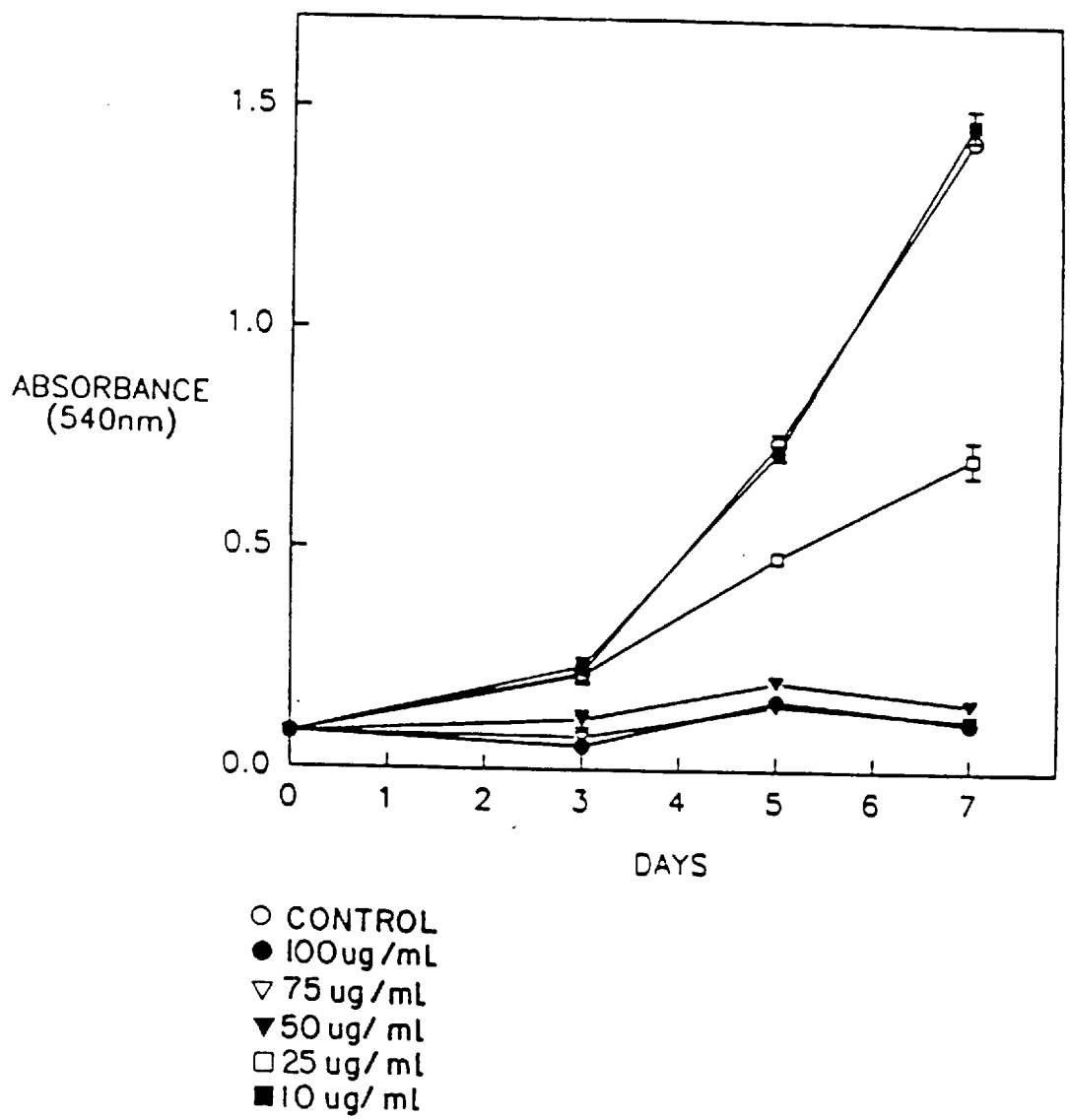
Figure 15J:
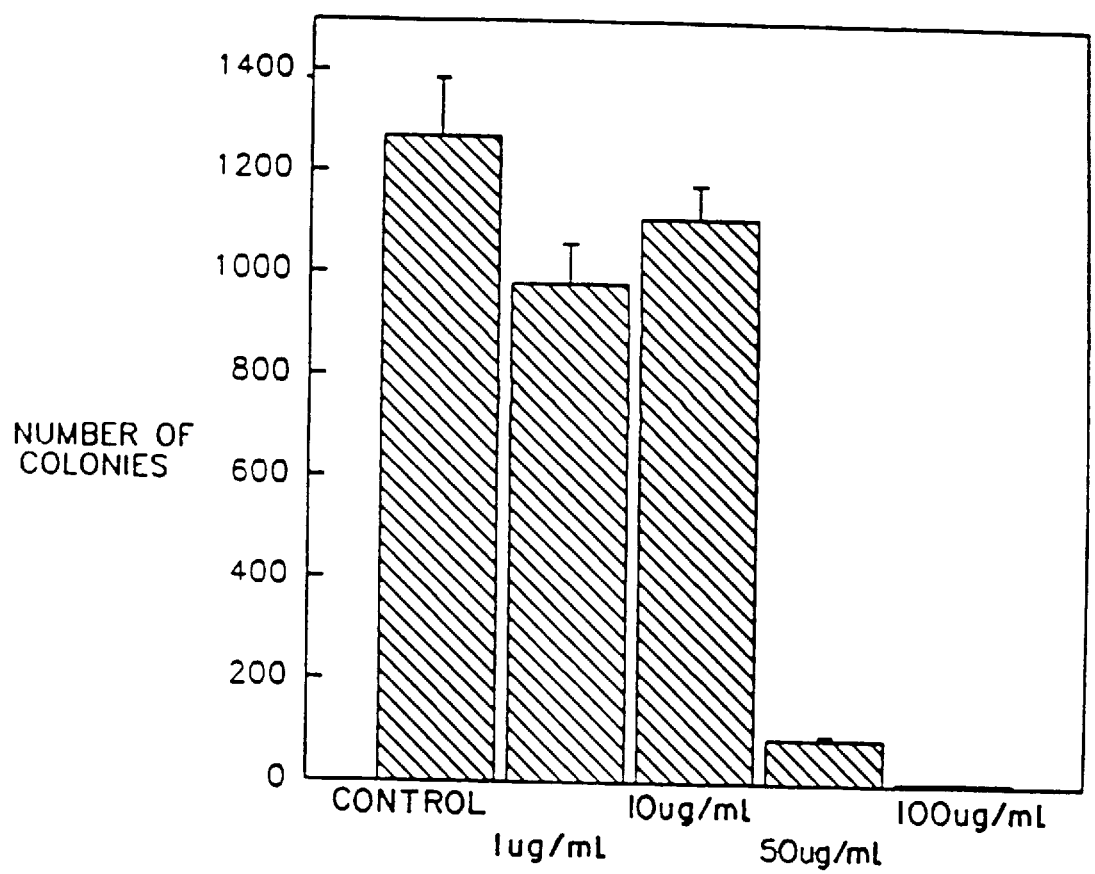
FIG. 15J shows typical dose-response relationships between cocoa procyanidin fraction D+E on Hela cells using the Soft Agar Cloning assay (bar chart; number of colonies vs. control, 1, 10, 50, and 100 µg/ml)
Figure 15N:
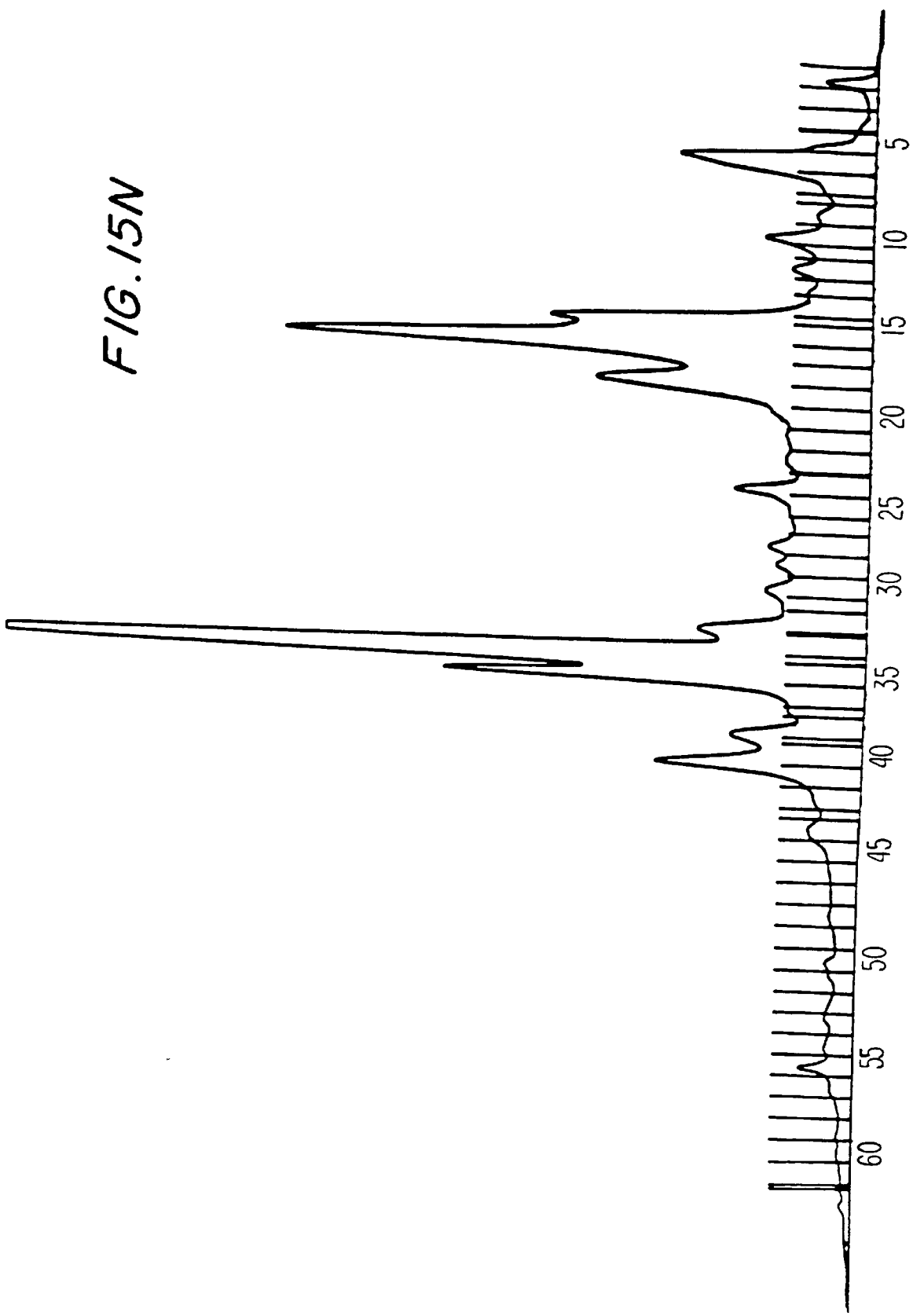
FIG. 15N shows a representative semi-preparative reverse phase HPLC separation for combined cocoa procyanidin fractions D and E.

A representative Semi-preparative HPLC trace is shown in FIG. 15N for the separation of procyanidins present in fraction D+E. Individual peaks or select chromatographic regions were collected on timed intervals or manually by fraction collection for further purification and subsequent evaluation. Injection loads ranged from 25–100 mg of material.

Method 2. Normal Phase separation

Procyanidin extracts obtained from Examples 2 and/or 3A were partially purified by semi-preparative HPLC. A Hewlett Packard 1050 HPLC system, Millipore-Waters Model 480 LC detector set at 254 nm was assembled with a Pharmacia Frac-100 Fraction Collector set in peak mode. Separations were effected on a Supelco $5\mu$ Supelcosil LC-Si column (250×10 mm) connected with a Supelco $5\mu$ Supelguard LC-Si guard column (20×4.6 mm). Procyanidins were eluted by a linear gradient under the following conditions: (Time, % A, % B); (0,82,14), (30, 67.6, 28.4), (60, 46, 50), (65, 10, 86), (70, 10, 86) followed by a 10 min. re-equilibration. Mobile phase composition was A=dichloromethane; B=methanol; and C=acetic acid: water (1:1). A flow rate of 3 mL/min was used. Components were detected by UV at 254 nm, and recorded on a Kipp & Zonan BD41 recorder. Injection volumes ranged from 100–250 $\mu$L of 10 mg of procyanidin extracts dissolved in 0.25 mL 70% aqueous acetone. A representative semi-preparative HPLC trace is shown in FIG. 15O. Individual peaks or select chromatographic regions were collected on timed intervals or manually by fraction collection for further purification and subsequent evaluation.

| HPLC Conditions: | 250 × 10 mm Supelco Supelcosil LC-Si (5 $\mu$m) Semipreparative Column |
|---|---|
| | 20 × 4.6 mm Supelco Supelcosil LC-Si (5 $\mu$m) Guard Column |
| | Detector: Waters LC Spectrophotometer Model 480 @ 254 nm |
| | Flow rate: 3 mL/min, |
| | Column Temperature: ambient, |
| | Injection: 250 $\mu$L of 70% aqueous acetone extract. |

| Gradient: Time (min) | $CH_2Cl_2$ | Methanol | Acetic Acid/$H_2O$ (1:1) |
|---|---|---|---|
| 0 | 82 | 14 | 4 |
| 30 | 67.6 | 28.4 | 4 |
| 60 | 46 | 50 | 4 |
| 65 | 10 | 86 | 4 |
| 70 | 10 | 86 | 4 |

The fractions obtained were as follows:

| FRACTION | TYPE |
|---|---|
| 1 | dimers |
| 2 | trimers |
| 3 | tetramers |
| 4 | pentamers |

-continued

| FRACTION | TYPE |
|---|---|
| 5 | hexamers |
| 6 | heptamers |
| 7 | octamers |
| 8 | nonamers |
| 9 | decamers |
| 10 | undecamers |
| 11 | dodecamers |
| 12 | higher oligomers |

Example 4

Figure 2A:
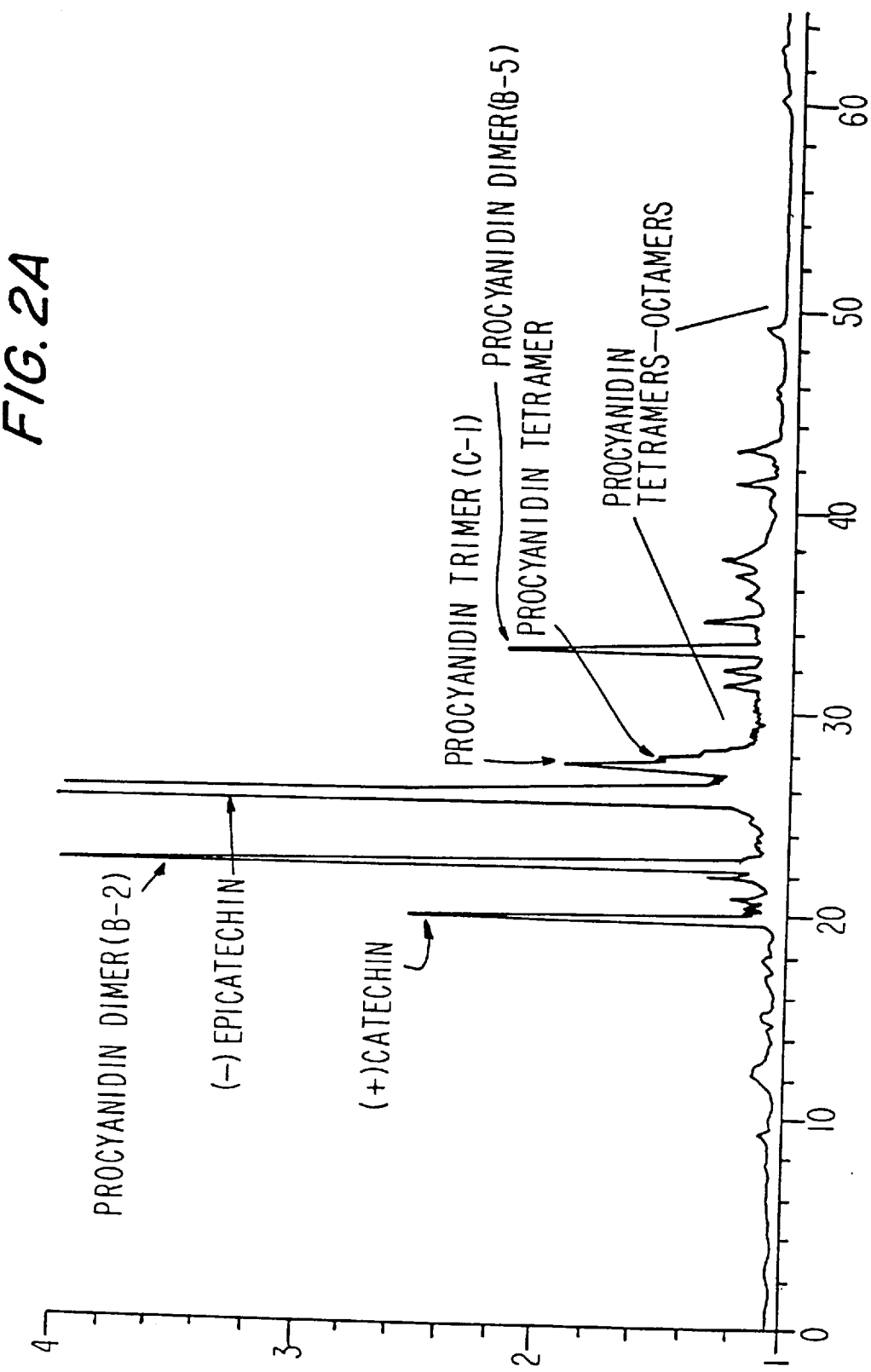
FIG. 2A shows a representative reverse-phase HPLC chromatogram showing the separation (elution profile) of cocoa procyanidins extracted from unfermented cocoa.

Analytical HPLC Analysis of Procyanidin Extracts
Method 1: Reverse Phase Separation Procyanidin extracts obtained from Example 3 were filtered through a $0.45\mu$ filter and analyzed by a Hewlett Packard 1090 ternary HPLC system equipped with a Diode Array detector and a HP model 1046A Programmable Fluorescence Detector. Separations were effected at 45° C. on a Hewlett-Packard $5\mu$ Hypersil ODS column (200×2.1 mm). The flavanols and procyanidins were eluted with a linear gradient of 60% B into A followed by a column wash with B at a flow rate of 0.3 mL/min. The mobile phase composition was B=0.5% acetic acid in methanol and A=0.5% acetic acid in deionized water. Acetic acid levels in A and B mobile phases can be increased to 2%. Components were detected by fluorescence, where $\lambda_{ex}$=276 nm and $\lambda_{em}$=316 nm. Concentrations of (+)-catechin and (−)-epicatechin were determined relative to reference standard solutions. Procyanidin levels were estimated by using the response factor for (−)-epicatechin. A representative HPLC chromatogram showing the separation of the various components is shown in FIG. 2A for one cocoa genotype. Similar HPLC profiles were obtained from the other cocoa genotypes.

| HPLC Conditions: | Column: | 200 × 2.1 mm Hewlett Packard Hypersil ODS ($5\mu$) |
|---|---|---|
| | Guard column: | 20 × 2.1 mm Hewlett Packard Hypersil ODS ($5\mu$) |
| | Detectors: | Diode Array @ 289 nm Fluorescence $\lambda_{ex}$ = 276 nm; $\lambda_{em}$ = 316 nm. |
| | Flow rate: | 3 mL/min. |
| | Column Temperature: 45° C. | |

| Gradient: Time (min) | 0.5% Acetic Acid in deionized water | 0.5% Acetic acid in methanol |
|---|---|---|
| 0 | 100 | 0 |
| 50 | 40 | 60 |
| 60 | 0 | 100 |

Method 2: Normal Phase Separation

Figure 2B:
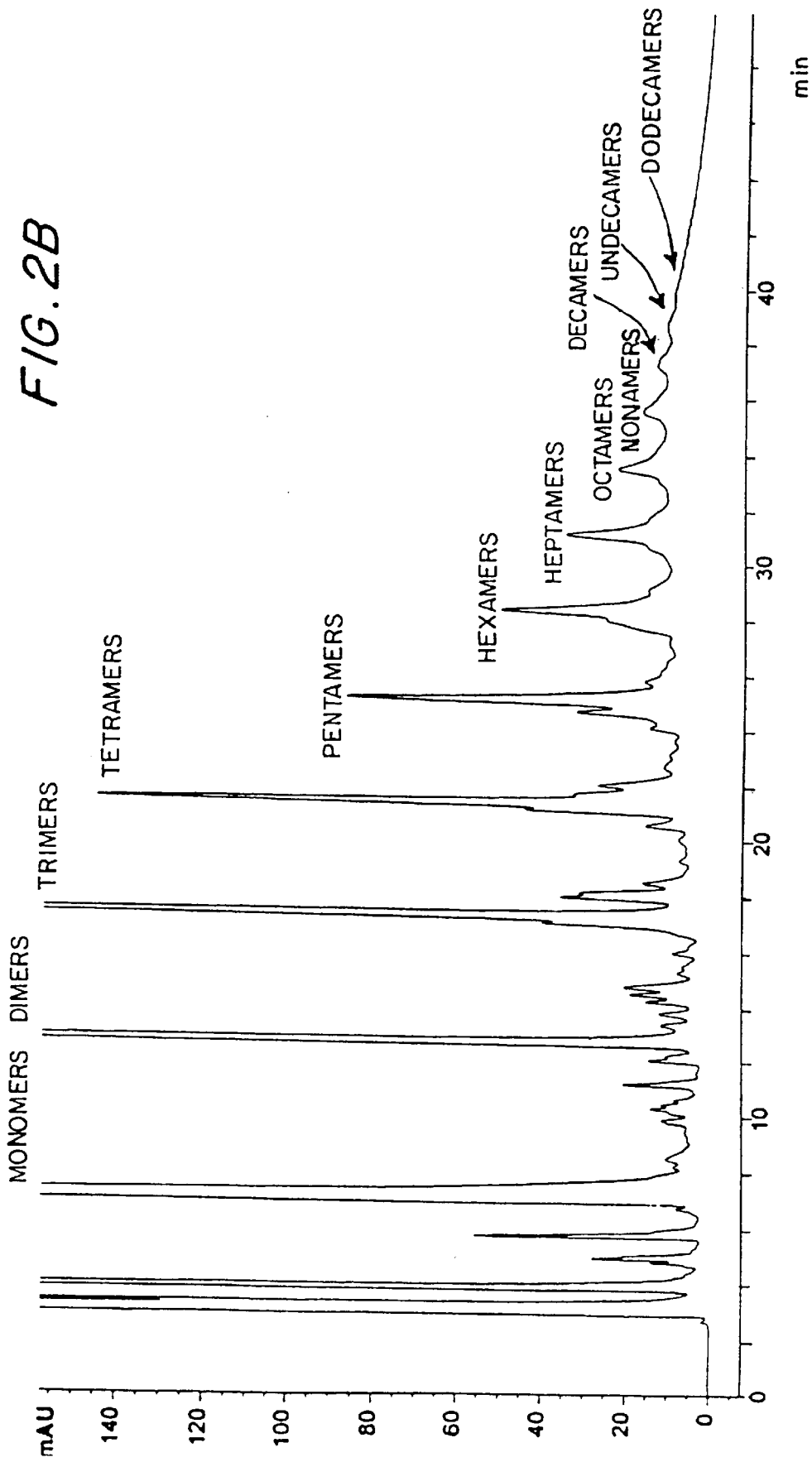
FIG. 2B shows a representative normal phase HPLC separation of cocoa procyanidins extracted from unfermented cocoa.
Figure 4B:
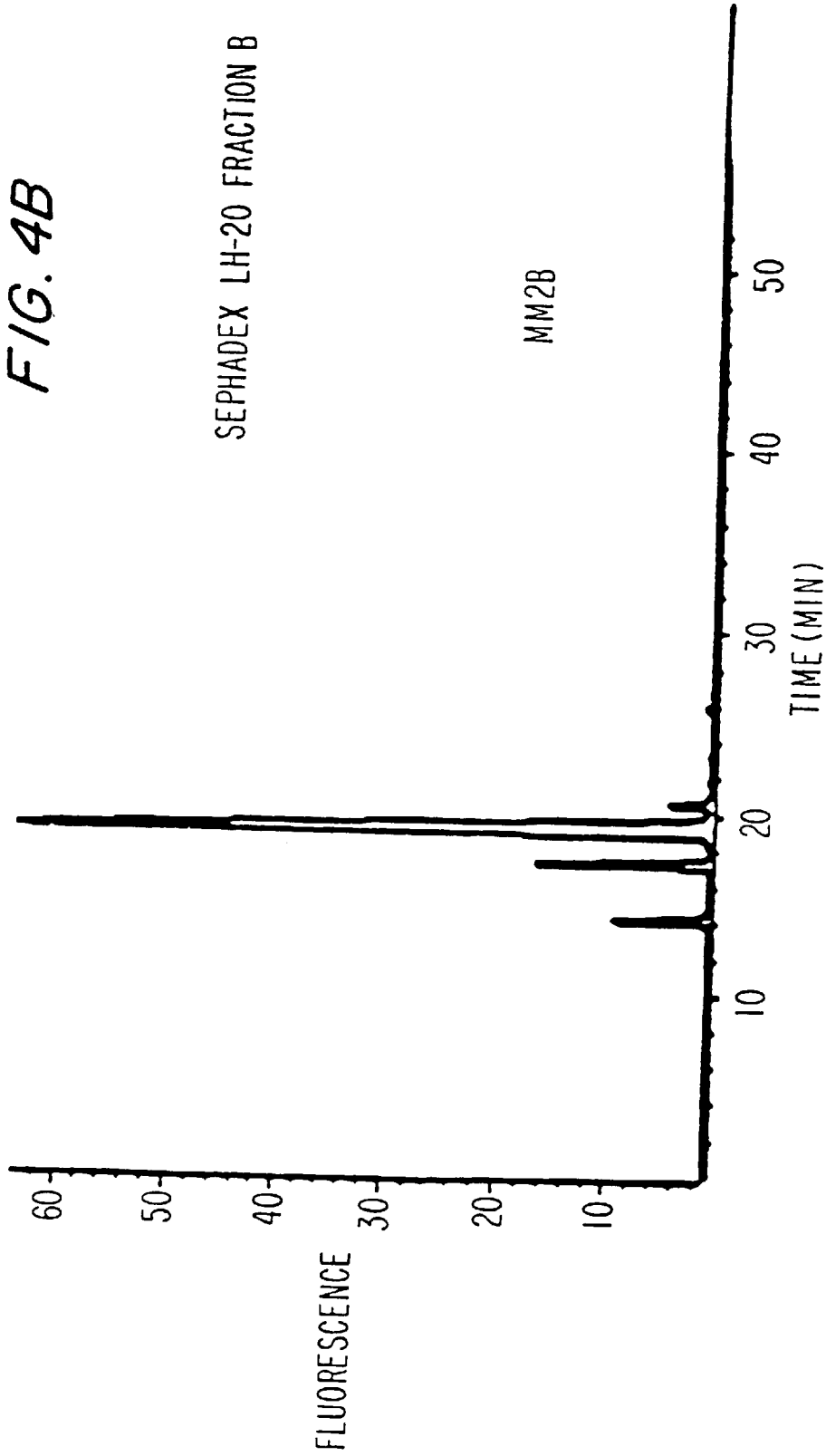
Figure 4E:
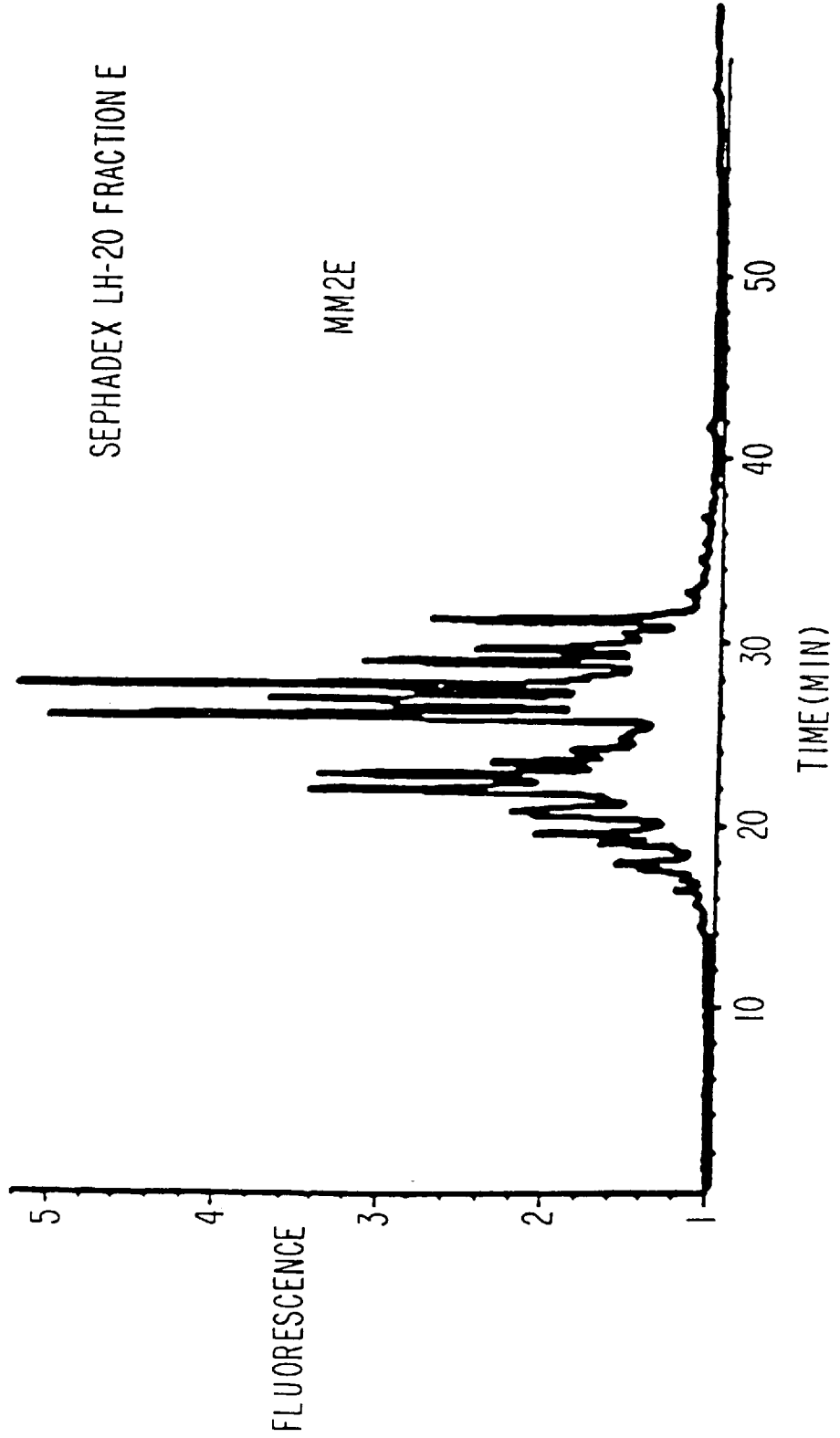

Procyanidin extracts obtained from Examples 2 and/or 3 were filtered through a $0.45\mu$ filter and analyzed by a Hewlett Packard 1090 Series II HPLC system equipped with a HP model 1046A Programmable Fluorescence detector and Diode Array detector. Separations were effected at 37° C. on a $5\mu$ Phenomenex Lichrosphere Silica 100 column (250×3.2 mm) connected to a supelco Supelguard LC-Si $5\mu$ guard column (20×4.6 mm). Procyanidins were eluted by linear gradient under the following conditions: (Time, % A, % B); (0, 82, 14), (30, 67.6, 28.4), (60, 46, 50), (65, 10, 86), (70, 10, 86) followed by an 8 min. re-equilibration. Mobile phase composition was A=dichloromethane, B=methanol, and C=acetic acid: water at a volume ratio of 1:1. A flow rate of 0.5 mL/min. was used. Components were detected by fluorescence, where $\lambda_{ex}$=276 nm and $\lambda_{em=316}$ nm or by UV at 280 nm. A representative HPLC chromatogram showing the separation of the various procyanidins is shown in FIG. 2B for one genotype. Similar HPLC profiles were obtained from other cocoa genotypes.

| HPLC Conditions: |
|---|
| 250 × 3.2 mm Phenomenex Lichrosphere Silica 100 column ($5\mu$) 20 × 4.6 mm Supelco Supelguard LC-Si ($5\mu$) guard column |
| Detectors: Photodiode Array @ 280 nm Fluorescence $\lambda_{ex}$ = 276 nm; $\lambda_{em}$ = 316 nm. |
| Flow rate: 0.5 mL/min. |
| Column Temperature: 37° C. |

| Gradient: Time (min.) | $CH_2$—$Cl_2$ | Methanol | Acetic Acid/Water (1:1) |
|---|---|---|---|
| 0 | 82 | 14 | 4 |
| 30 | 67.6 | 28.4 | 4 |
| 60 | 46 | 50 | 4 |
| 65 | 10 | 86 | 4 |
| 70 | 10 | 86 | 4 |

Example 5

Identification of Procyanidins

Procyanidins were purified by liquid chromatography on Sephadex LH-20 (28×2.5 cm) columns followed by semi-preparative HPLC using a $10\mu$ $\mu$Bondapak C18 (100×8 mm) column or by semi-preparative HPLC using a $5\mu$ Supelcosil LC-Si (250×10 mm) column.

Partially purified isolates were analyzed by Fast Atom Bombardment—Mass Spectrometry (FAB-MS) on a VG ZAB-T high resolution MS system using a Liquid Secondary Ion Mass Spectrometry (LSIMS) technique in positive and negative ion modes. A cesium ion gun was used as the ionizing source at 30 kV and a "Magic Bullet Matrix" (1:1 dithiothreitol/dithioerythritol) was used as the proton donor.

Analytical investigations of these fractions by LSIMS revealed the presence of a number of flavan-3-ol oligomers as shown in Table 3.

TABLE 3

LSIMS (Positive Ion) Data from Cocoa Procyanidin Fractions

| Oligomer | $(M + 1)^+$ m/z | $(M + Na)^+$ m/z | Mol. Wt. |
|---|---|---|---|
| Monomers (catechins) | 291 | 313 | 290 |
| Dimer(s) | 577/579 | 599/601 | 576/578 |
| Trimer(s) | 865/867 | 887/889 | 884/866 |
| Tetramer(s) | 1155 | 1177 | 1154 |
| Pentamer(s) | 1443 | 1465 | 1442 |
| Hexamer(s) | 1731 | 1753 | 1730 |
| Heptamer(s) | — | 2041 | 2018 |
| Octamer(s) | — | 2329 | 2306 |
| Nonamer(s) | — | 2617 | 2594 |
| Decamer(s) | — | 2905 | 2882 |
| Undecamer(s) | — | — | 3170 |
| Dodecamer(s) | — | — | 3458 |

The major mass fragment ions were consistent with work previously reported for both positive and negative ion FAB-MS analysis of procyanidins (Self et al., 1986 and Porter et al., 1991). The ion corresponding to m/z 577 $(M+H)^+$ and its sodium adduct at m/z 599 (M+Na)+ suggested the presence of doubly linked procyanidin dimers in the isolates. It was interesting to note that the higher oligomers were more likely to form sodium adducts (M+Na)+ than their protonated molecular ions (M+H)+. The procyanidin isomers B-2, B-5 and C-1 were tentatively identified based on the work reported by Revilla et al. (1991), Self et al. (1986) and Porter et al. (1991). Procyanidins up to both the octamer and decamer were verified by FAB-MS in the partially purified fractions. Additionally, evidence for procyanidins up to the dodecamer were observed from normal phase HPLC analysis (see FIG. 2B). Without wishing to be bound by any particular theory, it is believed that the dodecamer is the limit of solubility in the solvents used in the extraction and purification schemes. Table 4 lists the relative concentrations of the procyanidins found in xanthine alkaloid free isolates based on reverse phase HPLC analysis. Table 5 lists the relative concentrations of the procyanidins based on normal phase HPLC analysis.

TABLE 4

Relative Concentrations of Procyanidins in the Xanthine Alkaloid Free Isolates

| Component | Molecular Weight | Amount |
| --- | --- | --- |
| (+)-catechin | 290 | 1.6% |
| (−)-epicatechin | 290 | 38.2% |
| B-2 Dimer | 578 | 11.0% |
| B-5 Dimer | 578 | 5.3% |
| C-1 Trimer | 866 | 9.3% |
| Doubly linked dimers | 576 | 3.0% |
| Tetramer(s) | 1154 | 4.5% |
| Pentamer-Octamer | 1442–2306 | 24.5% |
| Unknowns and higher oligomers | — | 2.6% |

TABLE 5

Relative Concentrations of Procyanidins in Aqueous Acetone Extracts

| Component | Molecular Weight | Amount |
| --- | --- | --- |
| (+)-catechin and (−)-epicatechin | 290 (same for each) | 41.9% |
| B-2 and B-5 Dimers | 578 | 13.9% |
| Trimers | 884/866 | 11.3% |
| Tetramers | 1154 | 9.9% |
| Pentamers | 1442 | 7.8% |
| Hexamers | 1730 | 5.1% |
| Heptamers | 2018 | 4.2% |
| Octamers | 2306 | 2.8% |
| Nonamers | 2594 | 1.6% |
| Decamers | 2882 | 0.7% |
| Undecamers | 3170 | 0.2% |
| Dodecamers | 3458 | <0.1% |

FIG. 3 shows several procyanidin structures and FIGS. 4A–4E show the representative HPLC chromatograms of the five fractions employed in the following screening for anti-cancer or antineoplastic activity. The HPLC conditions for FIGS. 4A–4E were as follows:

HPLC Conditions: Hewlett Packard 1090 ternary HPLC System equipped with HP Model 1046A Programmable Fluorescence Detector. Column: Hewlett Packard 5μ Hypersil ODS (200×30 2.1 mm) Linear Gradient of 60% B into A at a flow rate of 0.3 ml/min. B=0.5% acetic acid in methanol; A=0.5% acetic acid in deionized water. $\lambda_{ex}$=280 nm; $\lambda_{em}$=316 nm.

FIG. 15O shows a representative semi-prep HPLC chromatogram of an additional 12 fractions employed in the screening for anticancer or antineoplastic activity (HPLC conditions stated above).

Example 6

Anti-Cancer, Anti-Tumor or Antineoplastic Activity of Cocoa Extracts (Procyanidins)

The MTT (3-[4,5-dimethyl thiazol-2yl]-2,5-diphenyltetrazolium bromide)—microtiter plate tetrazolium cytotoxicity assay originally developed by Mosmann (1983) was used to screen test samples from Example 5. Test samples, standards (cisplatin and chlorambucil) and MTT reagent were dissolved in 100% DMSO (dimethyl sulfoxide) at a 10 mg/mL concentration. Serial dilutions were prepared from the stock solutions. In the case of the test samples, dilutions ranging from 0.01 through 100 μg/mL were prepared in 0.5% DMSO.

All human tumor cell lines were obtained from the American Type Culture Collection. Cells were grown as mono layers in alpha-MEM containing 10% fetal bovine serum, 100 units/mL penicillin, 100 μg/mL streptomycin and 240 units/mL nystatin. The cells were maintained in a humidified, 5% $CO_2$ atmosphere at 37° C.

After trypsinization, the cells are counted and adjusted to a concentration of $50 \times 10^5$ cells/mL (varied according to cancer cell line). 200 μL of the cell suspension was plated into wells of 4 rows of a 96-well microtiter plate. After the cells were allowed to attach for four hours, 2 μL of DMSO containing test sample solutions were added to quadruplicate wells. Initial dose-response finding experiments, using order of magnitude test sample dilutions were used to determine the range of doses to be examined. Well absorbencies at 540 nm were then measured on a BIO RAD MP450 plate reader. The mean absorbance of quadruplicate test sample treated wells was compared to the control, and the results. expressed as the percentage of control absorbance plus/minus the standard deviation. The reduction of MTT to a purple formazan product correlates in a linear manner with the number of living cells in the well. Thus, by measuring the absorbance of the reduction product, a quantitation of the percent of cell survival at a given dose of test sample can be obtained. Control wells contained a final concentration of 1 DMSO.

Figure 5:
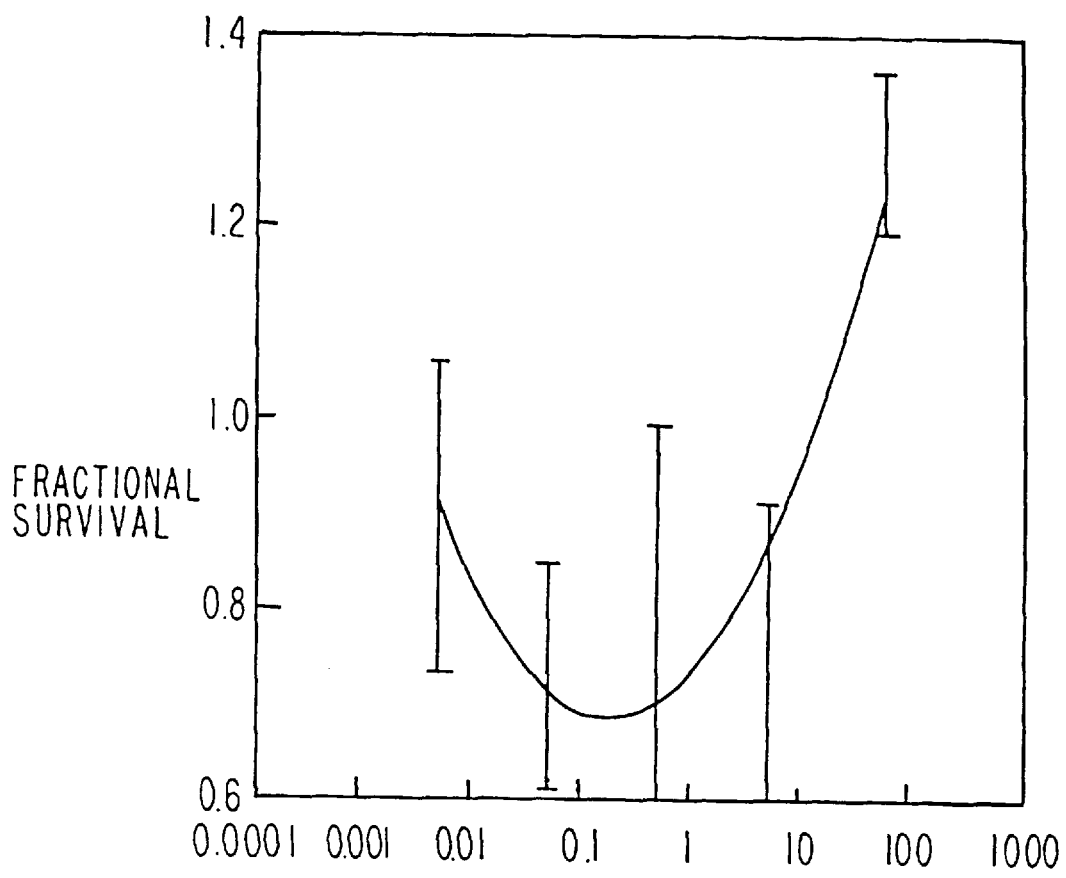
FIGS. 5 and 6A–6D show the dose-response relationship between cocoa extracts and cancer cells ACHN (FIG. 5) and PC-3 (FIGS. 6A–6D) (fractional survival vs. dose, µg/ml); M&M2 F4/92, M&MA+E U12P1, M&MB+E Y192P1, M&MC+E U12P2, M&MD+E U12P2.
Figure 6A:
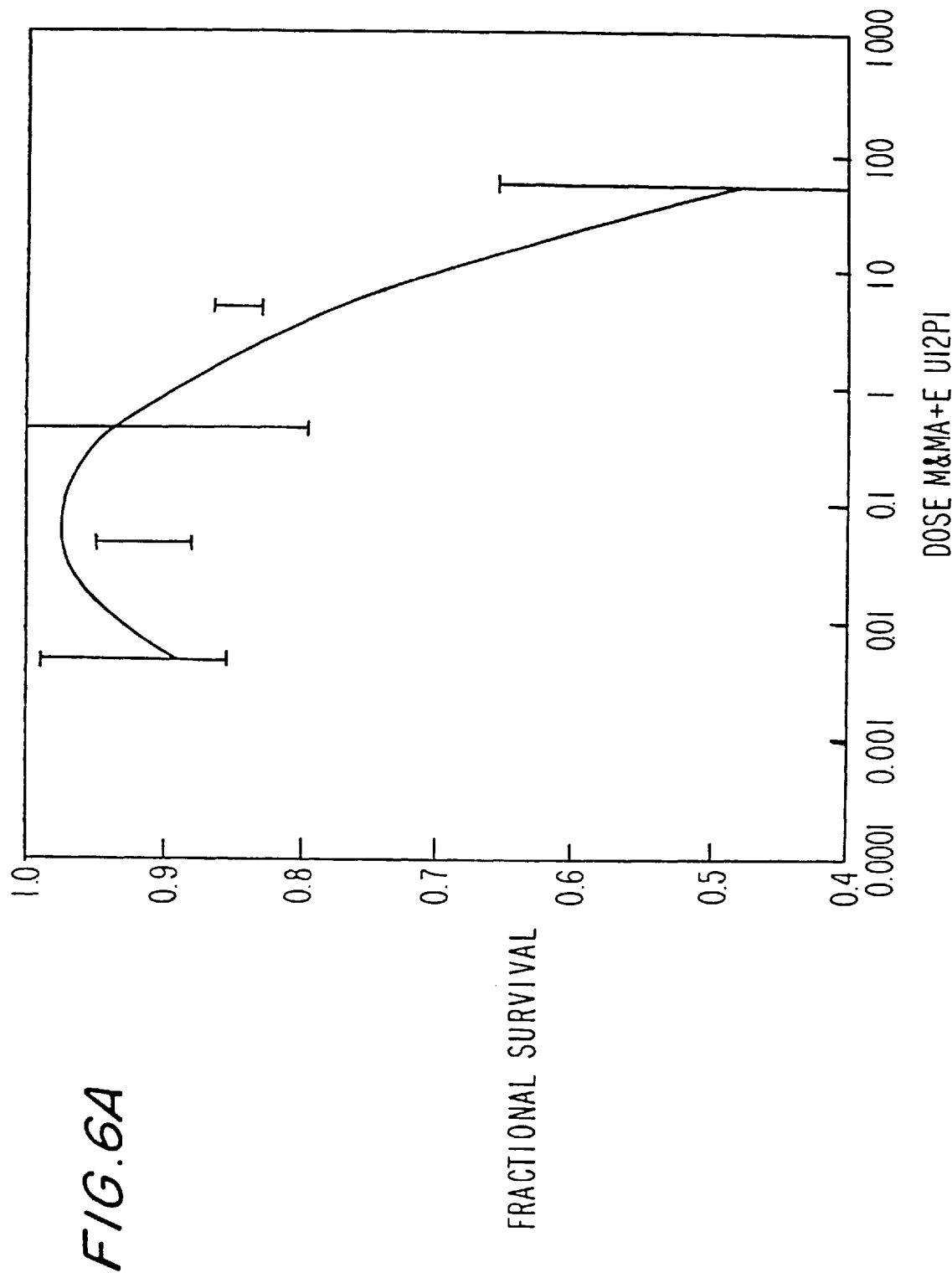
Figure 6B:
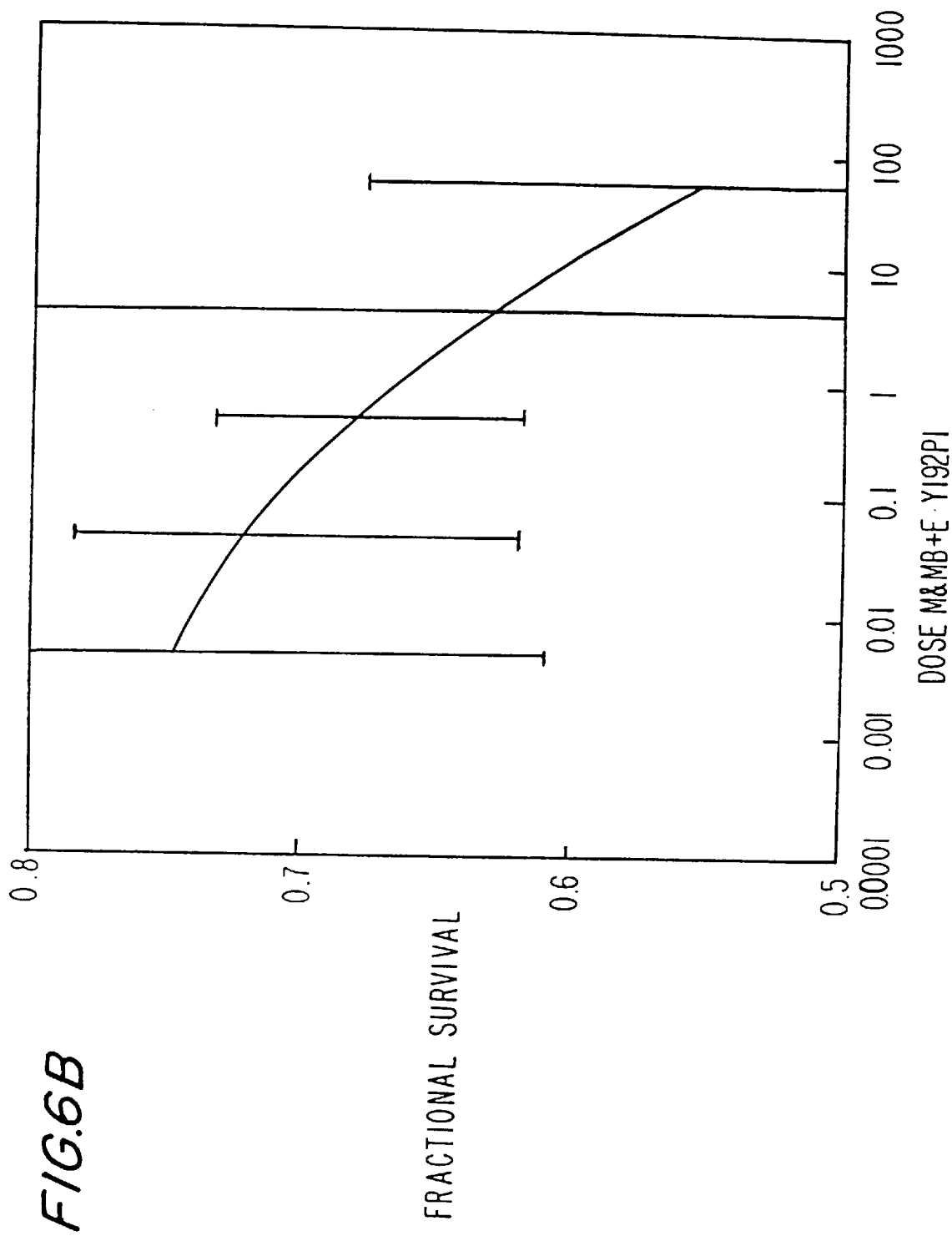
Figure 6C:
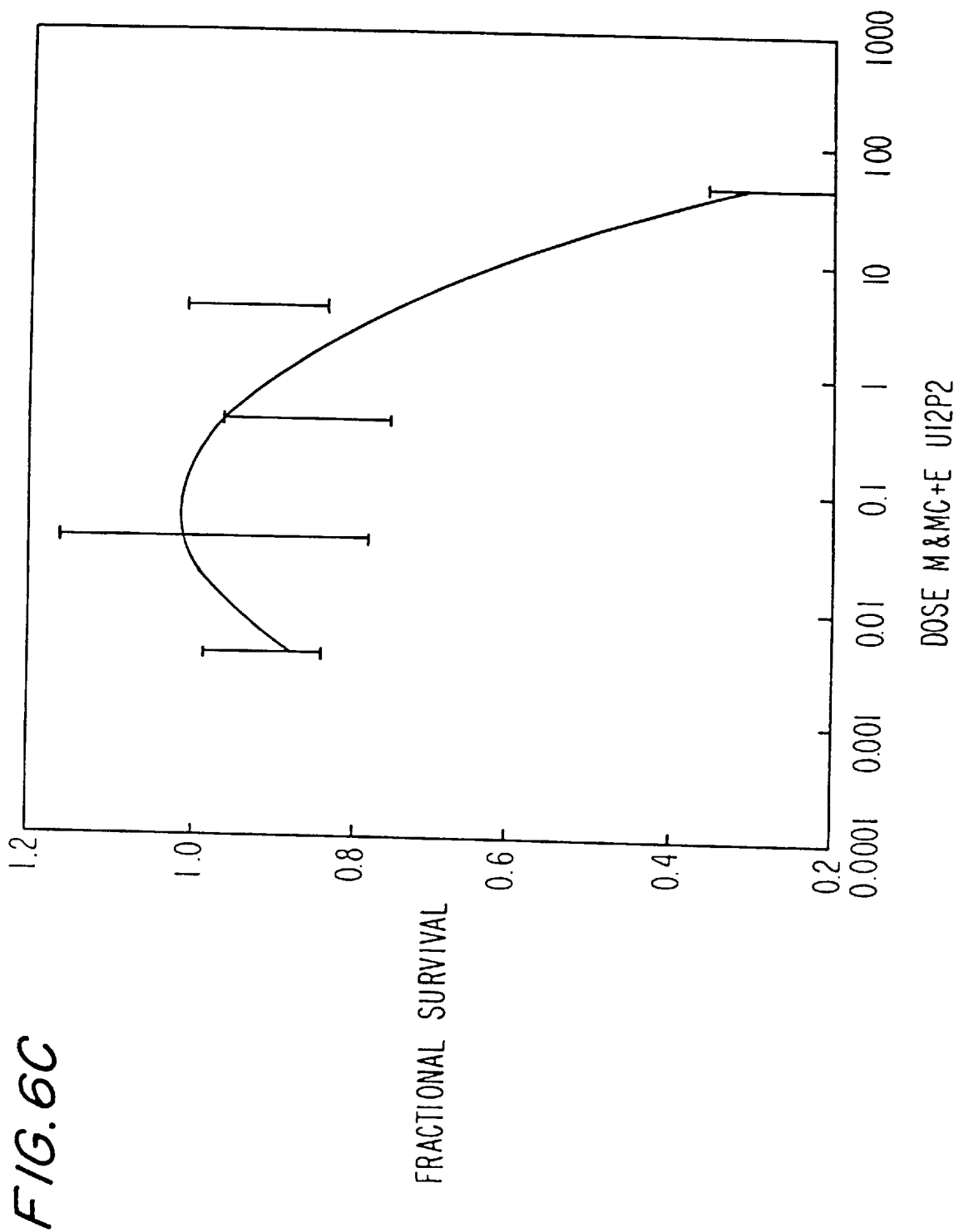
Figure 6D:
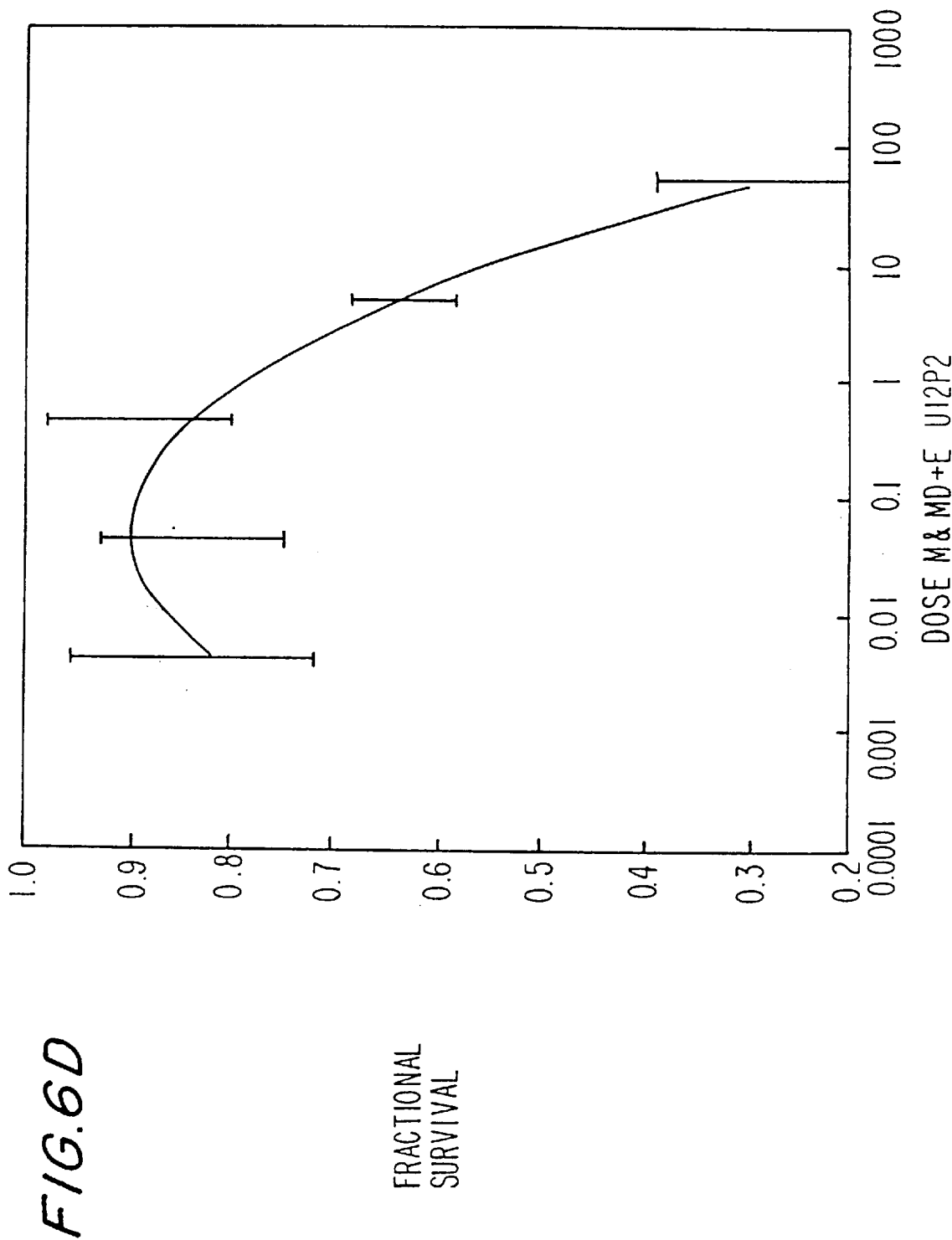

Two of the samples were first tested by this protocol. Sample MM1 represented a very crude isolate of cocoa procyanidins and contained appreciable quantities of caffeine and theobromine. Sample MM2 represented a cocoa procyanidin isolate partially purified by gel permeation chromatography. Caffeine and theobromine were absent in MM2. Both samples were screened for activity against the following cancer cell lines using the procedures previously described:

HCT 116 colon cancer
ACHN renal adenocarcinoma
SK-5 melanoma
A498 renal adenocarcinoma
MCF-7 breast cancer
PC-3 prostate cancer
CAPAN-2 pancreatic cancer Little or no activity was observed with MM1 on any of the cancer cell lines investigated. MM2 was found to have activity against HCT-116, PC-3 and ACHN cancer cell lines. However, both MM1 and MM2 were found to interfere with MTT such that it obscured the decrease in absorbance that would have reflected a decrease in viable cell number. This interference also contributed to large error bars, because the chemical reaction appeared to go more quickly in the wells along the perimeter of the plate. A typical example of these effects is shown in FIG. 5. At the high concentrations of test material, one would have expected to observe a large decrease in survivors rather than the high survivor levels shown. Nevertheless, microscopic examinations revealed that cytotoxic effects occurred, despite the MTT interference effects. For instance, an $IC_{50}$ value of 0.5 µg/mL for the effect of MM2 on the ACHN cell line was obtained in this manner.

These preliminary results, in the inventors' view, required amendment of the assay procedures to preclude the interference with MTT. This was accomplished as follows. After incubation of the plates at 37° C. in a humidified, 5% $CO_2$ atmosphere for 18 hours, the medium was carefully aspirated and replaced with fresh alpha-MEM media. This media was again aspirated from the wells on the third day of the assay and replaced with 100 µL of freshly prepared McCoy's medium. 11 µL of a 5 mg/mL stock solution of MTT in PBS (Phosphate Buffered Saline) were then added to the wells of each plate. After incubation for 4 hours in a humidified, 5% $CO_2$ atmosphere at 37° C., 100 µL of 0.04N HCl in isopropanol was added to all wells of the plate, followed by thorough mixing to solubilize the formazan produced by any viable cells. Additionally, it was decided to subfractionate the procyanidins to determine the specific components responsible for activity.

The subfractionation procedures previously described were used to prepare samples for further screening. Five fractions representing the areas shown in FIG. 1 and component(s) distribution shown in FIGS. 4A–4E were prepared. The samples were coded MM2A through MM2E to reflect these analytical characterizations and to designate the absence of caffeine and theobromine.

Each fraction was individually screened against the HCT-116, PC-3 and ACHN cancer cell lines. The results indicated that the activity did not concentrate to any one specific fraction. This type of result was not considered unusual, since the components in "active" natural product isolates can behave synergistically. In the case of the cocoa procyanidin isolate (MM2), over twenty detectable components comprised the isolate. It was considered possible that the activity was related to a combination of components present in the different fractions, rather than the activity being related to an individual component(s).

On the basis of these results, it was decided to combine the fractions and repeat the assays against the same cancer cell lines. Several fraction combinations produced cytotoxic effects against the PC-3 cancer cell lines. Specifically, $IC_{50}$ values of 40 µg/mL each for MM2A and MM2E combination, and of 20 µg/mL each for MM2C and MM2E combination, were obtained. Activity was also reported against the HCT-116 and ACHN cell lines, but as before, interference with the MTT indicator precluded precise observations. Replicate experiments were repeatedly performed on the HCT-116 and ACHN lines to improve the data. However, these results were inconclusive due to bacterial contamination and exhaustion of the test sample material. FIGS. 6A–6D show the dose-response relationship between combinations of the cocoa extracts and PC-3 cancer cells.

Nonetheless, from this data, it is clear that cocoa extracts, especially cocoa polyphenols or procyanidins, have significant anti-tumor; anti-cancer or antineoplastic activity, especially with respect to human PC-3 (prostate), HCT-116 (colon) and ACHN (renal) cancer cell lines. In addition, those results suggest that specific procyanidin fractions may be responsible for the activity against the PC-3 cell line.

Example 7

Anti-Cancer, Anti-Tumor or Antineoplastic Activity of Cocoa Extracts (Procyanidins)

To confirm the above findings and further study fraction combinations, another comprehensive screening was performed.

All prepared materials and procedures were identical to those reported above, except that the standard 4-replicates per test dose was increased to 8 or 12-replicates per test dose. For this study, individual and combinations of five cocoa procyanidin fractions were screened against the following cancer cell lines.

PC-3 Prostate
KB Nasopharyngeal/HeLa
HCT-116 Colon
ACHN Renal
MCF-7 Breast
SK-5 Melanoma
A-549 Lung
CCRF-CEM T-cell leukemia Individual screenings consisted of assaying different dose levels (0.01–100 µg/mL) of fractions A, B, C, D, and E (See FIGS. 4A–4E and discussion thereof, supra) against each cell line. Combination screenings consisted of combining equal dose levels of fractions A+B, A+C, A+D, A+E, B+C, B+D, B+E, C+D, C+E, and D+E against each cell line. The results from these assays are individually discussed, followed by an overall summary.

A. PC-3 Prostate Cell Line

Figure 7A:
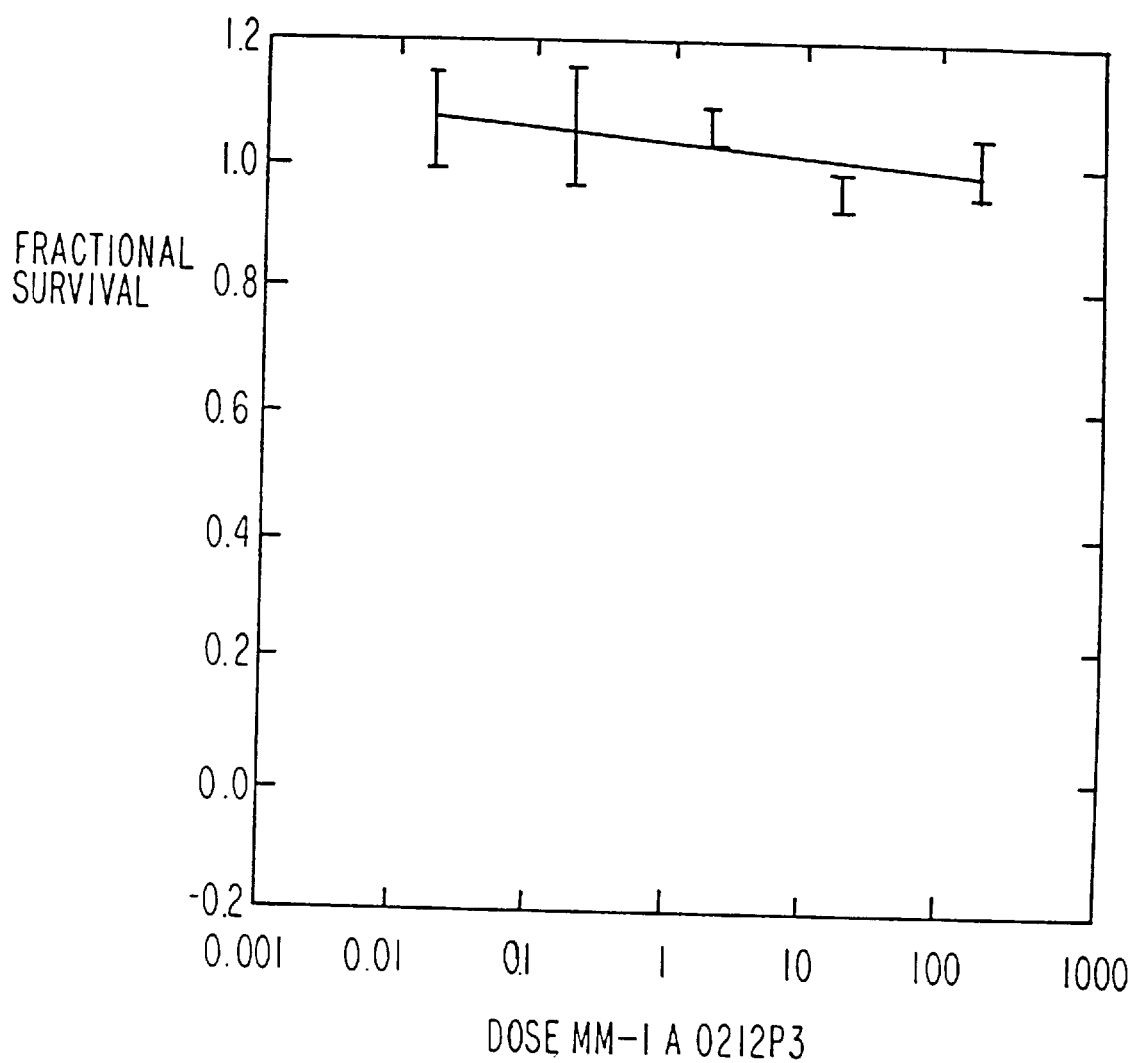
Figure 7B:
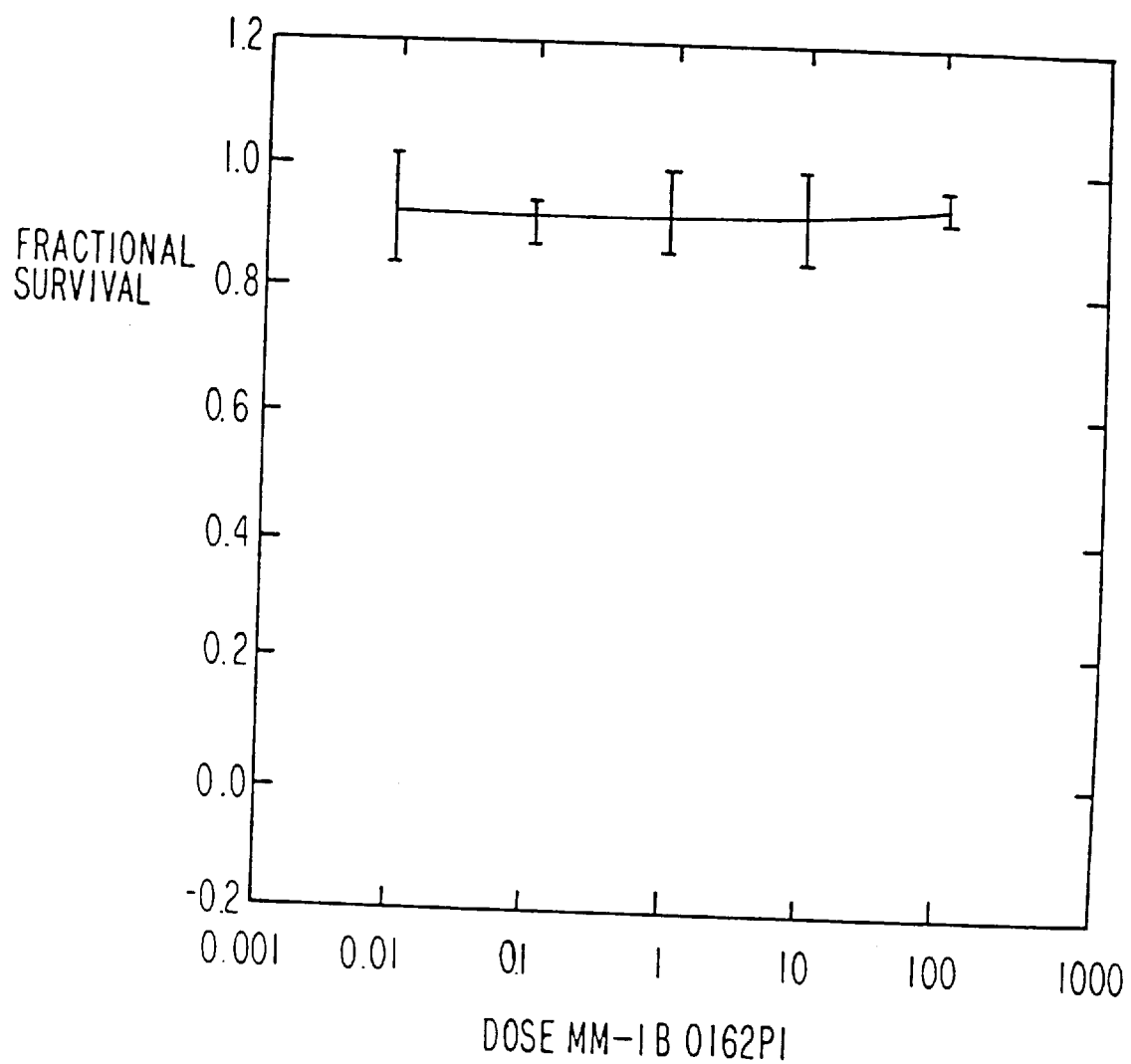
Figure 7C:
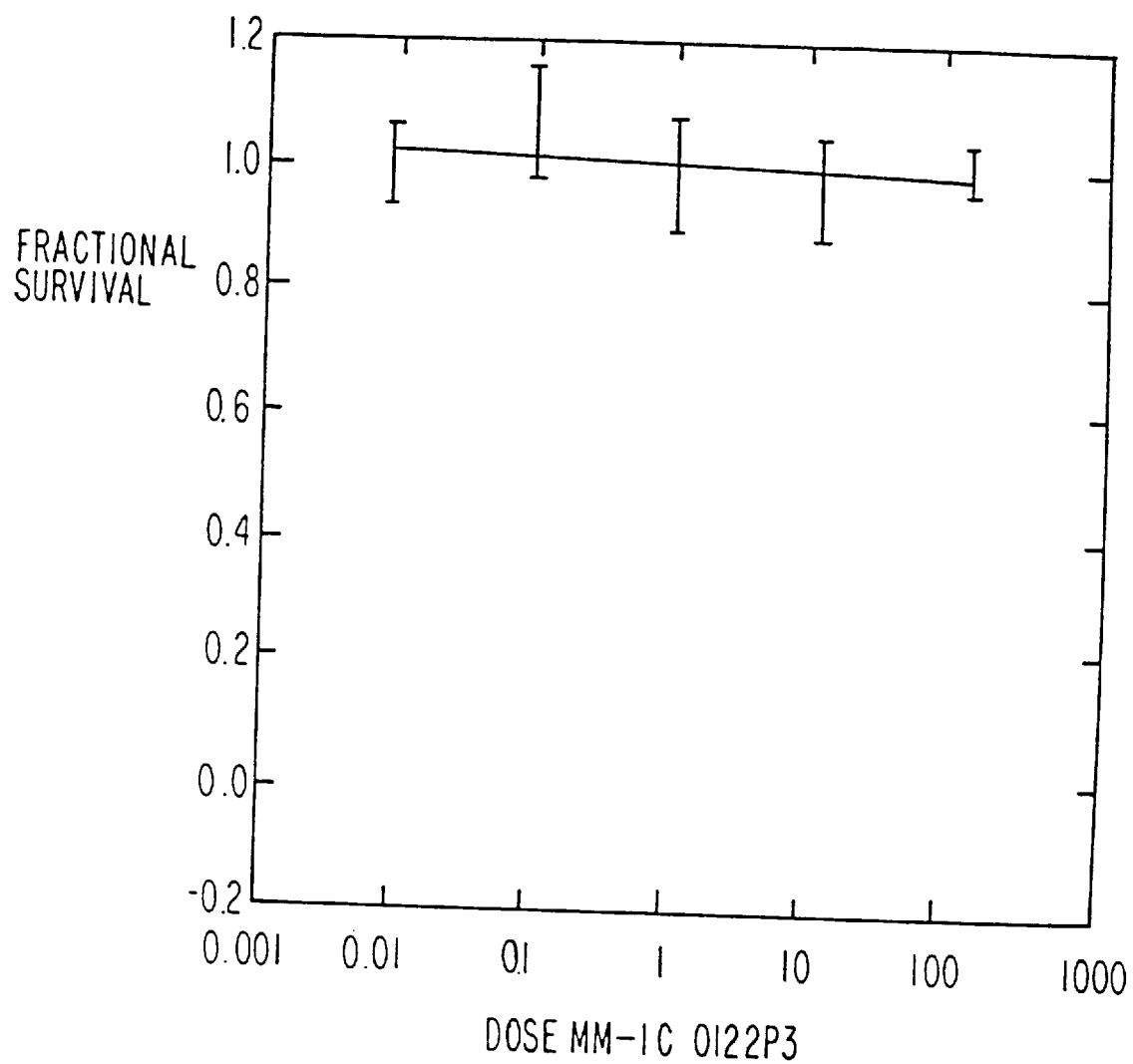
Figure 7E:
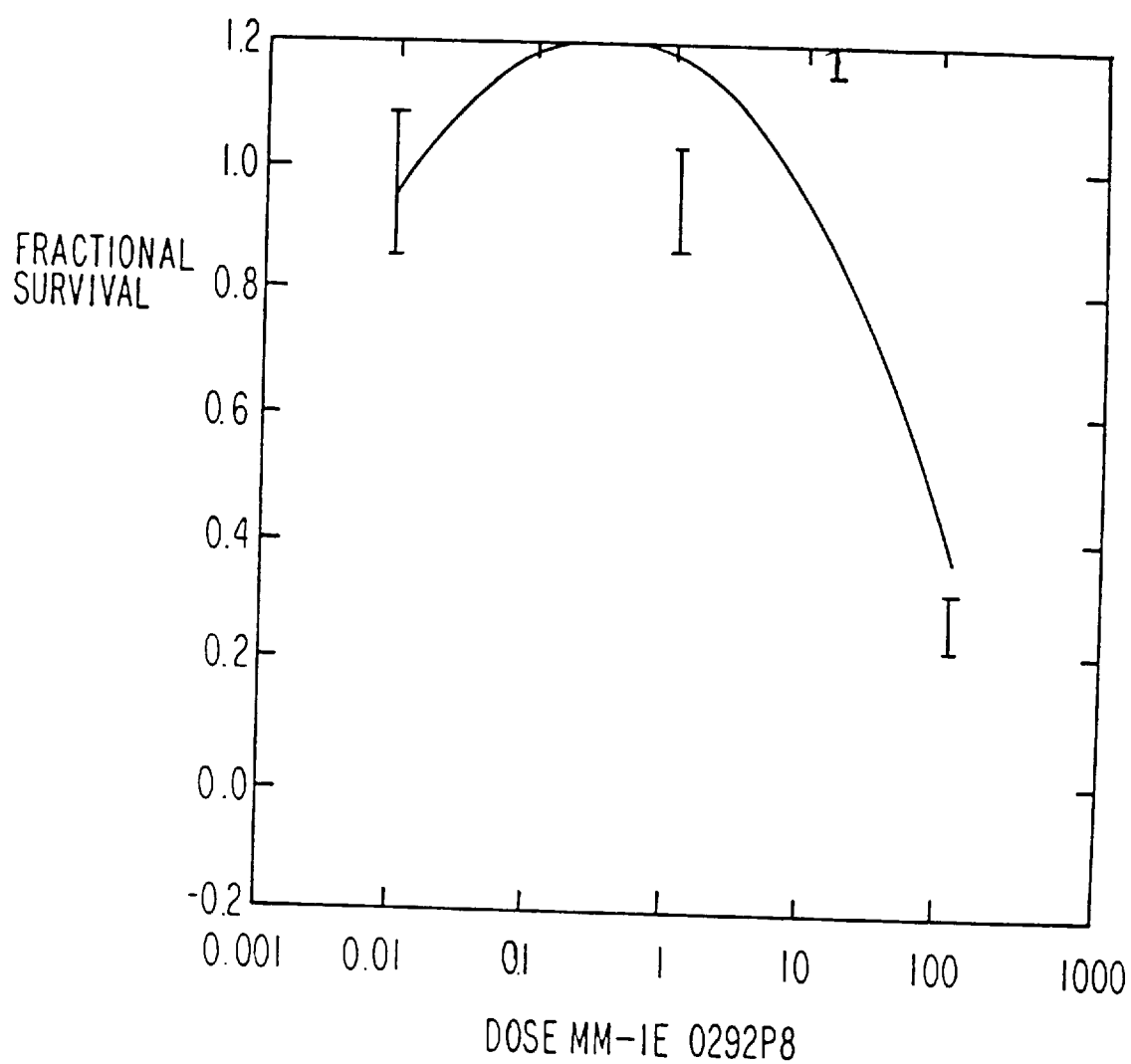
Figure 7G:
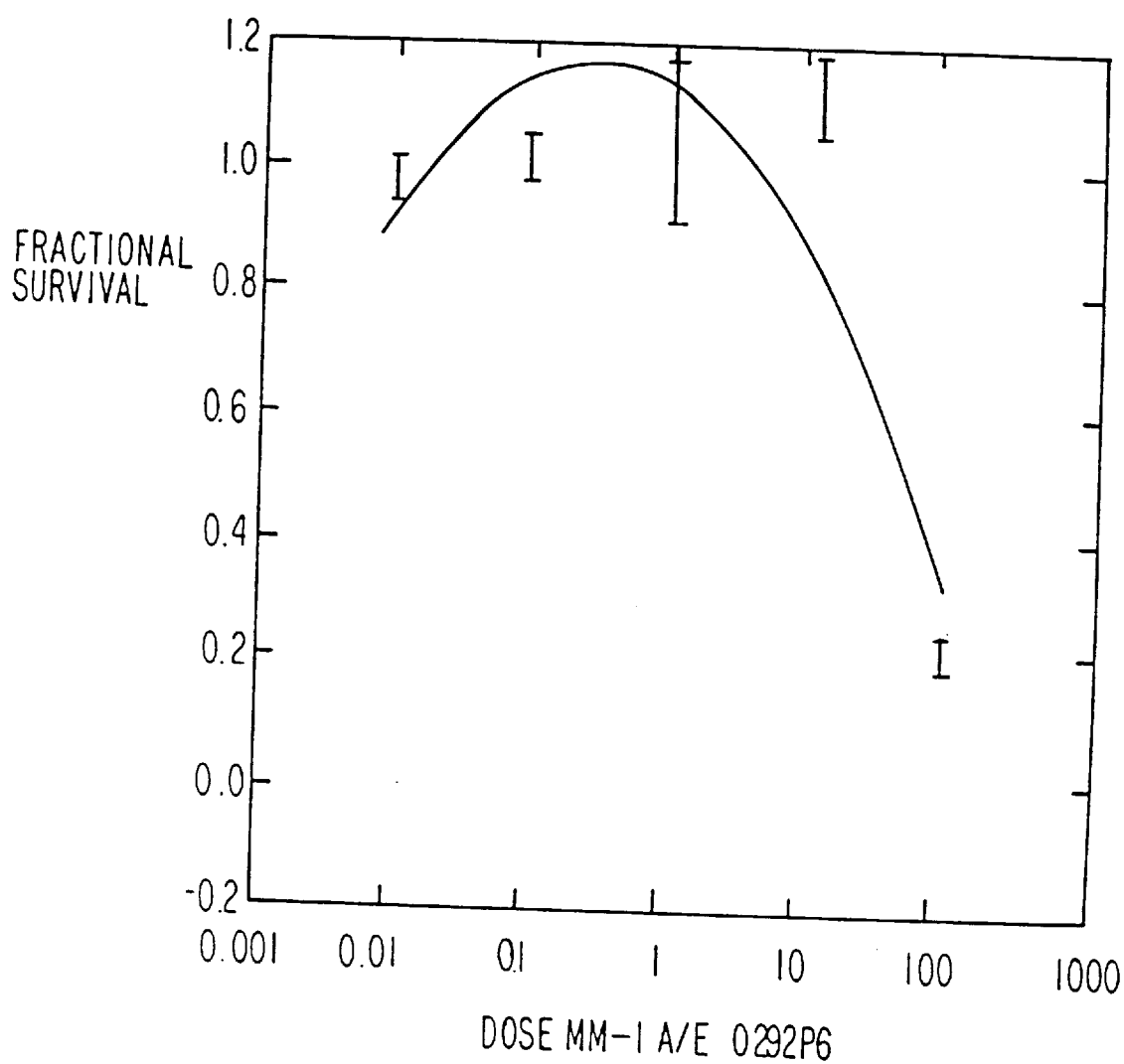
Figure 7H:
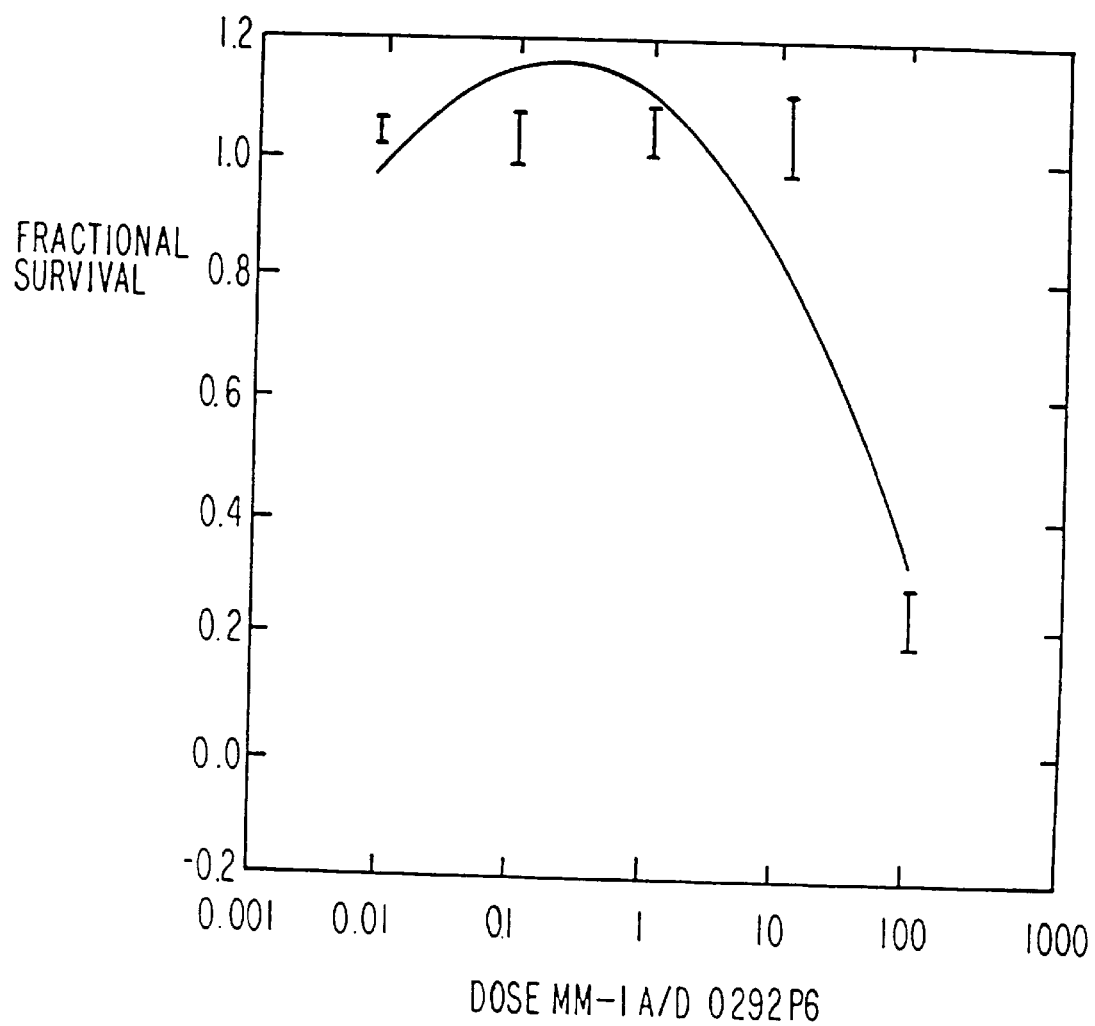

FIGS. 7A–7H show the typical dose response relationship between cocoa procyanidin fractions and the PC-3 cell line. FIGS. 7D and 7E demonstrate that fractions D and E were active at an $IC_{50}$ value of 75 µg/mL. The $IC_{50}$ values that were obtained from dose-response curves of the other procyanidin fraction combinations ranged between 60–80 µg/mL when fractions D or E were present. The individual $IC_{50}$ values are listed in Table 6.

B. KB Nasopharyngeal/HeLa Cell Line

Figure 8A:
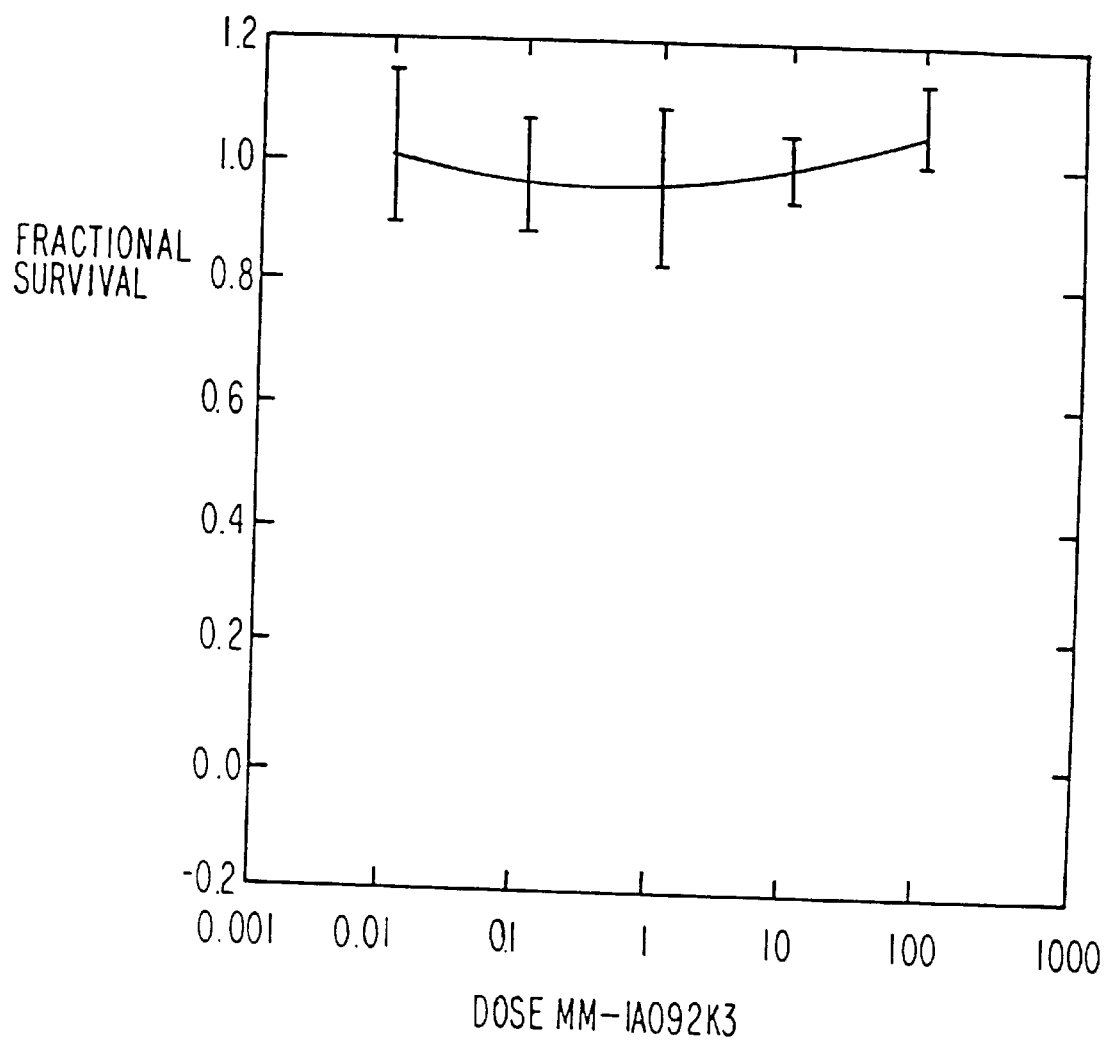
Figure 8B:
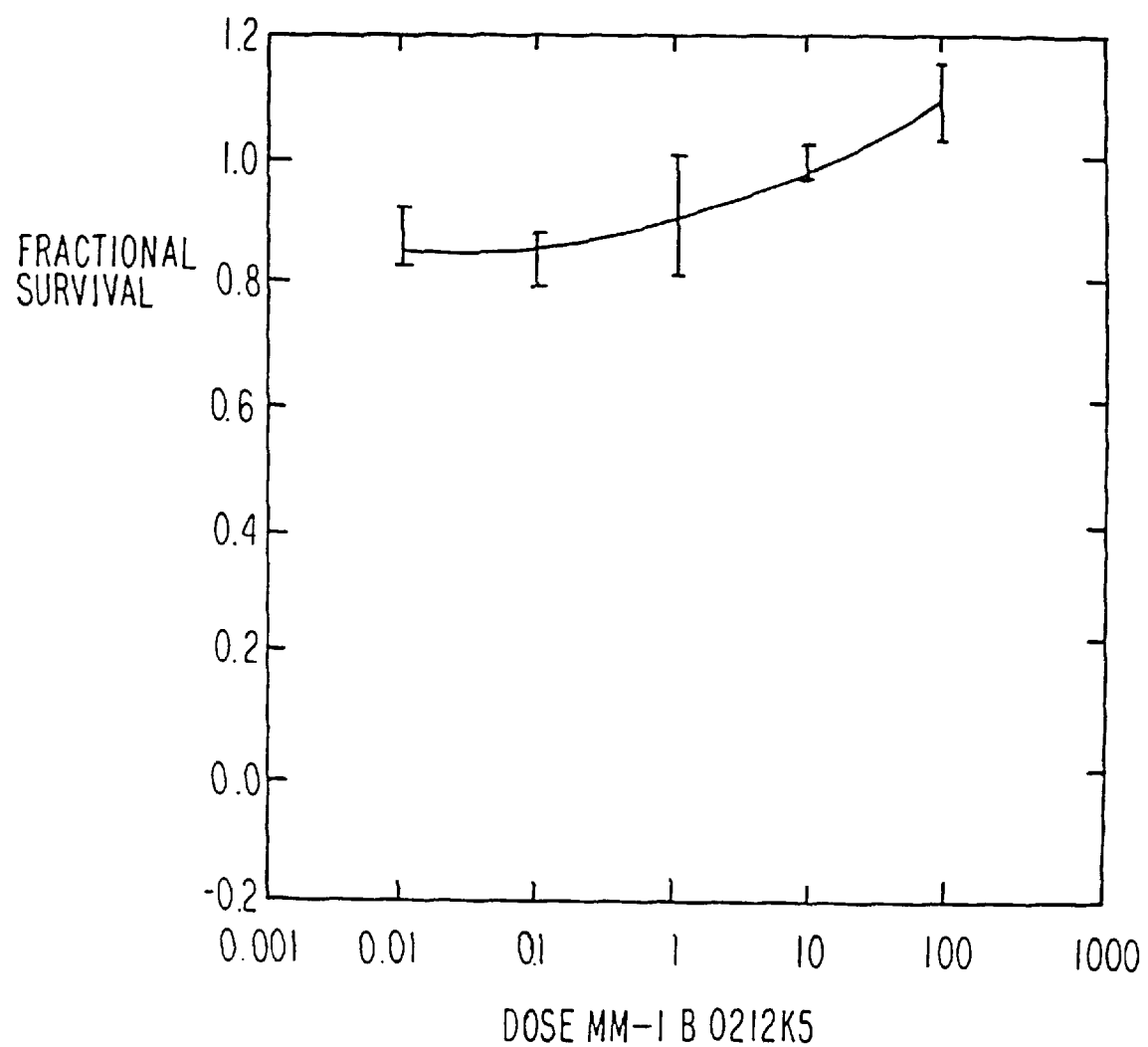
Figure 8C:
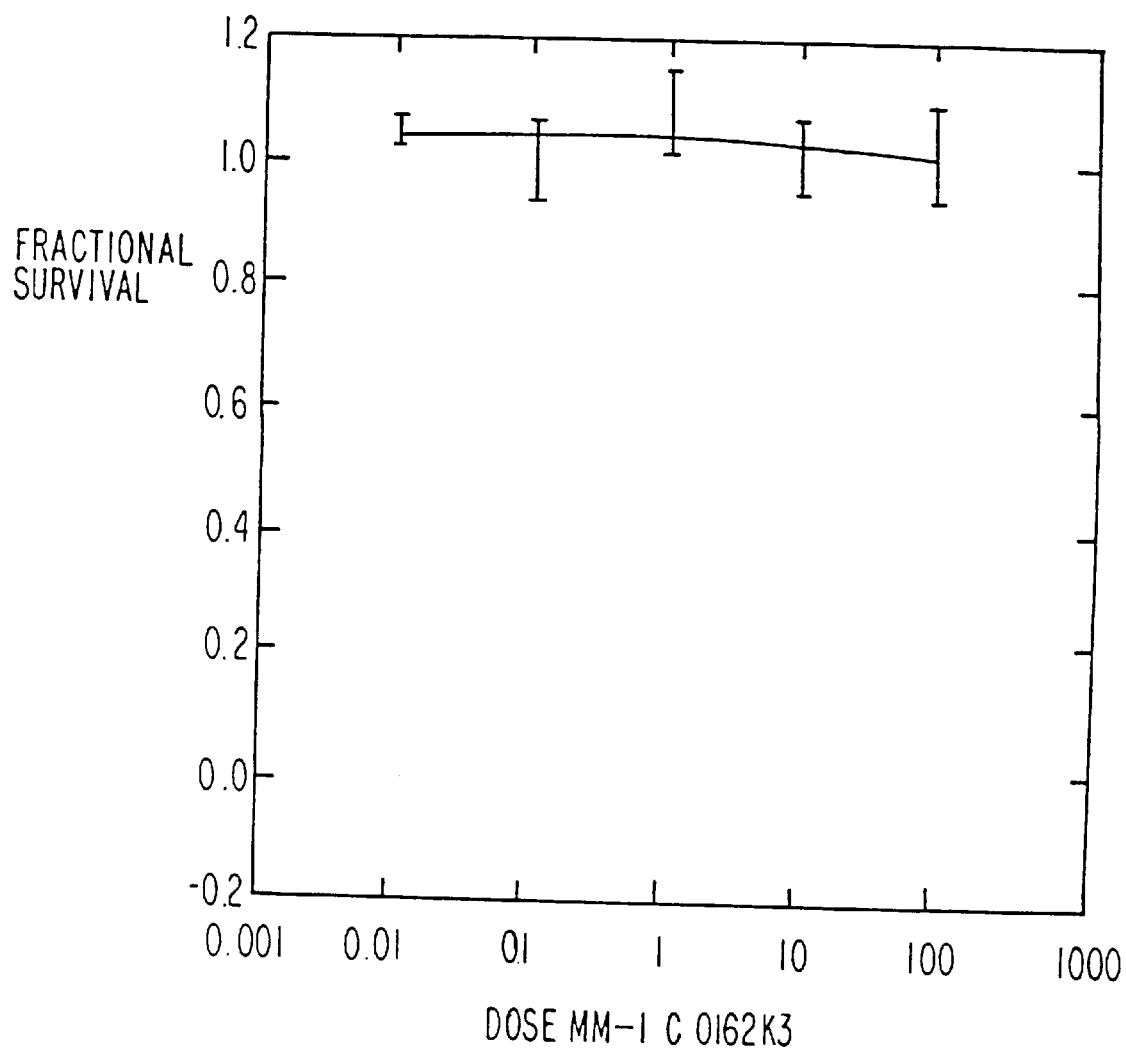
Figure 8E:
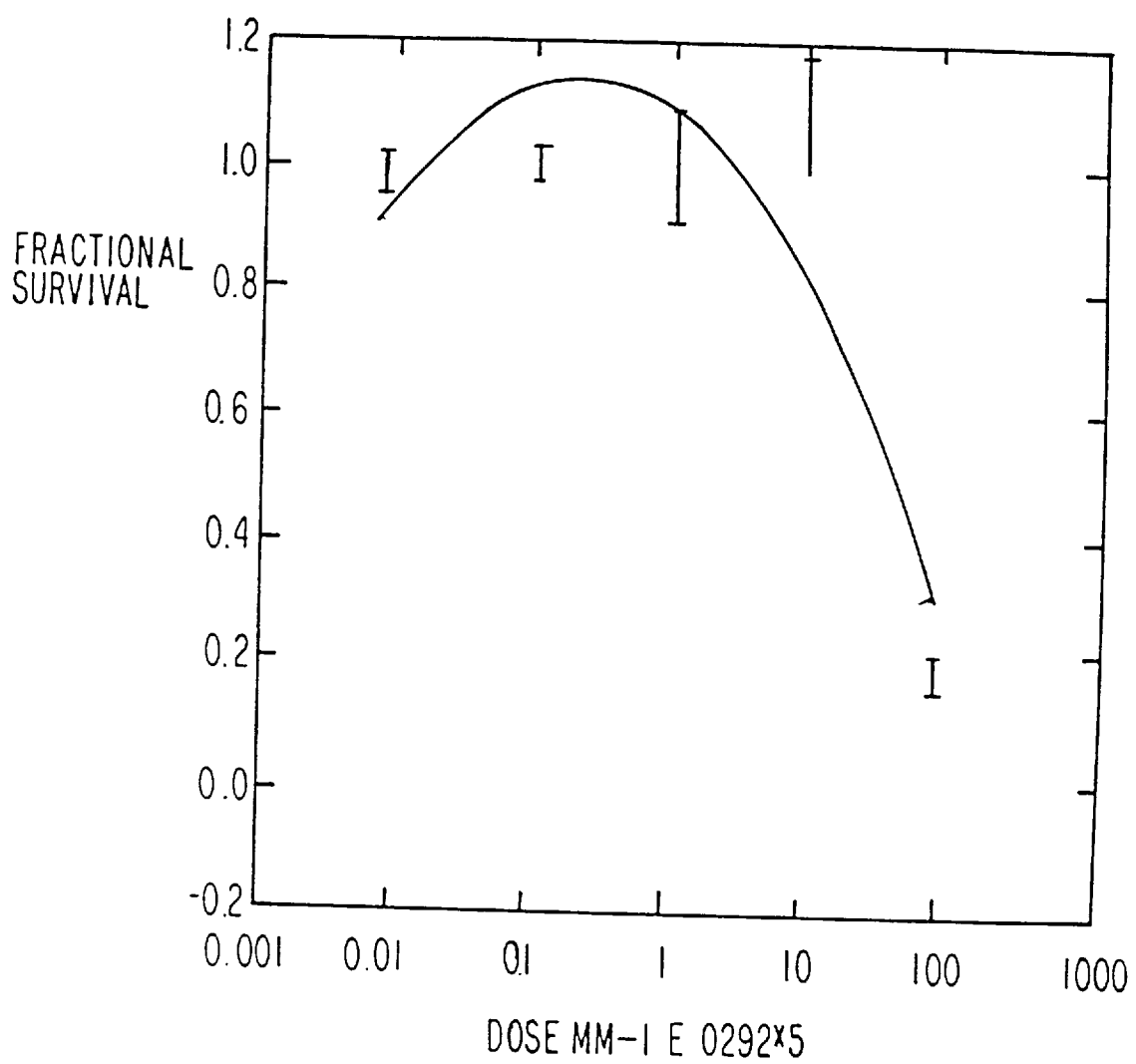
Figure 8F:
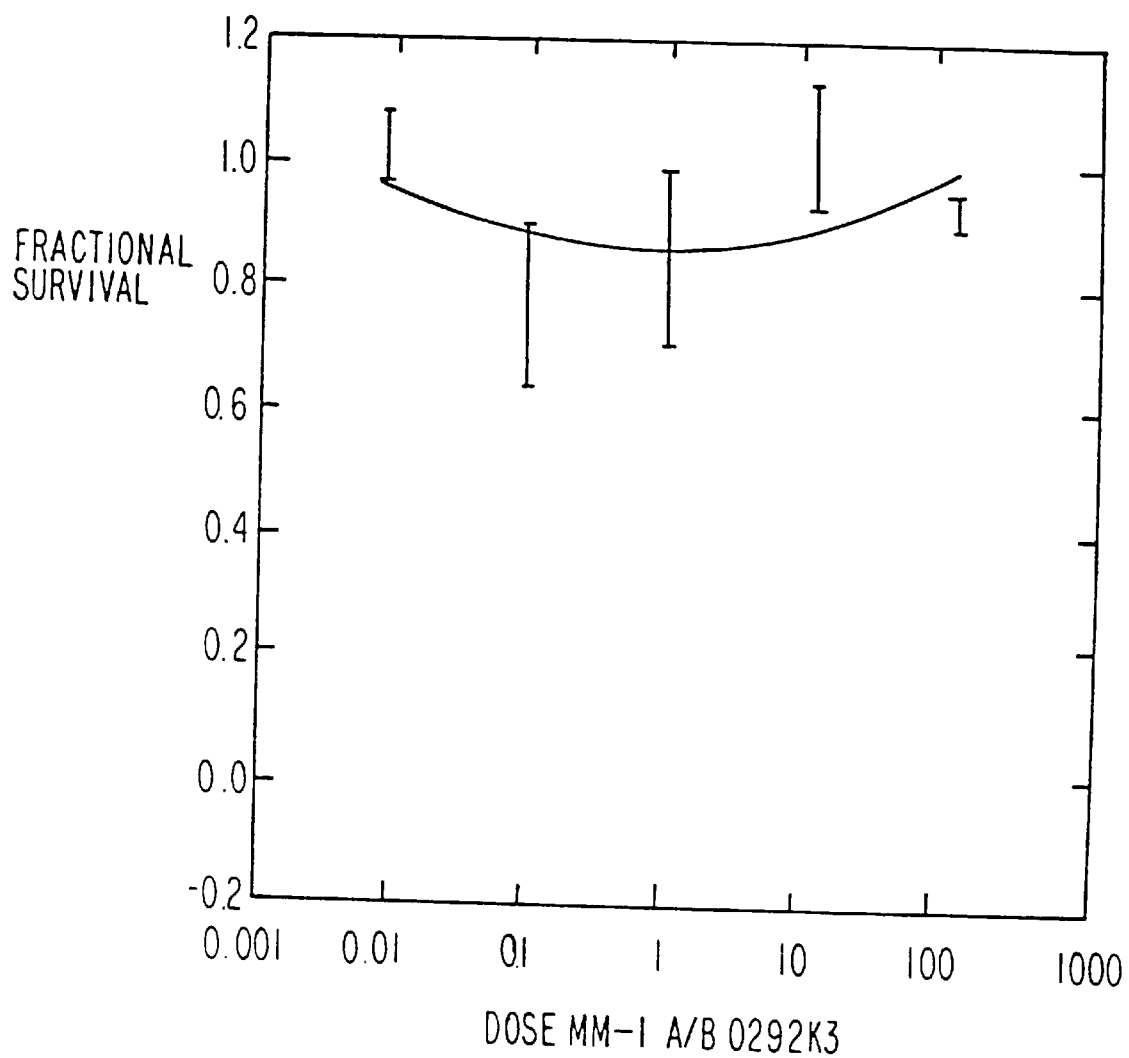
Figure 8G:
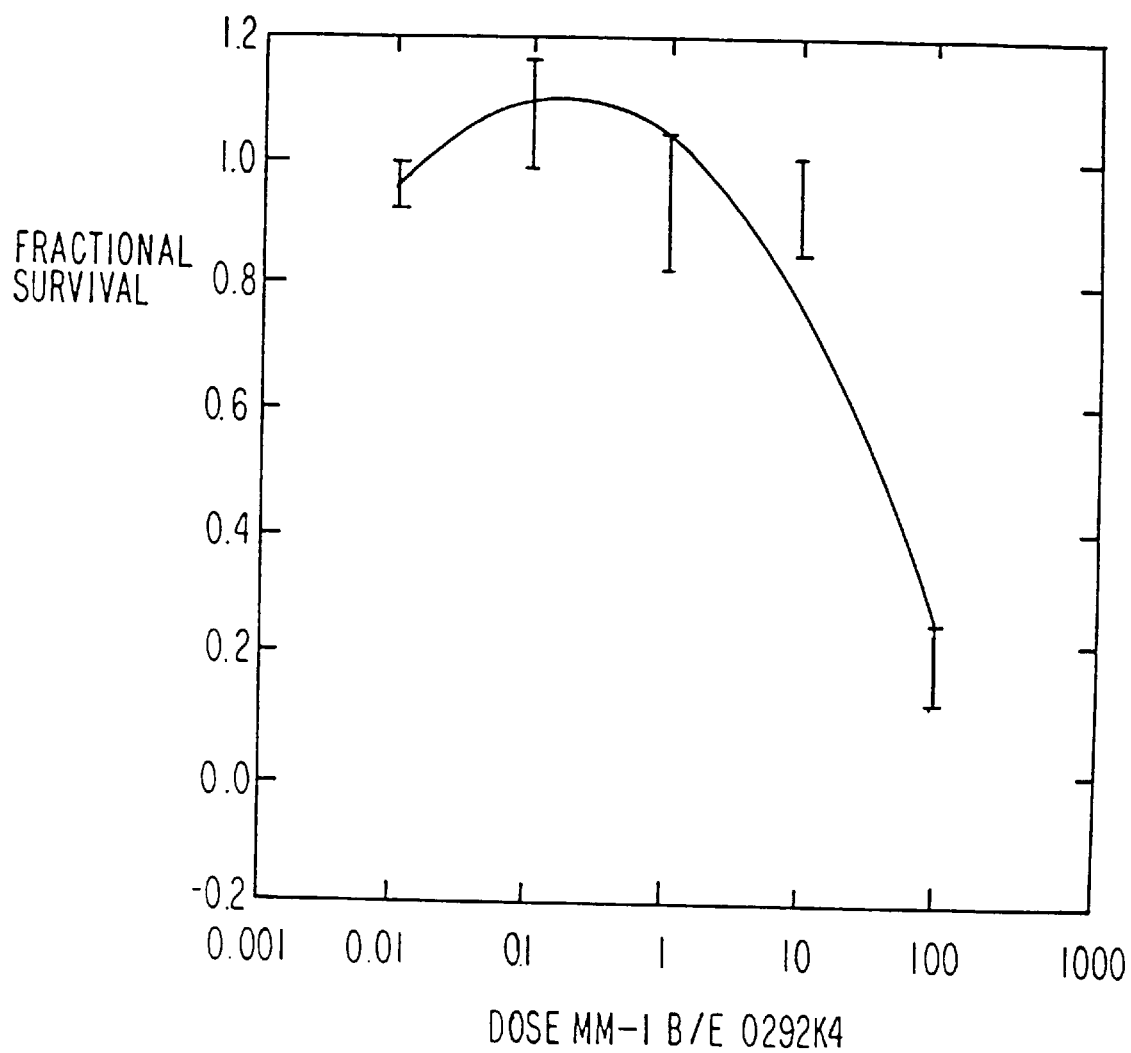
Figure 8H:
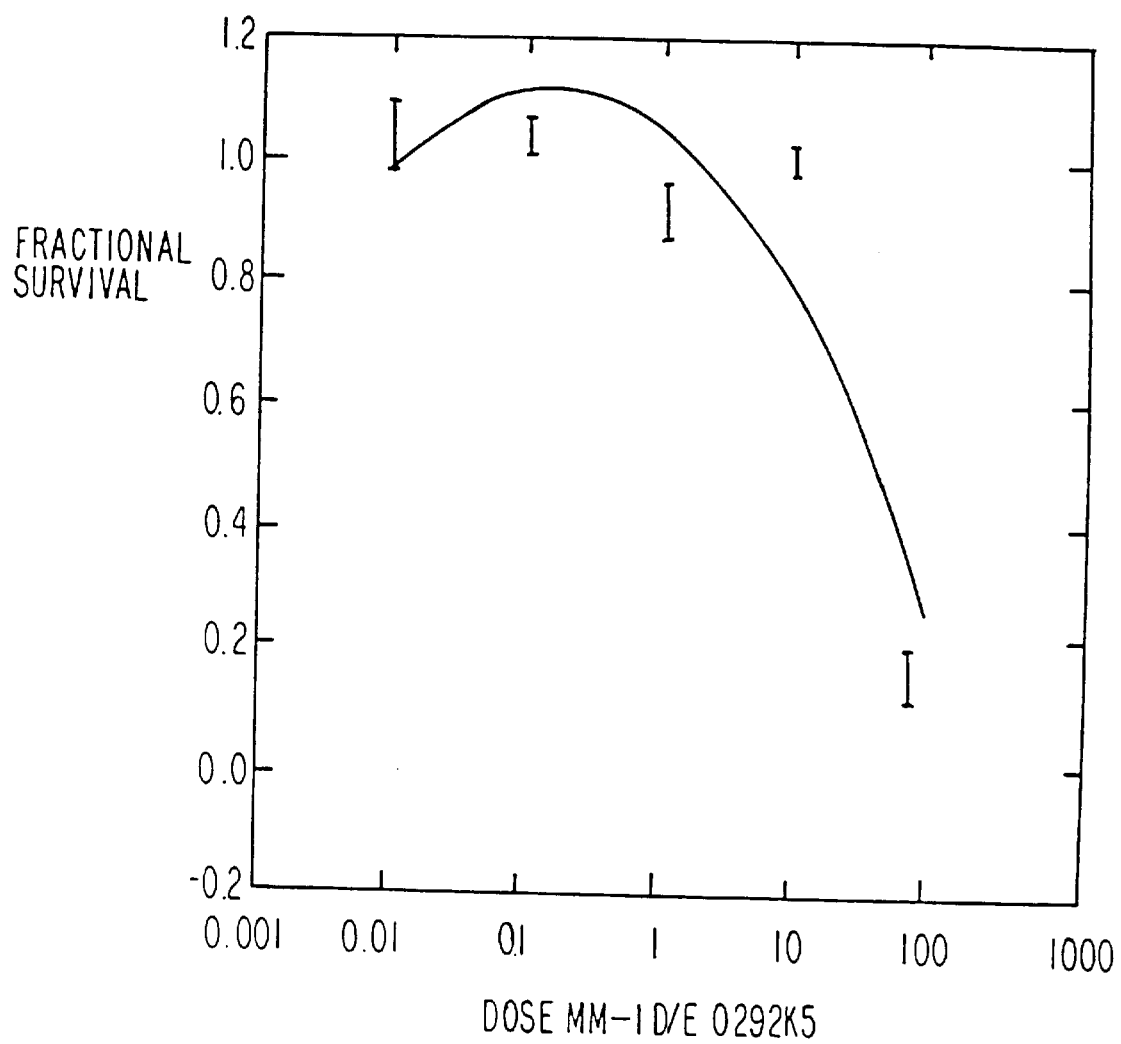

FIGS. 8A–8H show the typical dose response relationship between cocoa procyanidin fractions and the KB Nasopharyngeal/HeLa cell line. FIGS. 8D and 8E demonstrate that fractions D and E were active at an $IC_{50}$ value of 75 µg/mL. FIGS. 8F–8H depict representative results obtained from the fraction combination study. In this case, procyanidin fraction combination A+B had no effect, whereas fraction combinations B+E and D+E were active at an $IC_{50}$ value of 60 µg/mL. The $IC_{50}$ values that were obtained from other dose response curves from other fraction combinations ranged from 60–80 µg/mL when fractions D or E were present. The individual $IC_{50}$ values are listed in Table 6. These results were essentially the same as those obtained against the PC-3 cell line.

C. HCT-116 Colon Cell Line

Figure 9A:
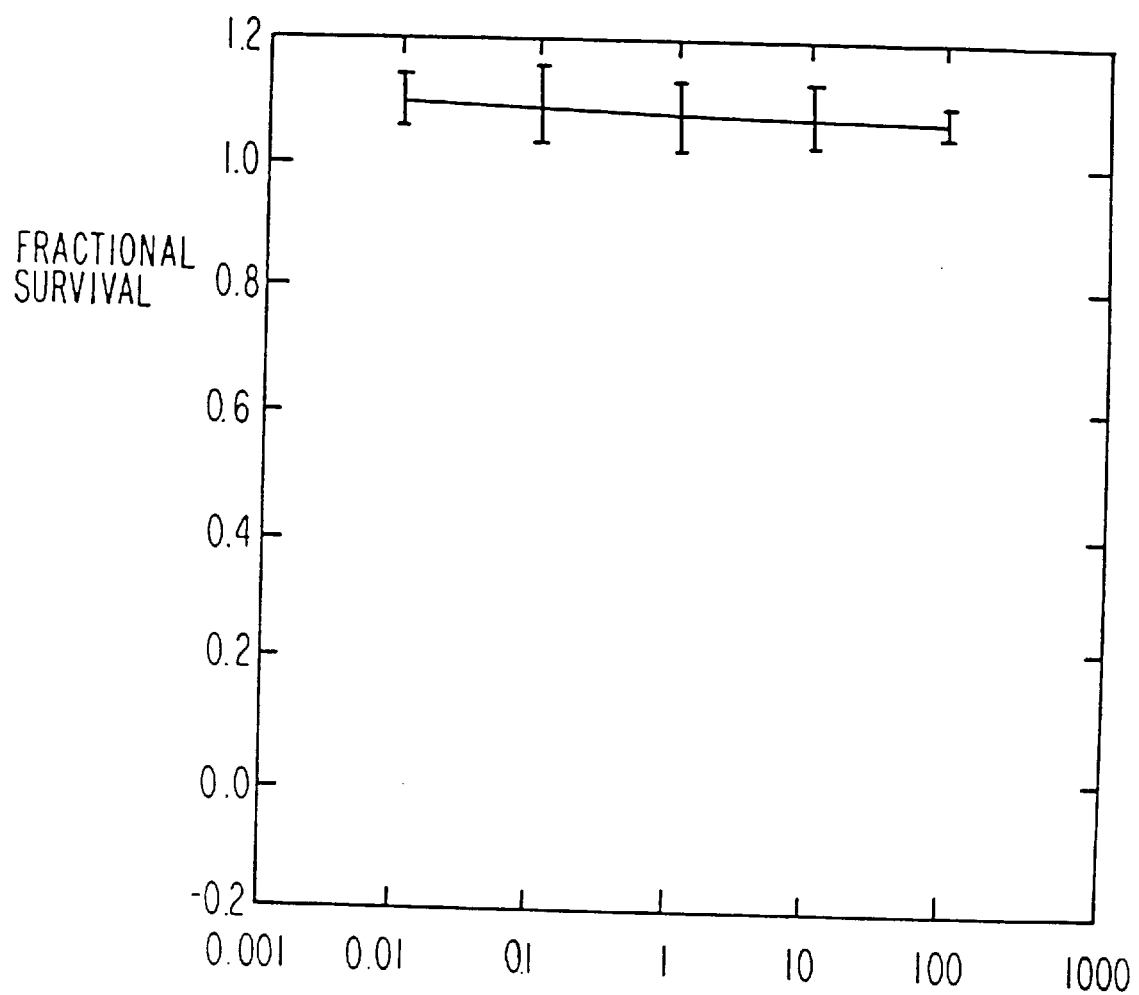
FIGS. 9A to 9H show the typical dose response relationship between cocoa procyanidin fractions A, B, C, D, E, B+D, A+E and D+E and the HCT-116 cell line (fractional survival vs. dose, µg/ml); MM-1 C 0192H5, D 0192H5, E 0192H5, MM-1 B&D 0262H2, A/E 0262H3, MM-1 D&E 0262H1.
Figure 9B:
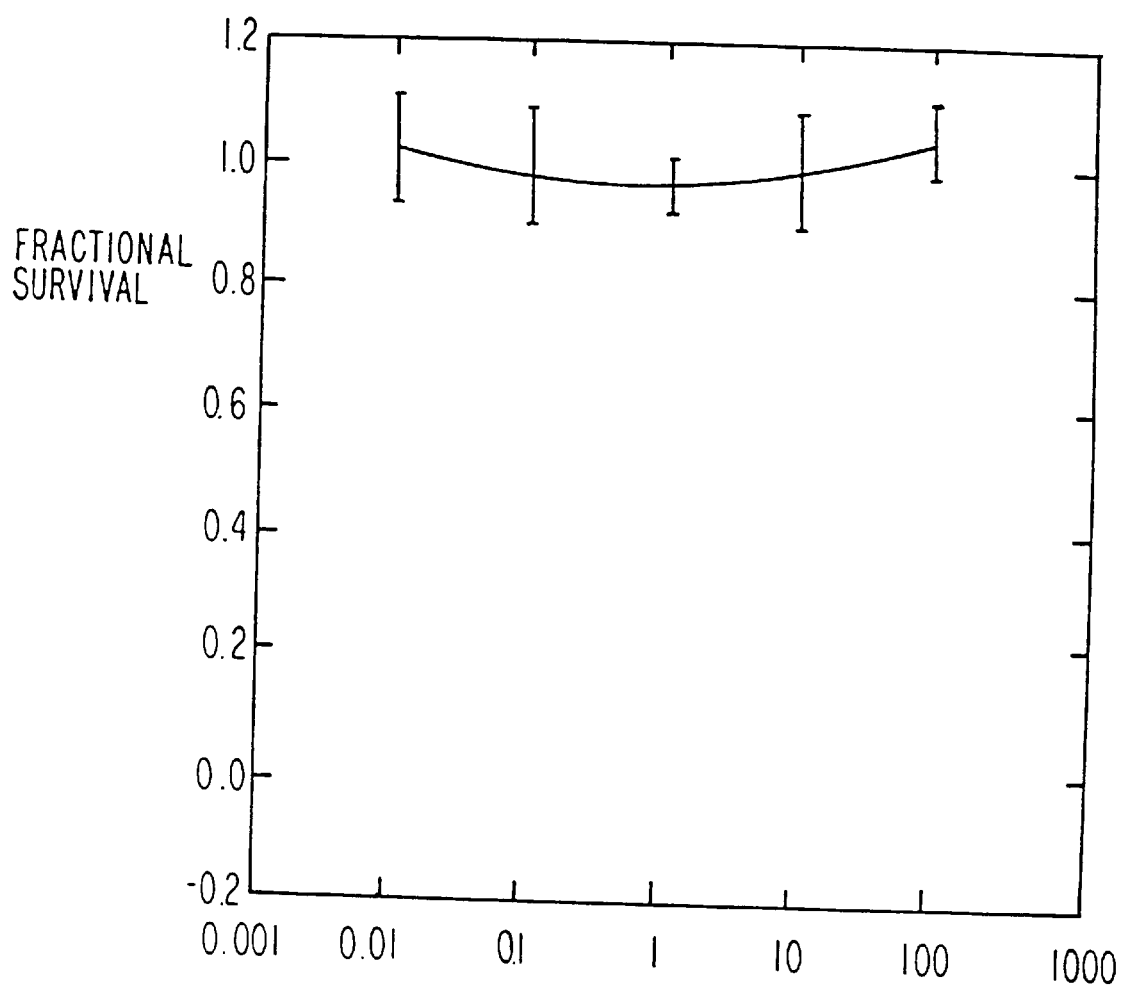
Figure 9C:
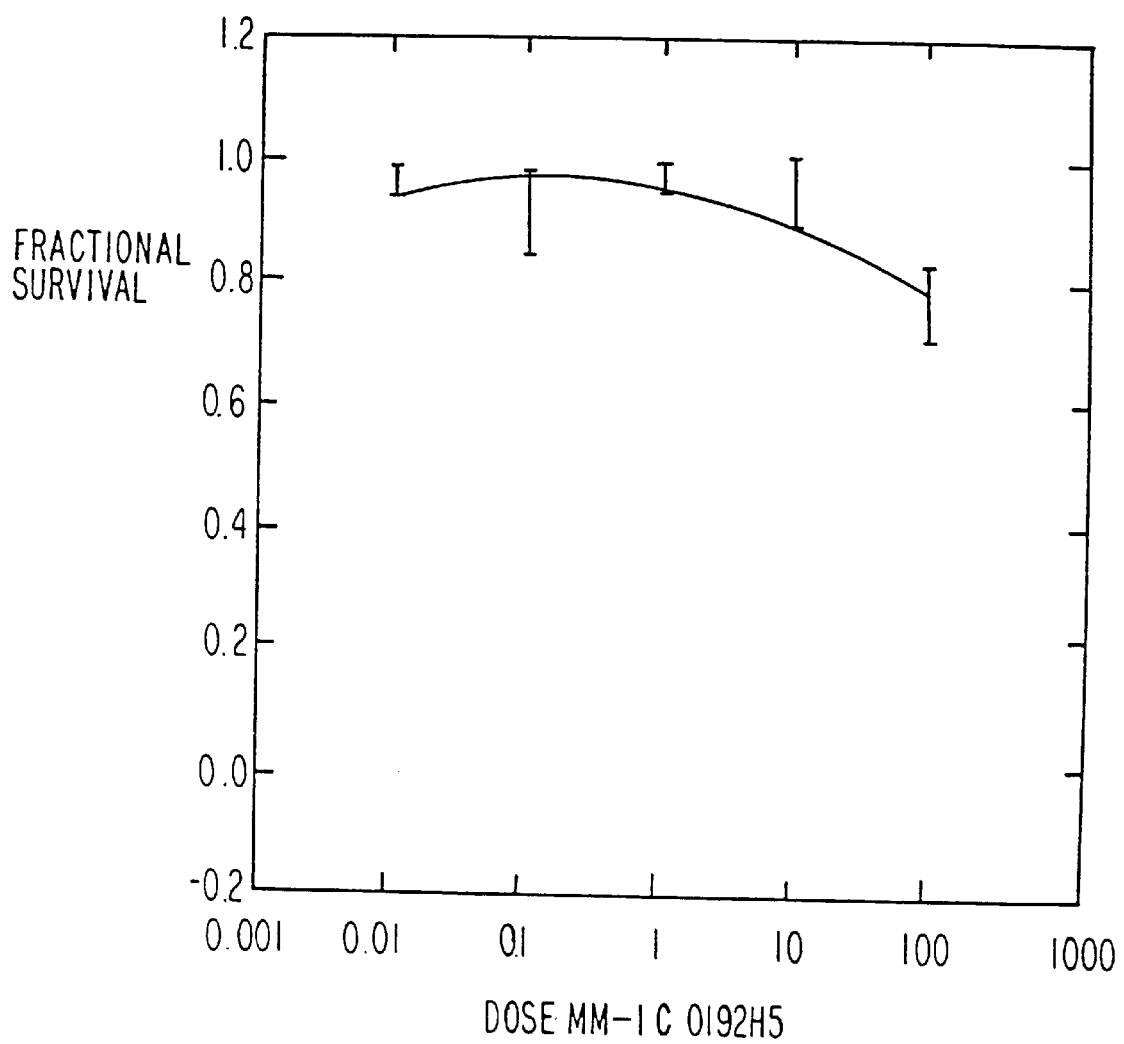
Figure 9D:
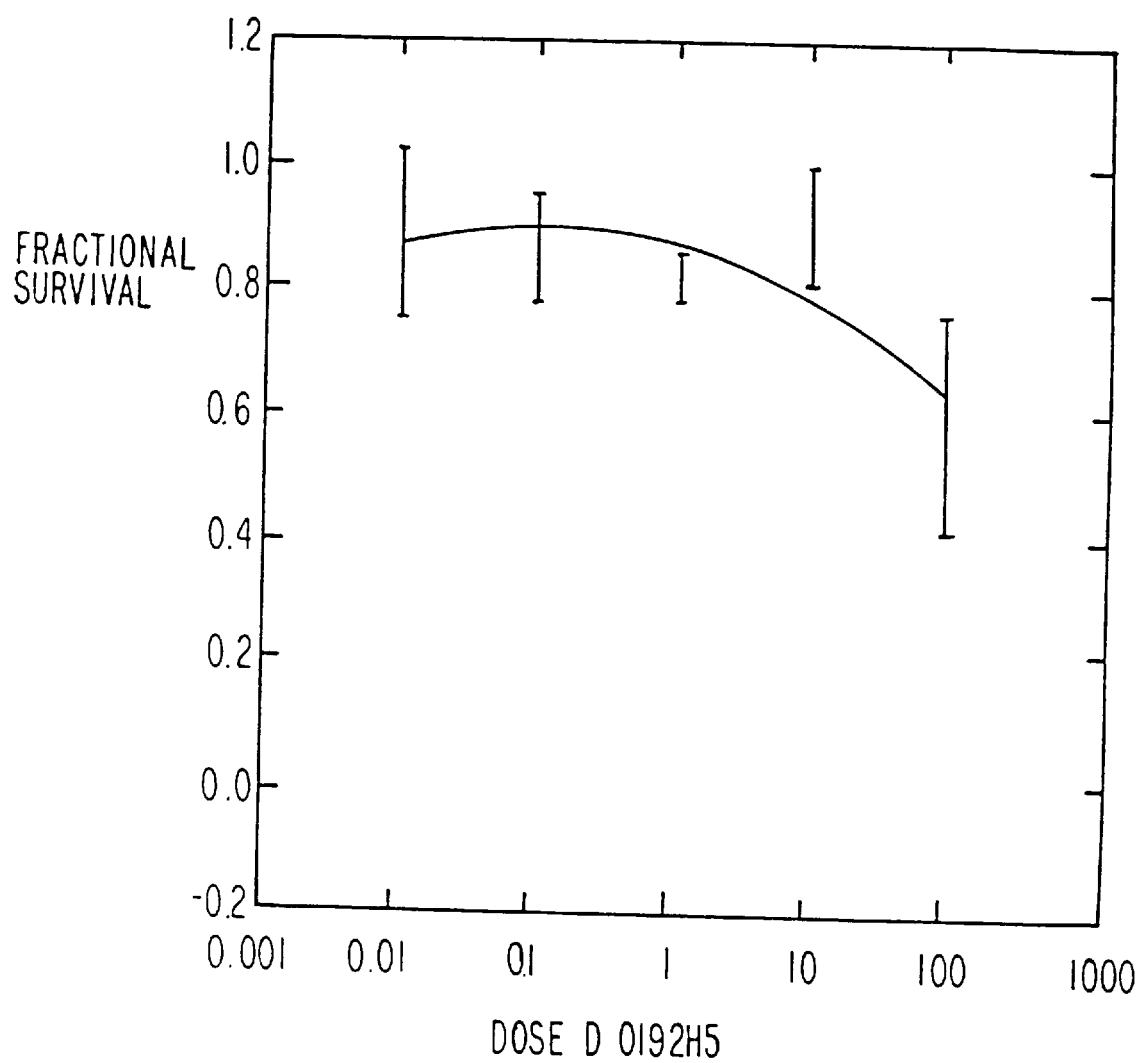
Figure 9E:
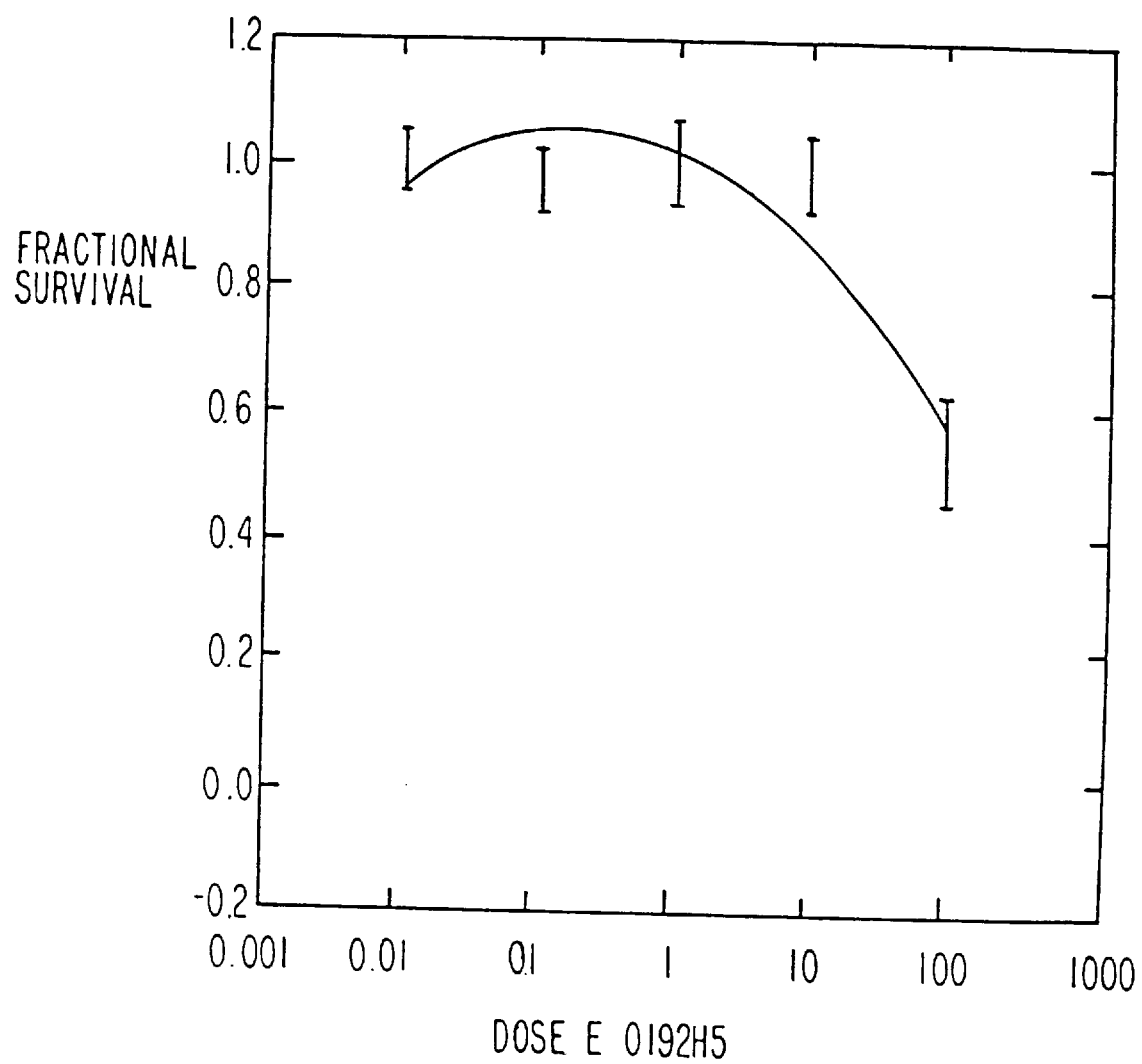
Figure 9F:
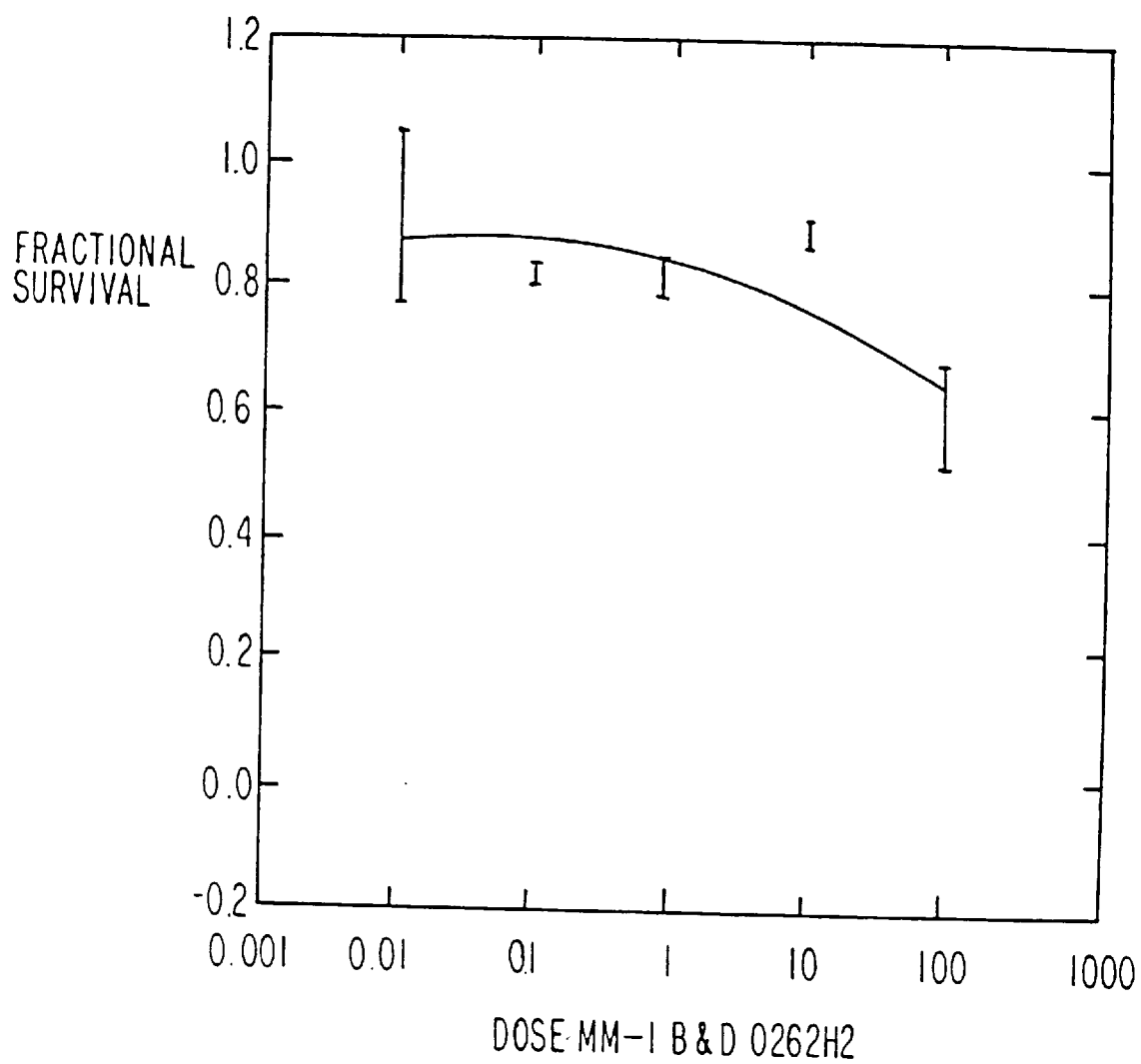
Figure 9G:
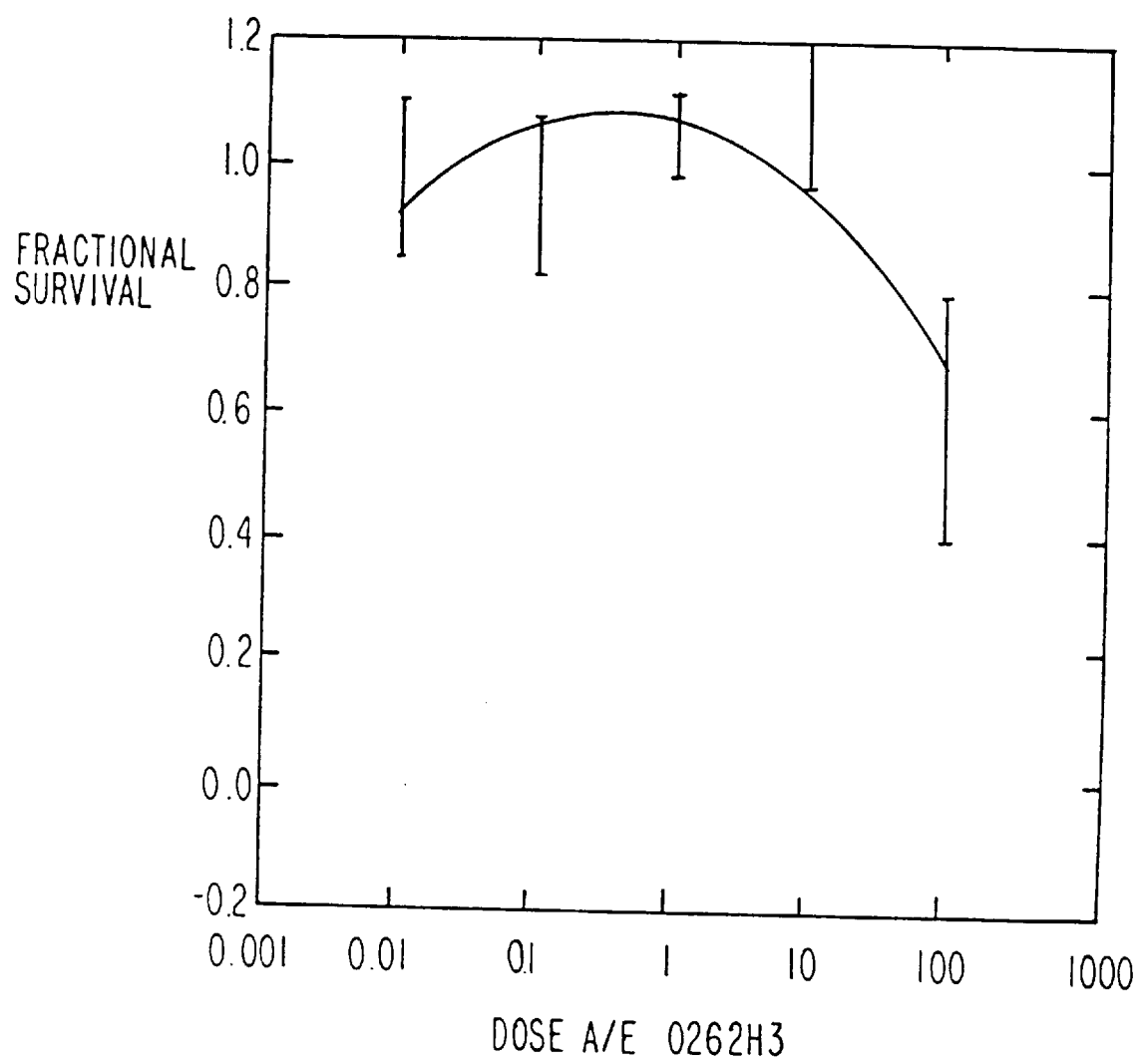
Figure 9H:
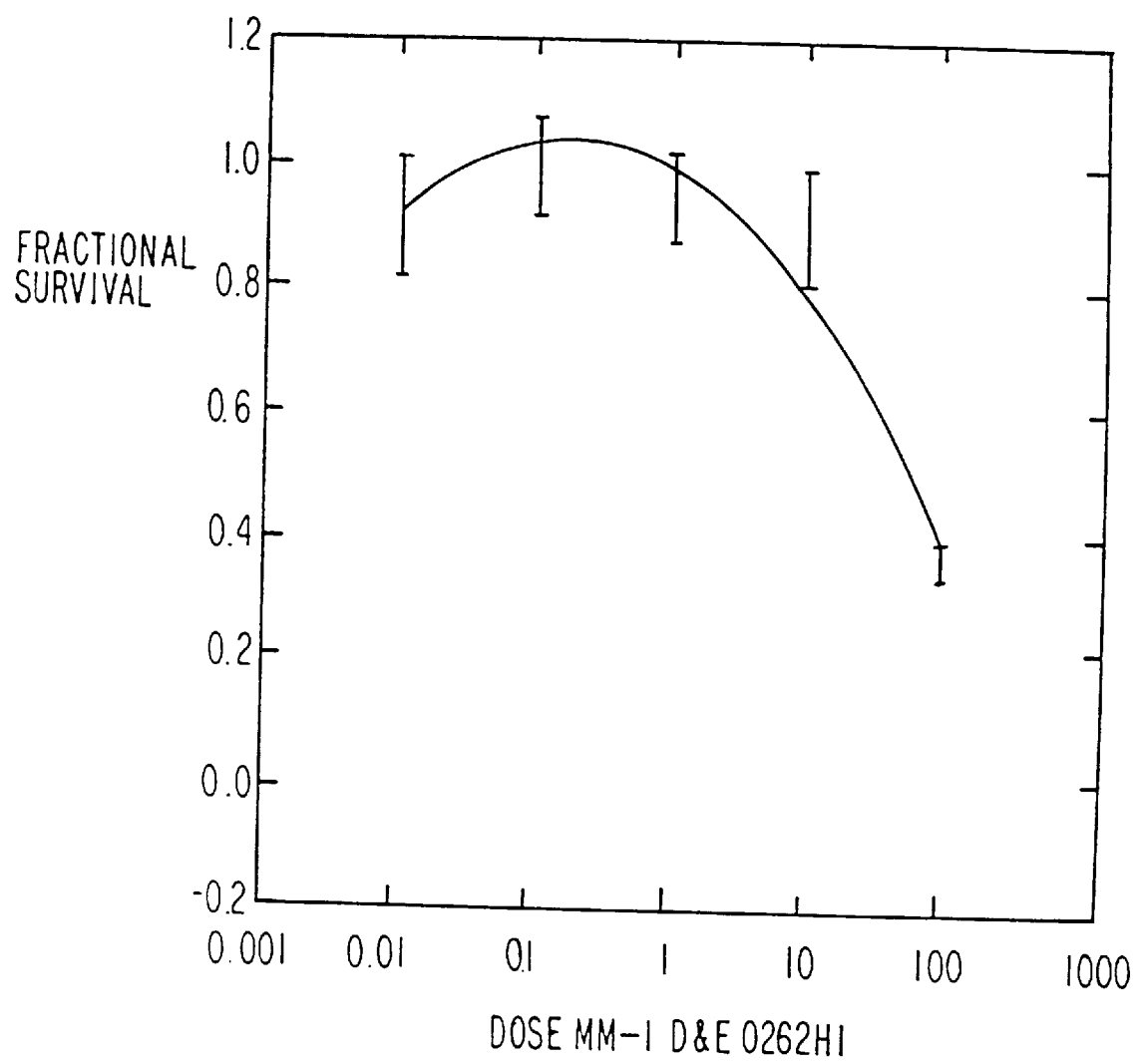

FIGS. 9A–9H show the typical dose response relationships between cocoa procyanidin fractions and the HCT-116 colon cell line. FIGS. 9D and 9E demonstrate that fraction E was active at an $IC_{50}$ value of approximately 400 µg/mL. This value was obtained by extrapolation of the existing curve. Note that the slope of the dose response curve for fraction D also indicated activity. However, no $IC_{50}$ value was determined from this plot, since the slope of the curve was too shallow to obtain a reliable value. FIGS. 9F–9H depict representative results obtained from the fraction combination study. In this case, procyanidin fraction combination B+D did not show appreciable activity, whereas fraction combinations A+E and D+E were active at $IC_{50}$ values of 500 µg/mL and 85 µg/mL, respectively. The $IC_{50}$ values that were obtained from dose response curves of other fraction combinations averaged about 250 µg/mL when fraction E was present. The extrapolated $IC_{50}$ values are listed in Table 6.

D. ACHN Renal Cell Line

Figure 10B:
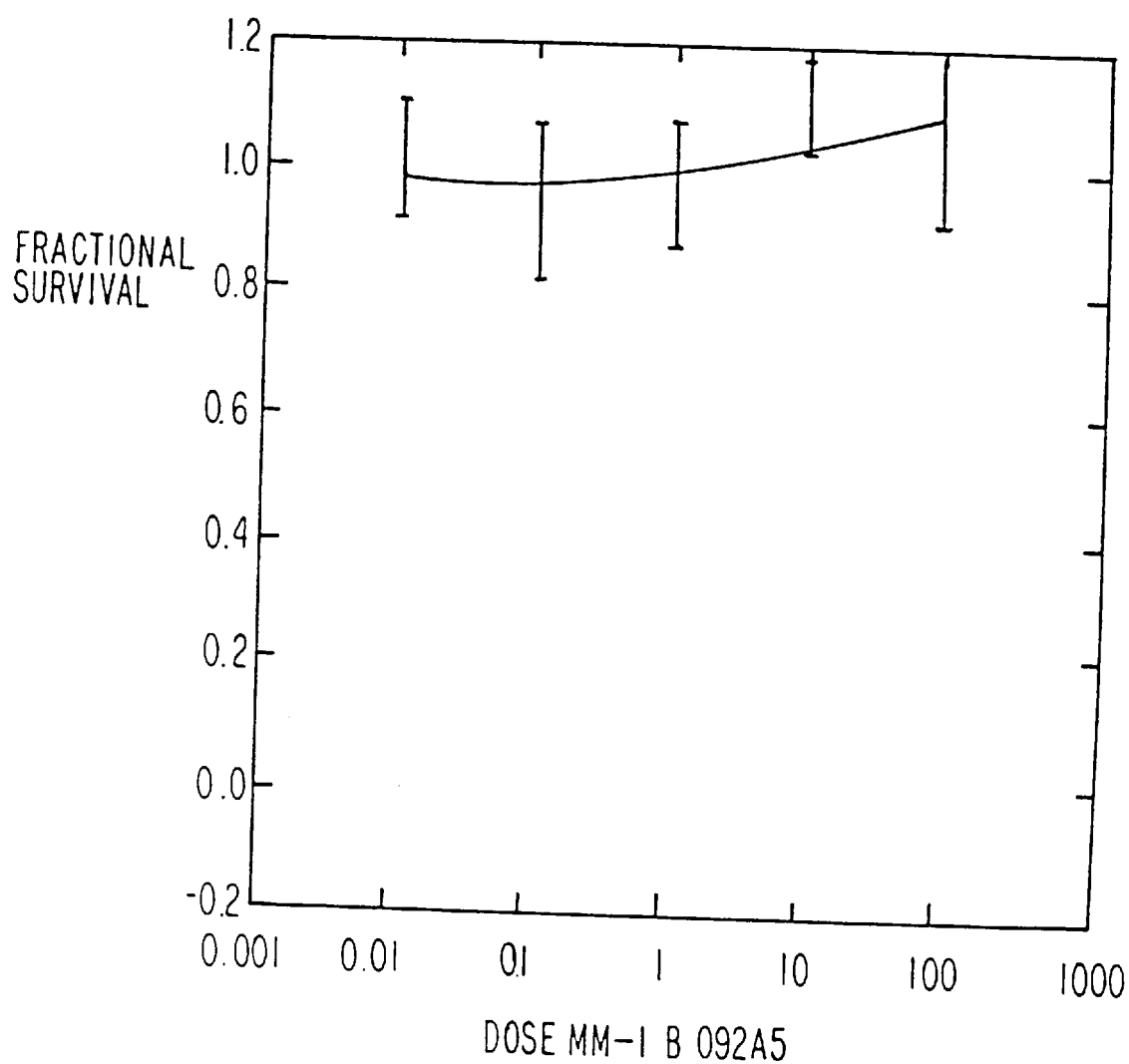
Figure 10C:
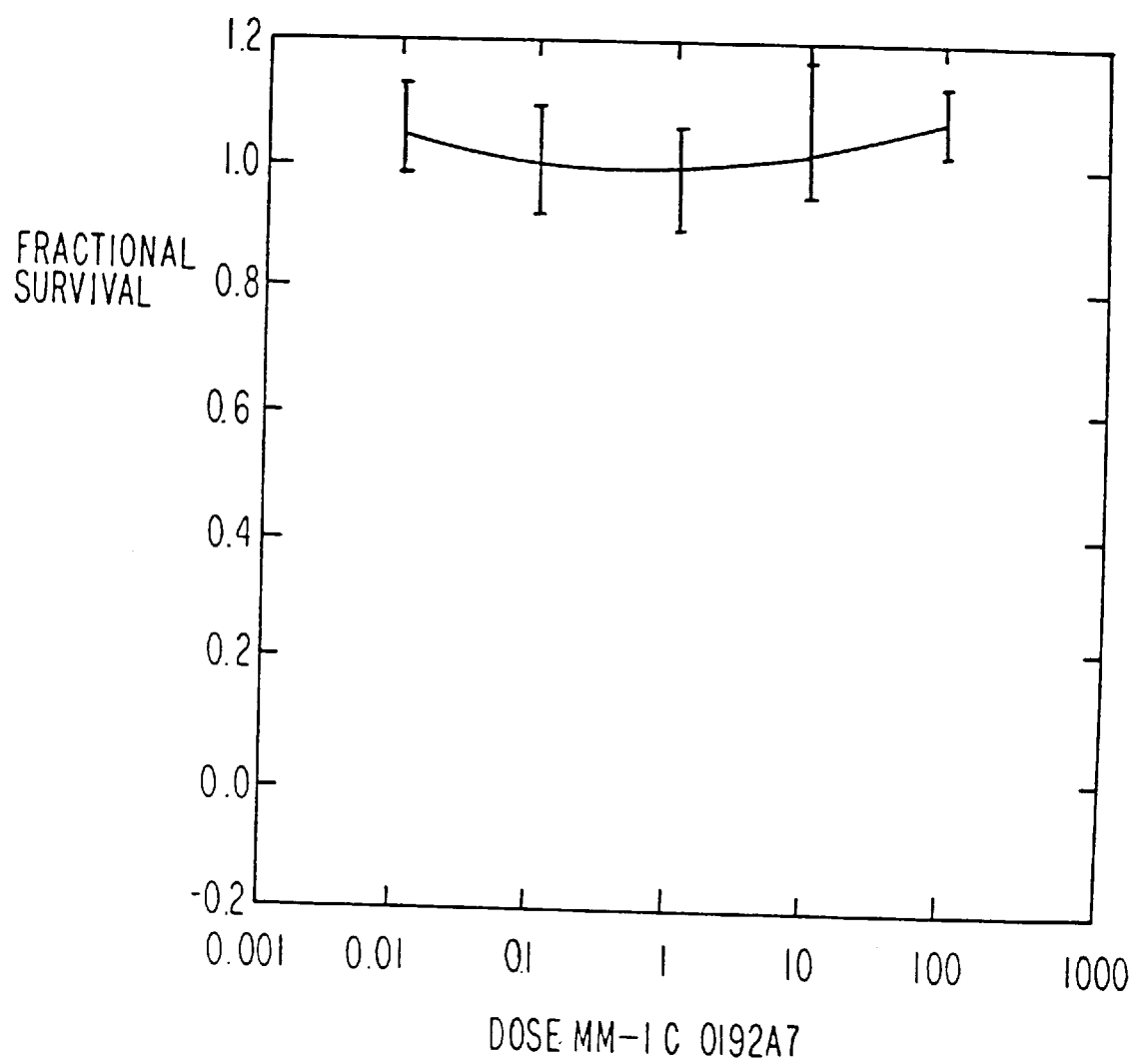
Figure 10D:
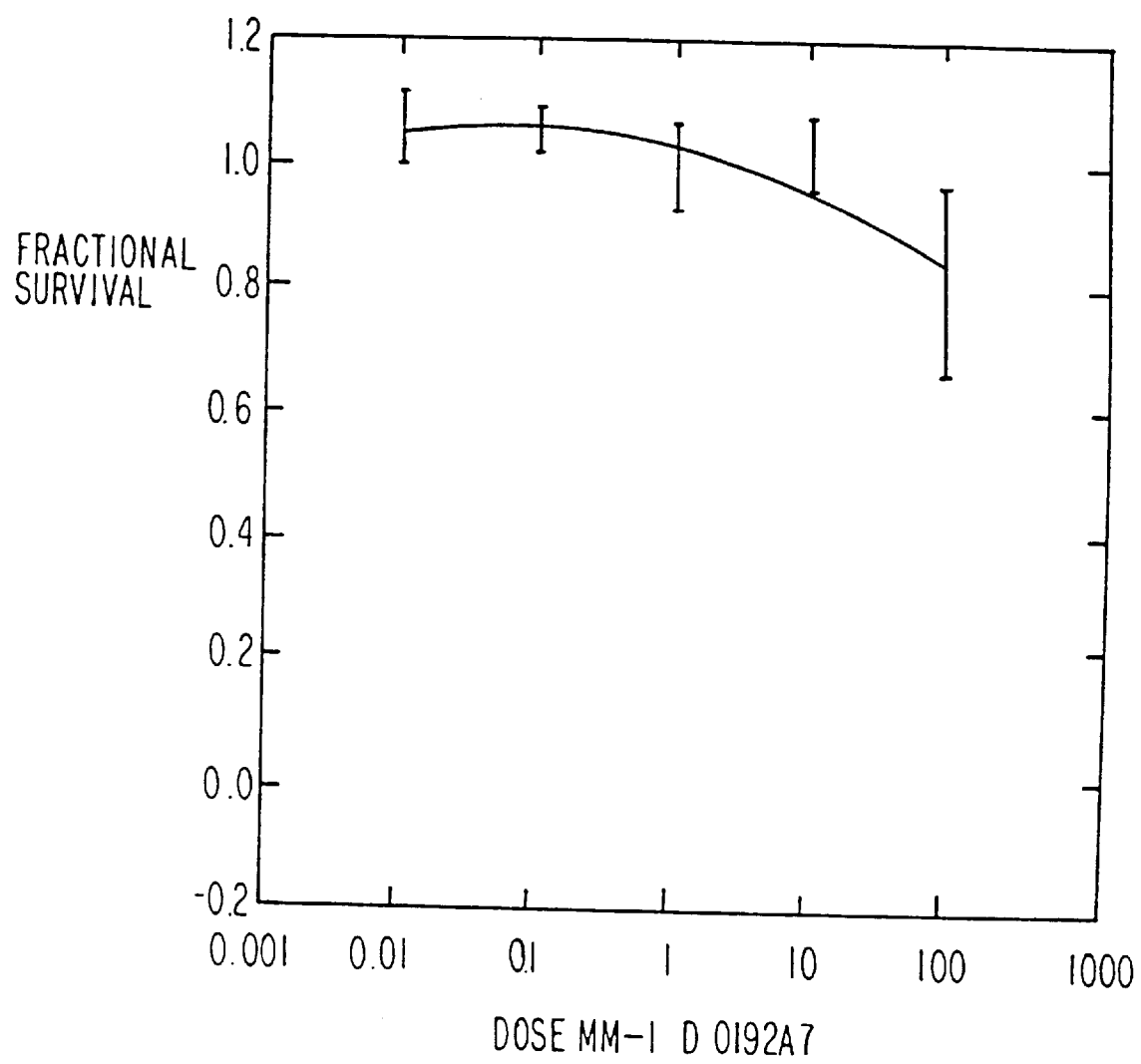
Figure 10E:
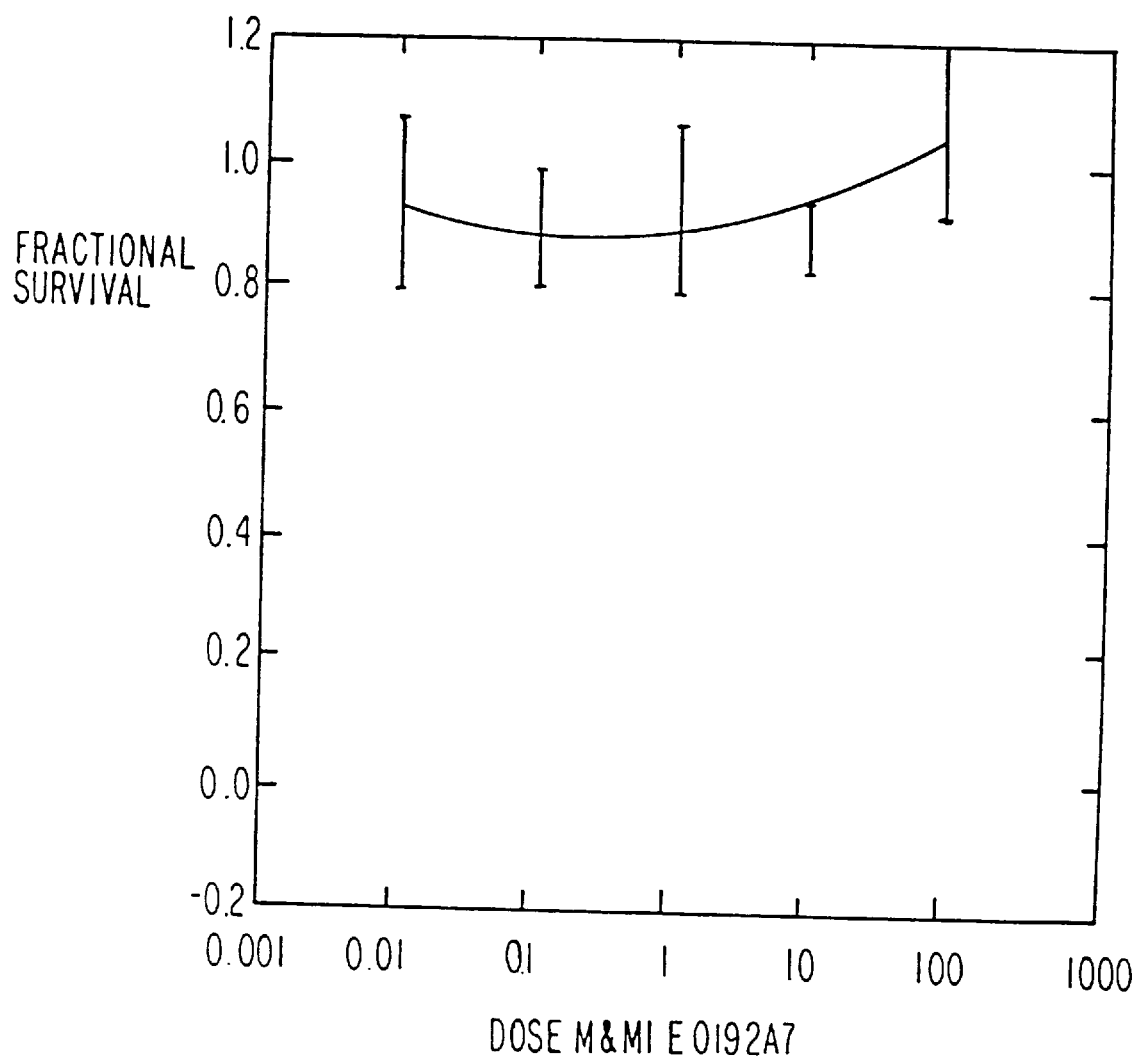
Figure 10F:
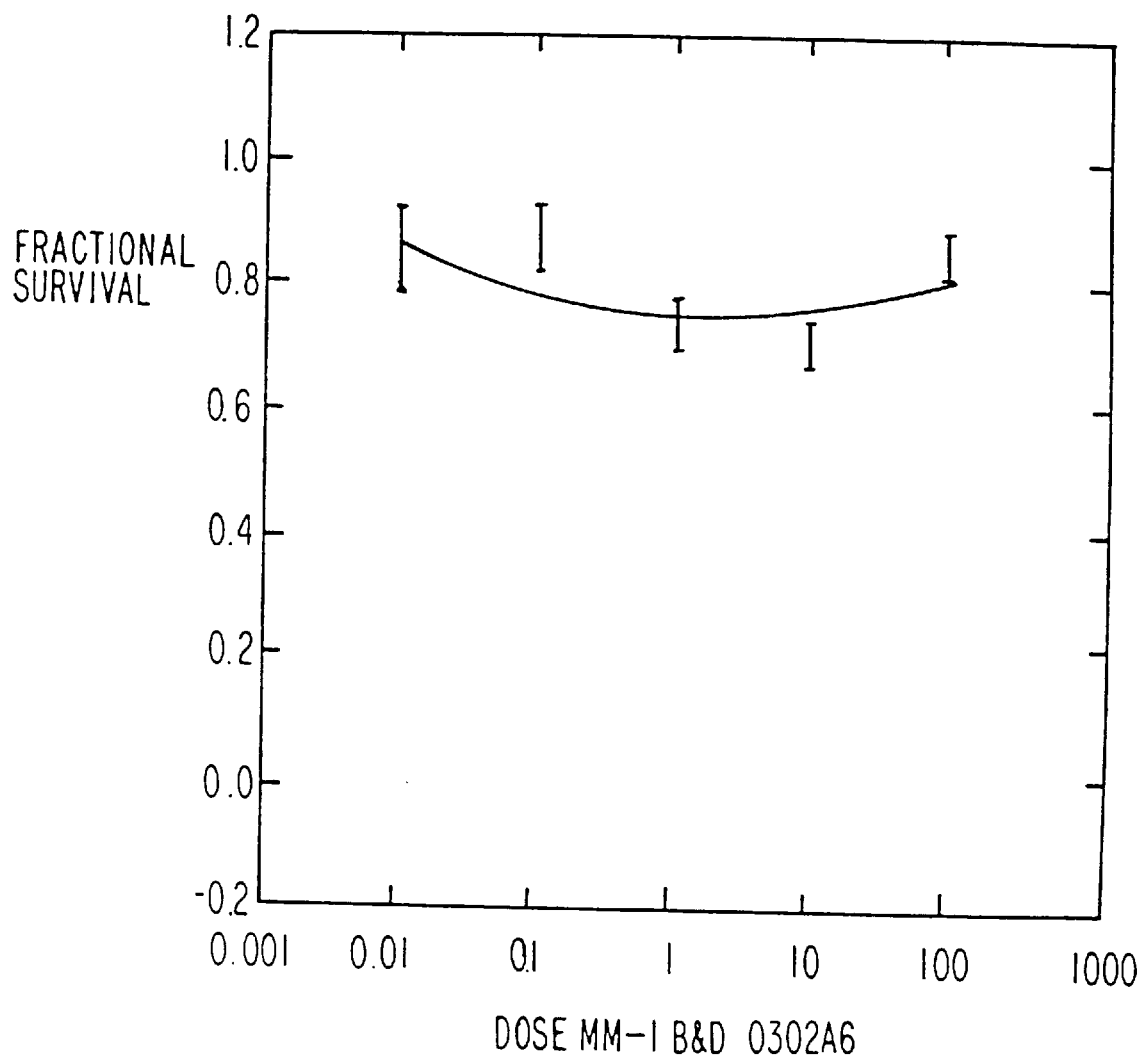
Figure 10G:
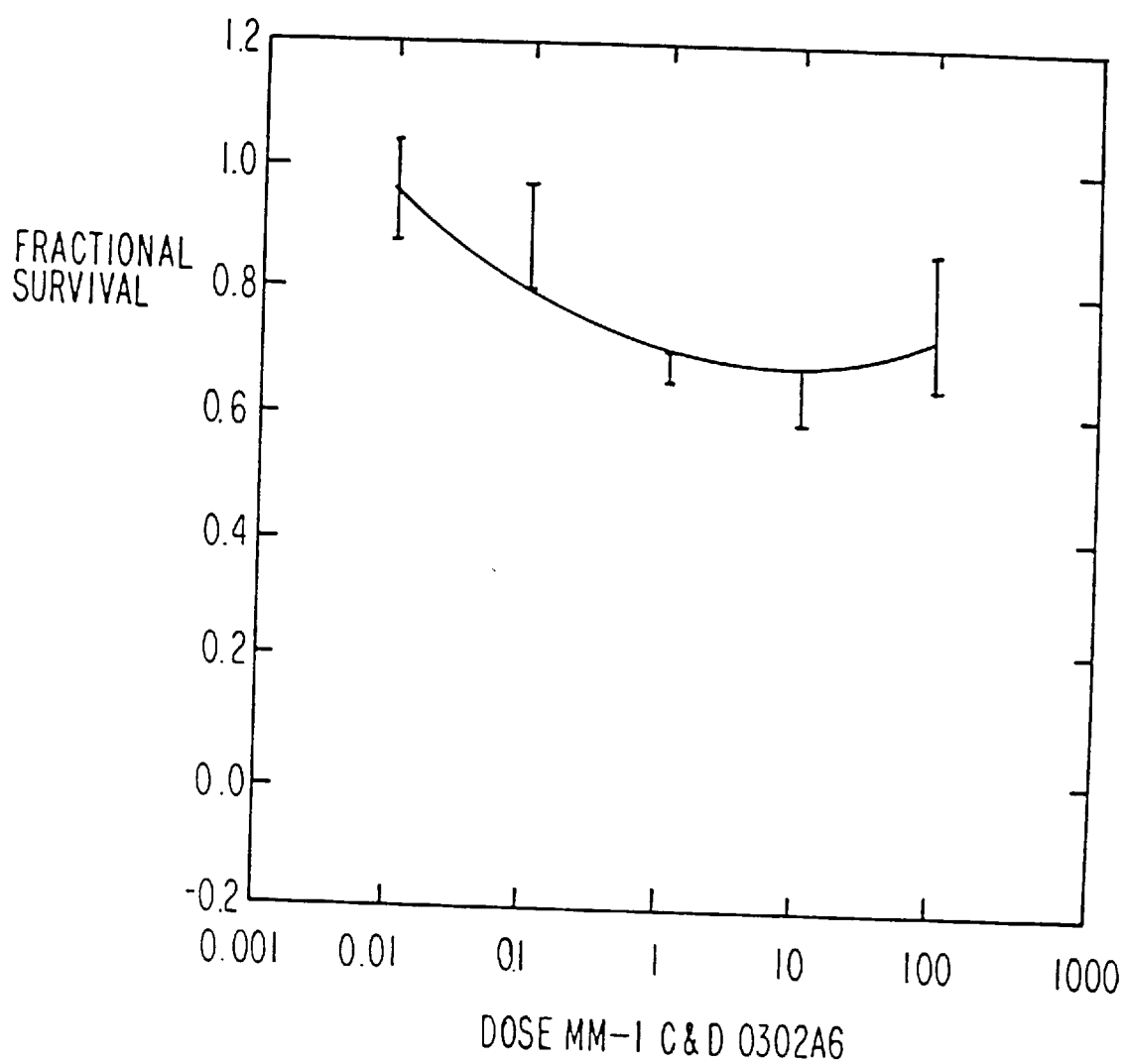
Figure 10H:
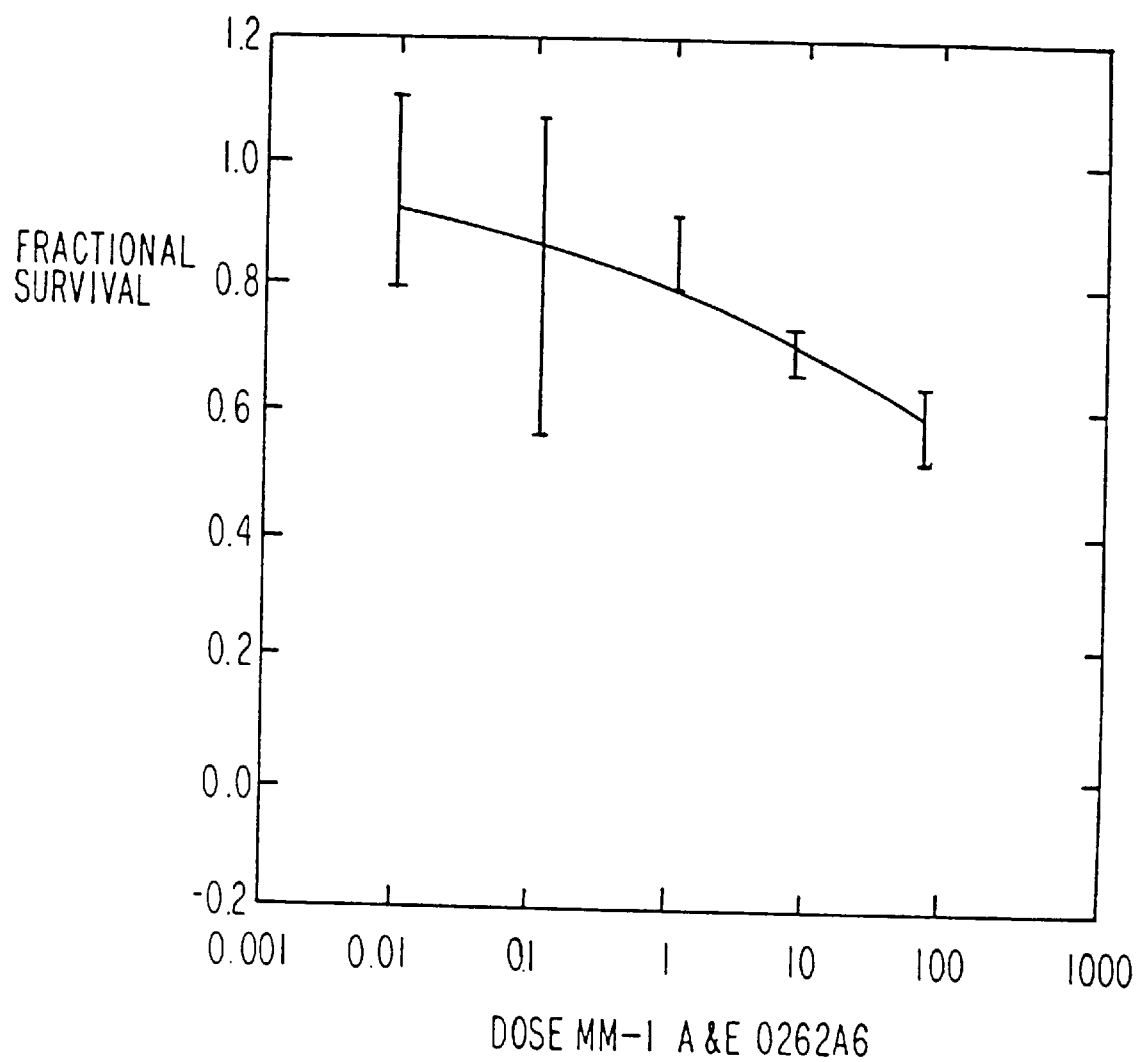
Figure 11A:
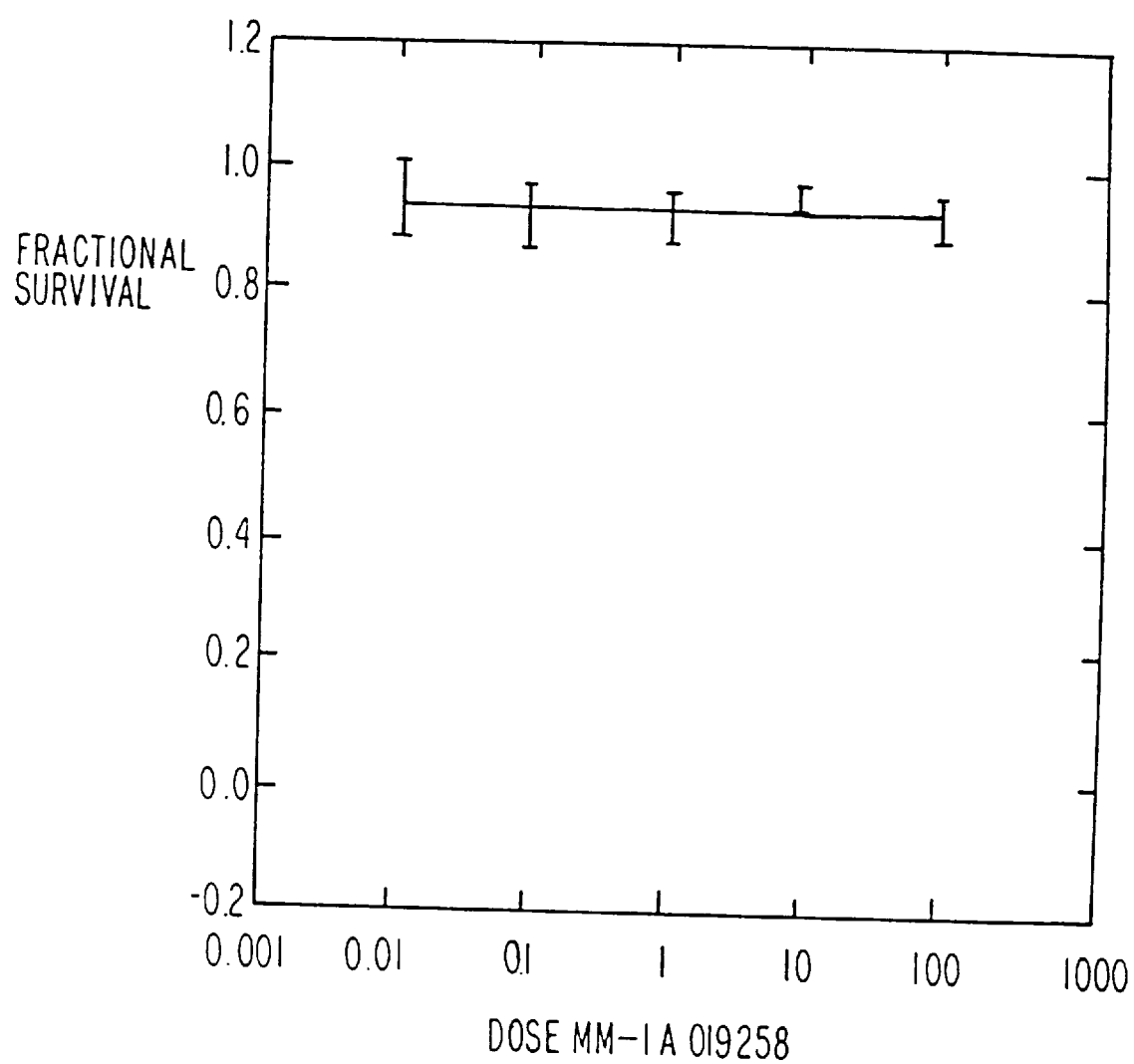
Figure 11B:
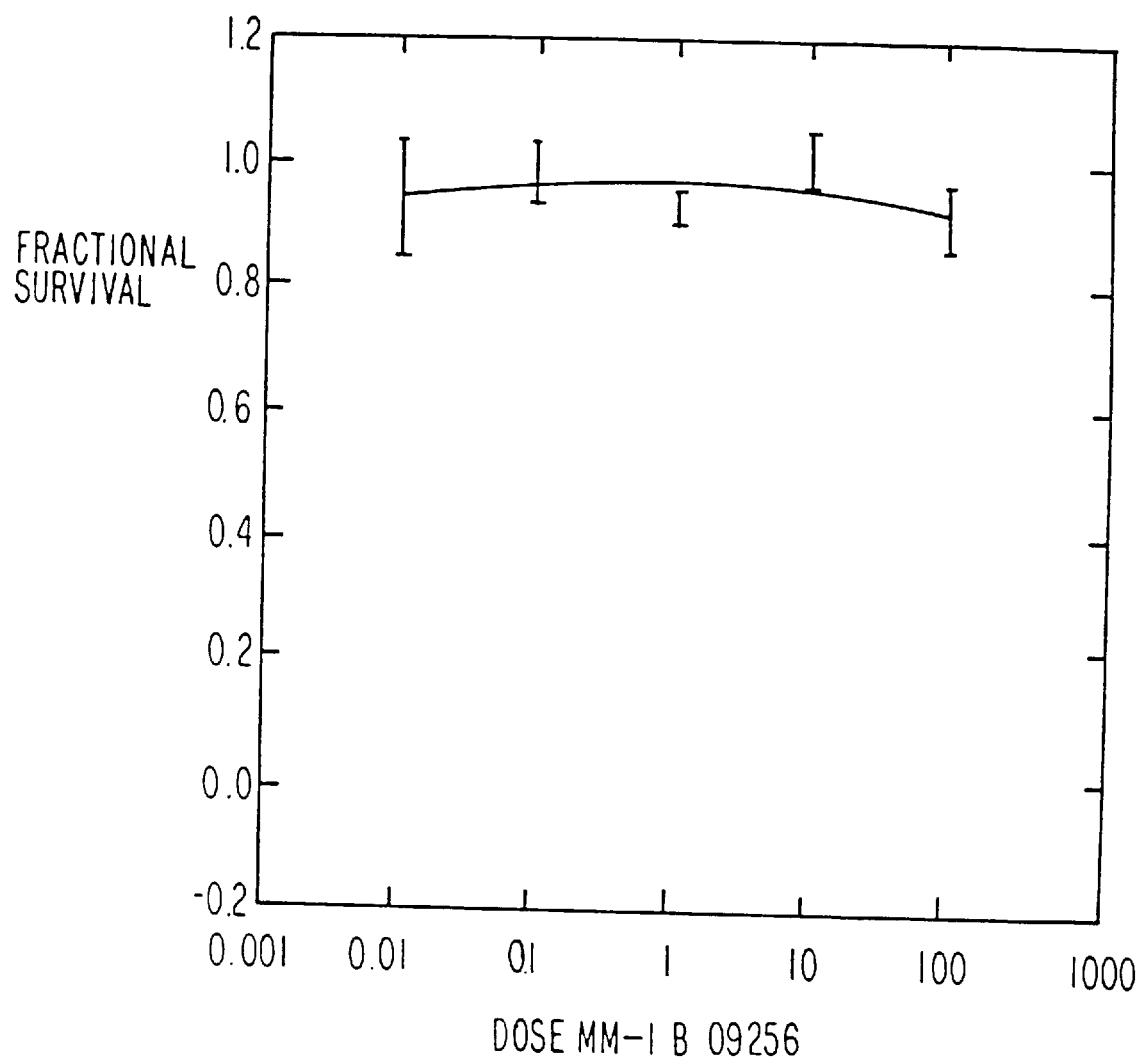
Figure 11C:
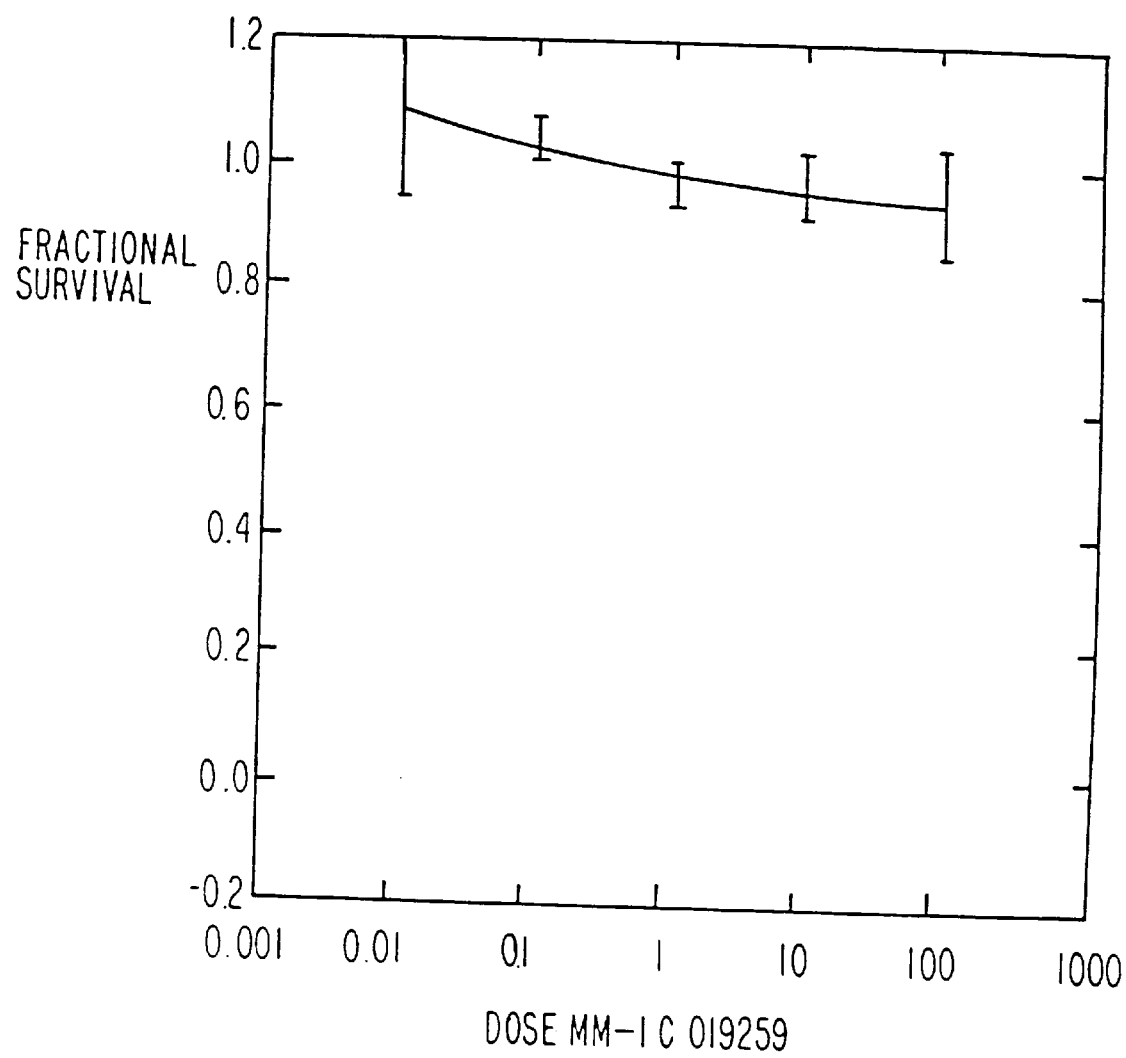
Figure 11D:
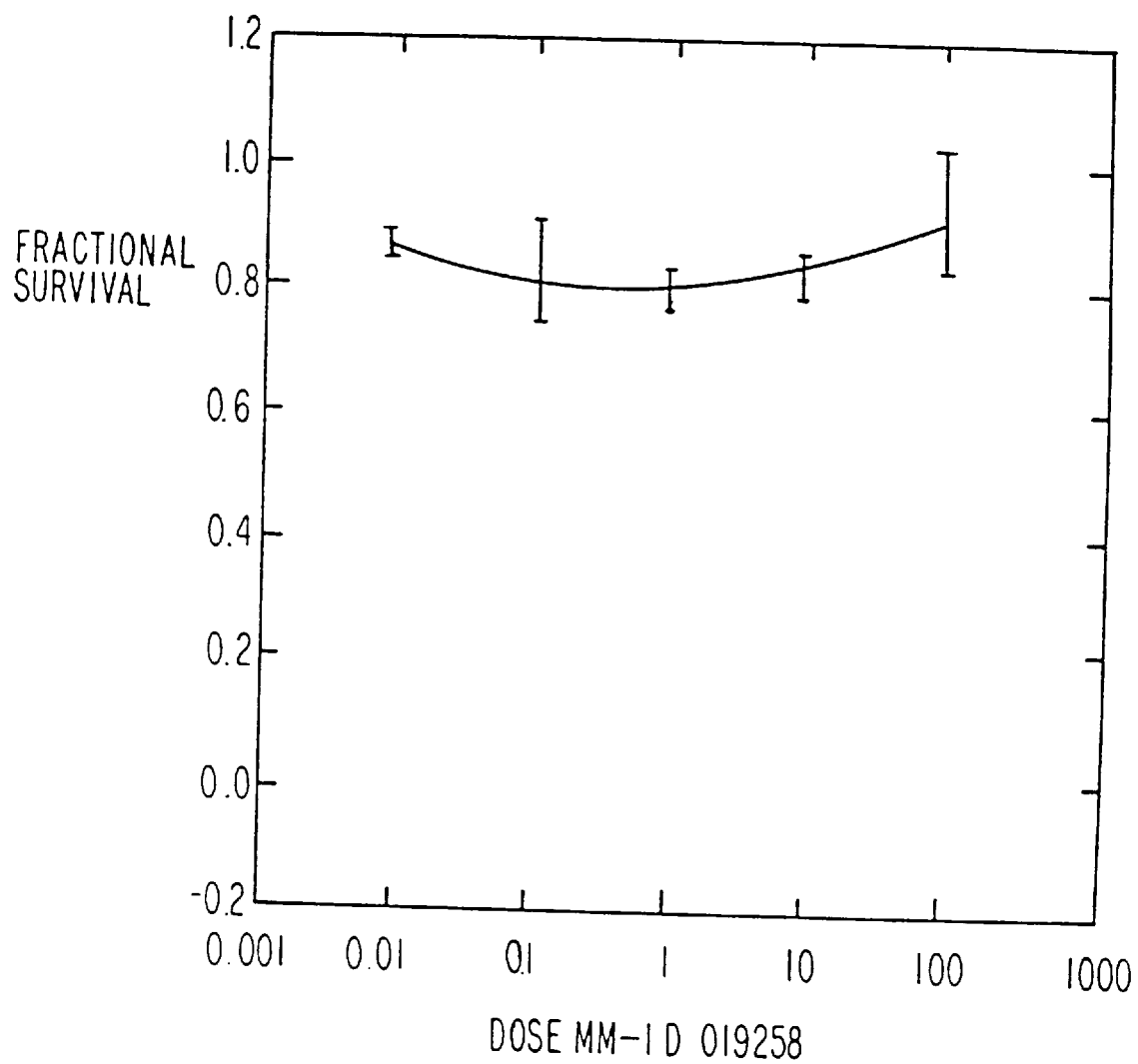
Figure 11E:
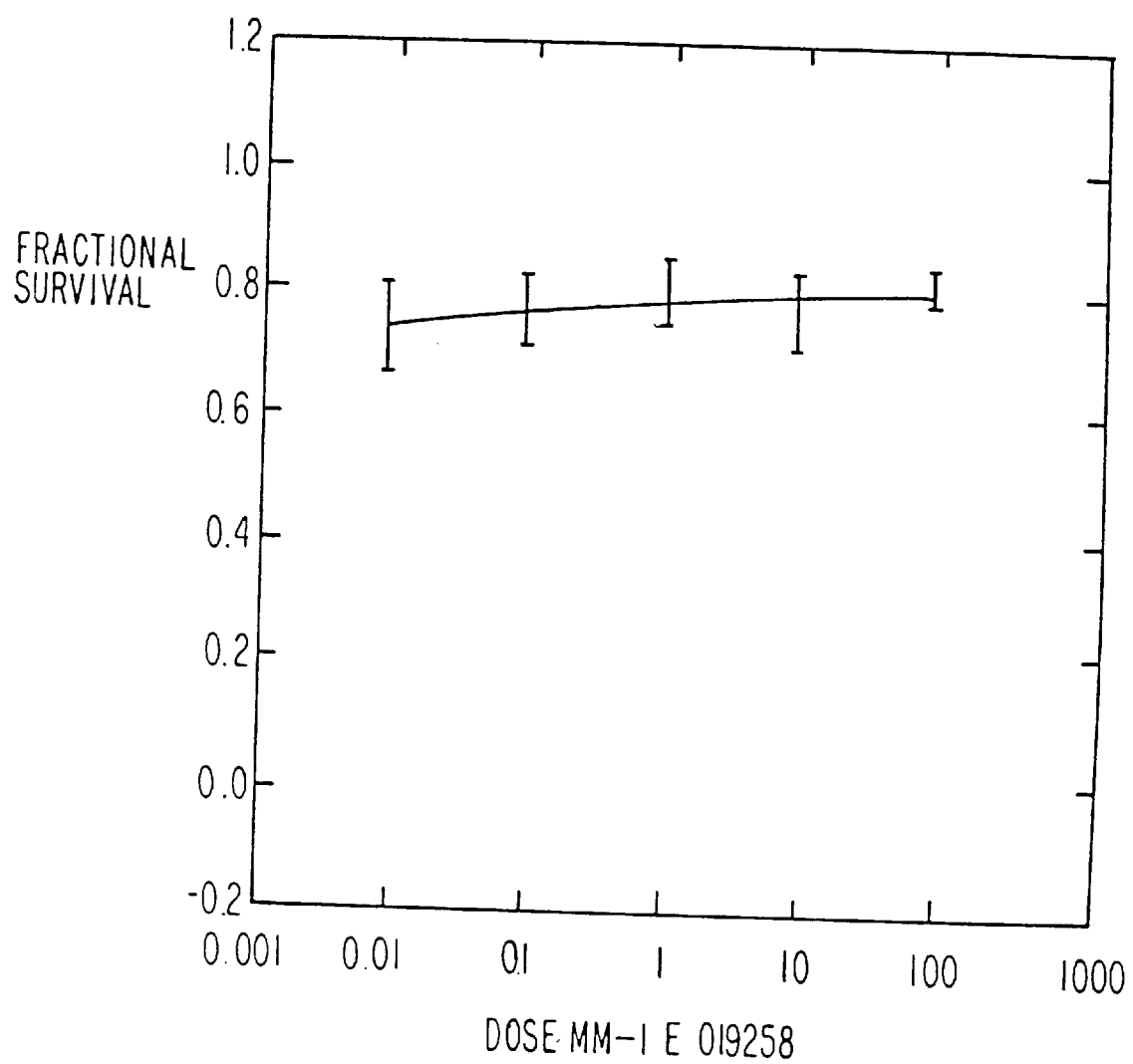
Figure 11F:
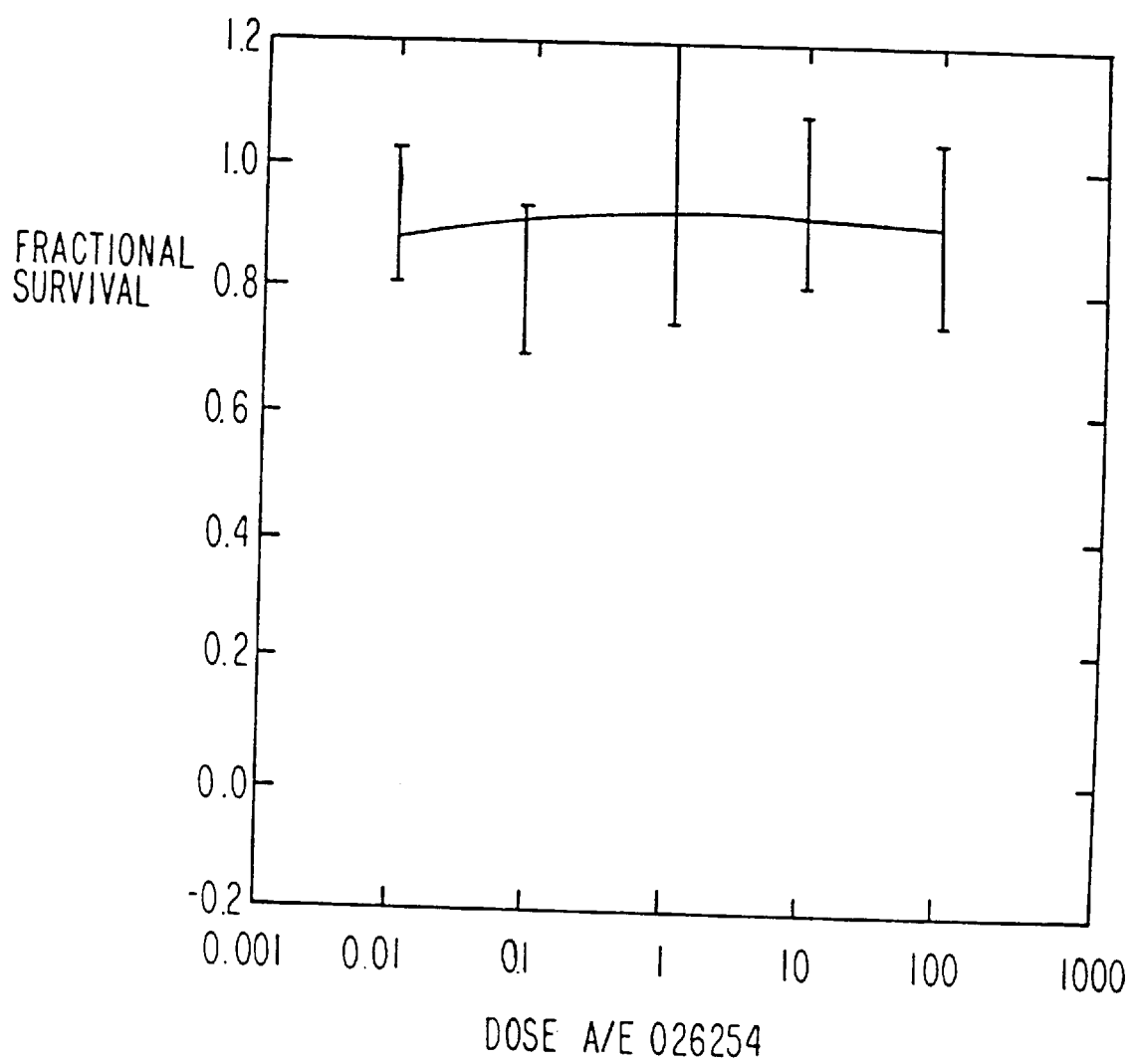
Figure 11H:
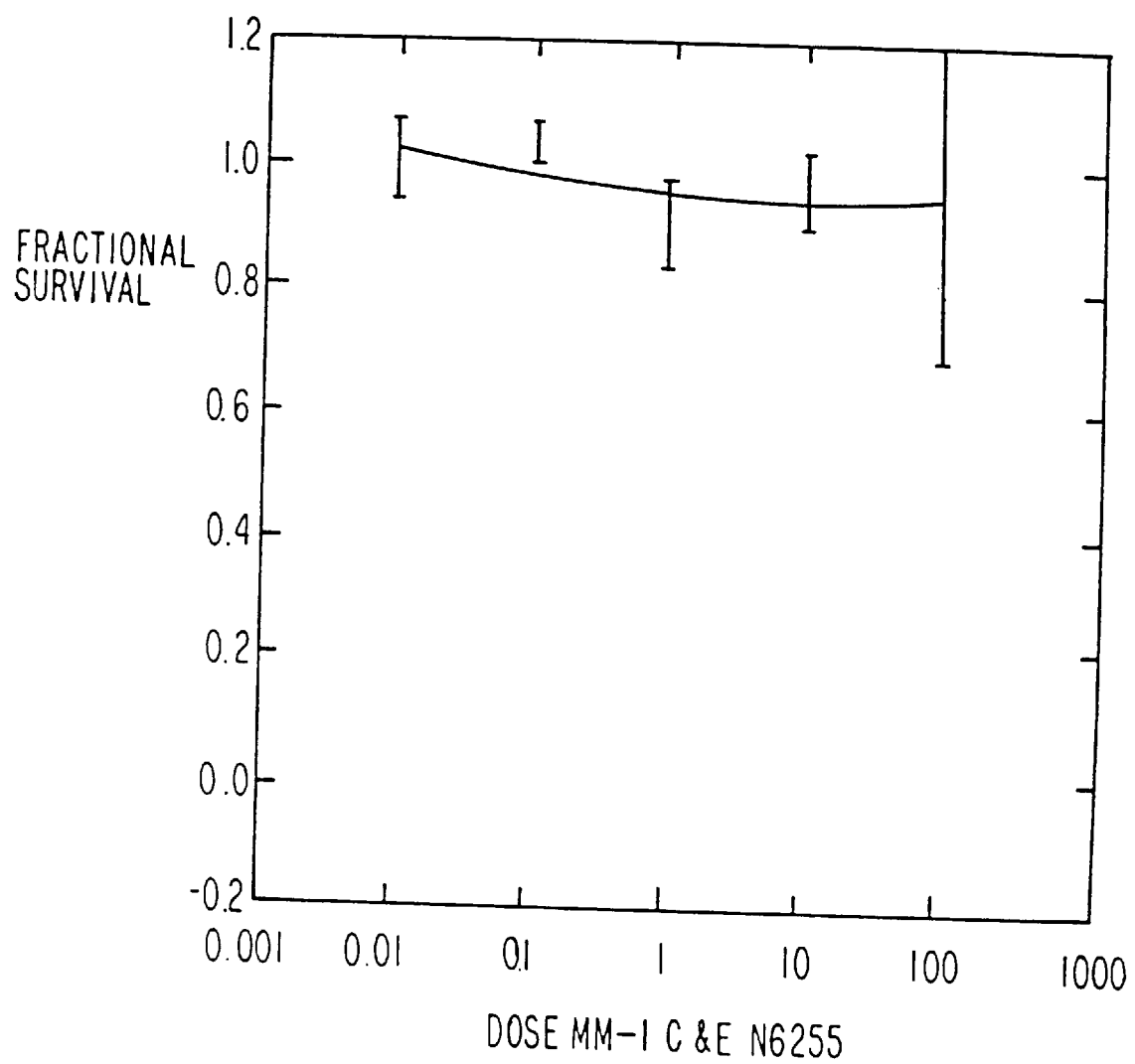
Figure 12B:
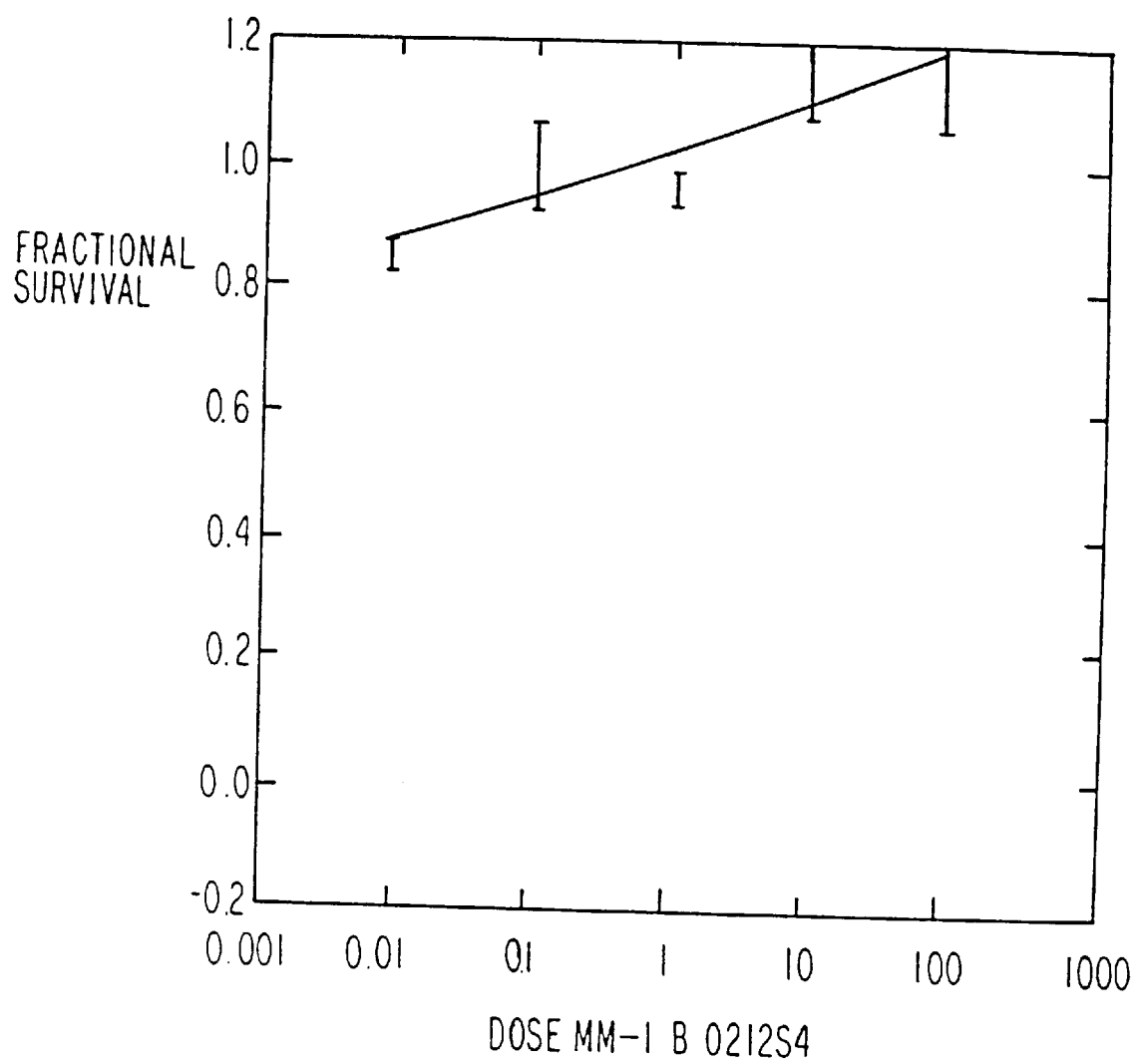
Figure 12C:
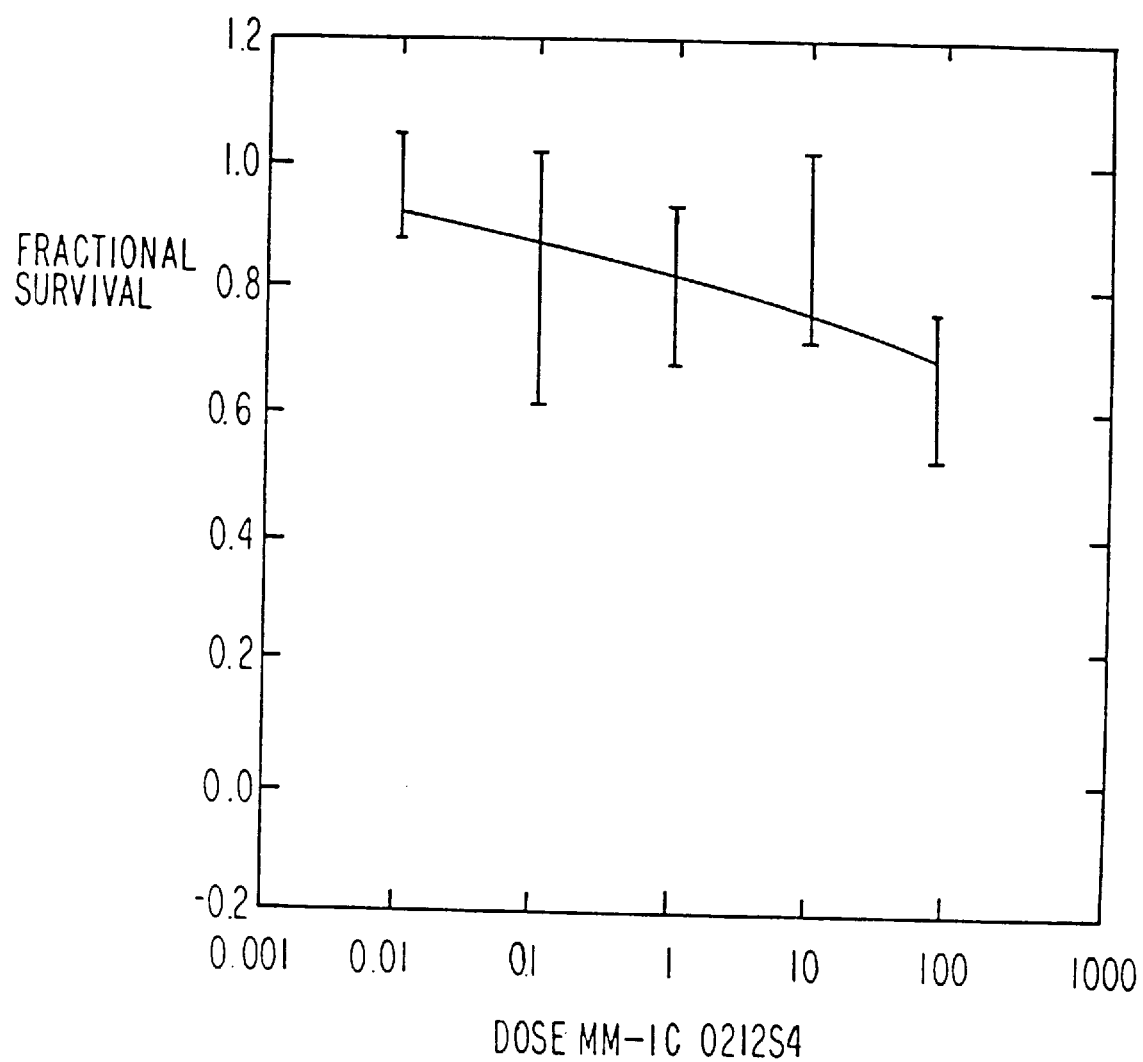
Figure 12D:
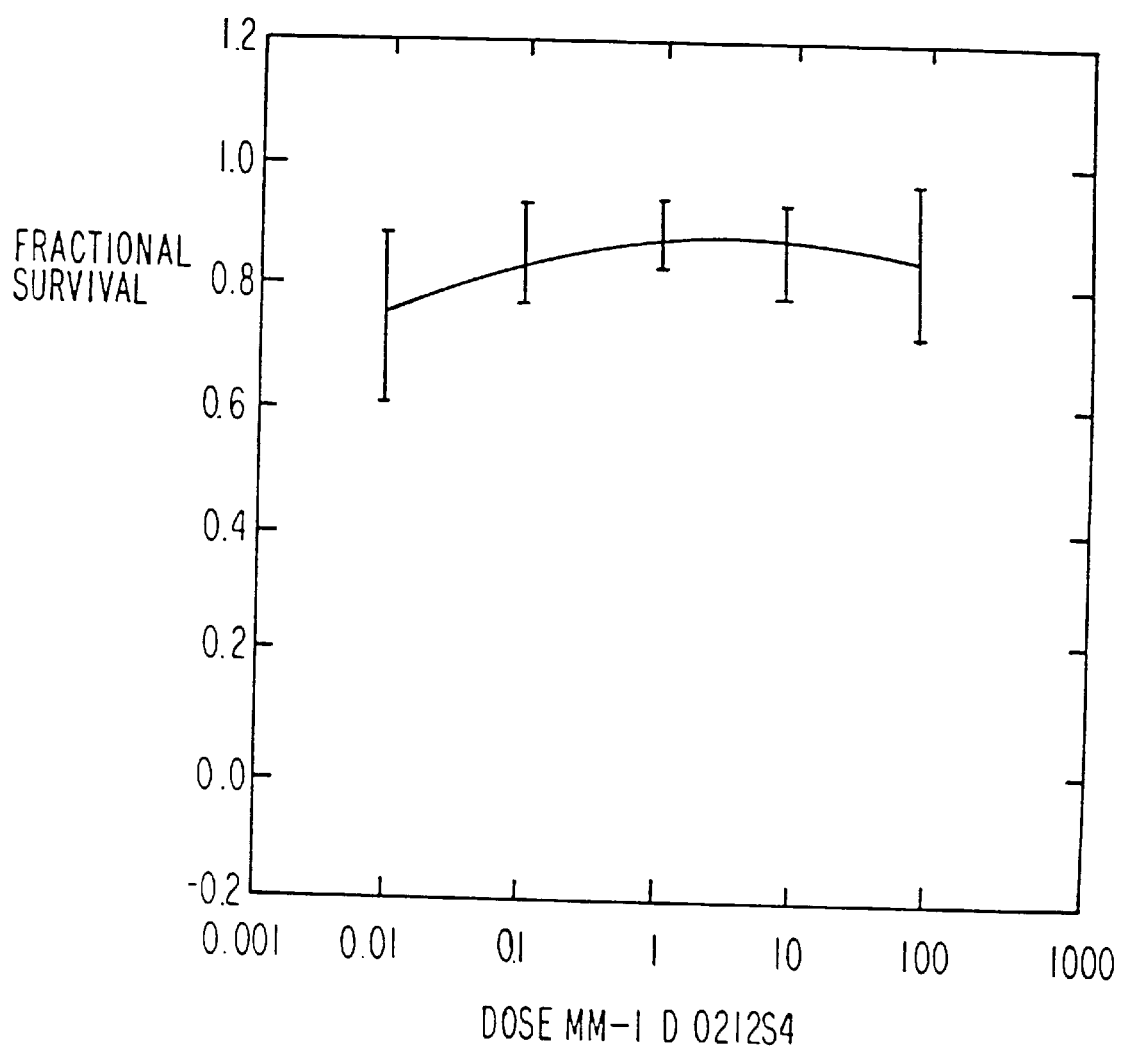
Figure 12E:
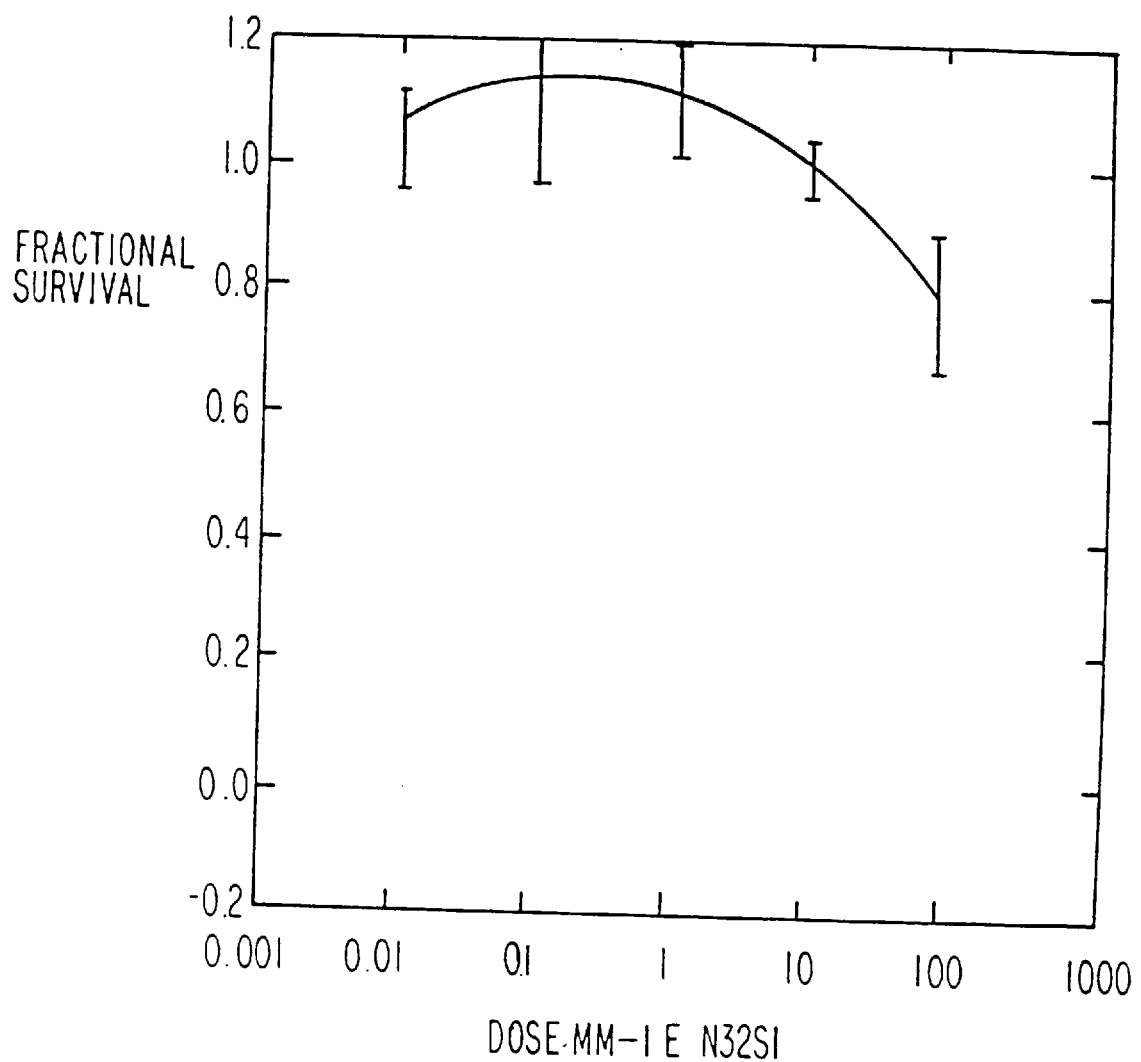
Figure 12F:
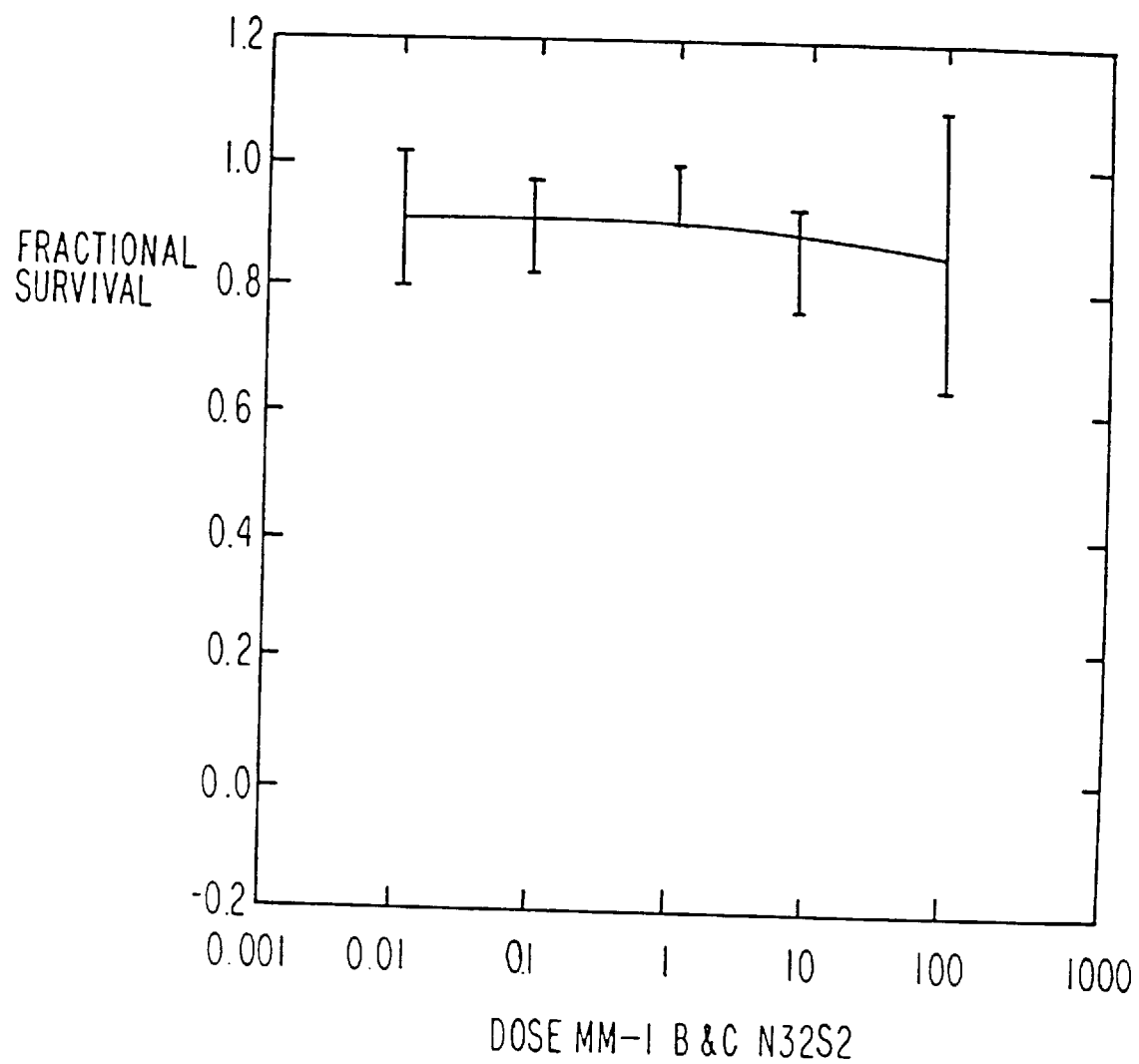
Figure 12G:
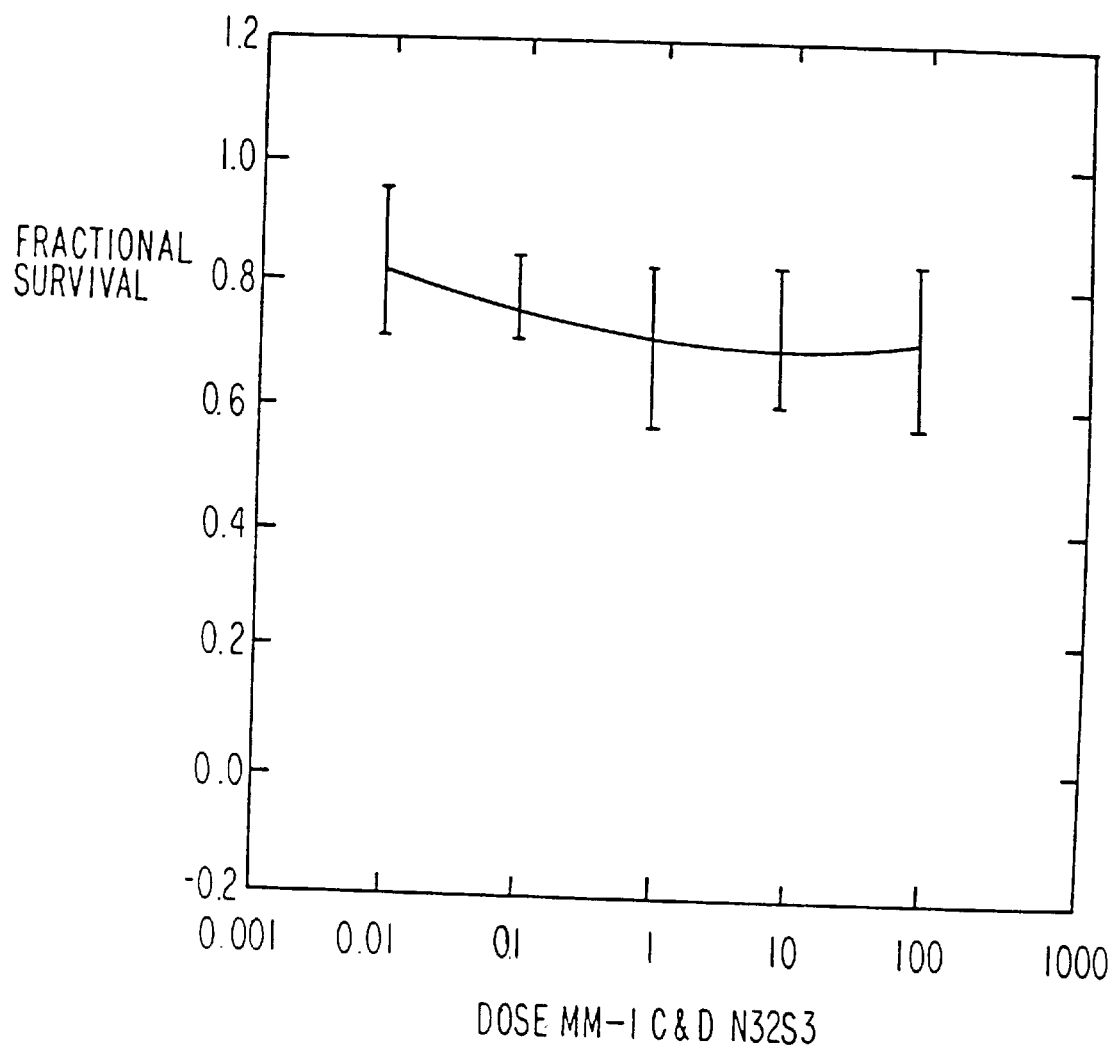
Figure 12H:
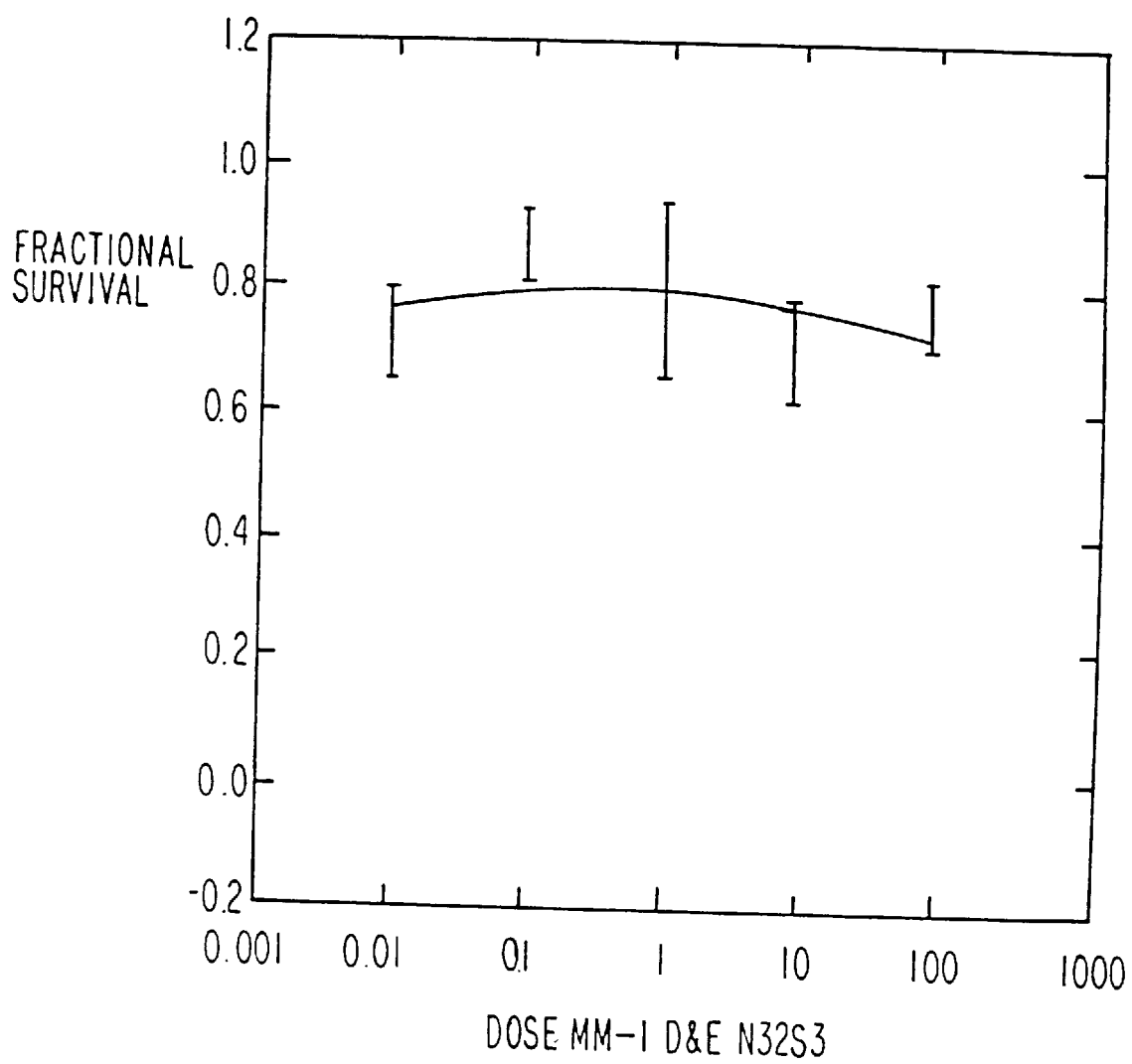
Figure 13A:
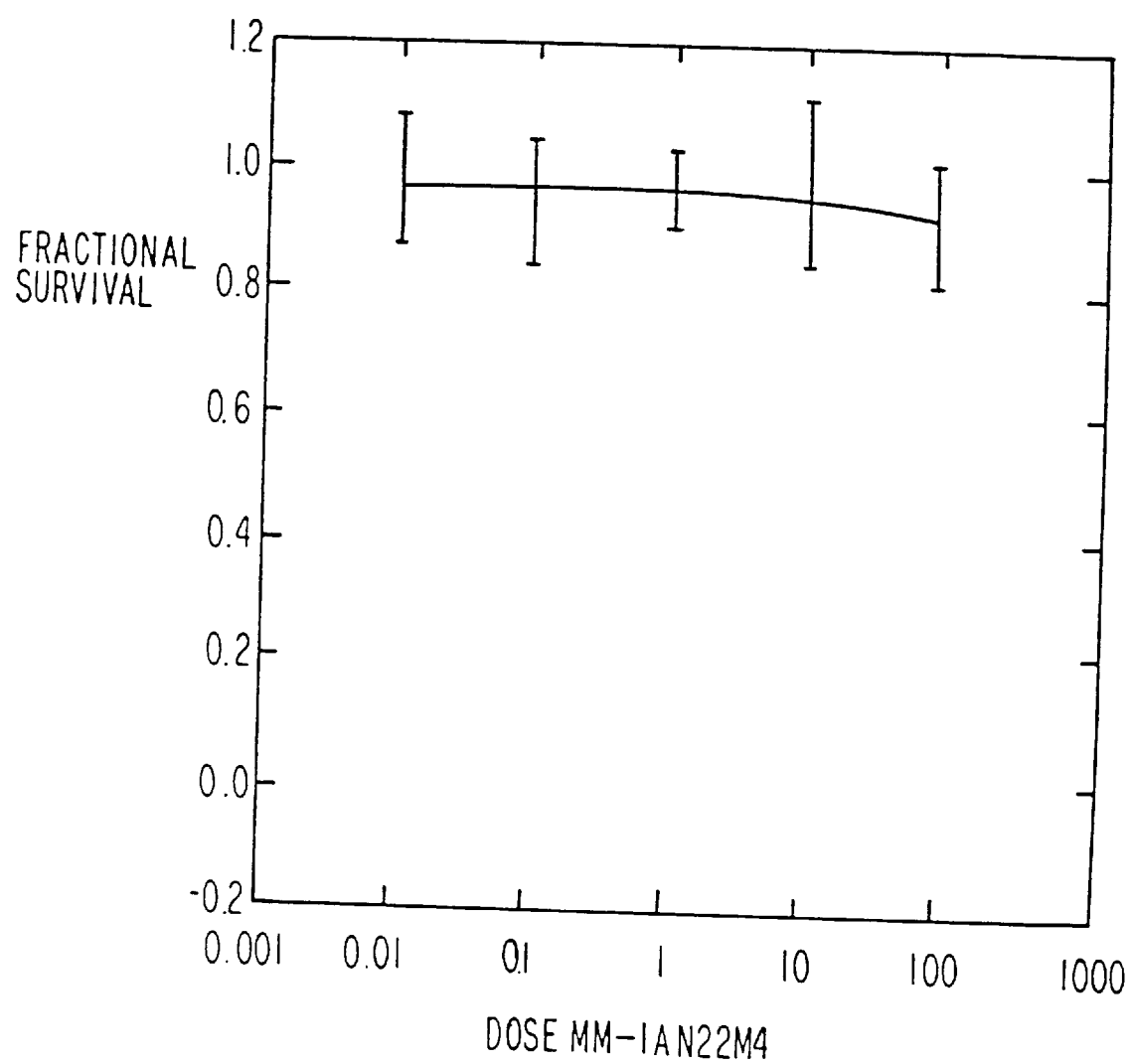
FIGS. 13A to 13H show typical dose response relationships between cocoa procyanidin fractions A, B, C, D, E, B+C, C+E, and D+E and the MCF-7 breast cell line (fractional survival vs. dose, µg/ml); MM-1 A N22M4, MM-1 B N22M4, MM-1 C N22M4, MM-1 D N22M3, MM-1 E 0302M2, MM-1 B/C 0302M4, MM-1 C&E N22M3, MM-1 D&E N22M3.
Figure 13B:
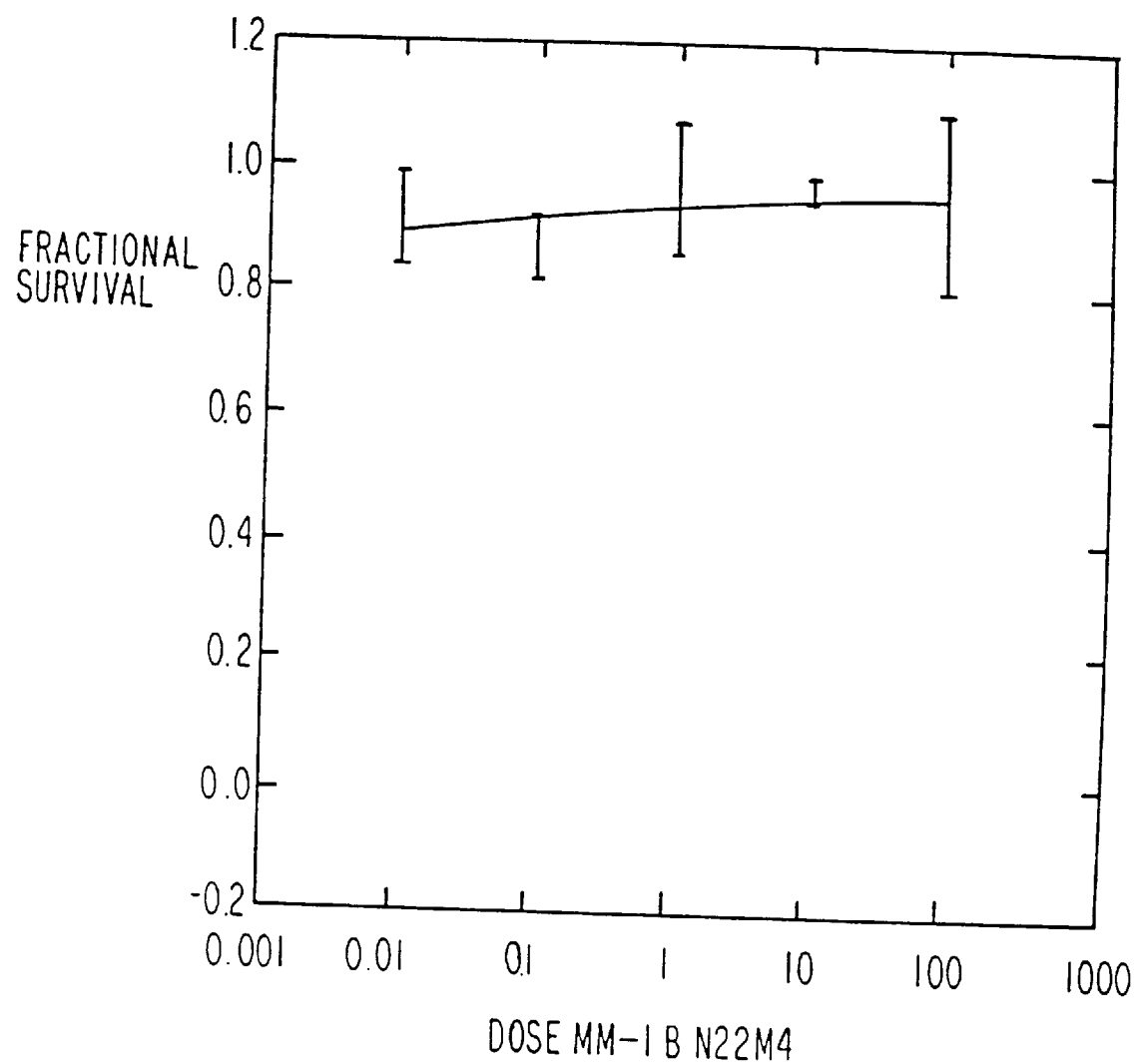
Figure 13C:
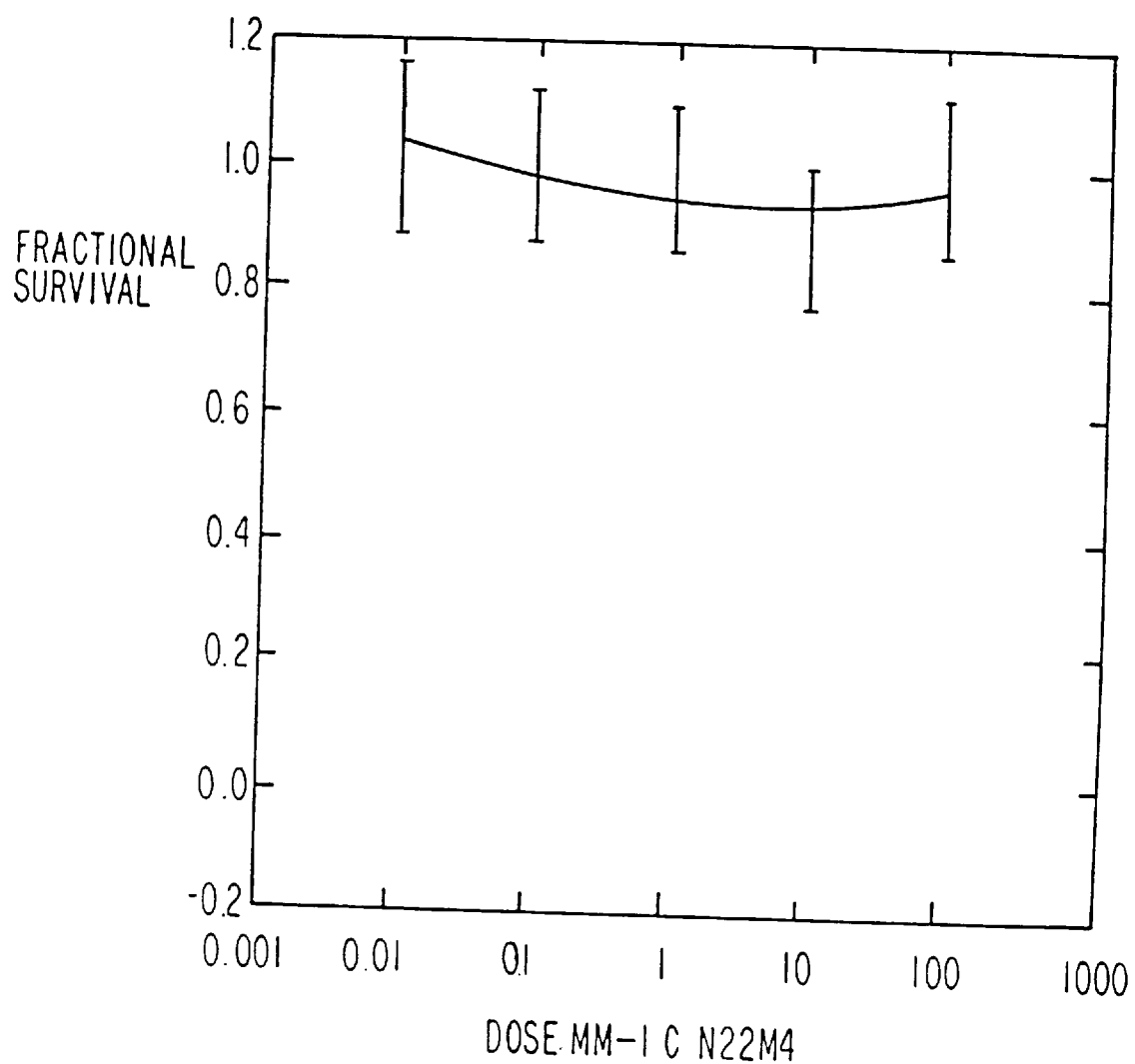
Figure 13D:
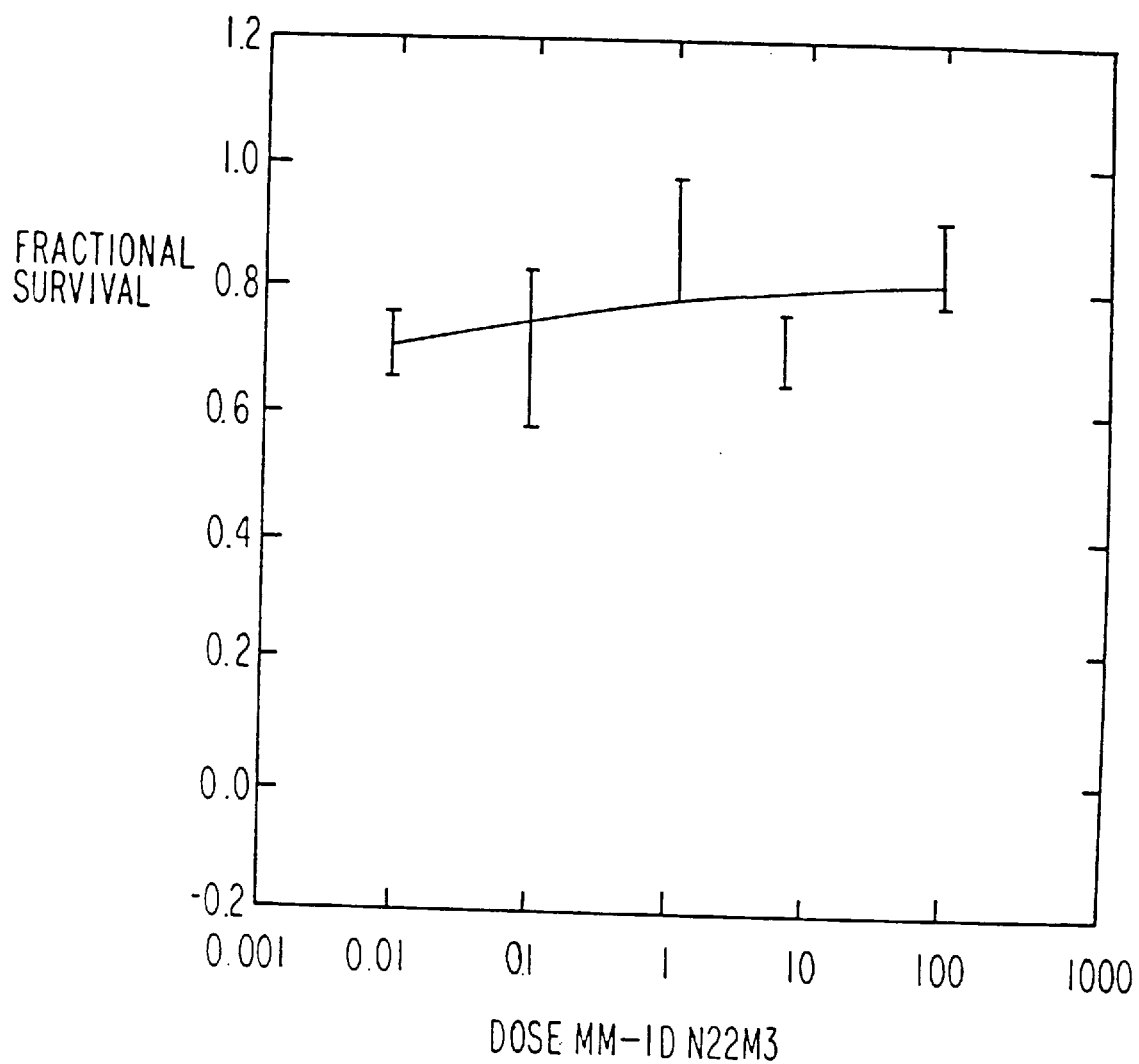
Figure 13E:
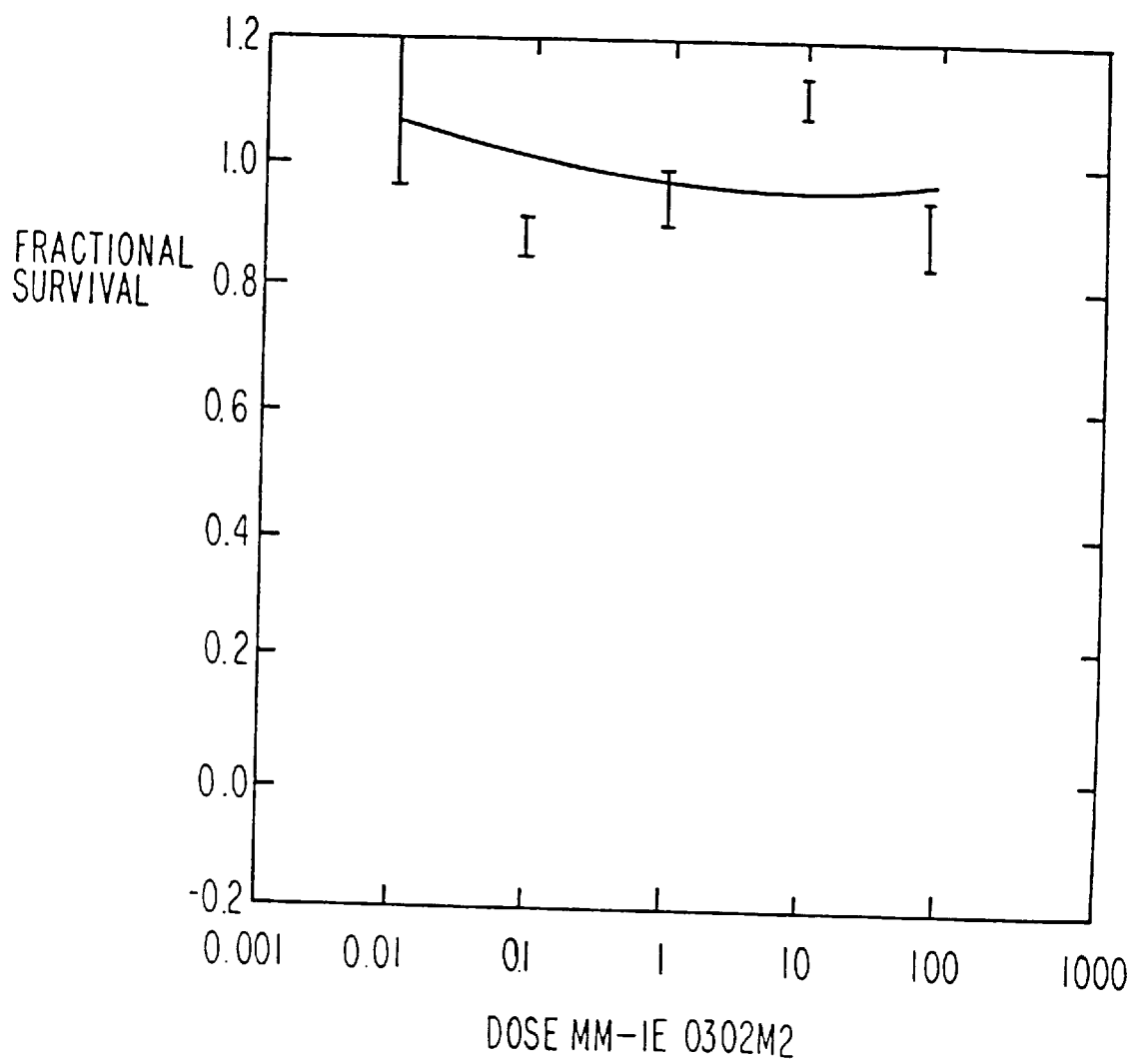
Figure 13F:
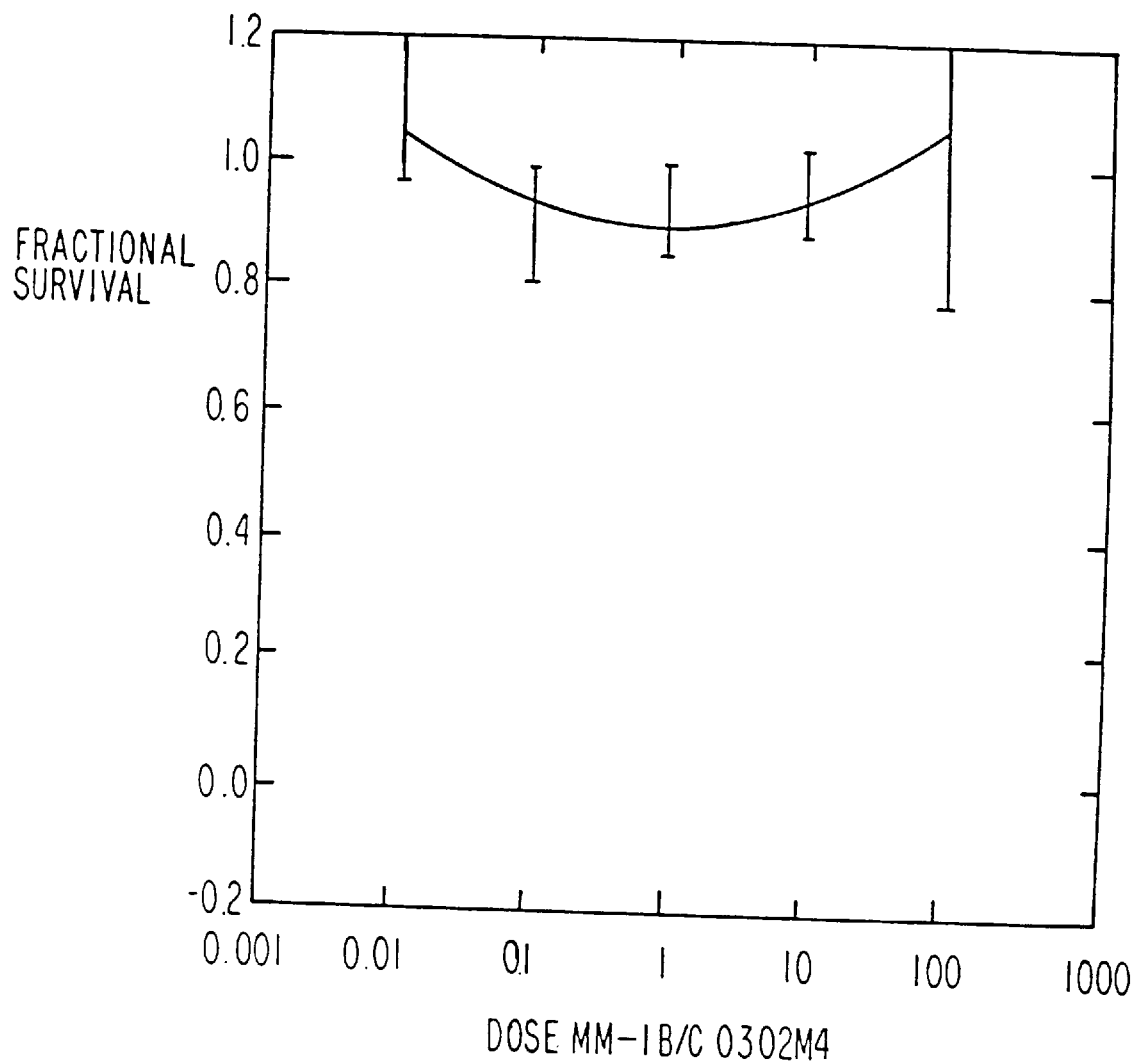
Figure 13G:
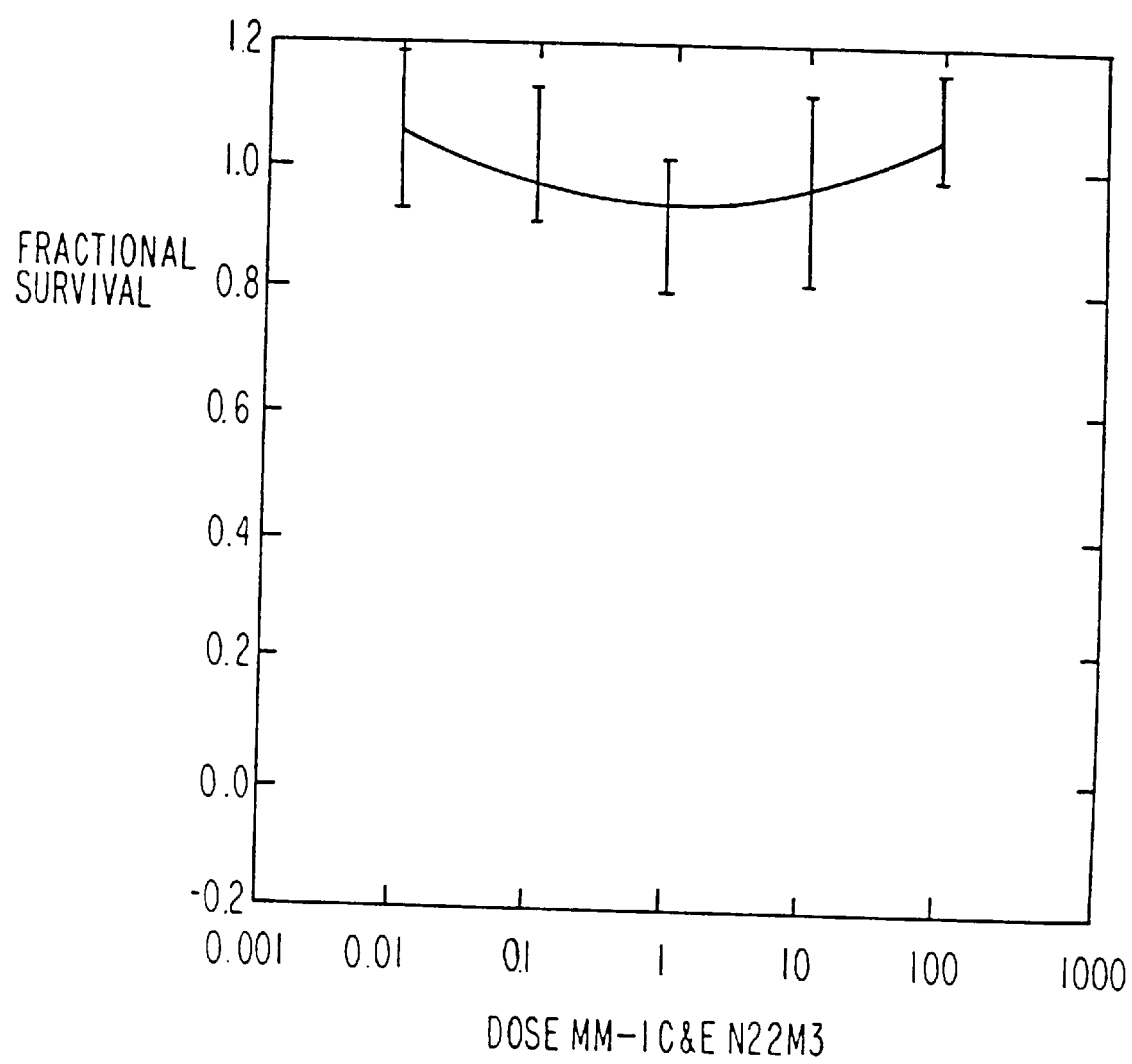
Figure 13H:
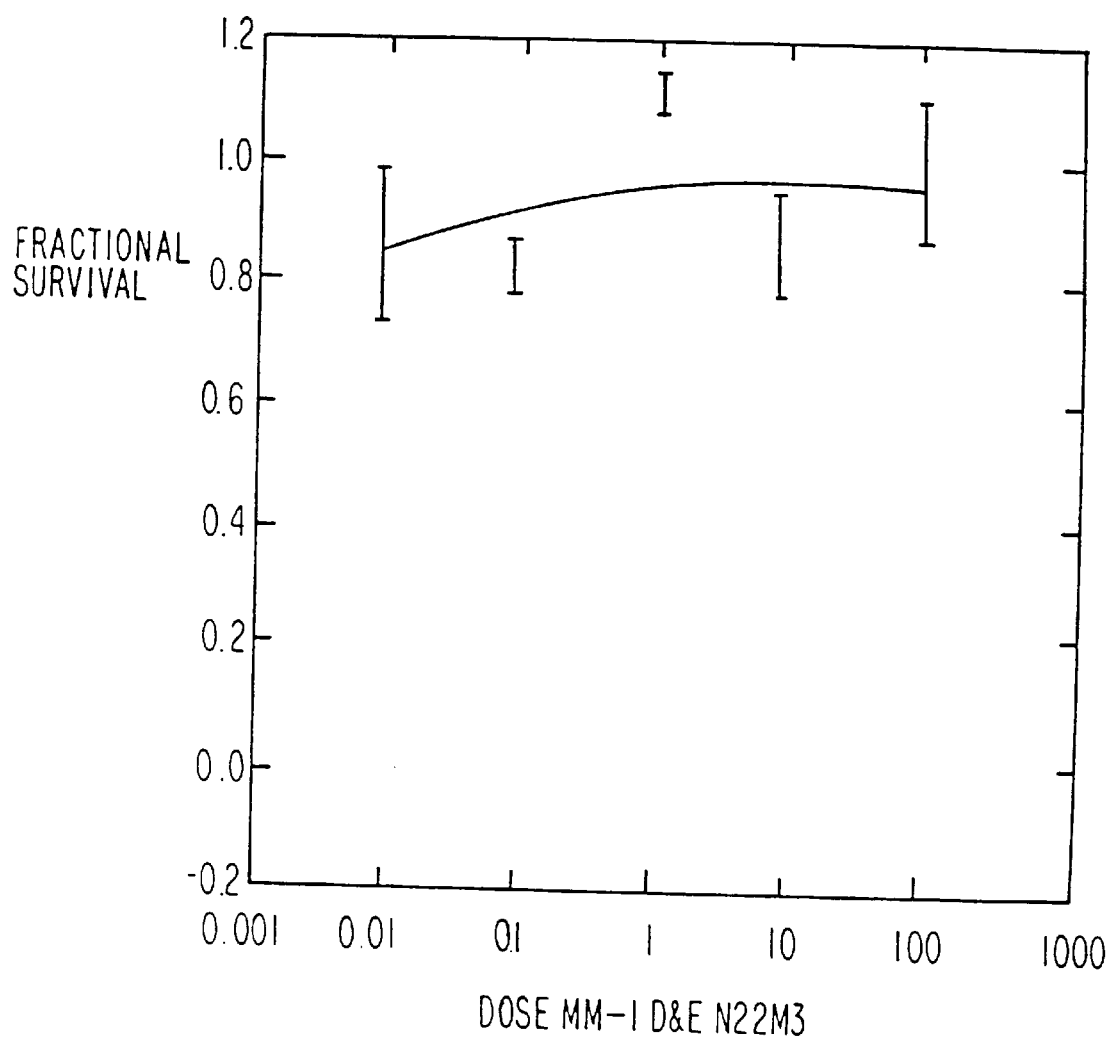

FIGS. 10A–10H show the typical dose response relationships between cocoa procyanidin fractions and the ACHN renal cell line. FIGS. 10A–10E indicated that no individual fraction was active against this cell line. FIGS. 10F–10H depict representative results obtained from the fraction combination study. In this case, procyanidin fraction combination B+C was inactive, whereas the fraction combination A+E resulted in an extrapolated $IC_{50}$ value of approximately 500 µg/mL. Dose response curves similar to the C+D combination were considered inactive, since their slopes were too shallow. Extrapolated $IC_{50}$ values for other fraction combinations are listed in Table 6.

E. A-549 Lung Cell Line

FIGS. 11A–11H show the typical dose response relationships between cocoa procyanidin fractions and the A-549 lung cell line. No activity could be detected from any individual fraction or combination of fractions at the doses used in the assay. However, procyanidin fractions may nonetheless have utility with respect to this cell line.

F. SK-5 Melanoma Cell Line

FIGS. 12A–12H show the typical dose response relationships between cocoa procyanidin fractions and the SK-5 melanoma cell line. No activity could be detected from any individual fraction or combination of fractions at the doses used in the assay. However, procyanidin fractions may nonetheless have utility with respect to this cell line.

G. MCF-7 Breast Cell Line

FIGS. 13A–13H show the typical dose response relationships between cocoa procyanidin fractions and the MCF-7 breast cell line. No activity could be detected from any individual fraction or combination of fractions at the doses used in the assay. However, procyanidin fractions may nonetheless have utility with respect to this cell line.

H. CCRF-CEM T-Cell Leukemia Line

Figure 14:
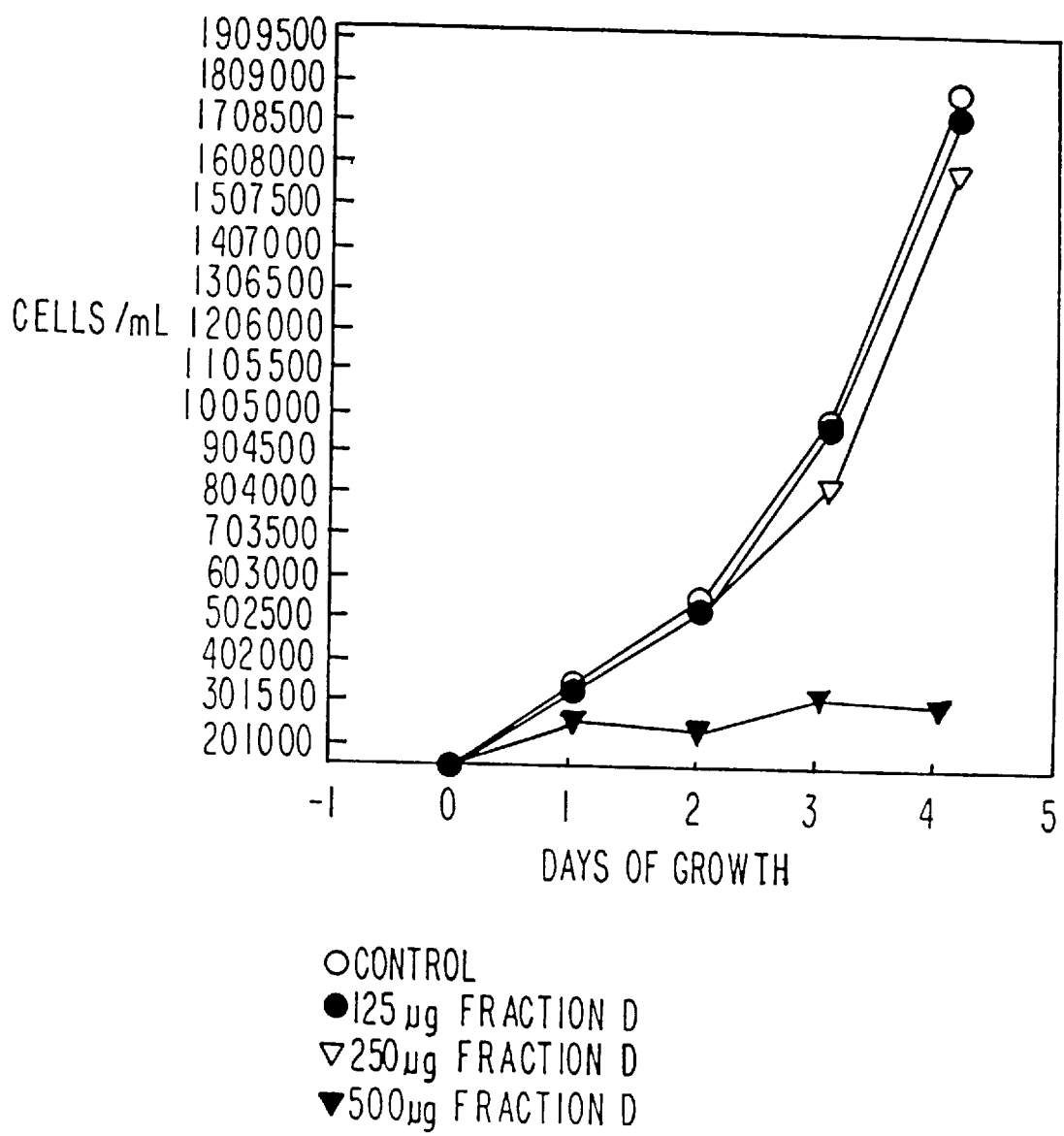
FIG. 14 shows typical dose response relationships for cocoa procyanidin (particularly fraction D) and the CCRF-CEM T-cell leukemia cell line (cells/ml vs. days of growth; open circle is control, darkened circle is 125 µg fraction D, open inverted triangle is 250 µg fraction D, darkened inverted triangle is 500 µg fraction D)

Atypical dose response curves were originally obtained against the CCRF-CEM T-cell leukemia line. However, microscopic counts of cell number versus time at different fraction concentrations indicated that 500 µg of fractions A, B and D effected an 80% growth reduction over a four day period. A representative dose response relationship is shown in FIG. 14.

I. Summary

The $IC_{50}$ values obtained from these assays are collectively listed in Table 6 for all the cell lines except for CCRF-CEM T-cell leukemia. The T-cell leukemia data was intentionally omitted from the Table, since a different assay procedure was used. A general summary of these results indicated that the most activity was associated with fractions D and E. These fractions were most active against the PC-3 (prostate) and KB (nasopharyngeal/HeLa) cell lines. These fractions also evidenced activity against the HCT-116 (colon) and ACHN (renal) cell lines, albeit but only at much higher doses. No activity was detected against the MCF-7 (breast), SK-5 (melanoma) and A-549 (lung) cell lines. However, procyanidin fractions may nonetheless have utility with respect to these cell lines. Activity was also shown against the CCRF-CEM (T-cell leukemia) cell line. It should also be noted that fractions D and E are the most complex compositionally. Nonetheless, from this data it is clear that cocoa extracts, especially cocoa procyanidins, have significant anti-tumor, anti-cancer or antineoplastic activity.

TABLE 6

$IC_{50}$ Values for Cocoa Procyanidin Fractions Against Various Cell Lines
($IC_{50}$ values in µg/mL)

| FRACTION | PC-3 | KB | HCT-116 | ACHN | MCF-7 | SK-5 | A-549 |
|---|---|---|---|---|---|---|---|
| A | | | | | | | |
| B | | | | | | | |
| C | | | | | | | |
| D | 90 | 80 | | | | | |
| E | 75 | 75 | 400 | | | | |
| A + B | | | | | | | |
| A + C | 125 | 100 | | | | | |
| A + D | 75 | 75 | | | | | |
| A + E | 80 | 75 | 500 | 500 | | | |
| B + C | | | | | | | |
| B + D | 75 | 80 | | | | | |
| B + E | 60 | 65 | 200 | | | | |
| C + D | 80 | 75 | | 1000 | | | |
| C + E | 80 | 70 | 250 | | | | |
| D + E | 80 | 60 | 85 | | | | |

Values above 100 µg/mL were extrapolated from dose response curves

Example 8

Anti-Cancer, Anti-Tumor or Antineoplastic Activity of Cocoa Extracts (Procyanidins)

Several additional in vitro assay procedures were used to complement and extend the results presented in Examples 6 and 7.

Method A. Crystal Violet staining Assay

All human tumor cell lines were obtained from the American Type Culture Collection. Cells were grown as monolayers in IMEM containing 10% fetal bovine serum without antibiotics. The cells were maintained in a humidified, 5% $CO_2$ atmosphere at 37° C.

After trypsinization, the cells were counted and adjusted to a concentration of 1,000–2,000 cells per 100 µL. Cell proliferation was determined by plating the cells (1,000–2,000 cells/well) in a 96 well microtiter plate. After addition of 100 µL cells per well, the cells were allowed to attach for 24 hours. At the end of the 24 hour period, various cocoa fractions were added at different concentrations to obtain dose response results. The cocoa fractions were dissolved in media at a 2 fold concentration and 100 µL of each solution was added in triplicate wells. On consecutive days, the plates were stained with 50 µL crystal violet (2.5 g crystal violet dissolved in 125 mL methanol, 375 mL water), for 15 min. The stain was removed and the plate was gently immersed into cold water to remove excess stain. The washings were repeated two more times, and the plates allowed to dry. The remaining stain was solubilized by adding 100 µL of 0.1M sodium citrate/50% ethanol to each well. After solubilization, the number of cells were quantitated on an ELISA plate reader at 540 nm (reference filter at 410 nm). The results from the ELISA reader were graphed with absorbance on the y-axis and days growth on the x-axis.

Method B. Soft Agar Cloning Assay

Cells were cloned in soft agar according to the method described by Nawata et al. (1981). Single cell suspensions were made in media containing 0.8% agar with various concentrations of cocoa fractions. The suspensions were aliquoted into 35 mm dishes coated with media containing 1.0% agar. After 10 days incubation, the number of colonies greater than 60 μm in diameter were determined on an Ominicron 3600 Image Analysis System. The results were plotted with number of colonies on the y-axis and the concentrations of a cocoa fraction on the x-axis.

Method C. XTT-Microculture Tetrazolium AssaY

The XTT assay procedure described by Scudiero et al. (1988) was used to screen various cocoa fractions. The XTT assay was essentially the same as that described using the MTT procedure (Example 6) except for the following modifications. XTT ((2,3-bis(2-methoxy-4-nitro-5-sulfophenyl)-5-[(phenylamino)carbonyl]-2H-tetrazolium hydroxide) was prepared at 1 mg/mL medium without serum, prewarmed to 37° C. PMS was prepared at 5 mM PBS. XTT and PMS were mixed together; 10 μL of PMS per mL XTT and 50 μL PMS-XTT were added to each well. After an incubation at 37° C. for 4 hr, the plates were mixed 30 min. on a mechanical shaker and the absorbance measured at 450–600 nm. The results were plotted with the absorbance on the y-axis and days growth or concentration on the x-axis.

For methods A and C, the results were also plotted as the percent control as the y-axis and days growth or concentration on the x-axis.

A comparison of the XTT and Crystal Violet Assay procedures was made with cocoa fraction D & E (Example 3B) against the breast cancer cell line MCF-7 p168 to determine which assay was most sensitive. As shown in FIG. 15A, both assays showed the same dose-response effects for concentrations >75 μ/mL. At concentrations below this value, the crystal violet assay showed higher standard deviations than the XTT assay results. However, since the crystal violet assay was easier to use, all subsequent assays, unless otherwise specified, were performed by this procedure.

Crystal violet assay results are presented (FIGS. 15B–15E) to demonstrate the effect of a crude polyphenol extract (Example 2) on the breast cancer cell line MDA MB231, prostate cancer cell line PC-3, breast cancer cell line MCF-7 p163, and cervical cancer cell line Hela, respectively. In all cases a dose of 250 μg/mL completely inhibited all cancer cell growth over a period of 5–7 days. The Hela cell line appeared to be more sensitive to the extract, since a 100 μg/mL dose also inhibited growth. Cocoa fractions from Example 3B were also assayed against Hela and another breast cancer cell line SKBR-3. The results (FIGS. 15F and 15G) showed that fraction D & E has the highest activity. As shown in FIGS. 15H and 15I, $IC_{50}$ values of about 40 μg/mL D & E were obtained from both cancer cell lines.

The cocoa fraction D & E was also tested in the soft agar cloning assay which determines the ability of a test compound(s) to inhibit anchorage independent growth. As shown in FIG. 15J, a concentration of 100 μg/mL completely inhibited colony-formation of Hela cells.

Crude polyphenol extracts obtained from eight different cocoa genotypes representing the three horticultural races of cocoa were also assayed against the Hela cell line. As shown in FIG. 15K all cocoa varieties showed similar dose-response effects. The UIT-1 variety exhibited the most activity against the Hela cell line. These results demonstrated that all cocoa genotypes possess a polyphenol fraction that elicits activity against at least one human cancer cell line that is independent of geographical origin, horticultural race, and genotype.

Another series of assays were performed on crude polyphenol extracts prepared on a daily basis from a one ton scale traditional 5-day fermentation of Brazilian cocoa beans, followed by a 4-day sun drying stage. The results shown in FIG. 15L showed no obvious effect of these early processing stages, suggesting little change in the composition of the polyphenols. However, it is known (Lehrian and Patterson, 1983) that polyphenol oxidase (PPO) will oxidize polyphenols during the fermentation stage. To determine what effect enzymically oxidized polyphenols would have on activity, another experiment was performed. Crude PPO was prepared by extracting finely ground, unfermented, freeze dried, defatted Brazilian cocoa beans with acetone at a ratio of 1 gm powder to 10 mL acetone. The slurry was centrifuged at 3,000 rpm for 15 min. This was repeated three times, discarding the supernatant each time with the fourth extraction being poured through a Buchner filtering funnel. The acetone powder was allowed to air dry, followed by assay according the procedures described by McLord and Kilara, (1983). To a solution of crude polyphenols (100 mg/10 mL Citrate-Phosphate buffer, 0.02M, pH 5.5) 100 mg of acetone powder (4,000 μ/mg protein) was added and allowed to stir for 30 min. with a stream of air bubbled through the slurry. The sample was centrifuged at 5,000×g for 15 min. and the supernatant extracted 3× with 20 mL ethyl acetate. The ethyl acetate extracts were combined, taken to dryness by distillation under partial vacuum and 5mL water added, followed by lyophilization. The material was then assayed against Hela cells and the dose-response compared to crude polyphenol extracts that were not enzymically treated. The results (FIG. 15M) showed a significant shift in the dose-response curve for the enzymically oxidized extract, showing that the oxidized products were more inhibitory than their native forms.

Example 9

Antioxidant Activity of cocoa Extracts Containing Procyanidins

Evidence in the literature suggests a relationship between the consumption of naturally occurring antioxidants (Vitamins C, E and B-carotene) and a lowered incidence of disease, including cancer (Designing Foods, 1993; Caragay, 1992). It is generally thought that these antioxidants affect certain oxidative and free radical processes involved with some types of tumor promotion. Additionally, some plant polyphenolic compounds that have been shown to be anticarcinogenic, also possess substantial antioxidant activity (Ho et al., 1992; Huang et al., 1992).

To determine whether cocoa extracts containing procyanidins possessed antioxidant properties, a standard Rancimat method was employed. The procedures described in Examples 1, 2 and 3 were used to prepare cocoa extracts which were manipulated further to produce two fractions from gel permeation chromatography. These two fractions are actually combined fractions A through C, and D and E (See FIG. 1) whose antioxidant properties were compared against the synthetic antioxidants BHA and BHT.

Peanut Oil was pressed from unroasted peanuts after the skins were removed. Each test compound was spiked into the oil at two levels, ~100 ppm and ~20 ppm, with the actual levels given in Table 7. 50 μL of methanol solubilized antioxidant was added to each sample to aid in dispersion of the antioxidant. A control sample was prepared with 50 μL of methanol containing no antioxidant.

Figure 16:
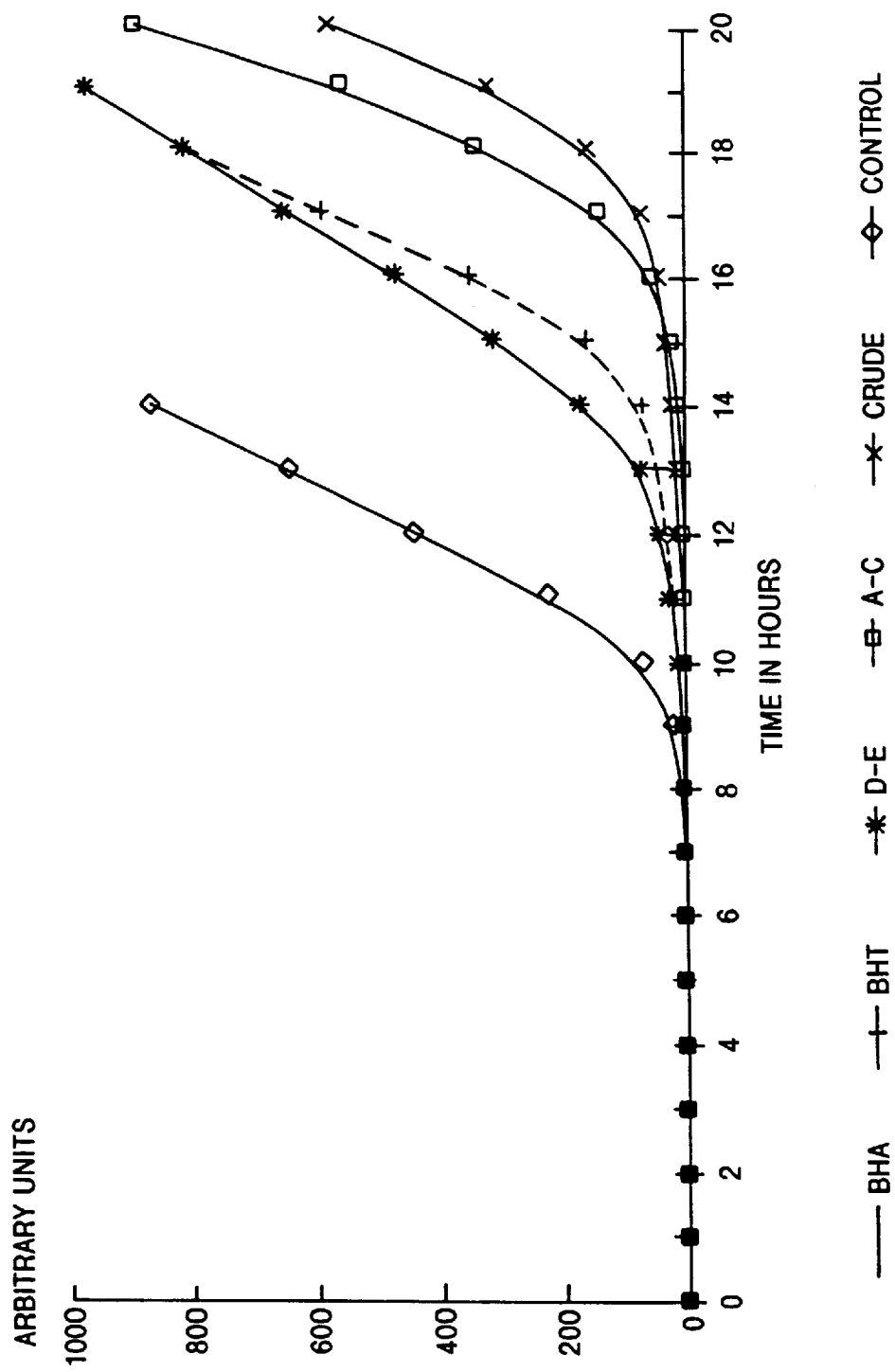
FIG. 16 shows typical Rancimat oxidation curves for cocoa procyanidin extract and fractions in comparison to the synthetic antioxidants BHA and BHT (arbitrary units vs. time; dotted line and cross (+) is BHA and BHT; * is D–E; x is crude; open square is A–C; and open diamond is control)

The samples were evaluated in duplicate, for oxidative stability using the Rancimat stability test at 100° C. and 20 cc/min of air. Experimental parameters were chosen to match those used with the Active Oxygen Method (AOM) or Swift Stability Test (Van Oosten et al., 1981). A typical Rancimat trace is shown in FIG. 16. Results are reported in Table 8 as hours required to reach a peroxide level of 100 meq.

TABLE 7

Concentrations of Antioxidants

| SAMPLE | LEVEL 1 | LEVEL 2 |
|---|---|---|
| | ppm | |
| Butylated Hydroxytoluene (BHT) | 24 | 120 |
| Butylated Hydroxyanisole (BHA) | 24 | 120 |
| Crude Ethyl Acetate Fraction of Cocoa | 22 | 110 |
| Fraction A–C | 20 | 100 |
| Fraction D–E | 20 | 100 |

TABLE 8

Oxidative Stability of Peanut Oil with Various Antioxidants

| SAMPLE | 20 ppm | 100 ppm |
|---|---|---|
| | average | |
| Control | 10.5 ± 0.7 | |
| BHT | 16.5 ± 2.1 | 12.5 ± 2.1 |
| BHA | 13.5 ± 2.1 | 14.0 ± 1.4 |
| Crude Cocoa Fraction | 18.0 ± 0.0 | 19.0 ± 1.4 |
| Fraction A–C | 16.0 ± 6.4 | 17.5 ± 0.0 |
| Fraction D–E | 14.0 ± 1.4 | 12.5 ± 0.7 |

These results demonstrated increased oxidative stability of peanut oil with all of the additives tested. The highest increase in oxidative stability was realized by the sample spiked with the crude ethyl acetate extract of cocoa. These results demonstrated that cocoa extracts containing procyanidins have antioxidant potential equal to or greater than equal amounts of synthetic BHA and BHT. Accordingly, the invention may be employed in place of BHT or BHA in known utilities of BHA or BHT, such as for instance as an antioxidant and/or food additive. And, in this regard, it is noted too that the invention is from an edible source. Given these results, the skilled artisan can also readily determine a suitable amount of the invention to employ in such "BHA or BHT" utilities, e.g., the quantity to add to food, without undue experimentation.

Example 10

Topoisomerase II Inhibition Study

DNA topoisomerase I and II are enzymes that catalyze the breaking and rejoining of DNA strands, thereby controlling the topological states of DNA (Wang, 1985). In addition to the study of the intracellular function of topoisomerase, one of the most significant findings has been the identification of topoisomerase II as the primary cellular target for a number of clinically important antitumor compounds (Yamashita et al., 1990) which include intercalating agents (m-AMSA, Adriamycin® and ellipticine) as well as nonintercalating epipodophyllotoxins. Several lines of evidence indicate that some antitumor drugs have the common property of stabilizing the DNA—topoisomerase II complex ("cleavable complex") which upon exposure to denaturing agents results in the induction of DNA cleavage (Muller et al., 1989). It has been suggested that the cleavable complex formation by antitumor drugs produces bulky DNA adducts that can lead to cell death.

According to this attractive model, a specific new inducer of DNA topoisomerase II cleavable complex is useful as an anti-cancer, anti-tumor or antineoplastic agent. In an attempt to identify cytotoxic compounds with activities that target DNA, the cocoa procyanidins were screened for enhanced cytotoxic activity against several DNA—damage sensitive cell lines and enzyme assay with human topoisomerase II obtained from lymphoma.

A. Decatenation of Kinetoplast DNA by Topoisomerase II

The in vitro inhibition of topoisomerase II decatenation of kinetoplast DNA, as described by Muller et al. (1989), was performed as follows. Nuclear extracts containing topoisomerase II activity were prepared from human lymphoma by modifications of the methods of Miller et al. (1981) and Danks et al. (1988). One unit of purified enzyme was enough to decatenate 0.25 µg of kinetoplast DNA in 30 min. at 34° C. Kinetoplast DNA was obtained from the trypanosome *Crithidia fasciculata*. Each reaction was carried out in a 0.5 mL microcentrifuge tube containing 19.5 µL $H_2O$, 2.5 µL 10× buffer (1× buffer contains 50 mM tris-HCl, pH 8.0, 120 mM KCl, 10 mM $MgCl_2$, 0.5 mM ATP, 0.5 mM dithiothreitol and 30 µg BSA/mL), 1 µL kinetoplast DNA (0.2 µg), and 1 µL DMSO-containing cocoa procyanidin test fractions at various concentrations. This combination was mixed thoroughly and kept on ice. One unit of topoisomerase was added immediately before incubation in a waterbath at 34° C. for 30 min.

Following incubation, the decatenation assay was stopped by the addition of 5 µL stop buffer (5% sarkosyl, 0.0025% bromophenol blue, 25% glycerol) and placed on ice. DNA was electrophoresed on a 1% agarose gel in TAE buffer containing ethidium bromide (0.5 µg/mL). Ultraviolet illumination at 310 nm wavelength allowed the visualization of DNA. The gels were photographed using a Polaroid Land camera.

FIG. 17 shows the results of these experiments. Fully catenated kinetoplast DNA does not migrate into a 1% agarose gel. Decatenation of kinetoplast DNA by topoisomerase II generates bands of monomeric DNA (monomer circle, forms I and II) which do migrate into the gel. Inhibition of the enzyme by addition of cocoa procyanidins is apparent by the progressive disappearance of the monomer bands as a function of increasing concentration. Based on these results, cocoa procyanidin fractions A, B, D, and E were shown to inhibit topoisomerase II at concentrations ranging from 0.5 to 5.0 µg/mL. These inhibitor concentrations were very similar to those obtained for mitoxanthrone and m-AMSA [4'-(9-acridinylamino)methanesulfon-m-anisidide].

B. Drug Sensitive Cell Lines

Cocoa procyanidins were screened for cytotoxicity against several DNA-damage sensitive cell lines. One of the cell lines was the xrs-6 DNA double strand break repair mutant developed by P. Jeggo (Kemp et al., 1984). The DNA repair deficiency of the xrs-6 cell line renders them particularly sensitive to x-irradiation, to compounds that produce DNA double strand breaks directly, such as bleomycin, and to compounds that inhibit topoisomerase II, and thus may indirectly induce double strand breaks as suggested by Warters et al. (1991). The cytotoxicity toward the repair deficient line was compared to the cytotoxicity against a DNA repair proficient CHO line, BR1. Enhanced cytotoxicity towards the repair deficient (xrs-6) line was interpreted as evidence for DNA cleavable double strand break formation.

The DNA repair competent CHO line, BR1, was developed by Barrows et al. (1987) and expresses $O^6$-alkylguanine-DNA-alkyltransferase in addition to normal CHO DNA repair enzymes. The CHO double strand break repair deficient line (xrs-6) was a generous gift from Dr. P. Jeggo and co-workers (Jeggo et al., 1989). Both of these lines were grown as monolayers in alpha-MEM containing serum and antibiotics as described in Example 6. Cells were maintained at 37° C. in a humidified 5% $CO_2$ atmosphere. Before treatment with cocoa procyanidins, cells grown as monolayers were detached with trypsin treatment. Assays were performed using the MTT assay procedure described in Example 6.

Figures 18A, 18B:
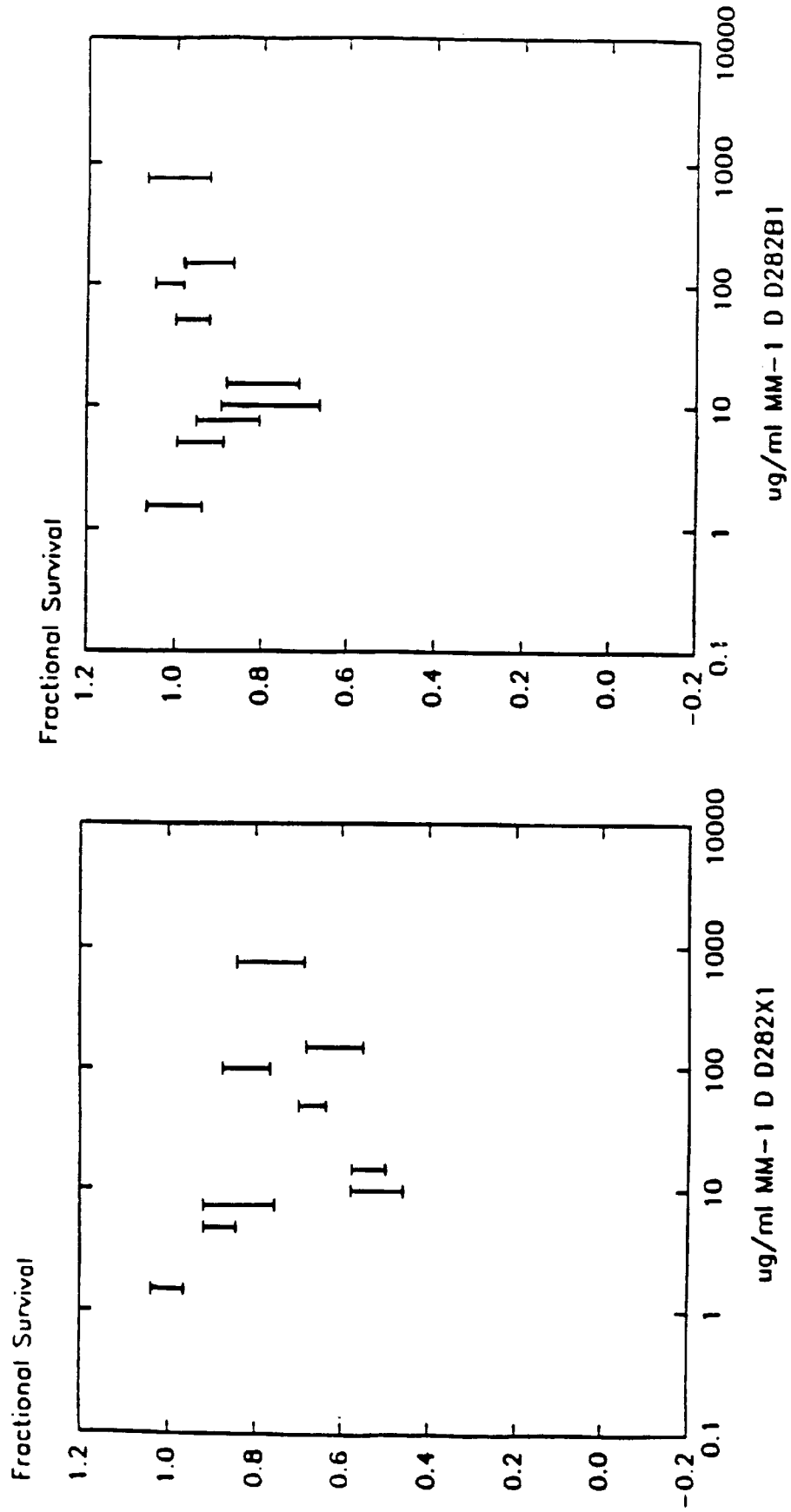
FIG. 18 shows dose response relationships of cocoa procyanidin fraction D against DNA repair competent and deficient cell lines (fractional survival vs. µg/ml; left side xrs-6 DNA Deficient Repair Cell Line, MM-1 D D282X1; right side BR1 Competent DNA Repair Cell Line, MM-1 D D282B1)

The results (FIG. 18) indicated no enhanced cytotoxicity towards the xrs-6 cells suggesting that the cocoa procyanidins inhibited topoisomerase II in a manner different from cleavable double strand break formation. That is, the cocoa procyanidins interact with topoisomerase II before it has interacted with the DNA to form a noncleavable complex.

Noncleavable complex forming compounds are relatively new discoveries. Members of the anthracyclines, podophyllin alkaloids, anthracenediones, acridines, and ellipticines are all approved for clinical anti-cancer, anti-tumor or anti-neoplastic use, and they produce cleavable complexes (Liu, 1989). Several new classes of topoisomerase II inhibitors have recently been identified which do not appear to produce cleavable complexes. These include amonafide (Hsiang et al., 1989), distamycin (Fesen et al., 1989), flavanoids (Yamashita et al., 1990), saintopin (Yamashita et al., 1991), membranone (Drake et al., 1989), terpenoids 5 (Kawada et al., 1991), anthrapyrazoles (Fry et al., 1985), dioxopiperazines (Tanabe et al., 1991), and the marine acridine-dercitin (Burres et al., 1989).

Since the cocoa procyanidins inactivate topoisomerase II before cleavable complexes are formed, they have chemotherapy value either alone or in combination with other known and mechanistically defined topoisomerase II inhibitors. Additionally, cocoa procyanidins also appear to be a novel class of topoisomerase II inhibitors, (Kashiwada et al., 1993) and may thus be less toxic to cells than other known inhibitors, thereby enhancing their utility in chemotherapy.

Figure 19:
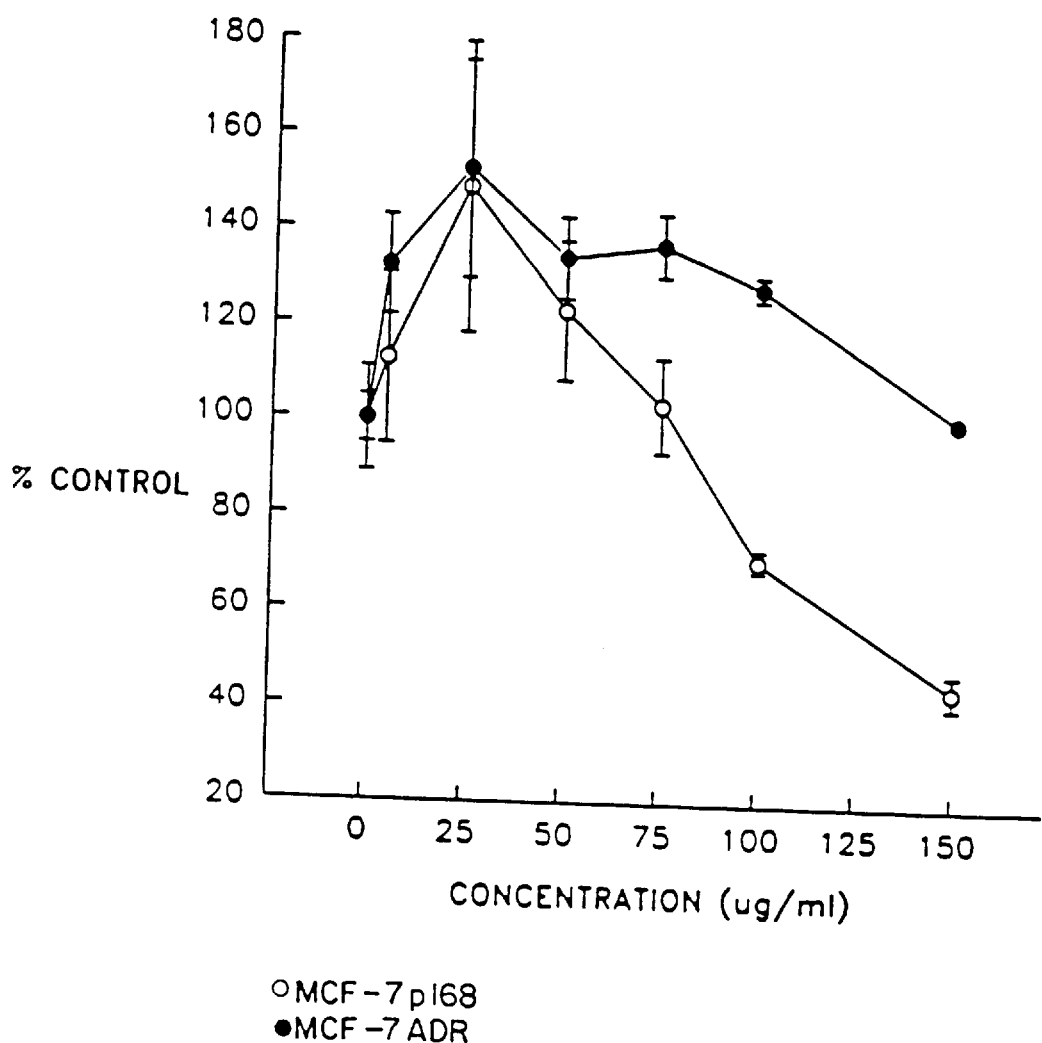
FIG. 19 shows the dose-response curves for Adriamycin resistant MCF-7 cells in comparison to a MCF-7 p168 parental cell line when treated with cocoa fraction D+E (% control vs. concentration, µg/ml; open circle is MCF-7 p168; darkened circle is MCF-7 ADR)

The human breast cancer cell line MCF-7 (ADR) which expresses a membrane bound glycoprotein (gp170) to confer multi-drug resistance (Leonessa et al., 1994) and its parental line MCF-7 p168 were used to assay the effects of cocoa fraction D & E. As shown in FIG. 19, the parental line was inhibited at increasing dose levels of fraction D & E, whereas the Adriamycin (ADR) resistant line was less effected at the higher doses. These results show that cocoa fraction D & E has an effect on multi-drug resistant cell lines.

Example 11

Synthesis of Procyanidins

The synthesis of procyanidins was performed according to the procedures developed by Delcour et al. (1983), with modification. In addition to condensing (+)-catechin with dihydroquercetin under reducing conditions, (−)-epicatechin was also used to reflect the high concentrations of (−)-epicatechin that naturally occur in unfermented cocoa beans. The synthesis products were isolated, purified, analyzed, and identified by the procedures described in Examples 3, 4 and 5. In this manner, the biflavanoids, triflavanoids and tetraflavanoids are prepared and used as analytical standards and, in the manner described above with respect to cocoa extracts.

Example 12

Assay of Normal Phase Semi-Preparative Fractions

Figure 20:
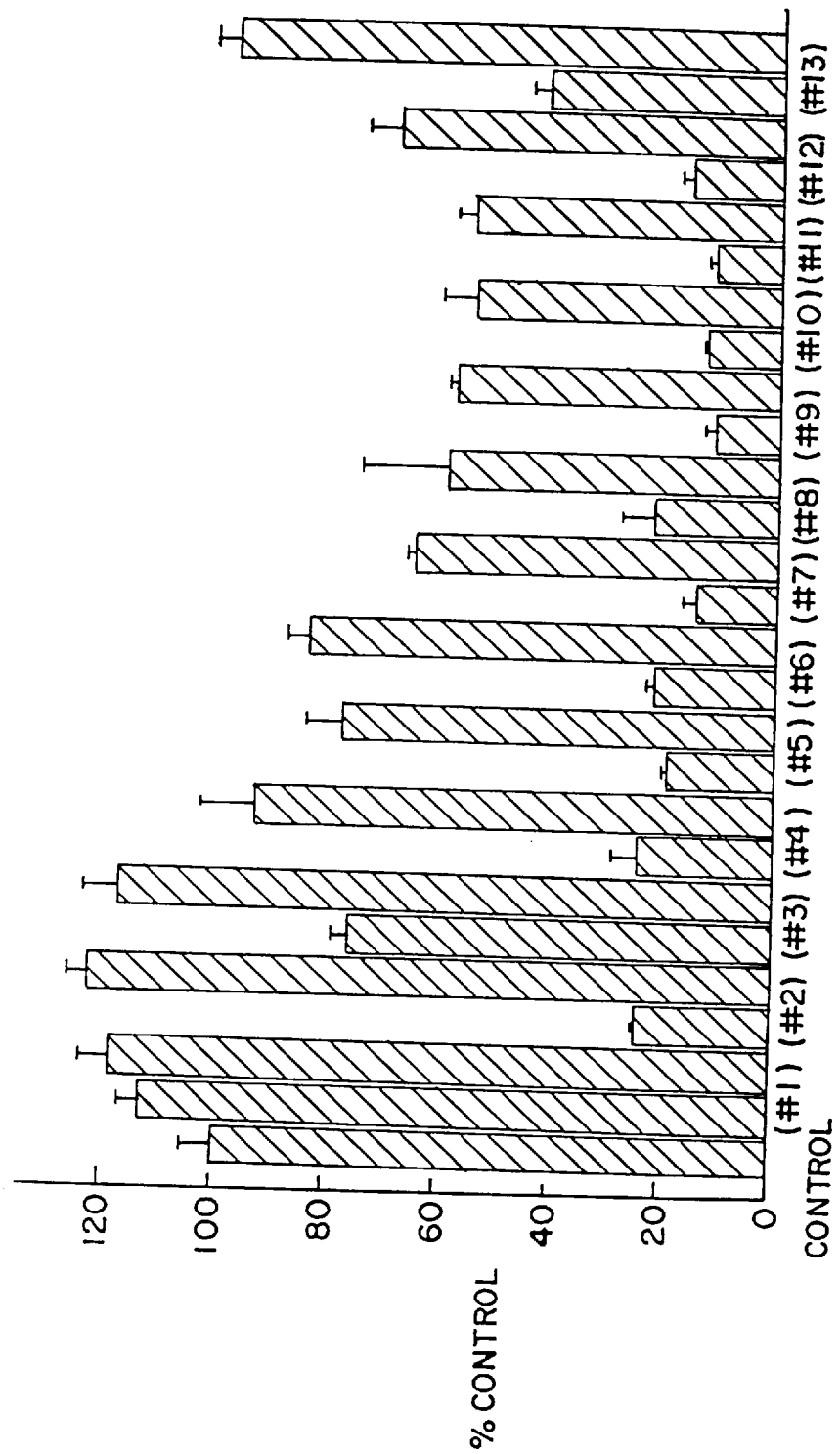
FIG. 20 shows the dose-response effects on Hela cells when treated at 100 µg/mL and 25 µg/mL levels of twelve fractions prepared by Normal phase semi-preparative HPLC (bar chart, % control vs. control and fractions 1–12).

Since the polyphenol extracts are compositionally complex, it was necessary to determine which components were active against cancer cell lines for further purification, dose-response assays and comprehensive structural identification. A normal phase semi preparative HPLC separation (Example 3B) was used to separate cocoa procyanidins on the basis of oligomeric size. In addition to the original extract, twelve fractions were prepared (FIGS. 2B and 15O) and assayed at 100 µg/mL and 25 µg/mL doses against Hela to determine which oligomer possessed the greatest activity. As shown in FIG. 20, fractions 4–11 (pentamer-dodecamer) demonstrated $IC_{50}$ values of approximately 25 µg/mL. These results indicated that these specific oligomers had the greatest activity against Hela cells. Additionally, normal phase HPLC analysis of cocoa fraction D & E indicated that this fraction was enriched with these oligomers.

From the foregoing, it is clear that the extract and cocoa polyphenols, as well as the compositions method and kit, of the invention have utility. In this regard, it is mentioned that the invention. is from an edible source and, that the activity in vitro can demonstrate at least some activity in vivo, especially considering the doses discussed above.

Additionally, the above description shows that the extract and cocoa polyphenols, as well as the compositions, method and kit have antioxidant activity like that of BHT and BHA, as well as oxidative stability. Thus, the invention can be employed in place of BHT or BHA in known utilities of BHA and BHT, such as an antioxidant, for instance, an antioxidant food additive. The invention can also be employed in place of topoisomerase-inhibitors in the presently known utilities therefor. Accordingly, there are many compositions and methods envisioned by the invention; for instance, antioxidant or preservative compositions, topoisomerase-inhibiting compositions, methods for preserving food or any desired item such as from oxidation, and methods for inhibiting topoisomerase which comprise either the extract and/or cocoa polyphenol(s) or which comprise contacting the food, item or topoisomerase with the respective composition or with the extract and/or cocoa polyphenol(s).

Having thus described in detail the preferred embodiments of the present invention, it is to be understood that the invention defined by the appended claims is not to be limited by particular details set forth in the above descriptions as many apparent variations thereof are possible without departing from the spirit or scope of the present invention.

REFERENCES

1. Barrows, L. R., Borchers, A. H., and Paxton, M. B., Transfectant CHO Cells Expressing $O^6$-alkylguanine-DNA-alkyltransferase Display Increased Resistance to DNA Damage Other than $O^6$-guanine Alkylation, Carcinogenesis, 8:1853 (1987).
2. Boukharta, M., Jalbert, G. and Castonguay, A., Efficacy of Ellagitannins and Ellagic Acid as Cancer Chemopreventive Agents—Presented at the XVI$^{th}$ International Conference of the Groupe Polyphenols, Lisbon, Portugal, Jul. 13–16, 1992.
3. Burres, N. S., Sazesh, J., Gunawardana, G. P., and Clement, J. J., Antitumor Activity and Nucleic Acid Binding Properties of Dercitin, a New Acridine Alkaloid Isolated from a Marine Dercitus species Sponge, Cancer Research, 49, 5267–5274 (1989).
4. Caragay, A. B., Cancer Preventive Foods and Ingredients, Food Technology, 46:4, 65–79 (1992).
5. Chu, S.-C., Hsieh, Y.-S. and Lim, J.-Y., Inhibitory Effects of Flavonoids on Maloney Murine Leukemia Virus Reverse Transcriptase Activity, J. of Natural Products, 55:2, 179–183 (1992).

6. Clapperton, J., Hammerstone, J. F. Jr., Romanczyk, L. J. Jr., Chan, J., Yow, S., Lim, D. and Lockwood, R., Polyphenols and Cocoa Flavor—Presented at the XVIth International Conference of the Groupe Polyphenols, Lisbon, Portugal, Jul. 13–16, 1992.
7. Danks, M. K., Schmidt, C. A., Cirtain, M. C., Suttle, D. P., and Beck, W. T., Altered Catalytic Activity of and DNA Cleavage by DNA Topoisomerase II from Human Leukemic Cells Selected for Resistance to VM-26, Biochem., 27:8861 (1988).
8. Delcour, J. A., Ferreira, D. and Roux, D. G., Synthesis of Condensed Tannins, Part 9, The Condensation Sequence of Leucocyanidin with (+)-Catechin and with the Resultant Procyanidins, J. Chem. Soc. Perkin Trans. I, 1711–1717 (1983).
9. Deschner, E. E., Ruperto, J., Wong, G. and Newmark, H. L., Quercitin and Rutin as Inhibitors of Azoxymethanol—Induced Colonic Neoplasia, Carcinogenesis, 7, 1193–1196 (1991).
10. Designing Foods, Manipulating Foods to Promote Health, Inform, 4:4, 344–369 (1993).
11. Drake, F. H., Hofmann, G. A., Mong., S.-M., Bartus, J. O., Hertzberg, R. P., Johnson, R. K., Mattern, M. R., and Mirabelli, C. K., In vitro and Intercellular Inhibition of Topoisomerase II by the Antitumor Agent Membranone, Cancer Research, 49, 2578–2583 (1989).
12. Engels J. M. M., Genetic Resources of Cacao: A Catalogue of the CATIE Collection, Tech. Bull. 7, Turrialba, Costa Rica (1981).
13. Enriquez G. A. and Soria J. V., Cocoa Cultivars Register IICA, Turrialba, Cost Rica (1967).
14. Ferreira, D., Steynberg, J. P., Roux, D. G. and Brandt, E. V., Diversity of Structure and Function in oligomeric Flavanoids, Tetrahedron, 48:10, 1743–1803 (1992).
15. Fesen, M. and Pommier, Y., Mammalian Topoisomerase II Activity is Modulated by the DNA Minor Groove Binder—Distainycin in Simian Virus 40 DNA, J. Biol. Chem., 264, 11354–11359 (1989).
16. Fry, D. W., Boritzki, T. J., Besserer, J. A., and Jackson, R.C., In vitro Strand Scission and Inhibition of Nucleic Acid Synthesis on L1210 Leukemia Cells by a New Class of DNA Complexes, the anthra [1, 9-CD]pyrazol-6(2H)-ones (anthrapyrazoles), Biochem. Pharmacol., 34, 3499–3508 (1985).
17. Hsiang, Y.-H., Jiang, J. B., and Liu, L. F., Topoisomerase II Mediated DNA Cleavage by Amonafide and Its Structural Analogs, Mol. Pharmacol., 36, 371–376 (1989).
18. Jalal, M. A. F. and Collin, H. A., Polyphenols of Mature Plant, Seedling and Tissue Cultures of Theobroma Cacoa, Phytochemistry, 6, 1377–1380 (1978).
19. Jeggo, P. A., Caldecott, K., Pidsley, S., and Banks, G. R., Sensitivity of Chinese Hamster ovary Mutants Defective in DNA Double Strand Break Repair to Topoisomerase II Inhibitors, Cancer Res., 49:7057 (1989).
20. Kashiwada, Y., Nonaka, G.-I., Nishioka, I., Lee, K. J.-H., Bori, I., Fukushima, Y., Bastow, K. F., and Lee, K.-H., Tannin as Potent Inhibitors of DNA Topoisomerase II in vitro, J. Pharm. Sci., 82:5, 487–492 (1993).
21. Kato, R., Nakadate, T., Yamamoto, S. and Sugimura, T., Inhibition of 12-O-tetradecanoylphorbol-13-acetate Induced Tumor Promotion and Ornithine Decarboxylase Activity by Quercitin: Possible Involvement of Lipoxygenase Inhibition, Carcinogenesis, 4, 1301–1305 (1983).
22. Kawada, S.-Z., Yamashita, Y., Fujii, N. and Nakano, H., Induction of Heat Stable Topoisomerase II-DNA Cleavable Complex by Nonintercalative Terpenoids, Terpentecin and Clerocidin, Cancer Research, 51, 2922–2929 (1991).
23. Kemp, L. M., Sedgwick, S. G. and Jeggo, P. A., X-ray Sensitive Mutants of Chinese Hamster Ovary Cells Defective in Double Strand Break Rejoining, Mutat. Res., 132:189 (1984).
24. Kikkoman Corporation, Antimutagenic Agent Containing Proanthocyanidin Oligomer Preferably Having Flavan-3-ol-Diol Structure, JP 04190774-A, Jul. 7, 1992.
25. Lehrian, D. W.; Patterson, G. R. In Biotechnology; Reed, G., Ed.; Verlag Chemie: Weinheim, 1983, Vol.5, Chapter 12.
26. Leonessa, F., Jacobson, M., Boyle, B., Lippman, J., McGarvey, M., and Clarke, R. Effect of Tamoxifen on the Multidrug-Resistant Phenotype in Human Breast Cancer Cells: Isobolograms, Drug Accumulation, and $M_r$ 170, 000 Glycoprotein (gp 170) Binding Studies, Cancer Research, 54, 441–447 (1994).
27. Liu, L. F., DNA Toposimerase Poisons as Antitumor Drugs, Ann. Rev. Biochem., 58, 351–375 (1989).
28. McCord, J. D. and Kilara A. Control of Enzymatic Browning in Processed Mushrooms (Agaricus bisporus). J. Food Sci., 48:1479 (1983).
29. Miller, K. G., Liu, L. F. and Englund, P. A., Homogeneous Type II DNA Topoisomerase from Hela Cell Nuclei, J. Biol. Chem., 256:9334 (1981).
30. Mosmann, T., Rapid Colorimetric Assay for Cellular Growth and Survival: Application to Proliferation and Cytoxicity Assays, J. Immunol. Methods, 65, 55 (1983).
31. Muller, M. T., Helal, K., Soisson, S. and Spitzer, J. R., A Rapid and Quantitative Microtiter Assay for Eukaryotic Topoisomerase II, Nuc. Acid Res., 17:9499 (1989).
32. Nawata, H., Chong, M. T., Bronzert, D. and Lippman, M. E. Estradiol-Independent growth of a Subline of MCF-7 Human Breast Cancer Cells in Culture, J. Biol. Chem., 256:13, 6895–6902 (1981).
33. Okuda, T., Yoshida, T., and Hatano, T., Molecular Structures and Pharmacological Activities of Polyphenols—Oligomeric Hydrolyzable Tannins and Others—Presented at the XVIth International Conference of the Groupe Polyphenols, Lisbon, Portugal, Jul. 13–16, 1992.
34. Phenolic Compounds in Foods and Their Effects on Health II. Antioxidants & Cancer Prevention, Huang, M.-T., Ho, C.-T., and Lee, C. Y. editors, ACS symposium Series 507, American Chemical Society, Washington, D.C. (1992).
35. Phenolic Compounds in Foods and Their Effects on Health I, Analysis, Occurrence & Chemistry, Ho, C.-T., Lee, C. Y., and Huang, M.-T editors, ACS Symposium Series 506, American Chemical Society, Washington, D.C. (1992).
36. Porter, L. J., Ma, Z. and Chan, B. G., Cocoa Procyanidins: Major Flavanoids and Identification of Some Minor Metabolites, Phytochemistry, 30, 1657–1663 (1991).
37. Revilla, E., Bourzeix, M. and Alonso, E., Analysis of Catechins and Procyanidins in Grape Seeds by HPLC with Photodiode Array Detection, Chromatographia, 31, 465–468 (1991).
38. Scudiero, D. A., Shoemaker, R. H., Paull, K. D., Monks, A., Tierney, S., Nofziger, T. H., Currens, M. J., Seniff, D., and Boyd, M. R. Evaluation of a Soluble Tetrazolium/Formazan Assay for Cell Growth and Drug Sensitivity in Culture Using Human and Other Tumor Cell Lines, Canur Research, 48, 4827–4833 (1988).
39. Self, R., Eagles, J., Galletti, G. C., Mueller-Harvey, I., Hartley, R. D., Lee, A. G. H., Magnolato, D., Richli, U., Gujur, R. and Haslam, E., Fast Atom Bombardment Mass Spectrometry of Polyphenols (syn. Vegetable Tannins), Biomed Environ. Mass Spec. 13, 449–468 (1986).

40. Tanabe, K., Ikegami, Y., Ishda, R. and Andoh, T., Inhibition of Topoisomerase II by Antitumor Agents bis (2,6-dioxopiperazine) Derivatives, cancer Research, 51, 4903–4908 (1991).
41. Van Oosten, C. W., Poot, C. and A. C. Hensen, The Precision of the Swift Stability Test, Fette, Seifen, Anstrichmittel, 83:4, 133–135 (1981).
42. Wang, J. C., DNA Topoisomerases, Ann. Rev. Biochem., 54, 665–697 (1985).
43. Warters, R. L., Lyons, B. W., Li, T. M. and Chen, D. J., Topoisomerase II Activity in a DNA Double-Strand Break Repair Deficient-Chinese Hamster Ovary Cell Line, Mutat. Res., 254:167 (1991).
44. Yamashita, Y., Kawada, S.-Z. and Nakano, H., Induction of Mammalian Topoismerase II Dependent DNA Cleavage by Nonintercalative Flavanoids, Genistein and Orbol., Biochem Pharm, 39:4, 737–744 (1990).
45. Yamashita, Y., Kawada, S.-Z., Fujii, N. and Nakano, H., Induction of Mammalian DNA Topoisomerase I and II Mediated DNA Cleavage by Saintopin, a New Antitumor Agent from Fungus, Biochem., 30, 5838–5845 (1991).

What is claimed is:

1. A method for treating a mammal in need of treatment with an antioxidant composition comprising administering to the mammal a substantially pure cocoa extract comprising at least one of cocoa procyanidins pentamers to dodecamers in an amount sufficient to effect said treatment.

2. The method of claim 1, wherein the cocoa procyanidin extract is prepared by a process comprising the steps of:
   (i) reducing cocoa beans to powder,
   (ii) defatting the cocoa powder,
   (iii) extracting the powder to provide the cocoa procyanidin extract, and
   (iv) purifying the cocoa procyanidins.

3. The method of claim , wherein the step of reducing cocoa beans to powder comprises:
   a) freeze drying beans and pulp,
   b) depulping the freeze dried mass,
   c) dehulling the freeze dried cocoa beans and
   d) grinding the dehulled beans to form powder.

4. The method of claim 3, wherein the process further comprises purifying the procyanidins of step (iv) by gel permeation chromatography and/or by preparative high performance liquid chromatography (HPLC).

5. The method of claim 4, wherein the process further comprises purifying the procyanidins of step (iv) by gel permeation chromatography and/or by preparative high performance liquid chromatography (HPLC).

6. A method for treating a mammal in need of treatment with an antioxidant composition comprising administering to the mammal at least one procyanidin pentamer through dodecamer in an amount sufficient to effect said treatment.

7. The method of claim 6, wherein the procyanidin is a pentameric polyphenol.

8. The method of claim 6, wherein the procyanidin is prepared by a process comprising the steps of:
   (i) reducing cocoa beans to powder,
   (ii) defatting the cocoa powder,
   (iii) extracting the powder to provide the cocoa procyanidin extract, and
   (iv) purifying the cocoa procyanidins.

9. The method of claim 8, wherein the step of reducing cocoa beans to powder comprises:
   a) freeze drying beans and pulp,
   b) depulping the freeze dried mass,
   c) dehulling the freeze dried cocoa beans and
   d) grinding the dehulled beans to form powder.

10. The method of claim 8, wherein the process further comprises purifying the procyanidins of step (iv) by gel permeation chromatography and/or by preparative high performance liquid chromatography (HPLC).

11. The method of claim 9, wherein the process further comprises purifying the procyanidins of step (iv) by gel permeation chromatography and/or by preparative high performance liquid chromatography (HPLC).

* * * * *

UNITED STATES PATENT AND TRADEMARK OFFICE
CERTIFICATE OF CORRECTION

PATENT NO. : 5,891,905
DATED : April 6, 1999
INVENTOR(S) : Leo J. Romanczyk, Jr. et al.

It is certified that error appears in the above-identified patent and that said Letters Patent is hereby corrected as shown below:

In the Drawings,
Sheet 31,
Figure 9A, under chart, insert, -- "DOSE MM-1 A 0192H5 --.

Sheet 32,
Figure 9B, under chart, insert, "DOSE MM-1 B 0192H5 --.

Sheet 73,
Figure 15B, "REPRESENTITIVE" should read -- REPRESENTATIVE --.

Sheet 84,
Figure 15m, "(WITH OUT") should read -- (WITHOUT --.

Item [56] REFERENCES CITED

U.S. Patent Documents, in "4,704,292," "Kattonberg" should read -- Kattenberg --.

Other Publications in "Drake, F.H.", "Membrane," should read -- Membranone, --.

In "Scudiero, D.A.,", "Canur" should read -- Cancer --.
In "Yamashita, Y.,", "(990)." should read -- (1990). --.

Item [57] Abstract,
Line 13, "topiosomerase-inhibiting" should read -- topoisomerase-inhibiting --.

Column 3,
Line 46, "ml); MM-1C" should read -- ml); MM-1A0192H5, MM-1B0192H5, MM-1C --.

UNITED STATES PATENT AND TRADEMARK OFFICE
CERTIFICATE OF CORRECTION

PATENT NO. : 5,891,905
DATED : April 6, 1999
INVENTOR(S) : Leo J. Romanczyk, Jr. et al.

It is certified that error appears in the above-identified patent and that said Letters Patent is hereby corrected as shown below:

Column 9,
Line 24, "step wise" should read -- stepwise --.
Line 48, "Chromatography-" should read -- Chromatography --.

Column 20,
Line 54, "Oil" should read -- oil --.

Column 23,
Line 45, "effected" should read -- affected --.

Column 24,
Line 3, "semi preparative" should read -- semi-preparative --.

Signed and Sealed this

Twenty-third Day of October, 2001

Attest:

NICHOLAS P. GODICI
Attesting Officer    Acting Director of the United States Patent and Trademark Office